(12) United States Patent
Gruskin et al.

(10) Patent No.: US 8,906,363 B2
(45) Date of Patent: *Dec. 9, 2014

(54) FUSION PROTEINS FOR THE TREATMENT OF CNS

(75) Inventors: Elliott A. Gruskin, Killingworth, CT (US); Anthony O. Caggiano, Larchmont, NY (US); Gargi Roy, Danbury, CT (US); Jennifer Iaci, Montville, NJ (US); Michael P. Zimber, Mamroneck, NY (US)

(73) Assignee: Acorda Therapeutics, Inc., Ardsley, NY (US)

( * ) Notice: Subject to any disclaimer, the term of this patent is extended or adjusted under 35 U.S.C. 154(b) by 1053 days.

This patent is subject to a terminal disclaimer.

(21) Appl. No.: 10/848,564

(22) Filed: May 17, 2004

(65) Prior Publication Data

US 2009/0028829 A1    Jan. 29, 2009

Related U.S. Application Data

(60) Provisional application No. 60/471,239, filed on May 16, 2003, provisional application No. 60/471,240, filed on May 16, 2003, provisional application No. 60/471,300, filed on May 16, 2003, provisional application No. 60/474,372, filed on May 29, 2003.

(51) Int. Cl.

| *A61K 38/51* | (2006.01) |
|---|---|
| *C12N 9/26* | (2006.01) |
| *C07K 19/00* | (2006.01) |
| *C12N 9/88* | (2006.01) |
| *A61K 38/00* | (2006.01) |

(52) U.S. Cl.
CPC .............. *C12N 9/2408* (2013.01); *A61K 38/51* (2013.01); *C07K 19/00* (2013.01); *C07K 2319/10* (2013.01); *C07K 2319/003* (2013.01); *A61K 38/00* (2013.01); *C12N 9/88* (2013.01); *C12Y 302/01035* (2013.01); *C12Y 302/01036* (2013.01); *C12Y 402/02001* (2013.01); *C12Y 402/02004* (2013.01)
USPC .......................... 424/94.5; 435/232; 424/93.7

(58) Field of Classification Search
None
See application file for complete search history.

(56) References Cited

U.S. PATENT DOCUMENTS

| 5,262,522 | A | 11/1993 | Gearing |
|---|---|---|---|
| 5,270,194 | A | 12/1993 | D'Alterio et al. |
| 5,496,718 | A | 3/1996 | Hashimoto |
| 5,498,536 | A | 3/1996 | Khandke |
| 5,578,480 | A | 11/1996 | Khandke |
| 5,652,122 | A | 7/1997 | Frankel et al. |
| 5,670,617 | A | 9/1997 | Frankel et al. |
| 5,674,980 | A | 10/1997 | Frankel et al. |
| 5,747,641 | A | 5/1998 | Frankel et al. |
| 5,763,205 | A | 6/1998 | Hashimoto et al. |
| 5,792,743 | A | 8/1998 | Schachner |
| 5,804,604 | A | 9/1998 | Frankel et al. |
| 5,869,301 | A | 2/1999 | Nghiem et al. |
| 5,997,863 | A | 12/1999 | Zimmermann et al. |
| 6,007,810 | A | 12/1999 | Ishikawa et al. |
| 6,063,378 | A | 5/2000 | Nohara et al. |
| 6,093,563 | A | 7/2000 | Bennett et al. |
| 6,153,187 | A | 11/2000 | Yacoby-Zeevi |
| 6,171,575 | B1 | 1/2001 | Okuyama |
| 6,184,023 | B1 | 2/2001 | Hashimoto et al. |
| 6,200,564 | B1 | 3/2001 | Lamont et al. |
| 6,248,562 | B1 | 6/2001 | Dunn et al. |
| 6,313,265 | B1 | 11/2001 | Phillips et al. |
| 6,326,166 | B1 | 12/2001 | Pomerantz et al. |
| 6,972,168 | B2 | 12/2005 | Muir |
| 7,008,783 | B1 | 3/2006 | Sato et al. |
| 7,163,545 | B2 | 1/2007 | Yaszemski et al. |
| 7,465,705 | B2 * | 12/2008 | Lee et al. ....................... 514/12 |
| 7,507,570 | B2 | 3/2009 | Prabhakar et al. |
| 7,560,106 | B2 | 7/2009 | Sasisekharan et al. |
| 2003/0040112 | A1 | 2/2003 | Muir et al. |
| 2003/0072749 | A1 | 4/2003 | Muir et al. |
| 2003/0077258 | A1 | 4/2003 | Muir |
| 2004/0033221 | A1 | 2/2004 | Masuda et al. |
| 2004/0265297 | A1 | 12/2004 | Gruskin et al. |
| 2005/0118157 | A1 | 6/2005 | McMahon et al. |
| 2005/0233419 | A1 | 10/2005 | Pojasek et al. |
| 2006/0078959 | A1 | 4/2006 | Prabhakar et al. |
| 2006/0153827 | A1 * | 7/2006 | Gruskin et al. ............ 424/94.63 |

(Continued)

FOREIGN PATENT DOCUMENTS

| AU | 2003/208466 B2 | 9/2003 |
|---|---|---|
| AU | 2003/265561 A8 | 3/2004 |

(Continued)

OTHER PUBLICATIONS

S.R. Schwarze et al. "In Vivo Protein Transduction: Delivery of a Biologically Active Protein into the Mouse", Science 285: 1569-1572. (Sep. 1999).*

L. Yick et al. "Chondroitinase ABC Promotes Axonal Regeneration of Clarke's Neurons After Spinal Cord Injury", Regenration and transplantation 11(5): 1063-1067. (Apr. 2000).*

Smiseth et al., Effect of Hyaluronidase on Substrate Exchange and Blood Flow in the Ischaemic Myocardium of the Dog, 1982, Clinical Physiology, 2(1):39-50.

(Continued)

*Primary Examiner* — Rebecca Prouty
(74) *Attorney, Agent, or Firm* — Pepper Hamilton LLP

(57) ABSTRACT

This disclosure relates to compositions capable of use in the treatment of spinal cord injuries and related disorders of the central nervous system (CNS), and in particular, compositions including proteoglycan degrading molecules and compositions capable of blocking and/or over coming the activity of neuronal growth inhibitory molecules, as well as fusion proteins which includes a proteoglycan degrading domain and a domain capable of blocking and or over coming the activity of neuronal growth inhibitory molecules.

8 Claims, 5 Drawing Sheets

(4 of 5 Drawing Sheet(s) Filed in Color)

(56) References Cited

U.S. PATENT DOCUMENTS

| | | |
|---|---|---|
| 2006/0233782 A1 | 10/2006 | Gruskin et al. |
| 2007/0104703 A1 | 5/2007 | Caggiano et al. |
| 2007/0274979 A1 | 11/2007 | Gruskin et al. |
| 2012/0207732 A1 | 8/2012 | Gruskin et al. |
| 2012/0308547 A1 | 12/2012 | Caggiano et al. |
| 2013/0210082 A1 | 8/2013 | Caggiano et al. |
| 2013/0243765 A1 | 9/2013 | Gruskin et al. |

FOREIGN PATENT DOCUMENTS

| | | |
|---|---|---|
| AU | 2004/241088 A2 | 12/2004 |
| AU | 2006/294755 | 4/2012 |
| CA | 2623635 | 4/2013 |
| EP | 0704532 A2 | 3/1996 |
| EP | 1631234 A2 | 3/2006 |
| EP | 1646353 A2 | 4/2006 |
| EP | 2353606 A2 | 8/2011 |
| EP | 2354155 A2 | 8/2011 |
| JP | H10-174598 | 6/1998 |
| JP | H11500308 | 1/1999 |
| JP | 2002-505873 | 2/2002 |
| JP | 2002-526028 | 8/2002 |
| JP | 2003-500016 | 1/2003 |
| JP | 2004-113166 | 4/2004 |
| WO | WO 91/06303 A | 5/1991 |
| WO | 94/25567 * | 11/1994 |
| WO | WO 95/13091 A1 | 5/1995 |
| WO | WO 95/14478 | 6/1995 |
| WO | WO 99/46368 A2 | 9/1999 |
| WO | WO 00/52149 A1 | 9/2000 |
| WO | WO 00/62067 A | 10/2000 |
| WO | 00/64482 * | 11/2000 |
| WO | WO 00/64482 A1 | 11/2000 |
| WO | WO 00/75319 A1 | 12/2000 |
| WO | WO 01/39795 A2 | 6/2001 |
| WO | WO 02/08285 A2 | 1/2002 |
| WO | WO 02/055684 A | 7/2002 |
| WO | WO 02/065136 A2 | 8/2002 |
| WO | WO 02/083179 A2 | 10/2002 |
| WO | WO 03/000901 A2 | 1/2003 |
| WO | WO 03/015612 A2 | 2/2003 |
| WO | WO 03/022882 A2 | 3/2003 |
| WO | WO 03/031578 A2 | 4/2003 |
| WO | WO 03/074080 A1 | 9/2003 |
| WO | WO 03/100031 A | 12/2003 |
| WO | WO 03/102160 A2 | 12/2003 |
| WO | WO 2004/017044 A | 2/2004 |
| WO | WO 2004/103299 A2 | 12/2004 |
| WO | WO 2004/108069 A2 | 12/2004 |
| WO | WO 2004/110359 A2 | 12/2004 |
| WO | WO 2004/110360 A2 | 12/2004 |
| WO | WO 2005/087920 A2 | 9/2005 |
| WO | WO 2005/112986 A2 | 12/2005 |
| WO | WO 2007/038548 A2 | 4/2007 |
| WO | WO 2008/045970 A2 | 4/2008 |

OTHER PUBLICATIONS

Sato et al., Cloning and Expression in *Escherichia coli* of the Gene Encoding the *Proteus vulgaris* Chondroitin ABC Lyase, Jan. 1, 1994, Appl. Microbiol. Biotechnol., 41:39-46.

Curinga et al., Mammalian-Produced Chondroitinase AC Mitigates Axon Inhibition by Chondroitin Sulfate Proteoglycans, Journal of Neurochemistry, 2007, 102:275-288.

Crespo et al., How does Chondroitinase Functional Recovery in the Damaged CNS?, Experimental Neurology, 2007, 206:159-171.

Hirschberg et al., Inflammation after axonal injury has conflicting consequences for recovery of function: rescue of spared axons is impaired but regeneration is supported, 1994, J. Neuroimmunol. 52(2):9 (abstract).

Zuo et al., Degradation of chondroitin sulfate proteoglycan enhances the neurite-promoting potential of spinal cord tissue, 1998, Exp. Neurol. 154(2):654-662.

Zuo et al., Regeneration of axons after nerve transaction repair is enhanced by degradation of chondroitin sulfate proteoglycan, 2002, Exp. Neurol. 176(1):221-228.

Krekoski et al., Axonal regeneration into acellular nerve grafts is enhanced by degradation of chondroitin sulfate proteoglycan, 2001, J. Neurocsi. 15:21(16):6206-6213.

Bradbury et al, Chondroitinase ABC promotes functional recovery after spinal cord injury, 2002, Nature 416:636-640.

Blight et al., Animal Modes of Spinal Cord Injury, 2000, Top. in Spinal Cord Injury Rehabil. 6(2):1-13.

Kwon et al., Animal Models Used in Spinal Cord Regeneration Research, 2002, Spine 27(14):1504-1510.

Hirschberg et al., Inflammation after axonal injury has conflicting consequences for recovery of function: rescue of spared axons is impaired but regeneration is supported, 1994, J. Neuroimmunol. 52(2):219 (abstract).

Yamagata et al., Purification and Properties of Bacterial Chondroitinases and Chondrosulfatases, 1968, J. Biol. Chem. 243:1523-1535.

Hiyama et al., Crystallization and Some Properties of Chondroitinase from Arthrobacter aurescens, 1975, J. Biol. Chem. 250:1824-1828.

Michelacci et al., A Comparative Study Between a Chondroitinase B and a Chondroitinase AC from *Flavobacterium heparinum*, 1976, Biochem. J. 80:121-129.

Michelacci et al., Isolation and Partial Characterization of an Induced Chondroitinase B from *Flavobacterium heparinum*, 1974, BioChemical and BioPhysical Research Communications 56(4):973-980.

Basso et al., A Sensitive and Reliable Locomotor Rating Scale for Open Field Testing in Rats, 1995, Journal of Neurotrauma, vol. 12(1):1-21.

Sato et al., Subunit Structure of Chondroitinase ABC from *Proteus vulgaris*, 1986, Agric. Biol. Chem. 50(4):1057-1059.

Jung et al., Transit Time of Leukocytes Rolling Through Venules Controls Cytokine-induced Inflammatory Cell Recruitment In Vivo, J. Clin. Invest., The American Society for Clinical Investigation, Inc., 102(8), Oct. 1998, 1526-1533.

Gennaro ed., Remington's Pharmaceutical Sciences, Mack Publishing Company, Philadelphia, PA, 17$^{th}$ Ed., 1985 (TOC).

Lodish, et al., Integrating cells into tissue, 2000, Molecular Cell Biology, 5$^{th}$ Ed., Chapter 6, (TOC).

Kubota et al., Functional Similarity of HIV-1 Rev and HTLV-1 Rex Proteins: Identification of a New Nucleolar-Targeting Signal in Rev Protein, 1989, Biochem. Biophys. Res. Commun., Aug. 15, 162(3):963-970.

Derossi et al., Cell Internalization of the Third Helix of the Antennapedia Homeodomain is Receptor-independent, 1996, J. Biol. Chem 271:18188-18193.

Avrameas et al., Polyreactive anti-DNA monoclonal antibodies and a derived peptide as vectors for the intracytoplasmic and intranuclear translocation of macromolecules, 1998, Proc. Natl. Acad. Sci. USA 95:5601-5606.

Elliott et al., Intercellular Trafficking and Protein Delivery by a Herpesvirus Structural Protein, 1997, Cell 88:223-233.

Fawell et al., Tat-mediated delivery of heterologous proteins into cells, 1994, Proc. Natl. Acad. Sci. USA 91:664-668.

Vives et al., A Truncated HIV-1 Tat Protein Basic Domain Rapidly Translocates through the Plasma Membrane and Accumulates in the Cell Nucleus, 1997, J. Biol. Chem. 272(25):16010-16017.

Mann et al., Endocytosis and Targeting of Exogenous HIV-1 Tat Protein, 1991, EMBO J., Jul. 10(7):1733-1739.

Vives et al., Effects of the Tat Basic Domain on Human Immunodiefieciency Virus Type 1 Transactivation, Using Chemically Synthesized Tat Protein and Tat Peptides, 1994, J. Virol., May, 68(5):3343-3353.

Jones, Taking a new TAK on Tat transactivation, 1997, Genes & Dev. 11:2593-2599.

Anderson et al., Tumor Cell Retention of Antibody Fab Fragments is Enhanced by an Attached HIV TAT Protein-Derived Peptide, 1993, Biochem. & Biophys. Res. Commun. 194(2):876-884.

Fahraeus et al., Inhibition of pRb phosphorylation and cell-cycle progression by a 20-residue peptide derived from p16$^{CDKN2/INk4A}$, 1996, Curr. Biol. 6(1):84-91.

(56) References Cited

OTHER PUBLICATIONS

Nagahara et al., Transduction of full-length TAT fusion proteins into mammalian cells: TAT-p27$^{Kip1}$ induces cell migration, 1998, Nat. Med. 4(12):1449-1452.
Efthymiadis et al., The HIV-1 Tat Nuclear Localization Sequence Confers Novel Nuclear Import Properties, 1998, J. Biol. Chem., Jan. 16, 273(3):1623-1628.
Frankel et al., Tat Protein from Human Immunodeficiency Virus Forms a Metal-Linked Dimer, 1988, Science, 240:70-73, esp (Abstract).
Accession P59807, Aug. 15, 2003 *UniProtKB/Swiss-Prot*.
Aldrich "Enzymer Explorer" 2009, URL:http://www.sigmaaldrich.com/life-science/metabolomics/enzyme-explorer/learning-center/carbohydrate-analysis/carbohydrate-analysis-iii.
Appel et al. "Several Extracellular Domains of the Neural Cell Adhesion Molecule L1 are Involved in Neurite Outgrowth and Cell Body Adhesion" 1993, *J. Neurosc.* 13(11): 4764-4775.
Banker et al. "Modern Pharmaceutics" 1979, *Marcel Dekker, Inc.* (TOC).
Banker et al. "Modern Pharmaceutics" 4th Ed., 2002, *Informa Healthcare*, New York (TOC).
Bao et al. "A Functional Dermatan Sulfate Epitope Containing Iduronate (2-O-sulfate) α1-3GalNAC (6-O-sulfate) Disaccharide in the Mouse Brain" 2005, *J. of Bio. Chem.* 280(24):23184-23193.
Ben-Bassat et al. "Processing of the Initiation Methionine from Proteins: Properties of the *Escherichia coli* Methionine Aminopeptidase and Its Gene Structure" 1987, *J. Bacteriol.* 169(2):751-757.
Bixby et al. "Neurite outgrowth on muscle cell surfaces involves extracellular matrix receptors as well as Ca2+-dependent and—independent cell adhesion molecules" 1987, *Proc. Natl. Acad. Sci. USA* 84:2555-2559.
Bowie et al. "Deciphering the Message in Protein Sequences: Tolerance to Amino Acid Substitutions" 1990, Science 247:1306-1319.
Bradbury et al. "Chondroitinase ABC Promotes Regeneration and Functional Recovery Following Spinal Cord Injury" 2001, *Soc. for Neuroscience Abstracts* 27(2):1835.
Bradbury et al. "NT-3 Promotes Growth of Lesioned Adult Rat Sens Ory Axons Ascending in the Dorsal Columns of the Spinal Cord" 1999, Eur. J. Neurosc. 11(11):3873-3783.
Bray et al., Neuronal and Nonneuronal Influences on Retinal Ganglion Cell Survival, Axonal Regrowth, and Connectivity after Axotomy, 1991, *Ann. NY Acad. Sci.*, 214-228.
Broach et al. "Experimental Manipulation of Gene Expression" M. Inouye ed., *Academic Press, New York*, pp. 83-117. 1983.
Burgess et al. "Possible Dissassociation of the Heparin-binding and Mitogenic Activities of Heparin-binding (Acidic Fibroblast) Growth Factor-1 From Its Receptor-binding Activities by Site-directed Mutagenesis of a Single Lysine Residue" 1990, *J. of Cell. Bio.* 111:2129-2138.
Cadelli et al. "Oligodendrocyte- and Myelin-Associated Inhibitors of Neurite Outgrowth: Their Involvement in the Lack of CNS Regeneration" 1992, *Exp. Neur.* 115:189-192.
Caggiano et al. "Chondroitinase ABCI Improves Locomotion and Bladder Function following Contusion Injury of the Rat Spinal Cord" 2005, *J. Neurotrauma* 22(2):226-239.
Cajal "Degeneration & Regeneration of the Nervous System" May ed., 1959, *Hafner Publ. Co.*, New York (TOC).
Chang et al. "Extension of Neurites on Axons is Impaired by Antibodies against Specific Neural Cell Surface Glycoproteins" 1987, *J. Cell. Biol.* 104:355-362.
Chen et al. "Peripheral nerve regeneration using silicone rubber chambers filled with collagen, laminin and fibronectin" 2000, *Biomat.* 21:1541-1547.
Daichi "Text Book of Physiology" 2000, 3rd Ed. 81.
Degrendele et al. "Requirement for CD44 in Activated T Cell Extravassation into an Inflammatory Site" 1997, *Science* 278:672-675.
Denuziere et al. "Chitosan-Chondroitin sulfate and chitosan-hyaluronate polyelectrolyte complexes: biological properties" 1998, *Biomaterials* 19:1275-1285.

Doppenberg et al. "Clinical Trials in Traumatic Brain Injury" 1998, *Ann. NY Acad. Sci.* 305-319.
Edelman "Cell Adhesion Molecules" 1983, *Science* 219:450-457.
Edelman et al. "Morphoregulatory Molecules" 1990, *Wiley, New York* (TOC).
Favre et al. "Hyaluronidase enhances recombinant adeno-associated virus (rAAV)-mediated gene transfer in the rat skeletal muscle" 2000, *Gene Ther.* 7(16):1417-1420.
Fawcett et al. "The glial scar and central nervous system repair" 1999, *Brain Res. Bull.* 49(6):377-391.
Fethiere et al. "Crystal Structure of Chondroitin AC Lyase, a Representative of a family of Glycosaminoglycan Degrading Enzymes" 1999, *J. Mol. Biol.* 288:635-647.
Fongmoon et al. "Chondroitinase-mediated Degradation of Rare 3-)-Sulfated Glucuronic Acid in Functional Oversulfated Chondroitin Sulfate K and E" 2007, *J. of Bio. Chem.* 282(51):36895-39904.
Frankish et al. "Spinal-cord Repair Moves a Step Closer" 2002, *The Lancet* 359(9314):1317.
Goodman et al. "The Pharmacological Basis of Therapeutics" 10th ed., 2001, *McGraw Hill*, New York (TOC).
Goodman et al. "The Pharmacological Basis of Therapeutics" 6th ed. 1980, *MacMillan Pub.*, New York (TOC).
Hamai et al. "Two Distinct Chondroitin Sulfate ABC Lyases" 1997, *J. Biol. Chem.* 272(14):9123-9130.
Hlavin et al. "Molecular Structure and Functional Testing of Human L1CAM: An Interspecies Comparison" 1991, *Genomics* 11:416-423.
Hoffman et al. "Chondroitin Sulfates" 1958, *Federation Proc.* 17:1078-1082.
Horstkorte et al. "The Fourth Immunoglobin-like Domain of NCAM Contains a Carbohydrate Recognition Domain for Oligomannosidic Glycans Implicated in Associated with L1 and Neurite Outgrowth" 1993, *J. Cell Biol.* 121(6):1409-1421.
Hou et al. "Endotoxin Removal by Anion-Exchange Polymeric Matrix" 1990, *Biotech. Appl. Biochem.* 12:315-324.
Huang et al. "Active Site of Chondroitin AC Lyase Revealed by the Structure of Enzyme-Oligosaccharide Complexes and Mutagenesis" Jan. 1, 2001, *Biochemistry*, 40(8):2359-2372.
Huang et al. "Crystal Structure of Chondroitinase B from *Flavobacterium heparinum* and its Complex with a Disaccharide Product at 107 a Resolution" 1999, *J. Mol. Biol.* 294:1257-1269.
Huang et al. "Crystal Structure of *Proteus vulgaris* Chondroitin Sulfate ABC Lyase I at 1.9 A Resolution" 2003, *J. Mol. Biol.* 328:623-634.
Iida et al. "Cell Surface Chondroitin Sulfate Proteoglycans in Tumor Cell Adhesion, Motility and Invastion" 1996, *Seminars in Cancer Biology* 7:155-162.
Iwai et al. "Axon Patterning Requires DN-cadherin, a Novel Neuronal Adhesion Receptor, in the Drosphila Embryonic CNS" 1997, *Neuron* 19:77-89.
Kadmon et al. "Functional Cooperation between the Neural Adhesion Molecules L1 and N-CAM is Carbohydrate Dependent" 1990, *J. Cell Biol.* 110:209-218.
Kadmon et al. "The Neural Cell Adhesion Molecule N-CAM Enhances L1-dependent Cell-Cell Interactions" 1990, *J. Cell Biol.* 110:193-208.
Khan et al. "Animal Models of Spinal Cord Contusion Injuries", 1999, Laboratory Animal Science 49: 161-172.
Kim et al. "Insertion and Deletion Mutants of FokI Restriction Endonuclease" 1994, *J. Biol. Chem.* 269(50):31978-31982.
Korn "The Degradation of Heparin by Bacterial Enzymes" 1957, *J. Biol. Chem.* 226:841-844.
Lagenaur et al. "An L1-like molecule, the 8D9 antigen, is a potent substrate for neurite extension" 1987, *Proc. Natl. Acad. Sci. USA* 84:7753-7757.
Lemons et al. "Chondroitin Sulfate Preteoglycan Immunoreactivity Increases Following Spinal Cord Injury and Transplantation" 1999, *Exper. Neurology* 160:51-65.
Lesley et al. "Variant Cell Lines Selected for Alterations in the Function of the Hyaluronan Receptor CD44 Show Differences in Glycosylation" 1995, *J. Exp. Med.* 182:431-437.
Li et al. "Delayed systemic Nogo-66 Receptor Antagonist Promotes Recovery from Spinal Cord Injury" 2003, *J. Neuroscience* 23(10):4219-4227.

(56) References Cited

OTHER PUBLICATIONS

Lindner et al. "L1 mono- and polyclonal antibodies modify cell migration in early postnatal mouse cerebellum" 1983, *Nature* 305:427-430.
Mahanthappa et al. "Glial Growth Factor 2, a Soluble Neuregulin, Directly Increases Schwann Cell Motility and Indirectly Promotes Neurite Outgrowth" 1996, *J. Neuroscience* 16(15):4673-4683.
Maniatis et al. "Molecular Cloning: A Laboratory Manual" 1982, *Cold Spring Harbor Lab*. (TOC).
Martinez et al. "Purification and Properties of the Enzyme Chondroitinase" 1959, *J. Biol. Chem.* 234(9):2236-2239.
Martini et al. "Restricted Localization of L1 and N-CAM Sites of Contact Between Schwann Cells and Neurites in Culture" 1994, *GLIA* 10:70-74.
Matinysn "Restoration of functions due to Enzyme Therepy After Complete Transaction of the Spinal Cord" 1965, *ZH EK SP KLIN MED* 5(3):3-13.
Matsumoto et al. "Peripheral nerve regeneration across an 80-mm gap bridged by a polyglycolic acid (PGA)-collagen tube filled with laminin-coated collagen fibers: a histilogical and electrophysiological evaluation of regenerated nerves" 2000, *Brain Res.* 868:315-328.
Matteuci et al. "Synthesis of Deoxyoligonucleotides on a Polymer Support" 1981, *J. Am. Chem. Soc.* 103:3185-3191.
Michelacci et al. "Chondroitinase C from *Flavobacterium haparinum*" 1976, *J. Biol. Chem.* 251(4):1154-1158.
Michelacci et al. "Isolation and characterization of an induced Chondroitinase ABC" 1987, *Biochem. Biophys. Acta* 923:291-301.
Miller et al. "N-terminal methionine-specific peptidase in *Salmonella typhimurium*" 1987, *PNAS* 84:2718-2722.
Miura et al. "Analysis of Glycosaminoglycan-Degrading Enzymes by Substrate Gel Electrophoresis (Zymography)" 1995, *Anal. Biochem.* 225:333-340.
Modena et al. "Hylauronidase-injectable microparticles intended for the treatment of extravasation" 1998, *J. Microencapsulation* 15(1):85-92.
Moon et al. "Regeneration of CNS axons back to their target following treatment of adult rat brain with chondroitinase ABC" 2001, *Nature Neurosc.* 4(5): 465-466.
Moos et al. "Neural adhesion molecule L1 as a member of the immunoglobulin superfamily with binding domains similar to fibronectin" 1988, *Nature* 334:701-703.
Netti et al. "Role of Extracellular Matrix Assembly in Interstitial Transport in Solid Tumors" 2000, *Cancer Res.* 60(9):2497-2503.
Nieke et al. "Expression of the neural cell adhesion molecules L1 and N-CAM and their common carbohydrate epitope L2/HNK-1 during development and after transaction of the mouse sciatic nerve" 1985, *Differentiation* 30:141-151.
Oermann et al. "The Use of Anti-inflammatory Medications in Cystic Fibrosis" 1999, *Chest* 115:1053-1058.
Olmarker et al. "Chondroitinase ABC (Pharmaceutical Grade) for Chemonucleolysis" 1996, *Spine* 21(17):1952-1956.
Pawson et al. "Assembly of Cell Regulatory systems Through Protein Interaction Domains" 2003, *Science* 300:445-452.
Pillwein et al. "Hyaluronidase Additional to Standard Chemotherapy Improves Outcome for Children with Malignant Tumors" 1998, *Cancer Letters* 131:101-108.
Pojasek et al. "Biochemical Characterization of the Chondroitinase B Active Site" Aug. 23, 2002, *J. Biol. Chem.* 277(34):31179-31186.
Pojasek et al. "Recombinant Expression, Purification, and Kinetic Characterization of Chondroitinase AC and Chondroitinase B from *Flavobacterium heparinum*" 2001, *Biochem, Biophys. Res. Commun.* 286:343-351.
Prabhakar et al. "Biochemical Characterization of the Chondroitinase ABC I Active Site" Aug. 23, 2005, *Biochem. J.* pp. 395-405.
Priestley et al. "Stimulating regeneration in the damaged spinal cord" 2002, *J. Phyl.* 96:123-133.
Rathjen et al. "Immunocytological and biochemical characterization of a new neuronal cell surface component (L1 antigen) which is involved in cell adhesion" 1984, *EMBO J.* 3(1):1-10.
Ratjen et al. "Cystic Fibrosis" 2003, *The Lancet* 361(9358):681-689.
Reich et al. "Small interfering RNA (siRNA) targeting VEGF effectively inhibits ocular neovascularization in a mouse model" 2003, *Molecular Vision* 9:210-216.
Reid et al. "Variants of Human L1 Cell Adhesion Molecule Arise through Alternate Splicing of RNA" 1992, *J. Mol. Neurosc.* 3:127-135.
Roy et al. "Generation of Substantially Smaller Deletion Mutants of Chondroitinase AC and B Those are Biologically Active" Nov. 8-12, 2003, Society for Neuroscience Abstract Viewer and Itinerary Planner, 33rd Annual Meeting of the Society of Neuroscience, New Orleans, LA, *Database Biosis*. (Abstract).
Saito et al. "Enzymatic Methods for the Determination of Small Quantities of Isomeric Chondroitin Sulfates" 1968, *J. Biol. Chem.* 243(7)1 536-1542.
Sambrook et al. "Molecular Cloning" 2nd ed., 1989, *Cold Spring Harbor Laboratory Press*, Ch. 16 and 17.
Schachner "Functional implications of glial cell recognition molecules" 1990, *Neurosc.* 2:497-507.
Schwab "Nerve fibre regeneration after traumatic lesions of the CNS; progress and problems" 1991, *Phil. Trans. R. Soc. Lond.* 331:303-306.
Seikagaku Biobus. Corp. "Chondroitinase AC II pamphlet" 2009, seikagakubb.co.jp/bio/cgi-bin/search/tenpu_pdf/100335.pdf.
Seilheimer et al. "Studies of Adhesion Molecules Mediating Interactions between Cells of Peripheral Nervous System Indicate a Major Role for L1 in Mediating Sensory Neuron Growth on Schwann Cells in Culture" 1988, *J. Cell Biol.* 107:341-351.
Silver et al. "Postnatally induced formation of the corpus callosum in acallosal mice on glia-coated cellulose bridges" 1983, *Science* 220:1067-1069.
Smith-Thomas et al. "Increased Axon Regeneration in Astrocytes Grown in the Presence of Proteoglycan Synthesis Inhibitors" 1995, *J. of Cell Science* 108(3):1307-1315.
Southern "Detection of Specific Sequences Among DNA Fragments Separated by Gel Electrophoresis" 1975, *J. Mol. Biol.* 98:503-517.
Stedman's Medical Dictionary 2008, Lippincott Williams & Wilkins, 27th Ed., entry for central nervous system.
Sterne et al. "Neurotrophin-3 Delivered Locally via Fibronectin Mats Enhances Peripheral Nerve Regeneration" 1997, *Eur. J. Neurosc.* 9:1388-1396.
Tona et al. "Effect of Hyaluronidase on Brain Extracellular Matrix in Vivo and Optic Nerve Regeneration" 1993, *J. Neurosc. Res.* 36:191-199.
Trigg et al. "Peripheral Nerve Regeneration: Comparison of Laminin and Acidic Fibroblast Growth Factor" 1998, *Am. J. Otolaryngology* 19(1):29-32.
Tsuda et al. "Substrate Specificity Studies of Flavobacterium Chondroitinase C and Heparitinases Towards the Glycosaminoglycan-protein Linkage region" 1999, *European J. of Biochem.* 262:127-133.
Williams et al. "Calcium Influx into Neurons Can Solely Account for Cell Contact-dependent Neurite Outgrowth Stimulated by Transfected L1" 1992, *J. Cell Biol.* 119(4):883-892.
Wood et al. "Inhibition of Schwann Cell Myelination in vitro by Antibody to the L1 Adhesion Molecule" 1990, *J. Neurosc.* 10(11):3635-3645.
Yamagata et al. "Repression of a Malignant Cell-Substratum Adhesion Phenotype by Inhibiting the Production of the Anti-Adhesive Proteoglycan, PG-M/Versican" 1994, *J. of Cell Science* 1007:2581-2590.
Yang et al. "Developmental Regulation of a Matrix Metalloproteinase during Regeneration of Axolotl Appendages" 1994, *Dev. Biol.* 166:696-703.
Yang et al. "Expression of Mmp-9 and Related Matrix Metalloproteinase Genes During Axolotl Limb Regeneration" 1999, *Dev. Dyn.* 216:2-9.
Yasuda et al. "Effect of Hyluronidase on Experimental Cerebral Infarct Size and Mortality" 1982, *Lab. Invest.* 46:400-404.
Yick et al. "Chondroitinase ABC Promotes Axonal Regrowth of Clarke's Neurons Into Peripheral Nerve Graft After Hemisection of the Spinal Cord" 1999, *Soc. for Neuroscience Abstracts* 25:747.

(56) References Cited

OTHER PUBLICATIONS

McGee et al. "The Nogo-66 Receptor:Focusing Myelin Inhibition of Axon Regeneration" 2003, *Trends in Neuroscience* 26(4):193-198.
Chau et al. "Chondroitinase ABC Enhances Axonal Regrowth Through Schwann Cell-seeded Guidance Channels After Spinal Cord Injury" Nov. 20, 2003 *FASEB J.* 18(1):1-24 (XP003008297).
Dimayuga et al. "The Neuregulin GGF2 Attenuates Free Radical Release from Activated Microglial Cell" Mar. 2003, *J. Neuroim.* 136(1-2):67-74 (XP002651543).
European Search Report for EP11152626 dated Jul. 21, 2011.
European Search Report for EP10184697 dated Jul. 12, 2011.
Grandpre et al. "Nogo-66 Receptor Antagonist Peptide Promotes Axonal Regeneration" May 30, 2002, *Nature* 417(6888):547-551 (XP002651544).
Hunt et al. "The Nogo Receptor, Its Ligands and Axonal Regeneration in the Spinal Cord; a Review" Feb. 2002, *J. Neurocytology* 31(2):93-120 (XP002651545).
Roy et al. "Treatment with Recombinant Chondroitinases AC and B Permits Neuronal Outgrowth Over Inhibitory Chondroitin Sulfate Proteoglycans (CSPGs)" Nov. 7, 2002, *Society for Neuroscience Abstract Archives* 2000-2005 (Abstract) (XP009150388).
Becker-Hapak et al. "TAT-Mediated Protein Transduction into Mammalian Cells" 2001, *Methods* 24:247-256.

\* cited by examiner

TAT fusion chondroitinase ABCI nucleic acid (SEQ ID NO: 61)

```
ggtcgtaaaa agcgtcgtca acgtcgtcgt ggtggtggtg gtggtgccac cagcaatcct gcatttgatc
ctaaaaatct gatgcagtca gaaatttacc attttgcaca aaataaccca ttagcagact tctcatcaga
taaaaactca atactaacgt tatctgataa acgtagcatt atgggaaacc aatctctttt atggaaatgg
aaaggtggta gtagctttac tttacataaa aaactgattg tccccaccga taaagaagca tctaaagcat
ggggacgctc atctaccccc gttttctcat tttggcttta caatgaaaaa ccgattgatg gttatcttac
tatcgatttc ggagaaaaac tcatttcaac cagtgaggct caggcaggct ttaaagtaaa attagatttc
actggctggc gtgctgtggg agtctcttta aataacgatc ttgaaaatcg agagatgacc ttaaatgcaa
ccaataccte ctctgatggt actcaagaca gcattgggcg ttctttaggt gctaaagtcg atagtattcg
ttttaaagcg ccttctaatg tgagtcaggg tgaaatctat atcgaccgta ttatgttttc tgtcgatgat
gctcgctacc aatggtctga ttatcaagta aaaactcgct tatcagaacc tgaaattcaa tttcacaacg
taaagccaca actacctgta acacctgaaa atttagcggc cattgatctt attcgccaac gtctaattaa
tgaatttgtc ggaggtgaaa aagagacaaa cctcgcatta gaagagaata tcagcaaatt aaaaagtgat
ttcgatgctc ttaatattca cactttagca aatgtggaa cgcaaggcag acatctgatc actgataaac
aaatcattat ttatcaacca gagaatctta actcccaaga taaacaacta tttgataatt atgttatttt
agtaattac acgacattaa tgtttaatat tagccgtgct tatgtgctgg aaaaagatcc cacacaaaag
gcgcaactaa agcagatgta cttattaatg acaaagcatt tattagatca aggctttgtt aaagggagtg
ctttagtgac aacccatcac tggggataca gttctcgttg gtggtatatt tccacgttat taatgtctga
tgcactaaaa gaagcgaacc tacaaactca agtttatgat tcattactgt ggtattcacg tgagtttaaa
agtagttttg atatgaaagt aagtgctgat agctctgatc tagattattt caataccta tctcgccaac
atttagcctt attattacta gagcctgatg atcaaaagcg tatcaactta gttaatactt tcagccatta
tatcactggc gcattaacgc aagtgccacc gggtggtaaa gatggtttac gccctgatgg tacagcatgg
cgacatgaag gcaactatcc gggctactct ttcccagcct ttaaaaatgc ctctcagctt atttatttat
tacgcgatac accatttca gtgggtgaaa gtggttggaa taacctgaaa aaagcgatgg tttcagcgtg
gatctacagt aatccagaag ttggattacc gcttgcagga agacacccit ttaactcacc ttcgttaaaa
tcagtcgctc aaggctatta ctggcttgcc atgtctgcaa aatcatcgcc tgataaaaca cttgcatcta
tttatcttgc gattagtgat aaaacacaaa atgaatcaac tgctattttt ggagaaacta ttacaccagc
gtctttacct caaggtttct atgcctttaa tggcggtgct tttggtattc atcgttggca agataaaatg
gtgacactga aagcttataa caccaatgtt tggtcatctg aaatttataa caaagataac cgttatggcc
gttaccaaag tcatggtgtc gctcaaatag tgagtaatgg ctcgcagctt tcacagggct atcagcaaga
aggttgggat tggaatagaa tgcaaggggc aaccactatt caccttcctc ttaaagactt agacagtcct
aaacctcata ccttaatgca acgtggagag cgtggattta gcggaacatc atcccttgaa ggtcaatatg
gcatgatggc attcgatctt attatcccg ccaatctgca gcgttttgat cctaatttca ctgcgaaaaa
gagtgtatta gccgctgata atcacttaat ttttattggt agcaatataa atagtagtga taaaataaa
aatgttgaaa cgaccttatt ccaacatgcc attactccaa cattaaatac cctttggatt aatggacaaa
agatagaaaa catgccttat caaacaacac ttcaacaagg tgattggtta attgatagca atggcaatgg
ttacttaatt actcaagcag aaaaagtaaa tgtaagtcgc caacatcagg tttcagcgga aaataaaaat
cgccaaccga cagaaggaaa ctttagctcg gcatggatcg atcacagcac tcgccccaaa gatgccagtt
atgagtatat ggtcttttta gatgcgacac ctgaaaaaat gggagagatg gcacaaaaat tccgtgaaaa
taatggtta tatcaggttc ttcgtaagga taagacgtt catattattc tcgataaact cagcaatgta
acgggatatg ccttttatca gccagcatca attgaagaca aatggatcaa aaaggttaat aaacctgcaa
ttgtgatgac tcatcgacaa aaagacactc ttattgtcac tgcagttaca cctgatttaa atatgactcg
ccaaaaagca gcaactcctg tcaccatcaa tgtcacgatt aatggcaaat ggcaatctgc tgataaaaat
agtgaagtga aatatcaggt ttctggtgat aacactgaac tgacgtttac gagttacttt ggtattccac
aagaaatcaa actctcgcca ctcccttgat ttaatcaaaa gaacgctctt gcgttccttt tttattgca
ggaaatctga ttatgctaat aaaaaaccct ttagccccacg cggttacatt aagcctctgt ttatcattac
ccgcacaagc attacccact ctgtctcatg aagcttcgg cgatatttat cttttgaag gtgaattacc
caataccctt accacttcaa ataataatca attatcgcta agcaaacagc atgctaaaga tggtgaacaa
tcactcaaat ggcaatatca accacaagca acattaacac taaataatat tgttaattac caagatgata
aaaatacagc cacaccactc acttttatga tgtggattta taatgaaaaa cctcaatctt ccccattaac
gttagcatt aaacaaaata ataaaattgc actaagtttt aatgctgaac ttaattttac ggggtggcga
ggtattgctg ttcctttcg tgatatgcaa ggctctgcga caggtcaact tgatcaatta gtgatcaccg
ctccaaacca agccggaaca ctcttttttg atcaaatcat catgagtgta ccgttagaca atcgttgggc
agtacctgac tatcaaacac cttacgtaaa taacgcagta aacacgatgg ttagtaaaaa ctggagtgca
ttattgatgt acgatcagat gtttcaagcc cattacccta cttttaactt cgatactgaa tttcgcgatg
accaaacaga aatggcttcg atttatcagc gctttgaata ttatcaagga attcc
```

FIG. 1

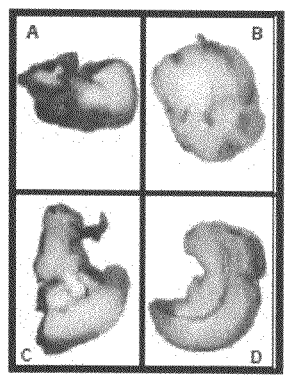
(I)
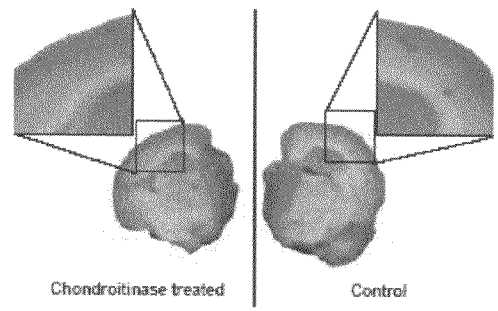
(II)
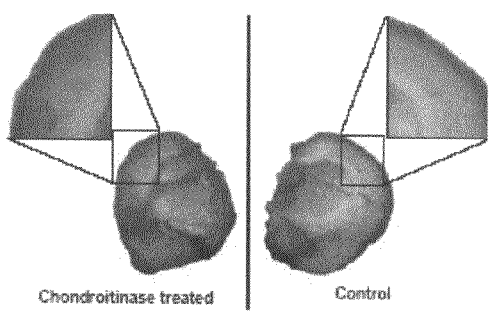
(III)
FIG. 2

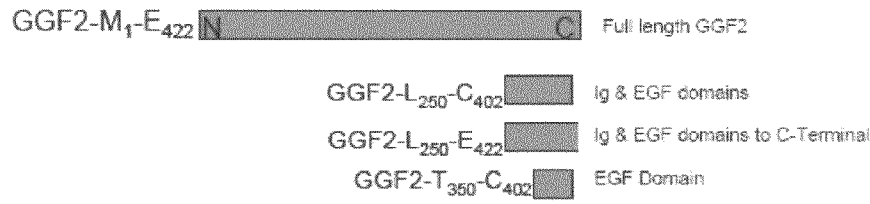
(A)
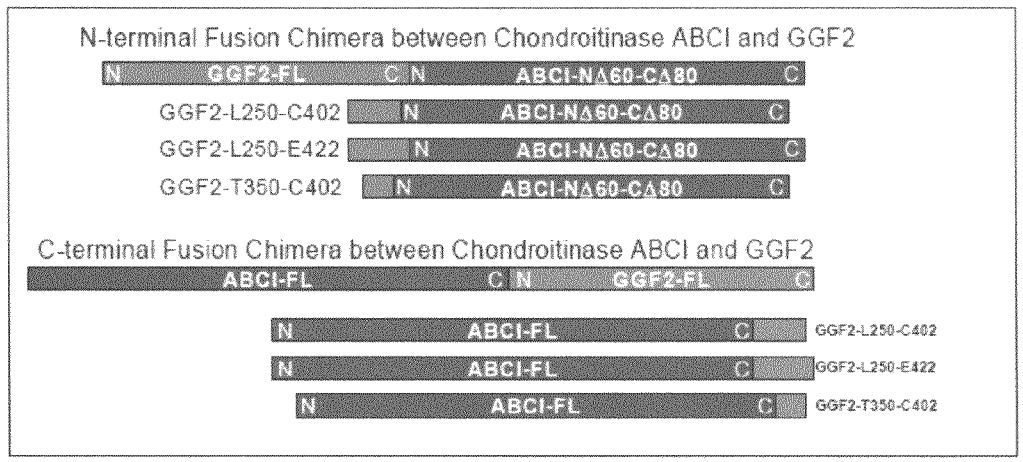
(B)
FIG. 3

(A) 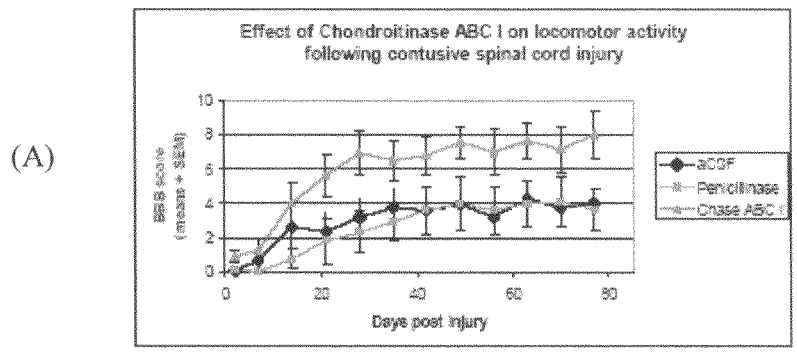
(B) 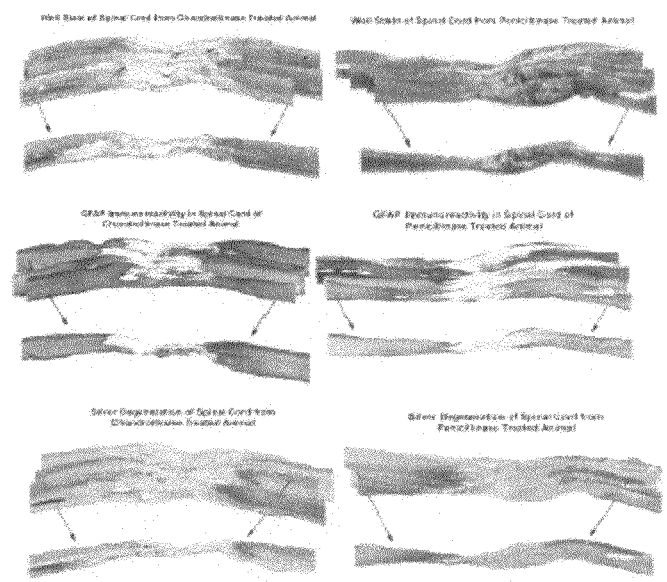
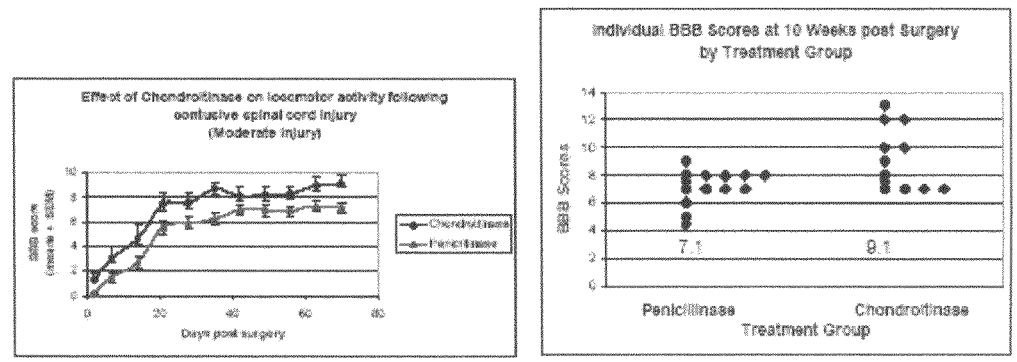
(D) (E)
Figure 5

FUSION PROTEINS FOR THE TREATMENT OF CNS

CROSS REFERENCE TO RELATED APPLICATIONS

This application claims the benefit and priority of U.S. Provisional Application Ser. No. 60/471,239, entitled "Fusion Proteins for Treatment of CNS", filed May 16, 2003; U.S. Provisional Application Ser. No. 60/471,240, entitled "Deletion Mutants for Treatment of CNS", filed May 16, 2003; U.S. Provisional Application Ser. No. 60/471,300, entitled "Methods of Facilitating Diffusion", filed May 16, 2003; and U.S. Provisional Application Ser. No. 60/474,372, entitled "Compositions for Treatment of CNS", filed May 29, 2003. These applications are hereby incorporated by reference in their entirety.

BACKGROUND AND SUMMARY

Spinal cord injury (SCI) inflicts trauma to the cells and tissues of the central nervous system (CNS) and causes a severe and debilitating condition in the individual. Following SCI, limited regeneration of injured neurons results in permanent disability characterized by some loss of sensation, paralysis and autonomic dysfunction. One reason that neurons fail to regenerate is their inability to traverse the glial scar that develops following SCI. This glial scar contains extracellular matrix molecules including chondroitin sulfate proteoglycans (CSPGs). In vitro studies show that neurons fail to extend processes over CSPG coated surfaces, while in vivo data correlate failure of regeneration with areas of CSPG expression. Within the adult central nervous system (CNS) myelin there are also several identified axon growth inhibitor compounds like myelin associated glycoprotein (MAG), OMgp, and Reticulon 4 or Nogo that have been shown to be inhibitory for the growth of neurons.

The proteglycan degrading enzyme chondroitinase ABC type I has been used to enhance neuronal growth in a dorsal column lesion model of spinal cord injury. It has also been reported that treating a spinal cord injury with NOGO receptor antagonist promotes a certain limited degree of neuronal regeneration. It has further been reported that creating a NOGO knock out mouse resulted in certain limited and inconsistent degrees of neuronal regeneration following dorsal hemisection of the spinal cord.

Experimental treatments for injury to the CNS have utilized the application of chondroitinase to the extracellular space, however the enzyme digests CSPG in the extracellular matrix and not intracellular stores. Furthermore, diffusion of chondroitinase within the parenchyma the essential and distinctive tissue of an organ or an abnormal growth as distinguished from its supportive framework) or between anatomical compartments is limited. The limited access of drugs, imaging agents, and anesthetics, etc. to target cells and/or tissues of the Central Nervous System (CNS) may reduce the usefulness or effectiveness of any of these substances.

The delivery of therapeutic and diagnostic molecules into cells and tissues is, in part, dependent upon extracellular matrices as well as carbohydrates and proteins linked to cell membranes. The extracellular matrix is composed in part of proteoglycans, among them are the chondroitin sulfated proteoglycans (CSPGs). CSPGs are a family of proteoglycans composed of a core protein and covalently linked sulfated glycosaminoglycans. Each proteoglycan is determined by the glycosaminoglycan side chains. For CSPGs these side chains are made up of approximately 40 to 100 sulfated disaccharides composed of chondroitin 4, 6 and dermatan sulfates. The protein component of the CSPG is ribosomally synthesized and the glycosylation occurs in the endoplasmic reticulum and Golgi apparatus. The sugar chains are then sulfated at the 4 or 6 positions by several glycosaminoglycan sulfotransferases.

Transduction proteins may be used to transport polypeptides and polynucleotides cargo across anatomical barriers and into cells. For example, the TAT protein (SEQ ID NO: 2) from the human immunodeficiency virus (HIV) contains a protein transduction domain (PTD) that is involved in the transduction of HIV into cells. The PTD contains an 11 amino acid domain (TAT Peptide) (SEQ ID NO: 3) that is responsible for the activity of the PTD. The TAT Peptide (SEQ ID NO: 3) can be linked to proteins and facilitate the transduction of the proteins into cells. The mechanism of transduction is independent of the molecular weight or chemical properties of the proteins that are linked to the TAT Peptide (SEQ ID NO: 3). In vivo studies show that if a fusion protein consisting of the TAT Peptide (SEQ ID NO: 3) linked to the 120 kd enzyme, beta-galactosidase (β-Gal), is injected into mice, then a robust delivery of β-Gal into a wide variety of cells is observed. When linked to the TAT transduction peptide (SEQ ID NO: 3), β-Gal activity was observed in the brain; without the TAT Peptide (SEQ ID NO: 3), β-Gal was not observed in the brain. Transport across the blood brain barrier is normally restricted to certain hydrophobic small molecules and particular low molecular weight lipophilic peptides. Transport of proteins as large as β-Gal into the brain is usually not possible without substantial disruption of the blood brain barrier, but the TAT Peptide (SEQ ID NO: 3) facilitates transport while leaving the blood brain barrier intact.

Chimeric proteins, also called fusion proteins, are hybrid proteins which combine at least parts of two or more precursor proteins or polypeptides. Chimeric proteins may be produced by recombinant technology, i.e. by fusing at least a part of the coding sequence of one gene to at least a part of the coding sequence of another gene. The fused gene may then be used to transform a suitable organism which then expresses the fusion protein.

Tat Peptide Complexes Frankel et al. (U.S. Pat. Nos. 5,804,604; 5,747,641; 5,674,980; 5,670,617; 5,652,122) discloses the use of Tat peptides to transport covalently linked biologically active cargo molecules into the cytoplasm and nuclei of cells. Frankel only discloses covalently linked cargo moieties that are (therapeutic, diagnostic or prophylactic), and does not teach or suggest the attachment of molecules that facilitate diffusion, plasticity, neurite growth, and axon regeneration. These molecules can include but are not limited to molecules that overcome neurite out growth inhibition, or promote nerve growth such as soluble NOGO antagonists like $NgR_{27-311}$, neural cell adhesion molecules like L1, neurotrophic factors, growth factors, phosphodiesterase inhibitors, and inhibitors of MAG or MOG. Additionally, deletion mutants may be combined with other compounds that promote remyelination such as neuregulins (GGF2) and antibodies that promote remyelination or proteoglycan degrading molecules to Tat peptides.

Regeneration following SCI is limited because of a variety of obstacles that include the deposition of CSPG at the glial scar, demyelination of axons, lack of trophic support and lack of axonal guidance. A single therapy directed against one aspect of SCI may not be as effective as a combinatorial approach. Fusion proteins with chondroitinase will allow combinatorial therapy with a single protein. Fusion partners for chondroitinase that will be constructed in this proposal were chosen from among proteins that have evidence for efficacy in SCI.

The use of a molecule that has the ability to both degrade extracellular matrix glycoproteins and to block or overcome the inhibitory nature of myelin components may be used to improve the ability of damaged neurons to grow or regenerate compared with either treatment alone. The proteoglycan degrading molecules may also be used advantageously to provide a method of facilitating access and diffusion of substances into cells or tissues through the use of at least one enzyme capable of cleaving proteoglycans and preferably degrading chondroitin sulfate proteoglycans (CSPG).

Embodiments of the present invention include compositions that comprise polypeptides which cleave proteoglycans, polypeptides that block and/or overcome the activity of neuronal growth inhibitory molecules, or a combination of these. The compositions containing the proteoglycan degrading molecule or neuronal growth inhibitory molecules may also include molecules for transduction of the polypeptides across cell membranes and the blood brain barrier. The compositions may be used in the treatment of spinal cord injuries and related disorders of the central nervous system (CNS). The compositions can be used in the regeneration of damaged neurological tissue and facilitate the diffusion and transport of therapeutic molecules capable of blocking and/or overcoming the activity of neuronal growth inhibitory molecules into damaged or diseased tissue.

Embodiments of the present invention include compositions and methods for their use to facilitate delivery and diffusion of therapeutics or diagnostic agents, and preferably agents that promote regeneration of nerves and axons, into cells or tissues. Preferably the composition includes the use of an enzyme capable of cleaving chondroitin sulfate proteoglycans (CSPG) to increase the diffusion of these agents into cells or tissues of the central nervous system.

Compositions of the present invention may include chimeric or fusion proteins capable of systemic use in the treatment of spinal cord injuries and related disorders of the central nervous system (CNS), and in particular, fusion proteins capable of crossing the blood brain barrier. The fusion protein may include a polypeptide transduction domain, a polypeptide domain capable of degrading a proteoglycan, preferably a domain cleaving chondroitin sulfate proteoglycan (CSPG), a polypeptide domain that blocks and or over comes the activity of neuronal growth inhibitory molecules, or any combination of these polypeptide domains that may be used in the treatment of spinal cord injuries and related disorders of the central nervous system (CNS). The various polypeptide domains may be linked or chemically bonded together by polypeptide linkers.

Compositions of the present invention include polynucleotides which encode for the chimeric or fusion proteins capable of systemic use in the treatment of spinal cord injuries and related disorders of the central nervous system (CNS), and in particular, they encode for fusion proteins capable of crossing the blood brain barrier. The polynucleotides which encode for these chimeric or fusion proteins may include a polynucleotide domain encoding for a polypeptide transduction domain, a polynucleotide domain encoding for a polypeptide domain capable of degrading a proteoglycan, preferably cleaving chondroitin sulfate proteoglycan (CSPG), a polynucleotide domain encoding for a polypeptide domain that blocks and or over comes the activity of neuronal growth inhibitory molecules, or any combination of these domains that may be used in the treatment of spinal cord injuries and related disorders of the central nervous system (CNS). The polynucleotide also includes one or more polynucleotide domains that encode for polypeptides that link the domains of the polypeptide together to form the fusion protein.

One embodiment of the present invention is a composition and a method for its use that facilitates the access and distribution of therapeutic and diagnostic agent in the composition into cells, through membranes or into tissues by the use of composition that includes at least one enzyme capable of cleaving proteoglycans, preferably the composition includes a fusion protein having an enzyme capable of cleaving CSPGs. The molecules or agents in the composition may include one or more of Growth factors including, Brain Derived Neurotrophic Factor, Insulin-like Growth Factor, Fibroblast Growth Factor, Ciliary Neurotrophic Factor, Glial Derived Neurotrophic Factor, Transforming Growth Factor, Glial Growth Factor 2, L1, GM1, Vascular Endothelial Growth Factor, Nerve Growth Factor, Immunophilins. Molecules in the composition can include fluorescent or contrast agents for imaging. The agents may include cells for transplant—stem cells, neurons, others, cells as delivery agents, chemotherapeutic agents, antibiotics, antibody therapies, Nogo receptor antagonists, other chondroitinase enzymes. The composition may include a transduction domain, an enzyme capable of cleaving proteoglycans, or both. Preferably the composition includes a fusion protein having a transduction domain, an enzyme domain capable of cleaving proteoglycans, or both. The fusion protein can facilitate the transport or modifies transport of such agents into cells, tissues, and/or otherwise inaccessible locations; and/or to enhance penetration rates, distance of penetration; or provide more even concentration distribution. Preferably the modified transport occurs through the use of at least one enzyme capable of cleaving CSPGs. The compositions can be used for treating a CNS injury, preferably the composition is used in the treatment of neuronal damage from a contusion injury.

Embodiments of the present invention include chimeric proteins of a proteoglycan degrading domain linked to a polypeptide that blocks the action of neuronal growth inhibitors such as but not limited to a Nogo-receptor antagonist ($NgR_{27-311}$) domain or variant linked to a chondroitinase like chondroitinase ABC I or a variant of chondroitinase having one or more N terminal amino acids deleted. The compound may include chimeric proteins of a proteoglycan degrading domain linked to a polypeptide that is a neural cell adhesion promoter such as an L1 neural cell adhesion promoter domain or variant linked to chondroitinase ABC I or a variant of chondroitinase having one or more N terminal amino acids deleted. The chimeric proteins may include chimeric proteins of a proteoglycan degrading domain linked to a polypeptide that is a glial cell stimulator, such as but not limited to a GGF2 glial cell stimulator or variant linked to chondroitinase ABCI or a variant of chondroitinase having one or more N terminal amino acids deleted.

An *E. Coli* recombinant expression system and purification process can be used to produce essentially pure and catalytically active chondroitinase ABCI. These methods may be modified for producing chimeras of proteoglycan degrading molecules and other agents.

The chimera may be assayed for chondroitinase enzymatic activity and the specific biological activity of each fusion partner. Methods to measure the activities of the chimera may be modified for those used to measure chondroitinase activity including a spectrophotometric assay, zymography, an HPLC assay to detect CSPG disaccharide digestion products and an in vito neurite outgrowth assay. A neuron growth cone collapse assay can be used to evaluate NOGO receptor antagonists and a neurite outgrowth assay can be used measure L1 activity. GGF2 activity may be measured using a Schwann cell proliferation assay.

The compositions and method of the present invention can be used for the treatment of spinal cord injuries and in the promotion of regeneration of axons. The compositions of the present invention can also be used to promote plasticity, regrowth, repair, and/or regeneration of dysfunctional neurons in the CNS that have been damaged as a result of disease, such as degenerative diseases including Alzheimer's and Parkinson's disease. Advantageously, the use of proteoglycan degrading polypeptides or membrane transducing polypeptides in the compositions of the present invention also promote diffusion and access of damage or diseased tissue to other therapeutic agents promoting the regeneration of neurons.

DESCRIPTION OF THE DRAWINGS

The file of this patent contains at least one drawing/photograph executed in color. Copies of this patent with color drawing(s)/photograph(s) will be provided by the Office upon request and payment of the necessary fee.

In part, other aspects, features, benefits and advantages of the embodiments of the present invention will be apparent with regard to the following description, appended claims and accompanying drawings where:

FIG. 1 is an illustrative example of a TAT-chondroitinase ABCI construct (SEQ ID NO: 61); the DNA sequence for the entire gene fragment (SEQ ID NO: 58) fused with the Tat sequence followed by the 5-glycine linker (SEQ ID NO: 45); the sense and antisense oligonucleotides having the sequences as 5'-tatgtatggtc gtaaaaagcgtc gtcaacgtcgtcgtgg tggtggtggtca-3' (SEQ ID NO: 92) and 5'-tatgaccaccaccaccaccacgac gacgttgacgac gcttttt acgaccataca-3' (SEQ ID NO: 93) were annealed and ligated at the NdeI site which is at the 5' end of ABCI gene cloned in pET15b (Novagen) at the NdeI and BamHI sites.

FIG. 2 are Brain section images; (I) illustrating lobes from adult rat which were incubated in beta-galactodidase alone (B&D), or with the addition of Choindroitinase ABCI (A, 0.5 U/ml or C, 0.005 U/ml); (II) Eosin Y penetration through the cortex of a Choindroitinase treated brain hemisphere and control showing approximately the same penetration, Eosin Y is a is a zwitterionic, having an overall negative charge at the low pH it was used at, and it is 692 kDa; (III) A saturate solution of Congo Red demonstrates greater penetration through the cortex of a Chondroitinase treated brain hemisphere as compared to untreated brain, Congo red is a negatively charged dye of 697 kDa;

FIG. 3 (A) is a diagram representing the full length GGF protein (GGF2-$M_1$-$E_{422}$) and the three GGF2 fragments containing the Ig and EGF domains GGF2-$L_{250}$-$C_{402}$, Ig and EGF domains GGF2-$L_{250}$-$E_{422}$ to C-terminal; and EGF domains GGF2-$T_{350}$-$C_{402}$; (B) a schematic presentation of chimeric proteins of a proteoglycan degrading molecule like chondroitinase ABCI and a neuregulin 1 gene isoform GGF2 such as N-terminal fusion chimera between chondroitinase ABCI-NΔ60-CΔ80 and GGF2-FL, between chondroitinase ABCI-NΔ60-CΔ80 and GGF2-$L_{250}$-$C_{402}$, between chondroitinase ABCI-NΔ60-CΔ80 and GGF2-$L_{250}$-$E_{422}$, and between chondroitinase ABCI-NΔ60-CΔ80 and GGF2-$T_{350}$-$C_{402}$, and C-terminal fusion chimera (lower) such as between chondroitinase ABCI-FL and GGF2-FL, between chondroitinase ABCI-FL and GGF2-$L_{250}$-$C_{402}$, between chondroitinase ABCI-FL and GGF2-$L_{250}$-$E_{422}$, and between chondroitinase ABCI-FL and GGF2-$T_{350}$-$C_{402}$.

FIG. 5 (A) BBB scores from spinal cord injured animals treated with chondroitinase (Chondroitinase ABC I), penicillinase or artificial cerebrospinal fluid (aCSF); (B) Parasagittal sections of spinal cords from injured animals treated with chondroitinase (left column) or penicillinase (right column). Sections were cut at 30 microns. Each set of images contains four parasagittal sections realigned with the rostral cord to the left and the caudal cord to the right. The most central section of each set has been removed and replaced below to aid visualization. Pairs of images are Weil stained, anti-GFAP and an amino cupric stain of neuronal degeneration (top to bottom). (C) and (D) Distribution of individual BBB scores according to treatment group. Scores are BBB scores at ten weeks post surgery. Group averages are shown below the data points.

DETAILED DESCRIPTION

Figure 4:
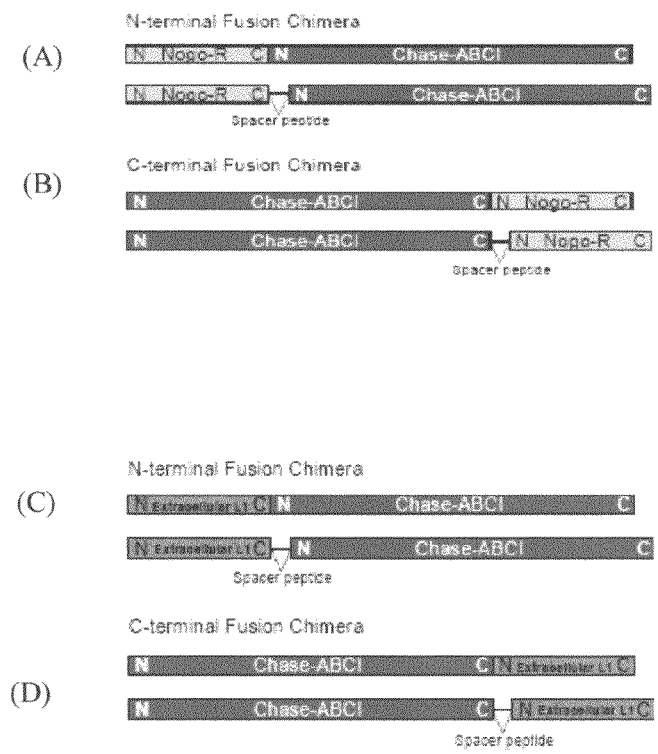
FIG. 4 illustrate the structure of (A) an $NgR_{27-311}$-N terminal chondroitinase ABCI chimeric protein without, and with, a peptide spacer or linking group; (B) an $NgR_{27-311}$-C terminal chondroitinase ABCI chimeric protein without, and with, a peptide spacer or linking group; (C) an extracellular domain L1 N-terminal chondroitinase ABCI chimeric protein without, and with, a spacer or linking peptide; (D) an extracellular domain L1 C-terminal chondroitinase ABCI chimeric protein without, and with, a spacer or linking peptide.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

"Optional" or "optionally" means that the subsequently described event or circumstance may or may not occur, and that the description includes instances where the event occurs and instances where it does not.

Suitable enzymes that cleave CSPGs include chondroitinase ABC type I, chondroitinase ABC Type II, chondroitinase AC, and chondroitinase B, or mammalian enzymes with chondroitinase-like activity such as hyaluronidase-1, hyaluronidase 2, hyaluronidase 3, hyaluronidase 4, cathepsins, ADAMTs and PH-20, or mixtures thereof.

CSPGs are a family of proteoglycans composed of a core protein and covalently linked sulfated glycosaminoglycans. The polysaccharide chains are cleaved by several enzymes, including a family of chondroitinases. To date, this enzyme family contains at least four members, Chondroitinase ABC I, ABC II, AC and B. Chondroitinase ABCI is an exo-lyase which cleaves both chondroitin and dermatan sulfates. It has been used extensively in the study of in vitro neuronal regeneration over CSPG-laden substrates and more recently in in vivo studies following CNS injury.

Proteins and polypeptide that may be used in the compositions and fusion proteins of the present invention are those which promote plasticity as well as the regeneration of injured or diseased neurons and axons. These regenerating proteins and polypeptides may include cell adhesion proteins, those which stimulate glial cells, and polypeptides which block the inhibitory effect of proteins that act as axon growth inhibitors.

Plasticity of the nervous system refers to any type of functional reorganization. This reorganization occurs with development, learning and memory and brain repair. The structural changes that occur with plasticity may include synapse formation, synapse removal, neurite sprouting and may even include strengthening or weakening existing synapses. Regeneration is generally differentiated from plasticity by the long range growth of axons in disrupted tracts that is characteristic of regeneration.

Proteins and polypeptides are capable of blocking the activity of neuronal growth inhibitory molecules may include peptides and polypeptides that block the inhibitory properties of peptide such as but not limited Nogo, MAG, and OMgp. Suitable compositions that overcome the activity of neuronal growth inhibitory molecules include but are not limited to Protein Kinase C family inhibitors, Rho Kinase family inhibitors and agents, such as phosphodiesterase inhibitors, that increase intracellular cyclic AMP, and L1. The ($NgR_{27-311}$) peptide has been shown to inhibit binding of Nogo66, OMgp, MAG, and MOG to membrane-bound NogoR and overcome the inhibitory effects of Nogo on the regeneration of nerve processes.

Proteins and polypeptides that affect cell adhesion or stimulate cells may include but are not limited to poly peptides such as L1 and GGF2. L1 is a neural cell adhesion protein that is a potent stimulator of neurite outgrowth in vitro for which has been found that treatment of acute SCI in rodents using a soluble form of L1 leads to an increase in the recovery of neurological function. GGF2 stimulates glial cells and has been shown to improve clinical outcome measures in a murine model of experimental allergic encephalomyelitis (EAE) likely as a result of the stimulation of oligodendrocytes to promote remyelination.

Cell membrane-permeant peptide sequences useful in practicing the present invention include, but are not limited to, RQARRNRRRRWRERQR-51 (HIV-1 Rev protein basic motif; (SEQ ID NO:43)); MPKTRRRPRRSQRKRPPTP-119 (HTLV-1 Rex protein basic motif; (SEQ ID NO:44)) (Kubota et al. 1989); the third helix of the homeodomain of Antennapedia (Derossi, et al., J. Biol. Chem. 271:18188-93, 1996) (43-RQIKIWFQNRRMKWKK-58 (SEQ ID NO:45)); a peptide derivable from the heavy chain variable region of an anti-DNA monoclonal antibody (Avrameas, et al., Proc. Natl. Acad. Sci. 95:5601-06, 1998) (VAYISRGGVSTYYS-DTVKGRFTRQKYNKRA (SEQ ID NO:46)); and the Herpes simplex virus VP22 protein (Elliot and O'Hare, Cell, 88:223-33, 1997) (1-MTSRRSVKSGPREVPRDEYED-LYYTPSSGMASPDSPPDTSRRGALQTRSRQR GEVR-FVQYDESDYALYGGSSSEDDEHPE-VPRTRRPVSGAVLSGPGPARAPPPP AGSGGAGRTPTTAPRAPRTQRVATKA-PAAPAAETTRGRKSAQPESAALPDAP ASRAPTVQL-WQMSRPRTDEDL-NELLGITHRVTVCEGKNLLQRANELVNPDV VQDVDAATATRGRSAASRPTERPRAPAR-SASRPRRPVE-246 (SEQ ID NO:47)). In a preferred embodiment, the basic peptide is derivable from the human immunodeficiency virus type 1 (HIV-1) Tat protein (Fawell et al., Proc. Natl. Acad. Sci., 91:664-68, 1994). In particular, the Tat peptide can comprise any sequential residues of the Tat protein basic peptide motif 37-72 (Vives et al. 1997) (37-CFITKALGISYGRKKRRQRRRPPQGSQTHQVSLSKQ-72 (SEQ ID NO:48)). The minimum number of amino acid residues can be in the range of from about three to about six, preferably from about three to about five, and most preferably about four, i.e., the minimal requirement for one alpha helical turn. A preferred embodiment comprises Tat protein residues 48-57 (GRKKRRQRRR) (SEQ ID NO:49).

Suitable PTD domains include those derived from the TAT protein (SEQ ID NO: 2). Tat proteins and peptides: Tat (SEQ ID NO: 2) is an 86-amino acid protein involved in the replication of human immunodeficiency virus type 1 (HIV-1). The HIV-1 Tat transactivation protein (SEQ ID NO: 2) is efficiently taken up by cells (Mann and Frankel 1991; Vives et al. 1994), and low concentrations (nM) are sufficient to transactivate a reporter gene expressed from the HIV-1 promoter (Mann and Frankel 1991). Exogenous Tat protein (SEQ ID NO: 2) is able to translocate through the plasma membrane and reach the nucleus to transactivate the viral genome.

A region of the Tat protein (SEQ ID NO: 2) centered on a cluster of basic amino acids is believed to be responsible for this translocation activity (Vives et al. 1997). Tat peptide-mediated cellular uptake and nuclear translocation have been demonstrated in several systems (Vives, et al., J Biol Chem 272:16010-16017, 1997; Jones, Genes Dev 11:2593-2599, 1997). Chemically coupling a Tat-derived peptide (residues 37-72) (SEQ ID NO:48) to several proteins results in their internalization in several cell lines or tissues (Fawell, et al., Proc Natl Acad Sci USA 91:664-668, 1994; Anderson, et al., Biochem Biophys Res Commun 194:876-8884, 1993; Fahraeus, et al., Curr Biol 6:84-91, 1996; Nagahara, et al., Nat Med 4:1449-1452, 1998). A synthetic peptide consisting of the Tat basic amino acids 48-60 with a cysteine residue at the C-terminus coupled to fluorescein maleimide translocates to the cell nucleus as determined by fluorescence microscopy (Vives et al. 1997). In addition, a fusion protein (Tat-NLS-.beta.-Gal) consisting of Tat amino acids 48-59 fused by their amino-terminus to .beta.-galactosidase amino acids 9-1023 translocates to the cell nucleus in an ATP-dependent, cytosolic factor-independent manner (Efthymiadis et al. 1998).

Chimeric proteins, also referred to in the art as fusion proteins, are hybrid proteins which combine at least parts of two or more precursor proteins or peptides. Chimeric proteins may be produced by recombinant technology, i.e. by fusing at least a part of the coding sequence of one gene to at least a part of the coding sequence of another gene. Where desirable, one or more genes for linker peptides may be fused to the coding sequence of genes for the other polypeptide domains in the fusion protein. The fused gene may then be used to transform a suitable organism such as but not limited to E. coli or CHO cells which then expresses the fusion protein.

Genes encoding either N or C terminal deletion mutants of polypeptide domains of the fusion proteins can be used in constructs for expression of the fusion proteins. Preferably the generated deletion mutants maintain their catalytic proteoglycan degrading activity, blocking activity, growth activity, or transduction activity. Generated deletion mutants of the proteoglycan degrading molecules like chondroitinase ABCI enzyme where the mutant is missing a certain number of amino acids from the N and or C-terminal are those that retain some proteoglycan degrading activity. N-terminal deletions of chondriotinase like chondroitinase ABC I maintain a histidine-tag that is attached to the N-terminus. It is expected that a TAT-deletion mutant chondroitinase ABC I fusion DNA construct can be expressed without removal of the TAT polypeptide during expression. For example a TAT peptide can be fused at the N-terminus of either ABCI-NΔ20 or ABCI-NΔ60 deletion mutant. Fragments of polypeptides, such as those shown in FIG. 3 for GGF2, may be used in the construction of chimeric fusion proteins.

Catalytically active deletion mutants of chondroitinase ABCI can be prepared for example but not limited to deleting 20, 40 and 60 amino acids respectively from the N-terminus of the mature ABCI protein. Deletion of 60 amino acids from the N terminal and 80 amino acids from the C-terminal end may also be used to make a deletion mutants of a proteoglycan degrading chondroitinase ABCI. These deletion mutants and those of other proteoglycan degrading molecules may be used for construction of N-terminal fusion chimeric protein. Detailed comparative biochemical studies can be done to determine the efficacy of mature chondroitinase ABCI versus various deletion mutant in compositions and fusion proteins with respect to the substrate specificity, substrate binding and tissue penetration.

A mutant of chondroitinase ABCI that has native protein structure, but lacks catalytic activity may be prepared as a null or a negative control for bioassays and SCI studies. Based on the crystal structure of chondroitinase ABCI a site-specific mutant designated H501a and Y508a to knock out catalytic activity in the putative active site can be prepared. Such mutants can be tested for inactivation of catalytic activity and SEC to compare to the wild-type enzyme. If the null activity mutant is successfully created it will provide a negative control for the various fusion proteins for use in bioassays and ultimately in SCI animal studies.

An *E. Coli* expression system may be used to make chondroitinase using PET expression vectors (Novagen). The GGF2-chondroitinase ABCI fusion protein may be expressed in *E. coli*. Constructs for Tat-chondroitinase deletion mutant fusion proteins, Tat-GGF2 fusion proteins, or Tat-chondroitinase-GGF2 fusion proteins may be expressed from *E. coli*. Other fusion proteins can be expressed in CHO cell lines.

Table 1 illustrates various non-limiting components which may be used in compositions of the present invention as a mixture, and preferably as a fusion or chimeric molecule. The composition or chimeric molecule described may include one or more of the molecules in Table 1. In the case of chimeric molecules one or more linker segments, preferably polypeptides are used.

TABLE 1

| Components of Compositions | | |
| --- | --- | --- |
| Transduction molecules | Proteoglycan degrading molecules | Therapeutic, diagnostic, receptor antagonist molecules |
| Tat protein residues 48-57 (SEQ ID NO: 49) HIV-1 Rev protein basic motif (SEQ ID NO: 43) HIV-1 Rev protein basic motif (SEQ ID NO: 43) Herpes simplex virus VP22 protein (SEQ ID NO: 47) | Any agent that degrades extracellular matrix glycoproteins including: Chrondroitinase ABC I (SEQ ID NO: 1 or 50), Chondroitinase ABC II (SEQ ID NO: 35), Chondroitinase AC (SEQ ID NO: 36), Chondroitinase B (SEQ ID NO: 37), Hyaluronidase 1 (SEQ ID NO: 38), Hyaluronidase 2 (SEQ ID NO: 39), Hyaluronidase 3, (SEQ ID NO: 40) Hyaluronidase 4, (SEQ ID NO: 41) PH20 (SEQ ID NO: 42) deletion and or substitution mutants of the above listed molecules that maintains enzymatic activity. | Any peptide that blocks the inhibitory properties of Nogo, MAG, OMgp including: Nogo peptide 1-40 (SEQ ID NO: 55) Any component of Nogo peptide 1-40 that maintains the ability to block the inhibitory properties of Nogo Other blocking peptides of Nogo Antibodies that recognize Nogo Blocking peptides of MAG Antibodies that recognize MAG Blocking peptides of OMgp Antibodies that recognize OMgp Antibodies that recognize the Nogo-66 receptor Blocking peptides of the p75 receptor Antibodies that recognize the p75 neurotrophin receptor Peptides or antibodies that block other receptors of Nogo, MAG and/or OMgp Peptide that overcomes the inhibitory properties of Myelin, Nogo, MAG, OMgp including: Protein Kinase C family inhibitors* Rho Kinase family inhibitors Agents that increase intracellular cAMP concentration L1 (SEQ ID NO: 5) |

A schematic illustration of non-limiting versions of chimeric fusion proteins of the present invention are illustrated in FIG. 4A and FIG. 4B.

A peptide component from any column in Table 1 could be linked by an oligopeptide linker that is well known in the art. A glycine rich peptide, for example Gly-Gly-Gly-Gly-Gly (SEQ ID NO: 56), or linkers prepared including any of the naturally occurring amino acids as well as substituted or beta or gamma amino acids like 4-aminobutyric acid or 6-aminocaproic acid can be used. Other linkers including but not limited to alkyl diamines, amino, or alkyl diols may also be used. Preferably the transduction component of the fusion protein is in a terminal position in the polypeptide. Other examples of common linkers may include but would not be limited to Gly-Gly-Ala-Gly-Gly (SEQ ID NO: 57), Gly/Ser rich linkers (for example $Gly_4Ser_3$ (SEQ ID NO: 94)), or Gly/Ala rich linkers. Additionally, linkers may be of any length and design to promote or restrict the mobility of components in the fusion protein.

The incorporation of non-natural amino acids, including synthetic non-native amino acids, substituted amino acids, or one or more D-amino acids into the peptides (or other components of the complexes) of the present invention (subsequently referred to herein as "D-peptides") is advantageous in a number of different ways. D-amino acid-containing peptides exhibit increased stability in vitro or in vivo compared to L-amino acid-containing counterparts. Thus, the construction of peptides incorporating D-amino acids can be particularly useful when greater intracellular stability is desired or required. More specifically, D-peptides are resistant to endogenous peptidases and proteases, thereby providing better oral transepithelial and transdermal delivery of linked drugs and conjugates, improved bioavailability of membrane-permeant complexes, and prolonged intravascular and interstitial lifetimes when such properties are desirable. The use of D-peptides can also enhance transdermal and oral transepithelial delivery of linked drugs and other cargo molecules.

In a spinal cord injury, the axons of ascending sensory and descending motor neurons are disrupted, that can result in the loss of sensation and paralysis. These axons fail to regenerate successfully leading to permanent disability. A scar envelopes the site of the injury which is believed to wall off the area of fragile tissue, stabilize the blood brain barrier, and prevent an overwhelming cascade of uncontrolled tissue damage. This scar is composed of hypertrophic glial cells and an extracellular matrix (ECM). Chondroitin sulfate proteoglycans (CSPGs) are one important component of the scar. They are expressed by glial cells and deposited in the ECM in regions of blood brain barrier breakdown. In vitro evidence demonstrates that these CSPGs are potently inhibitory for the growth of axons and without wishing to be bound by theory, are believed to contribute to the failure of the spinal cord axons to regenerate and reform functional synapses. In vivo studies have demonstrated that regenerating axons are able to grow into and even beyond the scar.

CSPGs and white matter components are generally accepted as molecular barriers that neurons must overcome in order to regenerate and reestablish functional connections after injury. Transplanted adult sensory neurons placed distal to a forming scar can regenerate robustly even along degenerating white matter pathways, however, regeneration ceases abruptly as axons enter the proteoglycan containing glial scar. Treatment of CNS white matter pathways with chondroitinase enhances the ability of neurons to grow in these substrates.

Central nervous system tissues are tightly compacted with cells and have limited extracelluar space. The proteins and carbohydrates of the extracellular matrix provide charge and osmotic forces as well as specific and non-specific binding sites which may prevent the penetration of therapeutic agents. The enzymatic cleavage of these matrix and cellular components may later or facilitate the access of compounds or cells through tissues. A proteoglycan degrading molecule like Chondroitinase ABC I that is an enzyme that digests chondroitin sulfate proteoglycans can be used to promote diffusion of therapeutic molecules into the CNS. Tat peptides transport covalently linked biologically active cargo molecules into the cytoplasm and nuclei of cells. In the case of a fusion protein having a protein transduction polypeptide domain like the HIV tat protein (SEQ ID NO: 3), therapeutic molecules for axon regeneration may be delivered across the blood brain barrier.

Treatment of SCI model injuries, preferably contusion model injury, can be used to determine the degree of regeneration and functional recovery achieved by compositions and method of the present invention. The degree of functional recovery can be demonstrated by improved corticospinal tract conduction, improved tape removal, beam walking, grid walking and paw placement following chondroitinase treatment of a dorsal column lesion. Motor skill improvement as well as autonomic function: bowel, bladder, sensor and sexual function may also be used as measures of function improvement and related to molecular structure and components in the compositions of the present invention.

In addition to the ability of chondroitinase to enhance regeneration, chondroitinase digests components of the perineuronal network (PNN). The density of the PNN is variable within the CNS and is particularly dense in the somatosensory, auditory, visual cortices and the hippocampus. PNN has also been demonstrated to be dense around spinal motor neurons. The inventors have discovered the dense PNN within the dorsal horn of the cord. Digestion of the PNN can enhance plasticity within the hippocampus and visual cortex. Plasticity within intact systems in incomplete SCI, especially in the region of the central pattern generators or in the reticular core, may support the function of damaged or destroyed systems. Promotion of plasticity in these systems may be one mechanism other than or in addition to regeneration by which chondroitinase can improve function following CNS injury. Furthermore, regeneration and plasticity may work in concert to affect recovery following injury; indeed, the corticospinal tract has been shown to be critical for modulation of spinal cord plasticity.

Recovery of neurological function following contusion injury in the CNS or a disease state may be promoted by administering the fusion proteins or mixtures including one or more of the components in Table 1, to cells, a tissue, or a subject having damaged or diseased neurons whether the injury or disease is immediate or long-standing.

The fusion proteins herein are administered in an amount effective to degrade CSPGs and thereby promote the recovery of neurological function. Once the proteins or polypeptides in the compositions have been purified to the extent desired, they may be suspended or diluted in an appropriate physiological carrier or excipient for SCI treatment. In models of SCI, effective intrathecal doses in rats have been about 0.06 units on alternate days for 14 days. A dose for a 70 kilogram human may be about 17 Units. At about 100 Units/milligram, this would equal about 170 micrograms. Doses of up to 20 Units appear safe in the rat. Compositions including a proteoglycan degrading molecule in a mixture or as part of a fusion protein diluted in a carrier or pharmaceutically acceptable excipient can be injected, generally at concentrations in the range of 1 µg to 500 mg/kg of host. Administering the agent can be by bolus injection, intravenous delivery, continuous infusion, sustained release from implants, or sustained release pharmaceuticals. Administration may be by injection, such as intramuscularly, peritoneally, subcutaneously, intravenously. Oral administration may include tablets or capsules, preferably the oral dosage is a sustained release formulation for once or twice daily administration. Percutaneous administration can be once per day, and is preferably less than once per day administration. Administration to the human patient or other mammalian subject may be continued until a measurable improvement in autonomic or motor function in the patient is achieved.

The chondroitinase PTD fusion proteins can be administered with a suitable pharmaceutical carrier. The administration of the compositions of the present invention as mixtures or chimeric proteins can be topical, local or systemic. The chimeric fusion proteins may also be secreted by genetically cells, preferably a chimeric fusion protein having a proteoglycan degrading portion like chondroitinase and a transduction polypeptide portion like TAT can be secreted by genetically modified cells that are implanted, either free or in a capsule, at or near the site of CNS injury.

Once the compositions either as mixtures or fusion proteins are administered, degradation of CSPGs removes the inhibitory molecules that block neurite outgrowth, and allow the regeneration of neurites into the affected area. For example, the chondroitinase AC and chondroitinase B degrade CS and DS, respectively, resulting in unsaturated sulfated disaccharides. Chondroitinase AC cleaves CS at 1, 4 glycosidic linkages between N-acetylgalactosamine and glucuronic acid in the polysaccharide backbone of CS. Cleavage occurs through beta-elimination in a random endolytic action pattern. Chondroitinase B cleaves the 1, 4 galactosamine iduronic acid linkage in the polysaccharide backbone of DS. The cleavage of both CS and DS occurs through a beta-elimination process which differentiates these enzymatic mechanisms from mammalian GAG degrading enzymes. Chondroitinase ABCI, and chondroitinase ABCII, are exo and endo lyases that cleave both CS and DS. The removal of CS and DS from the glial scar permits the regeneration of neurite outgrowths into the injured area.

Mixtures of any of these fusion polypeptides may be used to provide a therapeutic treatment for CNS injuries and disorders which may include but are not limited to contusion injury, traumatic brain injury, stroke, multiple sclerosis, brachial plexus injury, amblioplia, spinal cord injuries. Spinal cord injuries includes disease and traumatic injuries, such as the crushing of neurons brought about by an auto accident, fall, contusion, or bullet wound, as well as other injuries. Practice of the present methods can confer clinical benefits to the treated mammal, providing clinically relevant improvements in at least one of the subject's motor coordination functions and sensory perception. Clinically relevant improvements can range from a detectable improvement to a complete restoration of an impaired or lost function of the CNS.

The regeneration of the nerve cells into the affected CNS area allows the return of motor and sensory function. Clinically relevant improvement will range from a detectable improvement to a complete restoration of an impaired or lost nervous function, varying with the individual patients and injuries.

A variant of a protein or fragments thereof refer to a molecule substantially similar to either the entire protein or a fragment, which possesses biological activity that is substantially similar to a biological activity of the complement protein or fragments. A molecule is substantially similar to another molecule if both molecules have substantially similar structures or if both molecules possess a similar biological activity.

Variants of complement proteins or fragments thereof are produced by chemical or recombinant means. Variants of the polynucleotides constructed to express fusion proteins may also be made. The variants may include, for example, deletions from, or insertions or substitutions of, amino acid residues within the amino acid sequence, or deletion, substitution, or insertion of nucleic acids from a sequence encoding for a particular fusion protein or polypeptide domain in the fusion protein. For example, in some cases the removal of one or more amino acid residues from a chondroitinase polypeptide can be made without significant change in its CSPG degradation activity. Substantial changes in functional properties like proteoglycan degradation or blocking activity against axon growth inhibitors are made by selecting substitutions that are less conservative, ie. that differ more significantly in their effect on maintaining the structure, charge or hydrophobicity of the peptide backbone in the area of the substitution.

Most deletions, insertions, and substitutions are not expected to produce radical changes in the characteristics of the protein molecule; however, when it is difficult to predict the exact effect of the substitution, deletion, or insertion in advance of doing so, one skilled in the art will appreciate that the effect will be evaluated by routine screening assays. For example, a change in the axon regeneration character of the polypeptide molecule, through more or less proteoglycan degradation can be measured with functional recovery tests as well as HPLC assays to detect CSPG disaccharide digestion products.

The present invention relates to the use of a proteoglycan degrading molecule, an HIV tat protein, or a tat-derived polypeptide, or a combination of these as a mixture or fusion protein to deliver a molecule of interest into the CNS or a site in the CNS where neuronal tissue damage has occurred by disease or trauma. In particular the damage site in the CNS is where scaring has occurred as a result of a contusion injury. The molecule of interest, optionally referred to as an agent or cargo molecule can be a therapeutic molecule which promotes plasticity, axon growth, a diagnostic molecule, or a proteoglycan degrading molecule. In the case of a fusion protein having a protein transduction polypeptide domain like the HIV tat protein (SEQ ID NO: 3), therapeutic molecules for axon regeneration may be delivered across the blood brain barrier or proteoglycan degrading molecule can be delivered into cells to degrade cellular stores of proteoclycans and promote axon regeneration.

Transport polypeptides of this invention may be advantageously attached to cargo molecules by chemical cross-linking or by genetic fusion. A unique terminal cysteine residue is a preferred means of chemical cross-linking According to some preferred embodiments of this invention, the carboxy terminus of the transport moiety is genetically fused to the amino terminus of the cargo moiety. Embodiment of the present invention consists of an amino-terminal methionine followed by tat residues 47-58 (SEQ ID NO: 49), followed by a chondroitinase polypeptide.

It will be appreciated that the entire 86 amino acids which make up the tat protein may not be required for the uptake activity of tat. For example, a protein fragment or a peptide which has fewer than the 86 amino acids, but which exhibits uptake into cells and or can cross the blood brain barrier, can be used (a functionally effective fragment or portion of tat). For example, tat protein containing residues 1-72 can be sufficient for uptake activity and tat residues 1-67 can mediate the entry of a heterologous protein into cells. Synthetic peptide containing tat residues 1-58 can have uptake activity.

The tat peptide can be a single (i.e., continuous) amino acid sequence present in tat protein or it can be two or more amino acid sequences which are present in tat protein, but in the naturally-occurring protein are separated by other amino acid sequences. As used herein, tat protein includes a naturally-occurring amino acid sequence which is the same as that of naturally-occurring tat protein, its functional equivalent or functionally equivalent fragments thereof (peptides). Such functional equivalents or functionally equivalent fragments can possess uptake activity into the cell or across the blood brain barrier that is substantially similar to that of naturally-occurring tat protein. Tat protein can be obtained from naturally-occurring sources or can be produced using genetic engineering techniques or chemical synthesis.

The amino acid sequence of naturally-occurring HIV tat protein (SEQ ID NO: 2) can be modified, by addition, deletion and/or substitution of at least one amino acid present in the naturally-occurring tat protein, to produce modified tat protein (also referred to herein as tat protein or polypeptide). Modified tat protein or tat peptide analogs with increased stability can thus be produced using known techniques. Therefore, tat proteins or peptides may have amino acid sequences which are substantially similar, although not identical, to that of naturally-occurring tat protein or portions thereof. In addition, cholesterol or other lipid derivatives can be added to tat protein to produce a modified tat having increased membrane solubility.

Naturally-occurring HIV-1 tat protein (SEQ ID NO: 2) has a region (amino acids 22-37) wherein 7 out of 16 amino acids are cysteine. Those cysteine residues are capable of forming disulfide bonds with each other, with cysteine residues in the cysteine-rich region of other tat protein molecules and with cysteine residues in a cargo protein or the cargo moiety of a conjugate. Such disulfide bond formation can cause loss of the cargo's biological activity. Furthermore, even if there is no potential for disulfide bonding to the cargo moiety (for example, when the cargo protein has no cysteine residues), disulfide bond formation between transport polypeptides can lead to aggregation and insolubility of the transport polypeptide, the transport polypeptide-cargo conjugate, or both. The tat cysteine-rich region may be deleted to avoid disulfide bond formation and prevent aggregation and insolubility of the transport polypeptide, the transport polypeptide-cargo conjugate, or both.

Chondroitinase is also able to promote plasticity in regions of the CNS with significantly dense PNN, including cortex, tectum, hippocampus and spinal cord. It is reasonable to expect that some combination of effects, including regeneration, sprouting and plasticity are responsible for the improvement in function following SCI with chondroitinase treatment or treatment with fusion molecules including chondroitinase or other proteoglycan degrading molecule.

NbR$_{27-311}$: Nogo is a high molecular weight myelin component that inhibits neurite outgrowth. The amino terminal region (Nogo66) is the part of the molecule that is specifically associated with the inhibition of neurite outgrowth. Expression cloning methods revealed the receptor for Nogo66 (NgR) is a GPI anchored glycoprotein expressed mainly on neurons. NgR interacts not only with Nogo, but also with other myelin associated inhibitors such as MAG and MOG. Due to its central role in the inhibitory properties of myelin on neurons, NgR has been the target for approaches to antagonize its interactions with its ligands. The soluble segment of NgR interacts with Nogo66, MAG and MOG. The region spans residues 27-311 and this NgR fragment can therefore act as a decoy receptor that will interfere with myelin associated inhibition of neurons. If NgR$_{27-311}$ is linked to proteoglycan degrading molecule like chondroitinase ABCI to form a chimeric fusion protein, the NgR$_{27-311}$ polypeptide domain of the fusion protein would be expect to limit the myelin-associated inhibition of neurite outgrowth and promote axonal regeneration in chondroitinase digested regions of a spinal cord injury.

For cloned (NgR$_{27-311}$), the precise region of interest, or fragments can be derived from the initial clone. The biological activity of NgR$_{27-311}$, its fragments, and fusion polypeptides including NgR$_{27-311}$ may be confirmed using an in vitro assay for the collapse of growth cones on neurons. The growth cone collapse assay has been established and the addition of MAG or Nogo66 causes the collapse of growth cones in a dose dependent manner. If NgR$_{27-311}$, its fragments, and fusion polypeptides including NgR$_{27-311}$ are active is biologically active then they should inhibit the MAG and Nogo66 mediated growth cone collapse. Growth cone collapse data may be collected by the inspection of photomicrographs of DRG neurons in response to Nogo66 and MAG.

The L1 polypeptide is a member of the immunoglobulin superfamily of cell adhesion molecules and is expressed in growing axons, glial progenitor cells and Schwann cells throughout life, but has only limited expression in the CNS. L1 interacts with itself and with other extracellular molecules, such as the FGF receptor to promote neurite fasciculation and growth. Expression of L1 is generally associated with a permissive environment for axonal regeneration the, precise region of interest, or fragments of L1 can be derived from the initial clone. For example, Schwann cells that express L1 support peripheral nerve regeneration and axonal growth is observed in the optic nerves from transgenic mice that express L1 in astrocytes but not in wild-type optic nerves. Fibroblasts engineered to express L1 support axonal growth when transplanted into spinal cord. Finally, a soluble form of L1 linked to Fc promoted functional recovery following acute SCI. HU is linked to proteoglycan degrading molecule like chondroitinase ABCI in a fusion protein it is reasonable to expect the fusion protein to promote axonal regeneration in chondroitinase digested regions of a spinal cord injury.

The neuregulins and their receptors comprise a diverse growth factor and receptor tyrosine kinase system that has been demonstrated to be essential for organogenesis in the CNS, muscle epithelial and other tissues. GGF2 is a soluble isoform of the neuregulin 1 gene. It was initially characterized as a Schwann cell mitogen 32, but subsequent studies have demonstrated direct actions on oligodendrocytes, neurons and other cell types. GGF2 diminishes demyelination and inflammation and enhances remyelination in a mouse model for multiple sclerosis. Based on these results, it is reasonable to expect that a recombinant human GGF2 is a potential treatment for demyelination associated with SCI. With GGF2 is linked to a proteoglycan degrading molecule like chondroitinase ABCI it is reasonable to expect to promote remyelination of axons in chondroitinase-digested regions of a SCI.

TABLE 2

Examples of non-limiting GGF2 (SEQ ID NO: 6) fragments for expression in E. coli for use in compositions and fusion polypeptide compositions.

| Construct | Domain | Nucleotide Seq | Amino Acid Seq | Mol. Wt. |
| --- | --- | --- | --- | --- |
| GGF2-FL (SEQ ID NO: 6) | Full length GGF2 | | M1-E422 | 46 kDa |
| GGF2/1 (SEQ ID NO: 16) | Ig domain + EGF domain | 748-1206 | L250-C402 | 16.8 kDa |

TABLE 2-continued

Examples of non-limiting GGF2 (SEQ ID NO: 6) fragments for expression in
E. coli for use in compositions and fusion polypeptide compositions.

| Construct | Domain | Nucleotide Seq | Amino Acid Seq | Mol. Wt. |
|---|---|---|---|---|
| GGF2/2 (SEQ ID NO: 17) | Ig domain to C-terminus | 748-1266 | L250-E422 | 19 kDa |
| GGF2/3(SEQ ID NO: 18) | EGF domain | 1048-1206 | T350-C402 | 5.7 kDa |

The efficacy of a composition of the present invention, such as a proteoglycan degrading molecule and a molecule that blocks the activity of an axon growth inhibitor either as a mixture [of] or as a fusion protein can be evaluated using a validated rat SCI model at three different levels of SCI severity.

A proteoglycan degrading molecule like Chondroitinase ABCI is commercially available in small quantities as a naturally derived enzyme (Seikagaku Corporation) and can be made by a recombinant production system to have essentially the same activity as the enzyme purified from *Proteus vulgaris*. Genomic DNA can be isolated from *Proteus vulgaris* using DNeasy Tissue kit (Qiagen). PCR primers can be synthesized with an NdeI restriction site at the 5' end and a BamHI site at the 3' end having sequences 5'-CAT ATG GCC ACC AGC MT CCT GCA TTT G-3'(F2) (SEQ ID NO: 95) and 5'-GGA TCC TCA AGG GAG TGG CGA GAG-3'(R) (SEQ ID NO: 96) respectively, to synthesize the mature protein. The 3.0 kb PCR products can be ligated into pCR 2.1 vector (TOPO cloning kit, Invitrogen) and transformed into DH5a competent cells (Invitrogen). Plasmid DNA can be isolated from a number of clones screened by digestion with EcoRI restriction enzyme. The integrity of a gene prepared in this way can be confirmed by repeated DNA sequencing.

The chondroitinase ABCI sequence can cloned into a PET vector (Novogen) for expression in *E. Coli* After induction of gene expression with IPTG the bacteria can lysed by sonication with the concomitant extraction of chondroitinase ABCI with Triton X-114/PBS. The inventors discovered that the majority of recombinant chondroitinase ABCI was found in the cytosolic fraction of the bacterial cell lysate that enabled the development of a chondroitinase ABCI purification protocol that yields an enzyme with high activity at high yields. The protocol includes cation-exchange chromatography as a capture step and gel filtration as a polishing step. After these steps chondroitinase ABCI reaches a purity of ~95%. Anion exchange membrane filtration (Intercept Q, Millipore) can be used for endotoxin and host DNA removal. This step is expected to remove approximately 75% of the endotoxin. Following filtration, chondroitinase ABCI can be dialyzed into volatile buffer, pH 8.0 and lyophilized to dryness. The final product is stable at −70° C. for long term storage. The purified cABCI is a highly basic protein with pI~9.5 as determined by IEF-PAGE analysis of the samples from the crude cell lysate.

A variety of analytical methods can be used to compare the enzymatic activity of the recombinant version of chondroitinase ABCI to that of a commercially available form of the enzyme (Seikagaku Corporation) purified from *Proteus vulgaris*. The methods may be adapted to evaluate the activity of fusion proteins including proteoglycan degrading polypeptides like chondroitinase. Specific activity measurements were obtained using an accepted spectrophotometric assay that measures the change in absorbance due to the production of reaction products from the degradation of proteoglycans. The recombinant form of chondroitinase ABCI had approximately 25% higher specific activity than the Seikagaku chondroitinase ABCI. Size exclusion chromatography can be used to compare the hydrodynamic properties the enzymes. The elution profiles for recombinant enzyme was identical to that of the naturally derived enzyme.

A form of zymography can used to further characterize the enzyme and may be adapted for characterization of the fusion proteins. Polyacrylamide gels can be polymerized in the presence of aggrecan, a substrate for chondroitinase ABCI. Enzyme samples may be resolved on the aggrecan-impregnated gels by electrophoresis in the presence of SDS. The gels can then be subjected to a renaturation step wherein the SDS was extracted and the enzymes allowed to refold. Enzyme refolds and regains activity then digests aggrecan within the gel and the resulting loss of carbohydrate in that region of the gel can be visualized by a carbohydrate-specific stain. A similar loss of carbohydrate in the gel would be expected for active forms of a fusion protein including a proteoglycan degrading polypeptide portion. In the case of recombinant Chondroitinase ABCI, its activity can be visualized as a clear spot in the zymogram. The zymography results were consistent with the spectrophotometric analysis that demonstrates that the recombinant form of chondroitinase ABCI has the same or greater specific activity as the naturally occurring form.

HPLC methods may be used for detecting the four and six sulphated disaccharides ($\Delta$4DS and $\Delta$6DS, respectively) liberated as a result of chondroitinase ABCI digestion of CSPG. The two disaccharides can be effectively resolved by anion exchange chromatography. The HPLC assay has been validated by showing that the quantitation of $\Delta$4DS and $\Delta$6DS from chromatograms yields a linear relationship to the amounts injected into the HPLC. Production of $\Delta$4DS and $\Delta$6DS from CSPG digestion is directly related to the amount of chondroitinase specific activity as determined by the spectrophotometric assay described above. This assay may be used as a sensitive and accurate means to independently quantitate $\Delta$4DS and $\Delta$6DS released by chondroitinase digestion of a variety of substrates and may also be used to determine the activity of chondroitinase polypeptides in a fusion protein.

Another functional assay that can be performed to characterize proteoglycan polypeptide activity is where dorsal root ganglian (DRG) neurons are plated on aggrecan or aggrecan treated with a proteoglycan like chondroitinase ABCI. It is expected that neurons plated on aggrecan will failed to adhere to the plate and extend axons. In contrast, neurons plated on aggrecan treated with a proteoglycan degrading polypeptide like chondroitinase ABCI in a composition or as part of a fusion polypeptide would be expected to adhere to the surface and extend axons. The extensive axon growth, which is observed for chondroitinase ABCI is believed to be due to the digestion of the carbohydrates on the aggrecan core protein which creates a more permissive substrate for axon growth.

The rat contusion model of SCI is a clinically relevant model and may be used to evaluate the efficacy of fusion proteins and other compositions of the present invention for promoting axon regeneration. With a contusion SCI, cells are destroyed, hemorrhage ensues and inflammation begins. Destroyed cells are removed by macrophages and a reactive gliosis begins. A cystic cavity is formed and the gliosis matures into a glial scar. Myelin in the area is destroyed and many local neurons that are not destroyed are left in a demyelinated state.

The forceps compression model of SCI is a contusion model developed and characterized. This model has been validated and results in injuries that are very similar to the more widely used impactor models. The model can involves a forceps compression at vertebral level T9/T10. The forceps compress the cord to a width of 0.9, 1.3 or 1.7 mm for 15 seconds. These three levels of compression allow a severe, mild or moderate injury. This model has been validated using the open field locomotor testing and the Basso, Bresnahan and Beattie (BBB) scoring system. It was also characterized histologically. Behavioral testing and BBB scoring demonstrated that the forceps produce a highly reproducible injury, with recovery similar to that seen with impactor models. These testing and scoring data demonstrate that the forceps compression model is comparable to other contusion models and sufficiently reproducible to be used as an experimental model of SCI and may be used for the evaluation of compositions of the present invention.

Tissue from forceps compression injured animals can be processed histologically to examine white matter sparing, glial scar and cyst formation. As with other contusion SCI models, a central cyst is formed after injury, with a size that increases with increased injury severity (decrease forceps gap). Around the cyst a glial scar forms that is characterized by astrogliosis (GFAP), macrophage activation and myelin wasting.

Various aspects of the present invention will be illustrated with reference to the following non-limiting examples.

Example 1

This example illustrates how a proteoglycan degrading molecule may be administered, studied, and demonstrated to show a functional improvement in animals having a model contusion injury.

The forceps compression model of SCI is a contusion model developed and characterized. This model has been validated and results in injuries that are very similar to the more widely used impactor models. The model can involves a forceps compression at vertebral level T9/T10. The forceps compress the cord to a width of 0.9, 1.3 or 1.7 mm for 15 seconds. These three levels of compression allow a severe, mild or moderate injury.

Rats were injured with the forceps compression model at vertebral T9/T10/At the time of surgery an intrathecal catheter was placed for delivery of chondroitinase. Animals were treated every day for one week and then on alternating days for one week with 0.06 U/dose chondroitinase ABC I (Seikagaku), penicillinase or artificial cerebrospinal fluid (aCSF). Doses and controls were derived from Bradbury et al., 2002. Behavior was assessed using open-field locomotor testing and the BBB scoring system at day 2 and then weekly post injury for ten weeks.

FIG. 5A shown are mean BBB scores for animals treated with chondroitinase ABC I, penicillinase and aCSF. Rats treated with aCSF or penicillinase recovered to a mean BBB score of about 4. Rats treated with chondroitinase recovered to a mean BBB score of about 8. Multiple animals recovered to scores above 10, indicating supra-spinal input. The chondroitinase scores were significantly different from both control groups by ANOVA and post hoc Tukey.

Tissue from these animals was processed immunohistochemically for glial fibrillary acidic protein (GFAP) to assess general scar architecture. Tissue was also stained with a Weil stain and a silver degeneration stain to assess myelin and neuron degeneration, respectively. Interestingly no obvious differences in these parameters were noted between experimental and control treated tissues.

In FIG. 5B the large lesion comprising several segments and the sparing in the ventral cord. Weil staining revealed extensive demyelination in both the treated and untreated animals. The GFAP images (middle set) demonstrate the extent of the scar that is formed following forceps injury. The bottom amino cupric silver degeneration stain demonstrates the vast neural degeneration extending both rostrally and caudally after injury. Again, no obvious differences were noted between chondroitinase treated and control tissues.

Additional preliminary experiments have been performed at moderate injury levels and significant improvement in open-field locomotor activity was observed with chondroitinase treatment. Animals receiving chondroitinase ABCI recovered to a mean BBB score of 9.1 at ten weeks following injury, compared with 7.1 for the penicillinase controls. The consistency of the data (SEM's of 0.6 and 0.3, respectively) and the region of scores on the BBB scale make this 2 point change not only statistically significant, but also clinically meaningful. A score of 9 indicates plantar placement with weight support or frequent to consistent weight support with dorsal stepping while a score of 7 indicates movement of each joint in hind limb but with no weight support and no consistent sweeping of limbs. An examination of the individual animal scores at ten weeks shows that 6 of 12 animals in the chondroitinase group recovered to scores of 9 or above, while only one of 12 animals in the penicillinase group recovered to a score of 9. One animal from each group was removed from analysis because its score failed to ever rise above 2.5, indicating an injury severity outside the model norms. FIG. 5C and FIG. 5D includes a scatter plot of scores at 10 weeks for each animal in the penicillinase and chondroitinase treatment groups for the moderate injury. Group means are shown below.

The results show in this well controlled study, that chondroitinase improves open-field locomotor function in Rats that were injured with the forceps compression model at vertebral T9/T10. Animals recovered to mean BBB scores of 9.7 and 9.9 for the penicillinase and chondroitinase groups, respectively. This study demonstrates a significant effect at severe and moderate injury levels, but not mild injury levels. No significant differences were noted between any groups in the mild injury study (1.3 mm forceps). It is unclear if chondroitinase is not effective with mild injury, if chondroitinase effected changes not adequately assayed by the open-field locomotor testing such as stride length, paw placement, sensory or autonomic functions. Preliminary analysis of histology from animals in this study confirmed placement of the catheters and injuries in each animal. Ongoing experiments sacrificing animals at time points after injury with and without chondroitinase treatment will characterize the CSPG content of the scar and the effects of chondroitinase digestion on stub-antigen expression. Future experiments will expand the battery of behavior tests and examine the cord for evidence of regeneration with tract tracing.

Two acute toxicity studies were conducted in rats. The first was an intravenous (IV) study wherein rats were injected with 0, 0.2, 0.775 or 7.775 mg/kg chondroitinase ABCI. In the second study, intrathecal (IT) catheters were placed over the spinal cords using the same methods employed in the SCI animal studies and 0.06, 0.6 and 6.0 units of chondroitinase ABCI was delivered through the IT catheters. These doses were 1, 10, and 100-fold greater than the estimated local concentrations of chondroitinase ABCI achieved with IT catheters in the SCI experiments. Animals were monitored for pain and distress and body weights were acquired daily. No overt reactions were observed during or immediately after chondroitinase ABCI dosing. No swelling, inflammation, bruising or necrosis was noted at the injection site for the IV experiment. No changes in body temperature were observed in animals treated via the IT route. No alterations in feeding, grooming or vocalizations were noted. Animals were assessed for motor behavior in an open pool. No abnormalities were noted by the animal care staff or behavioral specialists. Animals displayed no signs of joint tenderness or swelling. There were no significant differences in weight change between the treatment groups. The results demonstrate that chondroitinase ABCI treatment is not associated with acute toxicity using IV and IT doses substantially greater than the efficacious IT doses.

Example 2

This example describes the preparation of Nogo-receptor agonist, L1 neural cell adhesion protein, and GGF2 polypeptide domains which can be used for compositions and fusion proteins of the present invention.

A soluble portion of the human Nogo receptor spanning amino acids 27 to 311 ($NgR_{27-311}$) was selected as it has been shown to inhibit the binding of Nogo66, MAG, and MOG to membrane-bound NgR. Primers were designed flanking this region, and RT-PCR was performed using human hippocampal RNA (BD Biosciences). The 1.05 kb region was successfully amplified and purified.

L1 was prepared through a CHO cell line from the laboratory of Dr. Melitta Schachner that secretes human L1 as a fusion protein with human Fc (L1-Fc). The cells were grown in roller bottles and then L1-Fc was purified from the conditioned media using protein A affinity column chromatography. The purity of L1-Fc was assessed by SDS-PAGE and a single band at the appropriate molecular weight was observed. The biological activity of L1-Fc was confirmed using a neurite outgrowth assay. Tissue culture plates were coated with either poly L-Lysine or L1-Fc and then cerebellar granule cells from postnatal day 10 rats were isolated and placed into culture on the substrates. It was observed that neurons plated on the L1-Fc substrate exhibited a substantial number of long neuritis compared to the polylysine substrate controls. These results demonstrate that the L1-Fc produced is biologically active in promoting neurite outgrowth. This neurite outgrowth assay will be used to assess the biological activity related to the L1 portion of the chondroitinase ABCI fusion protein.

A CHO cell line that secretes a soluble form of full length GGF2 glycoprotein was obtained from CeNes. Extensive optimization of media and purification methods was completed to obtain essentially pure and biologically active GGF2. A number of analytical methods were developed to characterize the GGF2 including SDS-PAGE, isoelectric focusing, peptide mapping and carbohydrate analysis. For example an SDS-PAGE gel of reduced and non-reduced GGF2; the isolate is essentially free of contaminating proteins and shows the expected molecular weight and monomeric structure. The biological activity of GGF2 was assayed using a primary rat Schwann cell proliferation method and the expected effect was reproducibly obtained with four independent batches of GGF2. Another functional assay was developed that measures the phosphorylation of Akt kinase, a downstream cell signaling component of the erbB receptor pathway. It was observed that there is a dose dependent phosphorylation of Akt kinase Example 3

This example illustrates the manipulation of chondroitinase ABCI for construction of chimeras.

Chondroitinase ABCI was cloned from *P. vulgans* and expressed in *E. coli*. Surprisingly repeated attempts to create N-terminal fusion proteins were not successful because the N-Terminal fusion portion was cleaved from chondroitinase ABCI during synthesis. However, catalytically active deletion mutants with N-terminal H is fusion tags designated ABC I-NΔ2O, ABC I-NΔ4O, and ABCI-NΔ6O were prepared by deleting 20, 40 and 60 amino acids respectively from the N-terminus of the mature ABCI protein. Unlike the full length chondroitinase ABCI, the N-terminal deletion mutants are capable of synthesizing a 6×His tag as an N-terminal fusion protein. It was also observed that deletion of 80 amino acids from the C-terminal end formed a mutant with proteoglycan degrading activity of chondroitinase ABCI as tested in a zymography assay.

Fusion proteins with $NgR_{27-311}$ or L1 with a proteoglycan degrading molecule such as chondroitinase ABCI will utilize mammalian expression and can be performed in CHO cells. The cDNA for chondroitinase ABCI has been cloned in pSECTag vector (Invitrogen) in the proper reading frame. A CHO cell line having secretary chondroitinase ABCI can be developed and the conditioned medium can be tested for catalytic activity by zymography assay to confirm that chondroitinase ABCI expressed in mammalian cells is functional. A mammalian cell codon optimized version of chondroitinase ABCI can be synthesized by methods known in the art for use for CHO cell expression.

GGF2 is a spliced variant of the NRG1 gene expressed in brain and spinal cord of adult humans. It is a glycosylated protein of molecular mass between 66-90 kDa. The inventors have discovered that recombinant GGF2 expressed in CHO cells is highly glycosylated and promotes Schwann cell proliferation in vitro and further that an EGF-like domain of NRG1 expressed in *E. coli* is fully functional in promoting myocyte proliferation and survival.

The inventors have expressed fragments of GGF2 in *E. coli* as described. The specific GGF2 domain responsible for Schwann cell proliferation and thereby remyelination can be determined. If the Ig and EGF domains together or separately show biological activity in vitro, then they can be used to form chimeric fusion proteins.

Cloning and expression of $NgR_{27-311}$ in CHO cells. An NgR fragment corresponding to residues 1-359 was isolated by RT-PCR from human hippocampus poly K RNA (BD Biosciences) and its structure can be confirmed by DNA sequencing. The gene fragment corresponding to residues 27-311 can be cloned from the larger fragment and then subcloned in pSECTag vector (Invitrogen) in the proper reading frame to express the fragment as a secretary protein in CHO cells. The plasmid DNA containing the $NgR_{27-311}$ gene can be transfected in CHO cells and the cell line producing $NgR_{27-311}$ can be selected under the selection pressure of hygromycine B. An $NgR_{27-311}$-ABCI chimera expression plasmid can be constructed for expression in a CHO cell expression system using methods known in the art.

Example 4

This example illustrates methods which may be used to purify and isolate expressed chondroitinase ABCI, and GGF2 domains expressed in *E. coli*. These method may be applied to purification of chimeric fusion proteins of the present invention.

An efficient *E. coli* recombinant expression system and a purification process for chondroitinase ABCI have been developed by the inventors that could be applied for the purification of chondroitinase ABCI chimeric derivatives.

For example, the expression of various GGF2 domains in the chondroitinase ABCI expression host, *E. coli* has been performed and the following peptides have been tested: aa250-402, aa250-422 and aa350-402. These expressed peptides were found in the soluble fraction of the *E. coli* lysates. It is reasonable to expect that final chimeric products of these peptides with chondroitinase ABCI in *E. coli* will also be soluble. In addition, it is expected that the charge characteristics of the chimeric products when compared to the recombinant chondroitinase ABCI will be similar. Thus, the theoretical isoelectric point (p1) values for the GGF2 peptides are 9.3 for aa250-402, 9.18 for aa250-422 and 7.55 for aa350-402. Fusing the first two peptides with chondroitinase ABCI is expected to result in chimeric proteins with p1 values still above 9. In this case SP chromatography is expected to perform well as the capturing step. The smallest GGF2 peptide, aa 350-402, will reduce the p1 of the final chondroitinase ABCI chimera to approximately 8.4. This change may require optimization of the capture step conditions.

The chimeric products of chondroitinase ABCI with $NgR_{27-311}$ and L1 peptides can be expressed in a CHO cell system. Prior to purification of the expressed chimeric proteins, the growth conditions for the cell line producing either the $NgR_{27-311}$ or L1 chimeric proteins will be optimized in serum-free medium. A detailed media optimization study can be performed to determine the highest production conditions. Scale-up volume can be decided based on the rate of production of the chimeric proteins (pg/cell/day). Conditioned media from the various chimera-producing cell lines can be collected and subjected to tangential flow filtration. Ion-exchange chromatography can be used for capturing the secreted proteins from conditioned media, gel filtration chromatography can be used as a polishing purification step and then anion-exchange membrane filtration can be used for endotoxin and DNA removal. At each step the efficiency of the purification will be analyzed by SDS-PAGE, and spectrophotometric quantitation of protein concentration.

Example 5

This prophetic example describes in vitro assessment of chimera biological activity: Each chimera can be assayed for chondroitinase enzymatic activity and the specific biological activity of each fusion partner.

The first step in analysis may employ conventional protein biochemical methodologies to confirm the fidelity of gene expression. These include SDSPAGE, 1EE, mass spectrometry and size exclusion chromatography.

Chondroitinase chimera specific activity can be determined using a standard and uniformly accepted spectrophotometric assay. The production of reaction products from the catalytic activity of a chondroitinase chimeric polypeptide can be determined by a measurement of the absorbance of the product at a wavelength of 232 nm. A typical reaction mixture consists of 120 microliters of reaction mixture (40 mM Tris, pH 8.0, 40 mM NaAcetate, 0.002% casein) combined with substrate (5 microliters of 50 mM chondroitin C) and 1.5 microliters of chondroitinase ABCI chimeric fusion polypeptide or test sample. The change in absorbance units is the initial rate which can be converted to a unit activity measurement.

Disaccharide HPLC assay: The catalytic activity of chondroitinase chimeric polypeptide on a CSPG substrate is expected to releases two species of sulphated disaccharides including α-Δ AUA-[1→3]-GalNAc-4S (Δ 4DS) and α-Δ AUA-[1→3]-GalNAc-6S (Δ 6DS). These species can be resolved by HPLC and the quantitation from the resulting chromatograms is a sensitive and accurate measure of chondroitinase activity. To perform the assay, samples from chondroitinase digestion reactions carried out with wild-type chondroitinase and chondroitinase fusion proteins can be clarified by centrifugation and then subjected to a validated anion exchange HPLC method as follows. A Dionex Carbo-Pac PA-10 analytical column (4×250 mm) fitted with a Dionex CarboPac PA-10 (4×50 mm) guard column can be used with a mobile phase consisting of a gradient of water at pH 3.5 (Buffer A) and 2M NaCl, at pH 3.5 (Buffer B). Detection may be set at a wavelength of 232 nm. A flow rate of 1 mL/minute and a 45 minute continuous gradient of 100% A to 100% B affords acceptable resolution of Δ4DS and Δ 6DS. Standard curves can be generated using known amounts of Δ4DS and Δ6DS.

Zymography allows resolution of proteins by molecular weight with a concomitant assessment of chondroitinase activity. A 10% polyacrylamide gel may be polymerized in the presence of 85 pg/ml of aggrecan. Samples can be boiled in an SDS-loading buffer and then the analytes can be resolved by electrophoresis. After separation the gel can be incubated for 1 hour at room temperature in 2.5% Triton X100 then 16 hours at 37° C. in fresh 2.5% Triton X-100. During these incubations, the SOS can be extracted from the gel and the chondroitinase refolds and digests the aggrecan in its immediate vicinity. After the refolding process the gel can be stained for carbohydrate: The gel can be first incubated in 0.2% Cetylpyridinium for 90 minutes at room temperature and then transferred into 0.2% Toludine Blue in 49:50:1 $H_2O$, Ethanol, and Acetic Acid for 30 minutes. The gel can then be fully destained. Following destaining the gel can be incubated overnight in a 50 microgram/ml solution of Stains-All (Sigma) in 50% ethanol. Chondroitinase activity can be detected as a clear spot in the gel that is coincident with the molecular weight of the enzyme. The size of the clearing has been shown to be almost linearly related to Unit activity.

The $NgR_{27-311}$-chondroitinase chimera can be assessed for the activity of the decoy Nogo receptor. The assay can be used to measures the collapse of growth cones: Dorsal root ganglia (DRG) are dissected from postnatal day 1 (P1) Sprague Dawley rat pups and dissociated in 200 U/ml collagenase I (Worthington) and 2.5 U/ml dispase (Boehringer/Roche)2 times for 30 min. at 37° C. Enzymes are removed and DNAse (0.5 mg/ml) can be added to the ganglia. Trituration may be done with a pipette tip attached to a 1000 µl Pipetman. The resulting cell suspension can be filtered through a 40 micron cell filter and centrifuged at 70×g for 5 min. Cells can be resuspended in DMEM/10% FBS and pre-plated for 2 hours on a non-coated tissue culture plate (100 mm diameter). Non-adherent neurons are removed and plated at 10,000 cells/well in a Poly-lysine/laminin-coated 24 well plate in serum-free Neurobasal/B27 with 50 ng/ml NGF. After 20 to 24 hours, MAG or Nogo66 can be added at varying concentrations for 1 hour at 37° C. to induce growth cone collapse. NgR$_{27-311}$-chondroitinase chimera can be added at various concentrations to compete with MAG and Nogo66 and thus protect the neurons from growth cone collapse. Cultures may be fixed by adding an equal volume of pre-warmed 8% paraformaldehyde/0.6 M sucrose to the medium for 20 min. while the cells are kept on a 37° C. hot plate. Growth cones may be labeled with AlexaS68 phalloidin (Molecular Probes). Briefly, cells can be permeabilized with 0.1% Triton-X 100 for 5 min. at RT, blocked for 20 min. in 1% BSA in PBS and incubated in phalloidin, diluted 1:40 in 1% BSA, in PBS for 20 mm at RT. Cells can be washed in PBS and mounted in Fluorescent Mounting Medium (DAKO). The percentage of collapsed growth cones is determined by analyzing a minimum of 100 growth cones per well under a 40× objective.

The biological activity L1 fusion proteins may be determined using a standardized neurite outgrowth assay. After etching a 25 mm circle in the center of a tissue culture-treated 35 mm dish, 1 ml of 10 μg/ml poly-lysine can be added to each etched circle and incubated at 37° C. for 60 minutes. The poly-lysine provides a negative control for neurite outgrowth. Etched circles may be washed 2 times with Hank's balanced salt solution plus calcium and magnesium (HBSS$^{++}$) after the last rinse; 1.2 μl of L1-Fc (0.6 μM, 0.3 μM, 0.15 μM, 0.075 μM) is spotted onto the petri dishes to serve as a positive control and various concentrations of the L1-chondroitinase fusion protein can be applied to the plates as test samples. The plates can be incubated for 1 hour at room temperature. The spots are lightly aspirated, so as not to dry them out, and immediately washed 2 times with 1 ml HBSS$^{++}$ and then 1 ml of 1% BSA in PBS is added to each etched circle. After about 15 minutes at room temperature the etched circles can be washed 2 times with HBSS$^{++}$, and once with bioassay medium (NeuralBasal (Gibco)+B27 supplements (Gibco)+L-glutamine+L-glutamic acid, penicillin and streptomycin (100 U/ml)+1% fetal bovine serum which will remain on the petri dishes until the time of the assay. To provide neurons to plate on the substrates Cerebellar granule cells from postnatal day (PND) 9 or 10 are harvested. The brain is removed from the cranium of 1 pup, and the cerebellum separated from the rest of the tissue. Meninges is removed, and the cerebellum is placed in ice cold HBSS$^{++}$. The tissue is minced and trypsinized using 0.25% trypsin for 15 minutes at 37° C. Trypsin action is inhibited by adding 0.5 mg/ml soybean trypsin inhibitor (Gibco). The tissue is rinsed with HBSS$^{++}$ and triturated using a flame narrowed Pasteur pipette coated with EBS. Dissociated cells are pelleted at 500×g for 3 minutes, the supernatant is decanted and the cells are resuspended in 2 ml of growth medium. After lightly triturating, the cell suspension is carefully layered on top of a 3.5% BSA (in PBS) cushion, and spun at 500×g for 3 minutes. Supernatant is aspirated and the pellet is resuspended in 2 ml growth media. A cell count is performed and the cells are diluted to a final working concentration of 1.5×105 cell/ml. A 300 μl aliquot of diluted cells is added to the center of each plate, resulting in the even distribution of 6×104 cells across the entire surface area of the etched circle. The cells are allowed to grow for 16 hours at 37° C. in a humidified environment supplemented with 5% CO2. The next day, plates are removed from the 37° C. incubator, cells are fixed with 4% paraformaldehyde and the outgrowth of neurites is recorded by photomicroscopy.

Biological activity assays for GGF2 may be performed using Schwann cell proliferation. Sciatic nerves are dissected from three day old Sprague Dawley rat pups and dissociated in L-15 medium (Invitrogen) containing 0.25% trypsin and 0.03% collagenase type I (SIGMA) for 15 minutes at 37° C. Nerves are centrifuged at 400×g for 5 minutes and dissociation medium is replaced by DMEM/10% FBS. Nerves are triturated using a 10 ml syringe with a 21 g needle and subsequently a 23 g needle. The cell suspension is filtered through a 40 μm mesh placed over the opening of a 50 ml conical tube. Cells can be centrifuged at 400×g for 5 min, plated in a poly-D-lysine (PDL) coated T-75 flask at a density of approximately 5 million cells in 15 ml of DMEM/10% FBS/PenStrep and incubated in a 37° C. incubator regulated with 10% $CO_2$. After a 24 hour incubation the cells can be washed twice with DMEM/10% FBS and re-fed with fibroblast inhibition medium consisting of DMEM/10% FBS and 10 μl/ml of 1 mM cytosine arabinoside (Ara-C). After an incubation time of 2 to 3 days the fibroblast inhibition medium is replaced with Schwann cell growth medium (DMEM/10% FBS/150 ng/ml of GGF2/5 μM forskolin). Cells can be expanded and aliquots of 2×106 cells/ml are frozen in DMEM/10% DMSO, 54% FBS in liquid nitrogen. At the time of use, Schwann cells are thawed and plated at a density of about 16,000 cells/well in a PDL-coated 96 well tissue culture plate in DMEM/5% FBS. After about 24 hours GGF2 is added in serial dilution ranging from 100 ng/ml to 0.78 ng/ml containing 5 μM forskolin to establish a standard curve. Samples of GGF2 fusion proteins can also be added in serial dilution together with 5 μM forskolin. BrdU is added at 10 μM. Cells are incubated for 48 hours in a 10% $CO_2$ incubator. A BrdU ELISA kit from Roche Applied Science can be used (Cat. No. 1 647 229) to detect Schwann cell proliferation. Medium is poured out of the plate and plate is tapped on tissue paper. A 200 μl/well aliquot of Fix/Denat is added and incubated for 30 min at 15-25° C. A 100 μl/well aliquot of anti-BrdU-POD working solution (lyophilized antibody is dissolved in 1.1 ml double distilled water and diluted 1:100 with antibody dilution solution) can be added and incubated for 90 min at room temperature. Wells may be washed 3 times with 200-300 μl/well of washing solution. A 100 μl aliquot of substrate solution is added and incubated for 15 minutes or until color development is sufficient for photometric detection. The Plates are read on a SpectraMax plate reader at 450 nm either before addition of stop solution at 370 nm or after addition of 50 ml 1N sulfuric acid to each well.

Akt [pS473] ELISA: C6 glioma cells, obtained from ATCC, are grown in DMEM/10% FBS in a T-75 flask to confluence. After trypsinization, cells are plated in a 24 well plate at a density of 500,000 cells/well in 0.5 ml of medium. One day after plating the cells are treated with GGF2 (batch: Glu from Lonza Biologics) at serial dilutions ranging from 0.78 to 100 ng/ml for 30 minutes at 37° C. to establish a standard curve. As a negative control, wortmannin, a PI3-kinase inhibitor, is added to cells at 10 nnM for 30 minutes before the addition of GGF2. Samples of GGF2 fusion proteins will also be added in serial dilution. The cells are washed with PBS and then extracted with 100 μl of cell extraction buffer (10 mM Tris, pH 7.4, 100 mM NaCl, 1 mM EDTA, 1 mM EGTA, 1 mM NaF, 20 mM $Na_4P_2O_7$, 2 mM $Na_3VO_4$, 1% Triton X-100, 10% glycerol, 0.1% SDS, 0.5% deoxycholate, 1 mM PMSF, protease inhibitor cocktail (Pierce)). Cell extracts are kept at −80° C. until further use. An ELISA kit from Biosource (Cat. #KHOO1 II) can be used to measure phosphorylated Akt kinase levels. Briefly, 100 μA of a 1:50 dilution of samples and a serial dilution of Akt [pS473] standards are loaded into wells pre-coated with anti-Akt antibody for 2 h at room temperature (RT) or overnight at 4° C. Wells are washed and anti-Akt [pS473] antibody is added and incubated for 1 hour. After washing, HRP-conjugated anti-rabbit antiserum is added to wells and incubated for 30 min. After washing, TMB chromogen is added to wells and incubated for 30 min at RT before the reaction is stopped with stop solution. The plate is read on a SpectraMax plate reader at 450 nm. The optical densities are plotted against the Akt [pS473] standards and the concentration of pAkt in the C6 samples are deduced from the standard curve.

Example 6

This example illustrates construction of a fusion protein of chondroitinase polypeptide and a TAT cellular transduction peptide.

The gene sequence encoding a chondroitinase enzyme can be functionally linked to the protein transduction domain from HIV called the TAT Peptide (SEQ ID NO: 61). The resultant chimeric gene TAT-chondroitinase ABCI fusion DNA construct is shown in FIG. 1. It was observed that during bacterial expression of this construct, the TAT peptide was removed from the chondroitinase enzyme at some processing point during the bacterial growth. The removal of n-terminal linked peptides was also observed during expression of an n-terminal histidine-tagged chondroitinase ABCI enzyme.

Deletion mutants of the chondroitinase ABCI enzyme were generated where the mutant was missing a certain number of amino acids from the n-terminal portion of the polypeptide but maintained it proteoglycan degrading activity. It was observed that these n-terminal deletion maintained a histidine-tag that was attached to the n-terminus. It is expected that various TAT-deletion mutant chondroitinase ABCI fusion DNA construct can be expressed without removal of the TAT polypeptide during expression. For example, the TAT peptide may be fused at the N-terminus of deletion mutants like ABCI-NΔ20 or ABCI-NΔ60 deletion mutant. Without wishing to be bound by theory, the inventors believe that the native proteoglycan degrading enzyme contains a signal sequence that is attached to the n-terminus. This signal sequence is removed during the natural production in bacteria and in production of the cloned enzyme in $E.$ $coli.$ It is thought that some signal within the n-terminal amino acids instructs the bacteria to remove anything attached to this end.

A DNA construct with the TAT-peptide attached to the N-terminus of one of the chondroitinase deletion mutants can be made and Western blot and protein gel showing this expressed protein and activity.

Example 7

This example illustrates the diffusion of molecules into cells and tissue using a proteoglycan degrading composition.

A brain from an adult Sprague Dawley rat was removed from the skull and quartered into Right frontal, left frontal, right rear and left rear sections, corresponding roughly to the frontal (front) and occipito-parietal (rear) lobes. (A) Right frontal quarter was placed in artificial cerebrospinal fluid (Catalog #59-7316; Harvard Apparatus, Holliston, Mass.) containing the beta-galactosidase enzyme (Catalog #, G 5160; Sigma, St. Louis, Mo.) and chondroitinase ABC I at 0.5 U/ml (Catalog #C 3667; Sigma, St. Louis, Mo.) for 2 hours at 37° C. Brain quarter was rinsed several times in phosphate buffered saline (PBS) and then processed with a Beta-Gal staining kit (Catalog #Gal-S; Sigma, St. Louis, Mo.). The substrate-enzyme reaction (blue product) was allowed to develop for 1 hour, and the brain was rinsed several times in PBS and slabs from the middle of each brain block cut using parallel straight razors. (B) Left frontal quarter was placed in artificial cerebrospinal fluid (Catalog #59-7316; Harvard Apparatus, Holliston, Mass.) containing the beta-galactosidase enzyme (Catalog #, G 5160; Sigma, St. Louis, Mo.) for 2 hours at 37° C. Brain quarter was rinsed several times in phosphate buffered saline (PBS) and then processed with a Beta-Gal staining kit (Catalog #Gal-S; Sigma, St. Louis, Mo.). The substrate-enzyme reaction (blue product) was allowed to develop for 1 hour, and the brain was rinsed several times in PBS and slabs from the middle of each brain block cut using parallel straight razors. (C) Right frontal quarter was placed in artificial cerebrospinal fluid (Catalog #59-7316; Harvard Apparatus, Holliston, Mass.) containing the beta-galactosidase enzyme (Catalog #, G 5160; Sigma, St. Louis, Mo.) and chondroitinase ABC I at 0.5 U/ml (Catalog #C 3667; Sigma, St. Louis, Mo.) for 2 hours at 37° C. Brain quarter was rinsed several times in phosphate buffered saline (PBS) and then processed with a Beta-Gal staining kit (Catalog #Gal-S; Sigma, St. Louis, Mo.). The substrate-enzyme reaction (blue product) was allowed to develop for 1 hour, and the brain was rinsed several times in PBS and slabs from the middle of each brain block cut using parallel straight razors. (D) Left rear quarter was placed in artificial cerebrospinal fluid (Catalog #59-7316; Harvard Apparatus, Holliston, Mass.) containing the beta-galactosidase enzyme (Catalog #, G 5160; Sigma, St. Louis, Mo.) for 2 hours at 37° C. Brain quarter was rinsed several times in phosphate buffered saline (PBS) and then processed with a Beta-Gal staining kit (Catalog #Gal-S; Sigma, St. Louis, Mo.). The substrate-enzyme reaction (blue product) was allowed to develop for 1 hour, and the brain was rinsed several times in PBS and slabs from the middle of each brain block cut using parallel straight razors. Images of brains were acquired on a scanner and are shown in FIG. 2(I)(A-D).

Adult rat brain hemispheres were soaked in buffer alone or containing 33 U/ml Chondroitinase ABCI (Acorda) for 2 hours at 37 degrees C. Hemispheres were rinsed and immediately placed in Eosin Y (Sigma) or a saturated solution of Congo Red (Sigma) in 70% ethanol. Slabs of tissue were cut and images were acquired on a scanner. See FIG. 2(II) Eosin and FIG. 2(III) Congo red.

FIG. 2(III) saturated solution of Congo Red demonstrates greater penetration through the cortex of a Chondroitinase treated brain hemisphere as compared to untreated brain. Congo Red is a negatively charged dye of 697 kDA. FIG. 2(II) Eosin Y penetration through the cortex of a Chondroitinase treated brain hemisphere looks slightly more diffuse, but penetration does not seem to be any deeper as compared to untreated brain. Eosin Y is zwitterionic, having an overall negative charged at the low pH it was used at, and it is 692 kDa. FIG. 2(I) Lobes from adult rat were incubated in beta-galactosidease alone (B&D), or with the addition of Chondroitinase ABCI (A, 0.5 U/ml or C, 0.005 U/m).

The results showed that chondroitinase treated tissue affected penetration of beta-galactosidase into CNS tissue. Chondroitinse had dramatic effects on the rate of Congo Red dye penetration but apparently not Eosin.

Example 8

This example illustrates a Chondroitinase ABCI Assay Protocol which may be modified to measure the activity of Chondroitinase ABCI deletion mutant-fusion proteins or the activity of other proteoglycan degrading polypeptide-fusion proteins of the present invention.

The production of reaction products from the catalytic activity of a proteoglycan degrading molecule or fusion protein is determined by a measurement of the absorbance of the product at a wavelength of 232 nm. A typical reaction mixture consists of 120 μl of reaction mixture (40 mM Tris, pH 8.0, 40 mM NaAcetate, 0.002% casein) combined with a substrate (5

µl of 50 mM chondroitin C) and 1.5 µl of chondroitinase ABCI or a fusion protein of a deletion mutant of chondroitinase ABCI-TAT. Seikagaku's cABCI reference: frozen at −20° C. in 5 ml aliquots, use 1 ml per reaction, 50 mM chondroitin C (MW 521) in water: frozen at −20° C. in 100 ml aliquots. Reaction mixture aliquots of about 120 µl can be prepared at 37° C. for 3 min or longer. A wavelength of 232 nm, is used with the spectrometer.

Knowing the extinction coefficient for the reaction product, measuring the change in the absorbance of the reaction product at 232 nm reading over time upon addition of a known amount of the Chondroitinase ABCI or other proteoglycan degrading polypeptide-fusion proteins to the 120 µl reaction mixture with 0.002% casein and chondroitin substrate added, the specific activity in µmol/min/mg of the proteoglycan degrading fusion protein can be determined. Seikagaku Chondroitinase ABCI has a specific activity under these assay conditions of about 450 µmmole/min/mg.

Although the present invention has been described in considerable detail with reference to certain preferred embodiments thereof, other versions are possible. Therefore the spirit and scope of the appended claims should not be limited to the description and the preferred versions contain within this specification.

```
                        SEQUENCE LISTING

<160> NUMBER OF SEQ ID NOS: 96

<210> SEQ ID NO 1
<211> LENGTH: 1021
<212> TYPE: PRT
<213> ORGANISM: Unknown
<220> FEATURE:
<223> OTHER INFORMATION: Proteus vulgaris Chondroitinase ABCI protein
      with gwra and dalni sequences

<400> SEQUENCE: 1

Met Pro Ile Phe Arg Phe Thr Ala Leu Ala Met Thr Leu Gly Leu Leu
1               5                   10                  15

Ser Ala Pro Tyr Asn Ala Met Ala Ala Thr Ser Asn Pro Ala Phe Asp
            20                  25                  30

Pro Lys Asn Leu Met Gln Ser Glu Ile Tyr His Phe Ala Gln Asn Asn
        35                  40                  45

Pro Leu Ala Asp Phe Ser Ser Asp Lys Asn Ser Ile Leu Thr Leu Ser
    50                  55                  60

Asp Lys Arg Ser Ile Met Gly Asn Gln Ser Leu Leu Trp Lys Trp Lys
65                  70                  75                  80

Gly Gly Ser Ser Phe Thr Leu His Lys Lys Leu Ile Val Pro Thr Asp
                85                  90                  95

Lys Glu Ala Ser Lys Ala Trp Gly Arg Ser Ser Thr Pro Val Phe Ser
            100                 105                 110

Phe Trp Leu Tyr Asn Glu Lys Pro Ile Asp Gly Tyr Leu Thr Ile Asp
        115                 120                 125

Phe Gly Glu Lys Leu Ile Ser Thr Ser Glu Ala Gln Ala Gly Phe Lys
    130                 135                 140

Val Lys Leu Asp Phe Thr Gly Trp Arg Ala Val Gly Val Ser Leu Asn
145                 150                 155                 160

Asn Asp Leu Glu Asn Arg Glu Met Thr Leu Asn Ala Thr Asn Thr Ser
                165                 170                 175

Ser Asp Gly Thr Gln Asp Ser Ile Gly Arg Ser Leu Gly Ala Lys Val
            180                 185                 190

Asp Ser Ile Arg Phe Lys Ala Pro Ser Asn Val Ser Gln Gly Glu Ile
        195                 200                 205

Tyr Ile Asp Arg Ile Met Phe Ser Val Asp Asp Ala Arg Tyr Gln Trp
    210                 215                 220

Ser Asp Tyr Gln Val Lys Thr Arg Leu Ser Glu Pro Glu Ile Gln Phe
225                 230                 235                 240

His Asn Val Lys Pro Gln Leu Pro Val Thr Pro Glu Asn Leu Ala Ala
                245                 250                 255

Ile Asp Leu Ile Arg Gln Arg Leu Ile Asn Glu Phe Val Gly Gly Glu
            260                 265                 270
```

```
Lys Glu Thr Asn Leu Ala Leu Glu Glu Asn Ile Ser Lys Leu Lys Ser
            275                 280                 285

Asp Phe Asp Ala Leu Asn Ile His Thr Leu Ala Asn Gly Gly Thr Gln
    290                 295                 300

Gly Arg His Leu Ile Thr Asp Lys Gln Ile Ile Tyr Gln Pro Glu
305                 310                 315                 320

Asn Leu Asn Ser Gln Asp Lys Gln Leu Phe Asp Asn Tyr Val Ile Leu
                325                 330                 335

Gly Asn Tyr Thr Thr Leu Met Phe Asn Ile Ser Arg Ala Tyr Val Leu
            340                 345                 350

Glu Lys Asp Pro Thr Gln Lys Ala Gln Leu Lys Gln Met Tyr Leu Leu
            355                 360                 365

Met Thr Lys His Leu Leu Asp Gln Gly Phe Val Lys Gly Ser Ala Leu
    370                 375                 380

Val Thr Thr His His Trp Gly Tyr Ser Ser Arg Trp Trp Tyr Ile Ser
385                 390                 395                 400

Thr Leu Leu Met Ser Asp Ala Leu Lys Glu Ala Asn Leu Gln Thr Gln
                405                 410                 415

Val Tyr Asp Ser Leu Leu Trp Tyr Ser Arg Glu Phe Lys Ser Ser Phe
            420                 425                 430

Asp Met Lys Val Ser Ala Asp Ser Ser Asp Leu Asp Tyr Phe Asn Thr
                435                 440                 445

Leu Ser Arg Gln His Leu Ala Leu Leu Leu Glu Pro Asp Asp Gln
            450                 455                 460

Lys Arg Ile Asn Leu Val Asn Thr Phe Ser His Tyr Ile Thr Gly Ala
465                 470                 475                 480

Leu Thr Gln Val Pro Pro Gly Gly Lys Asp Gly Leu Arg Pro Asp Gly
                485                 490                 495

Thr Ala Trp Arg His Glu Gly Asn Tyr Pro Gly Tyr Ser Phe Pro Ala
            500                 505                 510

Phe Lys Asn Ala Ser Gln Leu Ile Tyr Leu Leu Arg Asp Thr Pro Phe
    515                 520                 525

Ser Val Gly Glu Ser Gly Trp Asn Asn Leu Lys Lys Ala Met Val Ser
    530                 535                 540

Ala Trp Ile Tyr Ser Asn Pro Glu Val Gly Leu Pro Leu Ala Gly Arg
545                 550                 555                 560

His Pro Phe Asn Ser Pro Ser Leu Lys Ser Val Ala Gln Gly Tyr Tyr
                565                 570                 575

Trp Leu Ala Met Ser Ala Lys Ser Ser Pro Asp Lys Thr Leu Ala Ser
            580                 585                 590

Ile Tyr Leu Ala Ile Ser Asp Lys Thr Gln Asn Glu Ser Thr Ala Ile
            595                 600                 605

Phe Gly Glu Thr Ile Thr Pro Ala Ser Leu Pro Gln Gly Phe Tyr Ala
    610                 615                 620

Phe Asn Gly Gly Ala Phe Gly Ile His Arg Trp Gln Asp Lys Met Val
625                 630                 635                 640

Thr Leu Lys Ala Tyr Asn Thr Asn Val Trp Ser Ser Glu Ile Tyr Asn
                645                 650                 655

Lys Asp Asn Arg Tyr Gly Arg Tyr Gln Ser His Gly Val Ala Gln Ile
            660                 665                 670

Val Ser Asn Gly Ser Gln Leu Ser Gln Gly Tyr Gln Gln Glu Gly Trp
            675                 680                 685
```

```
Asp Trp Asn Arg Met Glu Gly Ala Thr Thr Ile His Leu Pro Leu Lys
    690                 695                 700

Asp Leu Asp Ser Pro Lys Pro His Thr Leu Met Gln Arg Gly Glu Arg
705                 710                 715                 720

Gly Phe Ser Gly Thr Ser Ser Leu Glu Gly Gln Tyr Gly Met Met Ala
            725                 730                 735

Phe Asn Leu Ile Tyr Pro Ala Asn Leu Glu Arg Phe Asp Pro Asn Phe
                740                 745                 750

Thr Ala Lys Lys Ser Val Leu Ala Asp Asn His Leu Ile Phe Ile
        755                 760                 765

Gly Ser Asn Ile Asn Ser Ser Asp Lys Asn Lys Asn Val Glu Thr Thr
770                 775                 780

Leu Phe Gln His Ala Ile Thr Pro Thr Leu Asn Thr Leu Trp Ile Asn
785                 790                 795                 800

Gly Gln Lys Ile Glu Asn Met Pro Tyr Gln Thr Thr Leu Gln Gln Gly
                805                 810                 815

Asp Trp Leu Ile Asp Ser Asn Gly Asn Gly Tyr Leu Ile Thr Gln Ala
            820                 825                 830

Glu Lys Val Asn Val Ser Arg Gln His Gln Val Ser Ala Glu Asn Lys
        835                 840                 845

Asn Arg Gln Pro Thr Glu Gly Asn Phe Ser Ser Ala Trp Ile Asp His
850                 855                 860

Ser Thr Arg Pro Lys Asp Ala Ser Tyr Glu Tyr Met Val Phe Leu Asp
865                 870                 875                 880

Ala Thr Pro Glu Lys Met Gly Glu Met Ala Gln Lys Phe Arg Glu Asn
                885                 890                 895

Asn Gly Leu Tyr Gln Val Leu Arg Lys Asp Lys Asp Val His Ile Ile
            900                 905                 910

Leu Asp Lys Leu Ser Asn Val Thr Gly Tyr Ala Phe Tyr Gln Pro Ala
        915                 920                 925

Ser Ile Glu Asp Lys Trp Ile Lys Lys Val Asn Lys Pro Ala Ile Val
930                 935                 940

Met Thr His Arg Gln Lys Asp Thr Leu Ile Val Ser Ala Val Thr Pro
945                 950                 955                 960

Asp Leu Asn Met Thr Arg Gln Lys Ala Ala Thr Pro Val Thr Ile Asn
                965                 970                 975

Val Thr Ile Asn Gly Lys Trp Gln Ser Ala Asp Lys Asn Ser Glu Val
            980                 985                 990

Lys Tyr Gln Val Ser Gly Asp Asn Thr Glu Leu Thr Phe Thr Ser Tyr
        995                 1000                1005

Phe Gly Ile Pro Gln Glu Ile Lys Leu Ser Pro Leu Pro
    1010                1015                1020

<210> SEQ ID NO 2
<211> LENGTH: 86
<212> TYPE: PRT
<213> ORGANISM: Unknown
<220> FEATURE:
<223> OTHER INFORMATION: Human immunodeficiency virus HIV-1 TAT protein

<400> SEQUENCE: 2

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30
```

```
His Cys Gln Val Cys Phe Ile Thr Lys Ala Leu Gly Ile Ser Tyr Gly
            35                  40                  45

Arg Lys Lys Arg Arg Gln Arg Arg Pro Pro Gln Gly Ser Gln Thr
 50                  55                  60

His Gln Val Ser Leu Ser Lys Gln Pro Thr Ser Gln Ser Arg Gly Asp
65                  70                  75                  80

Pro Thr Gly Pro Lys Glu
                85

<210> SEQ ID NO 3
<211> LENGTH: 11
<212> TYPE: PRT
<213> ORGANISM: Artificial
<220> FEATURE:
<223> OTHER INFORMATION: Synthetic peptide, amino acid residues 47-57 of
      (HIV-1) Tat protein, (Vives, et al.)

<400> SEQUENCE: 3

Tyr Gly Arg Lys Lys Arg Arg Gln Arg Arg Arg
1               5                   10

<210> SEQ ID NO 4
<211> LENGTH: 285
<212> TYPE: PRT
<213> ORGANISM: Artificial
<220> FEATURE:
<223> OTHER INFORMATION: Synthetic Peptide derived from Nogo-66 receptor
      antagonist Locus (Q9BZR6)

<400> SEQUENCE: 4

Cys Pro Gly Ala Cys Val Cys Tyr Asn Glu Pro Lys Val Thr Thr Ser
1               5                   10                  15

Cys Pro Gln Gln Gly Leu Gln Ala Val Pro Val Gly Ile Pro Ala Ala
            20                  25                  30

Ser Gln Arg Ile Phe Leu His Gly Asn Arg Ile Ser His Val Pro Ala
            35                  40                  45

Ala Ser Phe Arg Ala Cys Arg Asn Leu Thr Ile Leu Trp Leu His Ser
 50                  55                  60

Asn Val Leu Ala Arg Ile Asp Ala Ala Phe Thr Gly Leu Ala Leu
65                  70                  75                  80

Leu Glu Gln Leu Asp Leu Ser Asp Asn Ala Gln Leu Arg Ser Val Asp
                85                  90                  95

Pro Ala Thr Phe His Gly Leu Gly Arg Leu His Thr Leu His Leu Asp
            100                 105                 110

Arg Cys Gly Leu Gln Glu Leu Gly Pro Gly Leu Phe Arg Gly Leu Ala
            115                 120                 125

Ala Leu Gln Tyr Leu Tyr Leu Gln Asp Asn Ala Leu Gln Ala Leu Pro
        130                 135                 140

Asp Asp Thr Phe Arg Asp Leu Gly Asn Leu Thr His Leu Phe Leu His
145                 150                 155                 160

Gly Asn Arg Ile Ser Ser Val Pro Glu Arg Ala Phe Arg Gly Leu His
                165                 170                 175

Ser Leu Asp Arg Leu Leu Leu His Gln Asn Arg Val Ala His Val His
            180                 185                 190

Pro His Ala Phe Arg Asp Leu Gly Arg Leu Met Thr Leu Tyr Leu Phe
            195                 200                 205

Ala Asn Asn Leu Ser Ala Leu Pro Thr Glu Ala Leu Ala Pro Leu Arg
        210                 215                 220
```

```
Ala Leu Gln Tyr Leu Arg Leu Asn Asp Asn Pro Trp Val Cys Asp Cys
225                 230                 235                 240

Arg Ala Arg Pro Leu Trp Ala Trp Leu Gln Lys Phe Arg Gly Ser Ser
            245                 250                 255

Ser Glu Val Pro Cys Ser Leu Pro Gln Arg Leu Ala Gly Arg Asp Leu
        260                 265                 270

Lys Arg Leu Ala Ala Asn Asp Leu Gln Gly Cys Ala Val
275                 280                 285

<210> SEQ ID NO 5
<211> LENGTH: 1257
<212> TYPE: PRT
<213> ORGANISM: Unknown
<220> FEATURE:
<223> OTHER INFORMATION: Homo sapiens L1 protein

<400> SEQUENCE: 5

Met Val Val Ala Leu Arg Tyr Val Trp Pro Leu Leu Leu Cys Ser Pro
1               5                   10                  15

Cys Leu Leu Ile Gln Ile Pro Glu Glu Tyr Glu Gly His His Val Met
                20                  25                  30

Glu Pro Pro Val Ile Thr Glu Gln Ser Pro Arg Arg Leu Val Val Phe
            35                  40                  45

Pro Thr Asp Asp Ile Ser Leu Lys Cys Glu Ala Ser Gly Lys Pro Glu
50                  55                  60

Val Gln Phe Arg Trp Thr Arg Asp Gly Val His Phe Lys Pro Lys Glu
65                  70                  75                  80

Glu Leu Gly Val Thr Val Tyr Gln Ser Pro His Ser Gly Ser Phe Thr
                85                  90                  95

Ile Thr Gly Asn Asn Ser Asn Phe Ala Gln Arg Phe Gln Gly Ile Tyr
                100                 105                 110

Arg Cys Phe Ala Ser Asn Lys Leu Gly Thr Ala Met Ser His Glu Ile
            115                 120                 125

Arg Leu Met Ala Glu Gly Ala Pro Lys Trp Pro Lys Glu Thr Val Lys
130                 135                 140

Pro Val Glu Val Glu Glu Gly Glu Ser Val Val Leu Pro Cys Asn Pro
145                 150                 155                 160

Pro Pro Ser Ala Glu Pro Leu Arg Ile Tyr Trp Met Asn Ser Lys Ile
                165                 170                 175

Leu His Ile Lys Gln Asp Glu Arg Val Thr Met Gly Gln Asn Gly Asn
            180                 185                 190

Leu Tyr Phe Ala Asn Val Leu Thr Ser Asp Asn His Ser Asp Tyr Ile
        195                 200                 205

Cys His Ala His Phe Pro Gly Thr Arg Thr Ile Ile Gln Lys Glu Pro
210                 215                 220

Ile Asp Leu Arg Val Lys Ala Thr Asn Ser Met Ile Asp Arg Lys Pro
225                 230                 235                 240

Arg Leu Leu Phe Pro Thr Asn Ser Ser Ser His Leu Val Ala Leu Gln
                245                 250                 255

Gly Gln Pro Leu Val Leu Glu Cys Ile Ala Glu Gly Phe Pro Thr Pro
            260                 265                 270

Thr Ile Lys Trp Leu Arg Pro Ser Gly Pro Met Pro Ala Asp Arg Val
        275                 280                 285

Thr Tyr Gln Asn His Asn Lys Thr Leu Gln Leu Leu Lys Val Gly Glu
        290                 295                 300
```

```
Glu Asp Asp Gly Glu Tyr Arg Cys Leu Ala Glu Asn Ser Leu Gly Ser
305                 310                 315                 320

Ala Arg His Ala Tyr Tyr Val Thr Val Glu Ala Pro Tyr Trp Leu
            325                 330                 335

His Lys Pro Gln Ser His Leu Tyr Gly Pro Gly Glu Thr Ala Arg Leu
            340                 345                 350

Asp Cys Gln Val Gln Gly Arg Pro Gln Pro Glu Val Thr Trp Arg Ile
            355                 360                 365

Asn Gly Ile Pro Val Glu Glu Leu Ala Lys Asp Gln Lys Tyr Arg Ile
370                 375                 380

Gln Arg Gly Ala Leu Ile Leu Ser Asn Val Gln Pro Ser Asp Thr Met
385                 390                 395                 400

Val Thr Gln Cys Glu Ala Arg Asn Arg His Gly Leu Leu Leu Ala Asn
                405                 410                 415

Ala Tyr Ile Tyr Val Val Gln Leu Pro Ala Lys Ile Leu Thr Ala Asp
            420                 425                 430

Asn Gln Thr Tyr Met Ala Val Gln Gly Ser Thr Ala Tyr Leu Leu Cys
            435                 440                 445

Lys Ala Phe Gly Ala Pro Val Pro Ser Val Gln Trp Leu Asp Glu Asp
450                 455                 460

Gly Thr Thr Val Leu Gln Asp Glu Arg Phe Phe Pro Tyr Ala Asn Gly
465                 470                 475                 480

Thr Leu Gly Ile Arg Asp Leu Gln Ala Asn Asp Thr Gly Arg Tyr Phe
                485                 490                 495

Cys Leu Ala Ala Asn Asp Gln Asn Asn Val Thr Ile Met Ala Asn Leu
                500                 505                 510

Lys Val Lys Asp Ala Thr Gln Ile Thr Gln Gly Pro Arg Ser Thr Ile
            515                 520                 525

Glu Lys Lys Gly Ser Arg Val Thr Phe Thr Cys Gln Ala Ser Phe Asp
530                 535                 540

Pro Ser Leu Gln Pro Ser Ile Thr Trp Arg Gly Asp Gly Arg Asp Leu
545                 550                 555                 560

Gln Glu Leu Gly Asp Ser Asp Lys Tyr Phe Ile Glu Asp Gly Arg Leu
                565                 570                 575

Val Ile His Ser Leu Asp Tyr Ser Asp Gln Gly Asn Tyr Ser Cys Val
            580                 585                 590

Ala Ser Thr Glu Leu Asp Val Val Glu Ser Arg Ala Gln Leu Leu Val
            595                 600                 605

Val Gly Ser Pro Gly Pro Val Pro Arg Leu Val Leu Ser Asp Leu His
610                 615                 620

Leu Leu Thr Gln Ser Gln Val Arg Val Ser Trp Ser Pro Ala Glu Asp
625                 630                 635                 640

His Asn Ala Pro Ile Glu Lys Tyr Asp Ile Glu Phe Glu Asp Lys Glu
                645                 650                 655

Met Ala Pro Glu Lys Trp Tyr Ser Leu Gly Lys Val Pro Gly Asn Gln
            660                 665                 670

Thr Ser Thr Thr Leu Lys Leu Ser Pro Tyr Val His Tyr Thr Phe Arg
            675                 680                 685

Val Thr Ala Ile Asn Lys Tyr Gly Pro Gly Glu Pro Ser Pro Val Ser
            690                 695                 700

Glu Thr Val Val Thr Pro Glu Ala Ala Pro Glu Lys Asn Pro Val Asp
705                 710                 715                 720

Val Lys Gly Glu Gly Asn Glu Thr Thr Asn Met Val Ile Thr Trp Lys
```

-continued

```
                725                 730                 735
Pro Leu Arg Trp Met Asp Trp Asn Ala Pro Gln Val Gln Tyr Arg Val
            740                 745                 750
Gln Trp Arg Pro Gln Gly Thr Arg Gly Pro Trp Gln Glu Gln Ile Val
            755                 760                 765
Ser Asp Pro Phe Leu Val Val Ser Asn Thr Ser Thr Phe Val Pro Tyr
            770                 775                 780
Glu Ile Lys Val Gln Ala Val Asn Ser Gln Gly Lys Gly Pro Glu Pro
785                 790                 795                 800
Gln Val Thr Ile Gly Tyr Ser Gly Glu Asp Tyr Pro Gln Ala Ile Pro
            805                 810                 815
Glu Leu Glu Gly Ile Glu Ile Leu Asn Ser Ser Ala Val Leu Val Lys
            820                 825                 830
Trp Arg Pro Val Asp Leu Ala Gln Val Lys Gly His Leu Arg Gly Tyr
            835                 840                 845
Asn Val Thr Tyr Trp Arg Glu Gly Ser Gln Arg Lys His Ser Lys Arg
            850                 855                 860
His Ile His Lys Asp His Val Val Pro Ala Asn Thr Thr Ser Val
865                 870                 875                 880
Ile Leu Ser Gly Leu Arg Pro Tyr Ser Ser Tyr His Leu Glu Val Gln
                885                 890                 895
Ala Phe Asn Gly Arg Gly Ser Gly Pro Ala Ser Glu Phe Thr Phe Ser
            900                 905                 910
Thr Pro Glu Gly Val Pro Gly His Pro Glu Ala Leu His Leu Glu Cys
            915                 920                 925
Gln Ser Asn Thr Ser Leu Leu Leu Arg Trp Gln Pro Pro Leu Ser His
            930                 935                 940
Asn Gly Val Leu Thr Gly Tyr Val Leu Ser Tyr His Pro Leu Asp Glu
945                 950                 955                 960
Gly Gly Lys Gly Gln Leu Ser Phe Asn Leu Arg Asp Pro Glu Leu Arg
                965                 970                 975
Thr His Asn Leu Thr Asp Leu Ser Pro His Leu Arg Tyr Arg Phe Gln
            980                 985                 990
Leu Gln Ala Thr Thr Lys Glu Gly Pro Gly Glu Ala Ile Val Arg Glu
            995                1000                1005
Gly Gly Thr Met Ala Leu Ser Gly Ile Ser Asp Phe Gly Asn Ile
            1010                1015                1020
Ser Ala Thr Ala Gly Glu Asn Tyr Ser Val Val Ser Trp Val Pro
            1025                1030                1035
Lys Glu Gly Gln Cys Asn Phe Arg Phe His Ile Leu Phe Lys Ala
            1040                1045                1050
Leu Gly Glu Glu Lys Gly Gly Ala Ser Leu Ser Pro Gln Tyr Val
            1055                1060                1065
Ser Tyr Asn Gln Ser Ser Tyr Thr Gln Trp Asp Leu Gln Pro Asp
            1070                1075                1080
Thr Asp Tyr Glu Ile His Leu Phe Lys Glu Arg Met Phe Arg His
            1085                1090                1095
Gln Met Ala Val Lys Thr Asn Gly Thr Gly Arg Val Arg Leu Pro
            1100                1105                1110
Pro Ala Gly Phe Ala Thr Glu Gly Trp Phe Ile Gly Phe Val Ser
            1115                1120                1125
Ala Ile Ile Leu Leu Leu Leu Val Leu Leu Ile Leu Cys Phe Ile
            1130                1135                1140
```

```
Lys Arg Ser Lys Gly Gly Lys Tyr Ser Val Lys Asp Lys Glu Asp
    1145            1150                1155

Thr Gln Val Asp Ser Glu Ala Arg Pro Met Lys Asp Glu Thr Phe
    1160            1165                1170

Gly Glu Tyr Arg Ser Leu Glu Ser Asp Asn Glu Glu Lys Ala Phe
    1175            1180                1185

Gly Ser Ser Gln Pro Ser Leu Asn Gly Asp Ile Lys Pro Leu Gly
    1190            1195                1200

Ser Asp Asp Ser Leu Ala Asp Tyr Gly Gly Ser Val Asp Val Gln
    1205            1210                1215

Phe Asn Glu Asp Gly Ser Phe Ile Gly Gln Tyr Ser Gly Lys Lys
    1220            1225                1230

Glu Lys Glu Ala Ala Gly Gly Asn Asp Ser Ser Gly Ala Thr Ser
    1235            1240                1245

Pro Ile Asn Pro Ala Val Ala Leu Glu
    1250            1255

<210> SEQ ID NO 6
<211> LENGTH: 640
<212> TYPE: PRT
<213> ORGANISM: Unknown
<220> FEATURE:
<223> OTHER INFORMATION: Homo sapiens GGF2 protein

<400> SEQUENCE: 6

Met Ser Glu Arg Lys Glu Gly Arg Gly Lys Gly Lys Gly Lys Lys
1               5                   10                  15

Glu Arg Gly Ser Gly Lys Lys Pro Glu Ser Ala Ala Gly Ser Gln Ser
                20                  25                  30

Pro Ala Leu Pro Pro Arg Leu Lys Glu Met Lys Ser Gln Glu Ser Ala
                35                  40                  45

Ala Gly Ser Lys Leu Val Leu Arg Cys Glu Thr Ser Ser Glu Tyr Ser
            50                  55                  60

Ser Leu Arg Phe Lys Trp Phe Lys Asn Gly Asn Glu Leu Asn Arg Lys
65              70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
                100                 105                 110

Lys Val Ile Ser Lys Leu Gly Asn Asp Ser Ala Ser Ala Asn Ile Thr
            115                 120                 125

Ile Val Glu Ser Asn Glu Ile Ile Thr Gly Met Pro Ala Ser Thr Glu
            130                 135                 140

Gly Ala Tyr Val Ser Ser Glu Ser Pro Ile Arg Ile Ser Val Ser Thr
145             150                 155                 160

Glu Gly Ala Asn Thr Ser Ser Ser Thr Ser Thr Ser Thr Thr Gly Thr
                165                 170                 175

Ser His Leu Val Lys Cys Ala Glu Lys Glu Lys Thr Phe Cys Val Asn
                180                 185                 190

Gly Gly Glu Cys Phe Met Val Lys Asp Leu Ser Asn Pro Ser Arg Tyr
            195                 200                 205

Leu Cys Lys Cys Gln Pro Gly Phe Thr Gly Ala Arg Cys Thr Glu Asn
            210                 215                 220

Val Pro Met Lys Val Gln Asn Gln Glu Lys Ala Glu Glu Leu Tyr Gln
225             230                 235                 240
```

-continued

```
Lys Arg Val Leu Thr Ile Thr Gly Ile Cys Ile Ala Leu Leu Val Val
            245                 250                 255
Gly Ile Met Cys Val Val Ala Tyr Cys Lys Thr Lys Lys Gln Arg Lys
        260                 265                 270
Lys Leu His Asp Arg Leu Arg Gln Ser Leu Arg Ser Glu Arg Asn Asn
        275                 280                 285
Met Met Asn Ile Ala Asn Gly Pro His His Pro Asn Pro Pro Pro Glu
        290                 295                 300
Asn Val Gln Leu Val Asn Gln Tyr Val Ser Lys Asn Val Ile Ser Ser
305                 310                 315                 320
Glu His Ile Val Glu Arg Glu Ala Glu Thr Ser Phe Ser Thr Ser His
                325                 330                 335
Tyr Thr Ser Thr Ala His His Ser Thr Thr Val Thr Gln Thr Pro Ser
                340                 345                 350
His Ser Trp Ser Asn Gly His Thr Glu Ser Ile Leu Ser Glu Ser His
            355                 360                 365
Ser Val Ile Val Met Ser Ser Val Glu Asn Ser Arg His Ser Ser Pro
        370                 375                 380
Thr Gly Gly Pro Arg Gly Arg Leu Asn Gly Thr Gly Gly Pro Arg Glu
385                 390                 395                 400
Cys Asn Ser Phe Leu Arg His Ala Arg Glu Thr Pro Asp Ser Tyr Arg
                405                 410                 415
Asp Ser Pro His Ser Glu Arg Tyr Val Ser Ala Met Thr Thr Pro Ala
                420                 425                 430
Arg Met Ser Pro Val Asp Phe His Thr Pro Ser Ser Pro Lys Ser Pro
            435                 440                 445
Pro Ser Glu Met Ser Pro Pro Val Ser Ser Met Thr Val Ser Met Pro
        450                 455                 460
Ser Met Ala Val Ser Pro Phe Met Glu Glu Glu Arg Pro Leu Leu Leu
465                 470                 475                 480
Val Thr Pro Pro Arg Leu Arg Glu Lys Lys Phe Asp His His Pro Gln
                485                 490                 495
Gln Phe Ser Ser Phe His His Asn Pro Ala His Asp Ser Asn Ser Leu
                500                 505                 510
Pro Ala Ser Pro Leu Arg Ile Val Glu Asp Glu Glu Tyr Glu Thr Thr
            515                 520                 525
Gln Glu Tyr Glu Pro Ala Gln Glu Pro Val Lys Lys Leu Ala Asn Ser
        530                 535                 540
Arg Arg Ala Lys Arg Thr Lys Pro Asn Gly His Ile Ala Asn Arg Leu
545                 550                 555                 560
Glu Val Asp Ser Asn Thr Ser Ser Gln Ser Ser Asn Ser Glu Ser Glu
                565                 570                 575
Thr Glu Asp Glu Arg Val Gly Glu Asp Thr Pro Phe Leu Gly Ile Gln
                580                 585                 590
Asn Pro Leu Ala Ala Ser Leu Glu Ala Thr Pro Ala Phe Arg Leu Ala
            595                 600                 605
Asp Ser Arg Thr Asn Pro Ala Gly Arg Phe Ser Thr Gln Glu Glu Ile
        610                 615                 620
Gln Ala Arg Leu Ser Ser Val Ile Ala Asn Gln Asp Pro Ile Ala Val
625                 630                 635                 640

<210> SEQ ID NO 7
<211> LENGTH: 199
```

```
<212> TYPE: PRT
<213> ORGANISM: Unknown
<220> FEATURE:
<223> OTHER INFORMATION: Homo sapiens Brain derived neurotrophic factor
      protein

<400> SEQUENCE: 7

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
                100                 105                 110

Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
130                 135                 140

Ser Glu Trp Val Thr Ala Ala Asp Lys Arg His Trp Asn Ser Gln Cys
145                 150                 155                 160

Arg Thr Thr Gln Ser Tyr Val Arg Ala Leu Thr Met Asp Ser Lys Lys
                165                 170                 175

Arg Ile Gly Trp Arg Phe Ile Arg Ile Asp Thr Ser Cys Val Cys Thr
            180                 185                 190

Leu Thr Ile Lys Arg Gly Arg
        195

<210> SEQ ID NO 8
<211> LENGTH: 282
<212> TYPE: PRT
<213> ORGANISM: Unknown
<220> FEATURE:
<223> OTHER INFORMATION: Homo sapiens Insulin-like growth factor protein

<400> SEQUENCE: 8

Met Glu Arg Pro Ser Leu Arg Ala Leu Leu Leu Gly Ala Ala Gly Leu
1               5                   10                  15

Leu Leu Leu Leu Leu Pro Leu Ser Ser Ser Ser Ser Asp Thr Cys
                20                  25                  30

Gly Pro Cys Glu Pro Ala Ser Cys Pro Pro Leu Pro Pro Leu Gly Cys
            35                  40                  45

Leu Leu Gly Glu Thr Arg Asp Ala Cys Gly Cys Cys Pro Met Cys Ala
50                  55                  60

Arg Gly Glu Gly Glu Pro Cys Gly Gly Gly Ala Gly Arg Gly Tyr
65                  70                  75                  80

Cys Ala Pro Gly Met Glu Cys Val Lys Ser Arg Lys Arg Arg Lys Gly
                85                  90                  95

Lys Ala Gly Ala Ala Ala Gly Gly Pro Gly Val Ser Gly Val Cys Val
            100                 105                 110

Cys Lys Ser Arg Tyr Pro Val Cys Gly Ser Asp Gly Thr Thr Tyr Pro
```

```
                    115                 120                 125
Ser Gly Cys Gln Leu Arg Ala Ala Ser Gln Arg Ala Glu Ser Arg Gly
        130                 135                 140

Glu Lys Ala Ile Thr Gln Val Ser Lys Gly Thr Cys Glu Gln Gly Pro
145                 150                 155                 160

Ser Ile Val Thr Pro Pro Lys Asp Ile Trp Asn Val Thr Gly Ala Gln
                165                 170                 175

Val Tyr Leu Ser Cys Glu Val Ile Gly Ile Pro Thr Pro Val Leu Ile
            180                 185                 190

Trp Asn Lys Val Lys Arg Gly His Tyr Gly Val Gln Arg Thr Glu Leu
        195                 200                 205

Leu Pro Gly Asp Arg Asp Asn Leu Ala Ile Gln Thr Arg Gly Gly Pro
    210                 215                 220

Glu Lys His Glu Val Thr Gly Trp Val Leu Val Ser Pro Leu Ser Lys
225                 230                 235                 240

Glu Asp Ala Gly Glu Tyr Glu Cys His Ala Ser Asn Ser Gln Gly Gln
                245                 250                 255

Ala Ser Ala Ser Ala Lys Ile Thr Val Val Asp Ala Leu His Glu Ile
            260                 265                 270

Pro Val Lys Lys Gly Glu Gly Ala Glu Leu
        275                 280

<210> SEQ ID NO 9
<211> LENGTH: 155
<212> TYPE: PRT
<213> ORGANISM: Unknown
<220> FEATURE:
<223> OTHER INFORMATION: Homo sapiens Fibroblast growth factor protein

<400> SEQUENCE: 9

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 10
<211> LENGTH: 200
<212> TYPE: PRT
<213> ORGANISM: Unknown
<220> FEATURE:
<223> OTHER INFORMATION: Homo sapiens  Ciliary neurotrophic factor
``` protein

<400> SEQUENCE: 10

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Ala Asp Gly Met Pro Val Ala Ser Thr Asp Gln Trp
    50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200

<210> SEQ ID NO 11
<211> LENGTH: 211
<212> TYPE: PRT
<213> ORGANISM: Unknown
<220> FEATURE:
<223> OTHER INFORMATION: Homo sapiens Glial derived neurotrophic factor
      protein

<400> SEQUENCE: 11

Met Lys Leu Trp Asp Val Val Ala Val Cys Leu Val Leu Leu His Thr
1               5                   10                  15

Ala Ser Ala Phe Pro Leu Pro Ala Gly Lys Arg Pro Pro Glu Ala Pro
            20                  25                  30

Ala Glu Asp Arg Ser Leu Gly Arg Arg Arg Ala Pro Phe Ala Leu Ser
        35                  40                  45

Ser Asp Ser Asn Met Pro Glu Asp Tyr Pro Asp Gln Phe Asp Asp Val
    50                  55                  60

Met Asp Phe Ile Gln Ala Thr Ile Lys Arg Leu Lys Arg Ser Pro Asp
65                  70                  75                  80

Lys Gln Met Ala Val Leu Pro Arg Arg Glu Arg Asn Arg Gln Ala Ala
                85                  90                  95

Ala Ala Asn Pro Glu Asn Ser Arg Gly Lys Gly Arg Arg Gly Gln Arg
            100                 105                 110

Gly Lys Asn Arg Gly Cys Val Leu Thr Ala Ile His Leu Asn Val Thr
        115                 120                 125

Asp Leu Gly Leu Gly Tyr Glu Thr Lys Glu Glu Leu Ile Phe Arg Tyr

```
            130                 135                 140
Cys Ser Gly Ser Cys Asp Ala Glu Thr Thr Tyr Asp Lys Ile Leu
145                 150                 155                 160

Lys Asn Leu Ser Arg Asn Arg Arg Leu Val Ser Asp Lys Val Gly Gln
                165                 170                 175

Ala Cys Cys Arg Pro Ile Ala Phe Asp Asp Leu Ser Phe Leu Asp
                180                 185                 190

Asp Asn Leu Val Tyr His Ile Leu Arg Lys His Ser Ala Lys Arg Cys
                195                 200                 205

Gly Cys Ile
        210

<210> SEQ ID NO 12
<211> LENGTH: 414
<212> TYPE: PRT
<213> ORGANISM: Unknown
<220> FEATURE:
<223> OTHER INFORMATION: Homo sapiens Transforming growth factor protein

<400> SEQUENCE: 12

Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
                20                  25                  30

Met Arg Lys Arg Ile Glu Ala Ile Arg Gly Gln Ile Leu Ser Lys Leu
            35                  40                  45

Lys Leu Thr Ser Pro Pro Glu Asp Tyr Pro Glu Pro Glu Glu Val Pro
50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
            100                 105                 110

Pro Ser Glu Asn Ala Ile Pro Pro Thr Phe Tyr Arg Pro Tyr Phe Arg
        115                 120                 125

Ile Val Arg Phe Asp Val Ser Ala Met Glu Lys Asn Ala Ser Asn Leu
    130                 135                 140

Val Lys Ala Glu Phe Arg Val Phe Arg Leu Gln Asn Pro Lys Ala Arg
145                 150                 155                 160

Val Pro Glu Gln Arg Ile Glu Leu Tyr Gln Ile Leu Lys Ser Lys Asp
                165                 170                 175

Leu Thr Ser Pro Thr Gln Arg Tyr Ile Asp Ser Lys Val Val Lys Thr
            180                 185                 190

Arg Ala Glu Gly Glu Trp Leu Ser Phe Asp Val Thr Asp Ala Val His
        195                 200                 205

Glu Trp Leu His His Lys Asp Arg Asn Leu Gly Phe Lys Ile Ser Leu
    210                 215                 220

His Cys Pro Cys Cys Thr Phe Val Pro Ser Asn Asn Tyr Ile Ile Pro
225                 230                 235                 240

Asn Lys Ser Glu Glu Leu Glu Ala Arg Phe Ala Gly Ile Asp Gly Thr
                245                 250                 255

Ser Thr Tyr Thr Ser Gly Asp Gln Lys Thr Ile Lys Ser Thr Arg Lys
            260                 265                 270

Lys Asn Ser Gly Lys Thr Pro His Leu Leu Leu Met Leu Leu Pro Ser
```

```
            275                 280                 285
Tyr Arg Leu Glu Ser Gln Gln Thr Asn Arg Arg Lys Lys Arg Ala Leu
            290                 295                 300

Asp Ala Ala Tyr Cys Phe Arg Asn Val Gln Asp Asn Cys Cys Leu Arg
305                 310                 315                 320

Pro Leu Tyr Ile Asp Phe Lys Arg Asp Leu Gly Trp Lys Trp Ile His
                    325                 330                 335

Glu Pro Lys Gly Tyr Asn Ala Asn Phe Cys Ala Gly Ala Cys Pro Tyr
                340                 345                 350

Leu Trp Ser Ser Asp Thr Gln His Ser Arg Val Leu Ser Leu Tyr Asn
                355                 360                 365

Thr Ile Asn Pro Glu Ala Ser Ala Ser Pro Cys Cys Val Ser Gln Asp
370                 375                 380

Leu Glu Pro Leu Thr Ile Leu Tyr Tyr Ile Gly Lys Thr Pro Lys Ile
385                 390                 395                 400

Glu Gln Leu Ser Asn Met Ile Val Lys Ser Cys Lys Cys Ser
                    405                 410

<210> SEQ ID NO 13
<211> LENGTH: 1021
<212> TYPE: PRT
<213> ORGANISM: Unknown
<220> FEATURE:
<223> OTHER INFORMATION: Homo sapiens Chondroitinase ABCI protein

<400> SEQUENCE: 13

Met Pro Ile Phe Arg Phe Thr Ala Leu Ala Met Thr Leu Gly Leu Leu
1               5                   10                  15

Ser Ala Pro Tyr Asn Ala Met Ala Ala Thr Ser Asn Pro Ala Phe Asp
                20                  25                  30

Pro Lys Asn Leu Met Gln Ser Glu Ile Tyr His Phe Ala Gln Asn Asn
            35                  40                  45

Pro Leu Ala Asp Phe Ser Ser Asp Lys Asn Ser Ile Leu Thr Leu Ser
        50                  55                  60

Asp Lys Arg Ser Ile Met Gly Asn Gln Ser Leu Leu Trp Lys Trp Lys
65                  70                  75                  80

Gly Gly Ser Ser Phe Thr Leu His Lys Lys Leu Ile Val Pro Thr Asp
                85                  90                  95

Lys Glu Ala Ser Lys Ala Trp Gly Arg Ser Ser Thr Pro Val Phe Ser
                100                 105                 110

Phe Trp Leu Tyr Asn Glu Lys Pro Ile Asp Gly Tyr Leu Thr Ile Asp
            115                 120                 125

Phe Gly Glu Lys Leu Ile Ser Thr Ser Glu Ala Gln Ala Gly Phe Lys
        130                 135                 140

Val Lys Leu Asp Phe Thr Gly Trp Arg Ala Val Gly Val Ser Leu Asn
145                 150                 155                 160

Asn Asp Leu Glu Asn Arg Glu Met Thr Leu Asn Ala Thr Asn Thr Ser
                165                 170                 175

Ser Asp Gly Thr Gln Asp Ser Ile Gly Arg Ser Leu Gly Ala Lys Val
            180                 185                 190

Asp Ser Ile Arg Phe Lys Ala Pro Ser Asn Val Ser Gln Gly Glu Ile
        195                 200                 205

Tyr Ile Asp Arg Ile Met Phe Ser Val Asp Asp Ala Arg Tyr Gln Trp
    210                 215                 220

Ser Asp Tyr Gln Val Lys Thr Arg Leu Ser Glu Pro Glu Ile Gln Phe
```

-continued

```
            225                 230                 235                 240
His Asn Val Lys Pro Gln Leu Pro Val Thr Pro Glu Asn Leu Ala Ala
                245                 250                 255

Ile Asp Leu Ile Arg Gln Arg Leu Ile Asn Glu Phe Val Gly Gly Glu
                260                 265                 270

Lys Glu Thr Asn Leu Ala Leu Glu Glu Asn Ile Ser Lys Leu Lys Ser
                275                 280                 285

Asp Phe Asp Ala Leu Asn Ile His Thr Leu Ala Asn Gly Gly Thr Gln
                290                 295                 300

Gly Arg His Leu Ile Thr Asp Lys Gln Ile Ile Tyr Gln Pro Glu
305                 310                 315                 320

Asn Leu Asn Ser Gln Asp Lys Gln Leu Phe Asp Asn Tyr Val Ile Leu
                325                 330                 335

Gly Asn Tyr Thr Thr Leu Met Phe Asn Ile Ser Arg Ala Tyr Val Leu
                340                 345                 350

Glu Lys Asp Pro Thr Gln Lys Ala Gln Leu Lys Gln Met Tyr Leu Leu
                355                 360                 365

Met Thr Lys His Leu Leu Asp Gln Gly Phe Val Lys Gly Ser Ala Leu
                370                 375                 380

Val Thr Thr His His Trp Gly Tyr Ser Ser Arg Trp Trp Tyr Ile Ser
385                 390                 395                 400

Thr Leu Leu Met Ser Asp Ala Leu Lys Glu Ala Asn Leu Gln Thr Gln
                405                 410                 415

Val Tyr Asp Ser Leu Leu Trp Tyr Ser Arg Glu Phe Lys Ser Ser Phe
                420                 425                 430

Asp Met Lys Val Ser Ala Asp Ser Ser Asp Leu Asp Tyr Phe Asn Thr
                435                 440                 445

Leu Ser Arg Gln His Leu Ala Leu Leu Leu Glu Pro Asp Asp Gln
                450                 455                 460

Lys Arg Ile Asn Leu Val Asn Thr Phe Ser His Tyr Ile Thr Gly Ala
465                 470                 475                 480

Leu Thr Gln Val Pro Pro Gly Gly Lys Asp Gly Leu Arg Pro Asp Gly
                485                 490                 495

Thr Ala Trp Arg His Glu Gly Asn Tyr Pro Gly Tyr Ser Phe Pro Ala
                500                 505                 510

Phe Lys Asn Ala Ser Gln Leu Ile Tyr Leu Leu Arg Asp Thr Pro Phe
                515                 520                 525

Ser Val Gly Glu Ser Gly Trp Asn Asn Leu Lys Lys Ala Met Val Ser
                530                 535                 540

Ala Trp Ile Tyr Ser Asn Pro Glu Val Gly Leu Pro Leu Ala Gly Arg
545                 550                 555                 560

His Pro Phe Asn Ser Pro Ser Leu Lys Ser Val Ala Gln Gly Tyr Tyr
                565                 570                 575

Trp Leu Ala Met Ser Ala Lys Ser Ser Pro Asp Lys Thr Leu Ala Ser
                580                 585                 590

Ile Tyr Leu Ala Ile Ser Asp Lys Thr Gln Asn Glu Ser Thr Ala Ile
                595                 600                 605

Phe Gly Glu Thr Ile Thr Pro Ala Ser Leu Pro Gln Gly Phe Tyr Ala
                610                 615                 620

Phe Asn Gly Gly Ala Phe Gly Ile His Arg Trp Gln Asp Lys Met Val
625                 630                 635                 640

Thr Leu Lys Ala Tyr Asn Thr Asn Val Trp Ser Ser Glu Ile Tyr Asn
                645                 650                 655
```

```
Lys Asp Asn Arg Tyr Gly Arg Tyr Gln Ser His Gly Val Ala Gln Ile
            660                 665                 670

Val Ser Asn Gly Ser Gln Leu Ser Gln Gly Tyr Gln Gln Glu Gly Trp
        675                 680                 685

Asp Trp Asn Arg Met Glu Gly Ala Thr Thr Ile His Leu Pro Leu Lys
    690                 695                 700

Asp Leu Asp Ser Pro Lys Pro His Thr Leu Met Gln Arg Gly Glu Arg
705                 710                 715                 720

Gly Phe Ser Gly Thr Ser Ser Leu Glu Gly Gln Tyr Gly Met Met Ala
                725                 730                 735

Phe Asn Leu Ile Tyr Pro Ala Asn Leu Glu Arg Phe Asp Pro Asn Phe
            740                 745                 750

Thr Ala Lys Lys Ser Val Leu Ala Ala Asp Asn His Leu Ile Phe Ile
        755                 760                 765

Gly Ser Asn Ile Asn Ser Ser Asp Lys Asn Lys Asn Val Glu Thr Thr
    770                 775                 780

Leu Phe Gln His Ala Ile Thr Pro Thr Leu Asn Thr Leu Trp Ile Asn
785                 790                 795                 800

Gly Gln Lys Ile Glu Asn Met Pro Tyr Gln Thr Thr Leu Gln Gln Gly
                805                 810                 815

Asp Trp Leu Ile Asp Ser Asn Gly Asn Gly Tyr Leu Ile Thr Gln Ala
            820                 825                 830

Glu Lys Val Asn Val Ser Arg Gln His Gln Val Ser Ala Glu Asn Lys
        835                 840                 845

Asn Arg Gln Pro Thr Glu Gly Asn Phe Ser Ser Ala Trp Ile Asp His
    850                 855                 860

Ser Thr Arg Pro Lys Asp Ala Ser Tyr Glu Tyr Met Val Phe Leu Asp
865                 870                 875                 880

Ala Thr Pro Glu Lys Met Gly Glu Met Ala Gln Lys Phe Arg Glu Asn
                885                 890                 895

Asn Gly Leu Tyr Gln Val Leu Arg Lys Asp Lys Asp Val His Ile Ile
            900                 905                 910

Leu Asp Lys Leu Ser Asn Val Thr Gly Tyr Ala Phe Tyr Gln Pro Ala
        915                 920                 925

Ser Ile Glu Asp Lys Trp Ile Lys Lys Val Asn Lys Pro Ala Ile Val
    930                 935                 940

Met Thr His Arg Gln Lys Asp Thr Leu Ile Val Ser Ala Val Thr Pro
945                 950                 955                 960

Asp Leu Asn Met Thr Arg Gln Lys Ala Ala Thr Pro Val Thr Ile Asn
                965                 970                 975

Val Thr Ile Asn Gly Lys Trp Gln Ser Ala Asp Lys Asn Ser Glu Val
            980                 985                 990

Lys Tyr Gln Val Ser Gly Asp Asn  Thr Glu Leu Thr Phe  Thr Ser Tyr
        995                 1000                 1005

Phe Gly  Ile Pro Gln Glu Ile  Lys Leu Ser Pro Leu  Pro
    1010                 1015                 1020

<210> SEQ ID NO 14
<211> LENGTH: 232
<212> TYPE: PRT
<213> ORGANISM: Unknown
<220> FEATURE:
<223> OTHER INFORMATION: Homo sapiens Vascular endothelial growth factor
      protein
```

```
<400> SEQUENCE: 14

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230

<210> SEQ ID NO 15
<211> LENGTH: 240
<212> TYPE: PRT
<213> ORGANISM: Unknown
<220> FEATURE:
<223> OTHER INFORMATION: Homo sapiens  Nerve growth factor protein

<400> SEQUENCE: 15

Met Ser Met Leu Phe Tyr Thr Leu Ile Thr Ala Phe Leu Ile Gly Ile
1               5                   10                  15

Gln Ala Glu Pro His Ser Glu Ser Asn Val Pro Ala Gly His Thr Ile
            20                  25                  30

Pro Gln Val His Trp Thr Lys Leu Gln His Ser Leu Asp Thr Ala Leu
        35                  40                  45

Arg Arg Ala Arg Ser Ala Pro Ala Ala Ala Ile Ala Ala Arg Val Ala
    50                  55                  60

Gly Gln Thr Arg Asn Ile Thr Val Asp Pro Arg Leu Phe Lys Lys Arg
65                  70                  75                  80

Arg Leu Arg Ser Pro Arg Val Leu Phe Ser Thr Gln Pro Pro Arg Glu
                85                  90                  95

Ala Ala Asp Thr Gln Asp Leu Asp Phe Glu Val Gly Gly Ala Ala Pro
            100                 105                 110

Phe Asn Arg Thr His Arg Ser Lys Arg Ser Ser Ser His Pro Ile Phe
```

```
            115                 120                 125
His Arg Gly Glu Phe Ser Val Cys Asp Ser Val Ser Val Trp Val Gly
        130                 135                 140

Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
                165                 170                 175

Thr Lys Cys Arg Asp Pro Asn Pro Val Asp Ser Gly Cys Arg Gly Ile
            180                 185                 190

Asp Ser Lys His Trp Asn Ser Tyr Cys Thr Thr Thr His Thr Phe Val
        195                 200                 205

Lys Ala Leu Thr Met Asp Gly Lys Gln Ala Ala Trp Arg Phe Ile Arg
    210                 215                 220

Ile Asp Thr Ala Cys Val Cys Val Leu Ser Arg Lys Ala Val Arg Arg
225                 230                 235                 240

<210> SEQ ID NO 16
<211> LENGTH: 153
<212> TYPE: PRT
<213> ORGANISM: Artificial
<220> FEATURE:
<223> OTHER INFORMATION: Synthetic polypeptide, GGF2-L(sub)250-C(sub)402

<400> SEQUENCE: 16

Cys Ile Ala Leu Leu Val Val Gly Ile Met Cys Val Val Ala Tyr Cys
1               5                   10                  15

Lys Thr Lys Lys Gln Arg Lys Lys Leu His Asp Arg Leu Arg Gln Ser
            20                  25                  30

Leu Arg Ser Glu Arg Asn Asn Met Met Asn Ile Ala Asn Gly Pro His
        35                  40                  45

His Pro Asn Pro Pro Glu Asn Val Gln Leu Val Asn Gln Tyr Val
    50                  55                  60

Ser Lys Asn Val Ile Ser Ser Glu His Ile Val Glu Arg Glu Ala Glu
65                  70                  75                  80

Thr Ser Phe Ser Thr Ser His Tyr Thr Ser Thr Ala His His Ser Thr
                85                  90                  95

Thr Val Thr Gln Thr Pro Ser His Ser Trp Ser Asn Gly His Thr Glu
            100                 105                 110

Ser Ile Leu Ser Glu Ser His Ser Val Ile Val Met Ser Ser Val Glu
        115                 120                 125

Asn Ser Arg His Ser Ser Pro Thr Gly Gly Pro Arg Gly Arg Leu Asn
    130                 135                 140

Gly Thr Gly Gly Pro Arg Glu Cys Asn
145                 150

<210> SEQ ID NO 17
<211> LENGTH: 173
<212> TYPE: PRT
<213> ORGANISM: Artificial
<220> FEATURE:
<223> OTHER INFORMATION: Synthetic polypeptide, GGF2-L(sub)250-E(sub)422

<400> SEQUENCE: 17

Cys Ile Ala Leu Leu Val Val Gly Ile Met Cys Val Val Ala Tyr Cys
1               5                   10                  15

Lys Thr Lys Lys Gln Arg Lys Lys Leu His Asp Arg Leu Arg Gln Ser
            20                  25                  30
```

```
Leu Arg Ser Glu Arg Asn Asn Met Met Asn Ile Ala Asn Gly Pro His
             35                  40                  45

His Pro Asn Pro Pro Glu Asn Val Gln Leu Val Asn Gln Tyr Val
 50                  55                  60

Ser Lys Asn Val Ile Ser Ser Glu His Ile Val Glu Arg Ala Glu
65                  70                  75                  80

Thr Ser Phe Ser Thr Ser His Tyr Thr Ser Thr Ala His His Ser Thr
             85                  90                  95

Thr Val Thr Gln Thr Pro Ser His Ser Trp Ser Asn Gly His Thr Glu
            100                 105                 110

Ser Ile Leu Ser Glu Ser His Ser Val Ile Val Met Ser Ser Val Glu
            115                 120                 125

Asn Ser Arg His Ser Ser Pro Thr Gly Gly Pro Arg Gly Arg Leu Asn
130                 135                 140

Gly Thr Gly Gly Pro Arg Glu Cys Asn Ser Phe Leu Arg His Ala Arg
145                 150                 155                 160

Glu Thr Pro Asp Ser Tyr Arg Asp Ser Pro His Ser Glu
                165                 170

<210> SEQ ID NO 18
<211> LENGTH: 53
<212> TYPE: PRT
<213> ORGANISM: Artificial
<220> FEATURE:
<223> OTHER INFORMATION: Synthetic polypeptide, GGF2-T(sub)350-C(sub)402

<400> SEQUENCE: 18

Thr Pro Ser His Ser Trp Ser Asn Gly His Thr Glu Ser Ile Leu Ser
1                5                  10                  15

Glu Ser His Ser Val Ile Val Met Ser Ser Val Glu Asn Ser Arg His
            20                  25                  30

Ser Ser Pro Thr Gly Gly Pro Arg Gly Arg Leu Asn Gly Thr Gly Gly
        35                  40                  45

Pro Arg Glu Cys Asn
    50

<210> SEQ ID NO 19
<211> LENGTH: 1498
<212> TYPE: PRT
<213> ORGANISM: Artificial
<220> FEATURE:
<223> OTHER INFORMATION: Synthetic polypeptide, N terminal fusion
      chimera between ABCI-N (delta)60-C(delta)80 and GGF2-FL

<400> SEQUENCE: 19

Met Ser Glu Arg Lys Glu Gly Arg Gly Lys Gly Lys Gly Lys Lys Lys
1                5                  10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
            85                  90                  95

Leu Arg Ile Asn Lys Ala Ser Leu Ala Asp Ser Gly Glu Tyr Met Cys
```

```
            100                 105                 110
Lys Val Ile Ser Lys Leu Gly Asn Asp Ser Ala Ser Ala Asn Ile Thr
        115                 120                 125
Ile Val Glu Ser Asn Glu Ile Ile Thr Gly Met Pro Ala Ser Thr Glu
        130                 135                 140
Gly Ala Tyr Val Ser Ser Glu Ser Pro Ile Arg Ile Ser Val Ser Thr
145                 150                 155                 160
Glu Gly Ala Asn Thr Ser Ser Ser Thr Ser Thr Ser Thr Thr Gly Thr
                165                 170                 175
Ser His Leu Val Lys Cys Ala Glu Lys Glu Lys Thr Phe Cys Val Asn
                180                 185                 190
Gly Gly Glu Cys Phe Met Val Lys Asp Leu Ser Asn Pro Ser Arg Tyr
            195                 200                 205
Leu Cys Lys Cys Gln Pro Gly Phe Thr Gly Ala Arg Cys Thr Glu Asn
        210                 215                 220
Val Pro Met Lys Val Gln Asn Gln Glu Lys Ala Glu Glu Leu Tyr Gln
225                 230                 235                 240
Lys Arg Val Leu Thr Ile Thr Gly Ile Cys Ile Ala Leu Leu Val Val
                245                 250                 255
Gly Ile Met Cys Val Val Ala Tyr Cys Lys Thr Lys Lys Gln Arg Lys
                260                 265                 270
Lys Leu His Asp Arg Leu Arg Gln Ser Leu Arg Ser Glu Arg Asn Asn
            275                 280                 285
Met Met Asn Ile Ala Asn Gly Pro His His Pro Asn Pro Pro Pro Glu
        290                 295                 300
Asn Val Gln Leu Val Asn Gln Tyr Val Ser Lys Asn Val Ile Ser Ser
305                 310                 315                 320
Glu His Ile Val Glu Arg Glu Ala Glu Thr Ser Phe Ser Thr Ser His
                325                 330                 335
Tyr Thr Ser Thr Ala His His Ser Thr Thr Val Thr Gln Thr Pro Ser
                340                 345                 350
His Ser Trp Ser Asn Gly His Thr Glu Ser Ile Leu Ser Glu Ser His
            355                 360                 365
Ser Val Ile Val Met Ser Ser Val Glu Asn Ser Arg His Ser Ser Pro
        370                 375                 380
Thr Gly Gly Pro Arg Gly Arg Leu Asn Gly Thr Gly Gly Pro Arg Glu
385                 390                 395                 400
Cys Asn Ser Phe Leu Arg His Ala Arg Glu Thr Pro Asp Ser Tyr Arg
                405                 410                 415
Asp Ser Pro His Ser Glu Arg Tyr Val Ser Ala Met Thr Thr Pro Ala
                420                 425                 430
Arg Met Ser Pro Val Asp Phe His Thr Pro Ser Ser Pro Lys Ser Pro
            435                 440                 445
Pro Ser Glu Met Ser Pro Pro Val Ser Ser Met Thr Val Ser Met Pro
        450                 455                 460
Ser Met Ala Val Ser Pro Phe Met Glu Glu Glu Arg Pro Leu Leu Leu
465                 470                 475                 480
Val Thr Pro Pro Arg Leu Arg Glu Lys Lys Phe Asp His His Pro Gln
                485                 490                 495
Gln Phe Ser Ser Phe His His Asn Pro Ala His Asp Ser Asn Ser Leu
                500                 505                 510
Pro Ala Ser Pro Leu Arg Ile Val Glu Asp Glu Glu Tyr Glu Thr Thr
            515                 520                 525
```

```
Gln Glu Tyr Glu Pro Ala Gln Glu Pro Val Lys Lys Leu Ala Asn Ser
            530                 535                 540

Arg Arg Ala Lys Arg Thr Lys Pro Asn Gly His Ile Ala Asn Arg Leu
545                 550                 555                 560

Glu Val Asp Ser Asn Thr Ser Ser Gln Ser Ser Asn Ser Glu Ser Glu
                565                 570                 575

Thr Glu Asp Glu Arg Val Gly Glu Asp Thr Pro Phe Leu Gly Ile Gln
            580                 585                 590

Asn Pro Leu Ala Ala Ser Leu Glu Ala Thr Pro Ala Phe Arg Leu Ala
            595                 600                 605

Asp Ser Arg Thr Asn Pro Ala Gly Arg Phe Ser Thr Gln Glu Glu Ile
610                 615                 620

Gln Ala Arg Leu Ser Ser Val Ile Ala Asn Gln Asp Pro Ile Ala Val
625                 630                 635                 640

Phe Thr Leu His Lys Lys Leu Ile Val Pro Thr Asp Lys Glu Ala Ser
                645                 650                 655

Lys Ala Trp Gly Arg Ser Ser Thr Pro Val Phe Ser Phe Trp Leu Tyr
            660                 665                 670

Asn Glu Lys Pro Ile Asp Gly Tyr Leu Thr Ile Asp Phe Gly Glu Lys
            675                 680                 685

Leu Ile Ser Thr Ser Glu Ala Gln Ala Gly Phe Lys Val Lys Leu Asp
690                 695                 700

Phe Thr Gly Trp Arg Thr Val Gly Val Ser Leu Asn Asn Asp Leu Glu
705                 710                 715                 720

Asn Arg Glu Met Thr Leu Asn Ala Thr Asn Thr Ser Ser Asp Gly Thr
                725                 730                 735

Gln Asp Ser Ile Gly Arg Ser Leu Gly Ala Lys Val Asp Ser Ile Arg
            740                 745                 750

Phe Lys Ala Pro Ser Asn Val Ser Gln Gly Glu Ile Tyr Ile Asp Arg
            755                 760                 765

Ile Met Phe Ser Val Asp Asp Ala Arg Tyr Gln Trp Ser Asp Tyr Gln
770                 775                 780

Val Lys Thr Arg Leu Ser Glu Pro Glu Ile Gln Phe His Asn Val Lys
785                 790                 795                 800

Pro Gln Leu Pro Val Thr Pro Glu Asn Leu Ala Ala Ile Asp Leu Ile
                805                 810                 815

Arg Gln Arg Leu Ile Asn Glu Phe Val Gly Gly Lys Glu Thr Asn
            820                 825                 830

Leu Ala Leu Glu Glu Asn Ile Ser Lys Leu Lys Ser Asp Phe Asp Ala
            835                 840                 845

Leu Asn Thr His Thr Leu Ala Asn Gly Gly Thr Gln Gly Arg His Leu
850                 855                 860

Ile Thr Asp Lys Gln Ile Ile Tyr Gln Pro Glu Asn Leu Asn Ser
865                 870                 875                 880

Gln Asp Lys Gln Leu Phe Asp Asn Tyr Val Ile Leu Gly Asn Tyr Thr
                885                 890                 895

Thr Leu Met Phe Asn Ile Ser Arg Ala Tyr Val Leu Glu Lys Asp Pro
            900                 905                 910

Thr Gln Lys Ala Gln Leu Lys Gln Met Tyr Leu Leu Met Thr Lys His
            915                 920                 925

Leu Leu Asp Gln Gly Phe Val Lys Gly Ser Ala Leu Val Thr Thr His
930                 935                 940
```

-continued

His Trp Gly Tyr Ser Ser Arg Trp Trp Tyr Ile Ser Thr Leu Leu Met
945                 950                 955                 960

Ser Asp Ala Leu Lys Glu Ala Asn Leu Gln Thr Gln Val Tyr Asp Ser
                965                 970                 975

Leu Leu Trp Tyr Ser Arg Glu Phe Lys Ser Ser Phe Asp Met Lys Val
            980                 985                 990

Ser Ala Asp Ser Ser Asp Leu Asp Tyr Phe Asn Thr Leu Ser Arg Gln
        995                 1000                1005

His Leu Ala Leu Leu Leu Glu Pro Asp Asp Gln Lys Arg Ile
1010            1015                1020

Asn Leu Val Asn Thr Phe Ser His Tyr Ile Thr Gly Ala Leu Thr
1025                1030                1035

Gln Val Pro Pro Gly Gly Lys Asp Gly Leu Arg Pro Asp Gly Thr
1040                1045                1050

Ala Trp Arg His Glu Gly Asn Tyr Pro Gly Tyr Ser Phe Pro Ala
1055                1060                1065

Phe Lys Asn Ala Ser Gln Leu Ile Tyr Leu Leu Arg Asp Thr Pro
1070                1075                1080

Phe Ser Val Gly Glu Ser Gly Trp Asn Asn Leu Lys Lys Ala Met
1085                1090                1095

Val Ser Ala Trp Ile Tyr Ser Asn Pro Glu Val Gly Leu Pro Leu
1100                1105                1110

Ala Gly Arg His Pro Phe Asn Ser Pro Ser Leu Lys Ser Val Ala
1115                1120                1125

Gln Gly Tyr Tyr Trp Leu Ala Met Ser Ala Lys Ser Ser Pro Asp
1130                1135                1140

Lys Thr Leu Ala Ser Ile Tyr Leu Ala Ile Ser Asp Lys Thr Gln
1145                1150                1155

Asn Glu Ser Thr Ala Ile Phe Gly Glu Thr Ile Thr Pro Ala Ser
1160                1165                1170

Leu Pro Gln Gly Phe Tyr Ala Phe Asn Gly Gly Ala Phe Gly Ile
1175                1180                1185

His Arg Trp Gln Asp Lys Met Val Thr Leu Lys Ala Tyr Asn Thr
1190                1195                1200

Asn Val Trp Ser Ser Glu Ile Tyr Asn Lys Asp Asn Arg Tyr Gly
1205                1210                1215

Arg Tyr Gln Ser His Gly Val Ala Gln Ile Val Ser Asn Gly Ser
1220                1225                1230

Gln Leu Ser Gln Gly Tyr Gln Gln Glu Gly Trp Asp Trp Asn Arg
1235                1240                1245

Met Glu Gly Ala Thr Thr Ile His Leu Pro Leu Lys Asp Leu Asp
1250                1255                1260

Ser Pro Lys Pro His Thr Leu Met Gln Arg Gly Glu Arg Gly Phe
1265                1270                1275

Ser Gly Thr Ser Ser Leu Glu Gly Gln Tyr Gly Met Met Ala Phe
1280                1285                1290

Asn Leu Ile Tyr Pro Ala Asn Leu Glu Arg Phe Asp Pro Asn Phe
1295                1300                1305

Thr Ala Lys Lys Ser Val Leu Ala Ala Asp Asn His Leu Ile Phe
1310                1315                1320

Ile Gly Ser Asn Ile Asn Ser Ser Asp Lys Asn Lys Asn Val Glu
1325                1330                1335

Thr Thr Leu Phe Gln His Ala Ile Thr Pro Thr Leu Asn Thr Leu

-continued

```
                          1340                1345                1350

Trp Ile Asn Gly Gln Lys Ile Glu Asn Met Pro Tyr Gln Thr Thr
    1355                1360                1365

Leu Gln Gln Gly Asp Trp Leu Ile Asp Ser Asn Gly Asn Gly Tyr
    1370                1375                1380

Leu Ile Thr Gln Ala Glu Lys Val Asn Val Ser Arg Gln His Gln
    1385                1390                1395

Val Ser Ala Glu Asn Lys Asn Arg Gln Pro Thr Glu Gly Asn Phe
    1400                1405                1410

Ser Ser Ala Trp Ile Asp His Ser Thr Arg Pro Lys Asp Ala Ser
    1415                1420                1425

Tyr Glu Tyr Met Val Phe Leu Asp Ala Thr Pro Glu Lys Met Gly
    1430                1435                1440

Glu Met Ala Gln Lys Phe Arg Glu Asn Asn Gly Leu Tyr Gln Val
    1445                1450                1455

Leu Arg Lys Asp Lys Asp Val His Ile Ile Leu Asp Lys Leu Ser
    1460                1465                1470

Asn Val Thr Gly Tyr Ala Phe Tyr Gln Pro Ala Ser Ile Glu Asp
    1475                1480                1485

Lys Trp Ile Lys Lys Val Asn Lys Pro Ala
    1490                1495
```

<210> SEQ ID NO 20
<211> LENGTH: 1011
<212> TYPE: PRT
<213> ORGANISM: Artificial
<220> FEATURE:
<223> OTHER INFORMATION: Synthetic Polypeptide, N Terminal fusion
      chimera between ABCI-N(delta)60-C(delta)80 and
      GGF2-L(sub)250-C(sub)402

<400> SEQUENCE: 20

```
Cys Ile Ala Leu Leu Val Val Gly Ile Met Cys Val Val Ala Tyr Cys
1               5                   10                  15

Lys Thr Lys Lys Gln Arg Lys Lys Leu His Asp Arg Leu Arg Gln Ser
            20                  25                  30

Leu Arg Ser Glu Arg Asn Asn Met Met Asn Ile Ala Asn Gly Pro His
        35                  40                  45

His Pro Asn Pro Pro Glu Asn Val Gln Leu Val Asn Gln Tyr Val
    50                  55                  60

Ser Lys Asn Val Ile Ser Ser Glu His Ile Val Glu Arg Glu Ala Glu
65                  70                  75                  80

Thr Ser Phe Ser Thr Ser His Tyr Thr Ser Thr Ala His His Ser Thr
            85                  90                  95

Thr Val Thr Gln Thr Pro Ser His Ser Trp Ser Asn Gly His Thr Glu
        100                 105                 110

Ser Ile Leu Ser Glu Ser His Ser Val Ile Val Met Ser Ser Val Glu
    115                 120                 125

Asn Ser Arg His Ser Ser Pro Thr Gly Gly Pro Arg Gly Arg Leu Asn
130                 135                 140

Gly Thr Gly Gly Pro Arg Glu Cys Asn Phe Thr Leu His Lys Lys Leu
145                 150                 155                 160

Ile Val Pro Thr Asp Lys Glu Ala Ser Lys Ala Trp Gly Arg Ser Ser
            165                 170                 175

Thr Pro Val Phe Ser Phe Trp Leu Tyr Asn Glu Lys Pro Ile Asp Gly
        180                 185                 190
```

```
Tyr Leu Thr Ile Asp Phe Gly Glu Lys Leu Ile Ser Thr Ser Glu Ala
            195                 200                 205

Gln Ala Gly Phe Lys Val Lys Leu Asp Phe Thr Gly Trp Arg Thr Val
210                 215                 220

Gly Val Ser Leu Asn Asn Asp Leu Glu Asn Arg Glu Met Thr Leu Asn
225                 230                 235                 240

Ala Thr Asn Thr Ser Ser Asp Gly Thr Gln Asp Ser Ile Gly Arg Ser
            245                 250                 255

Leu Gly Ala Lys Val Asp Ser Ile Arg Phe Lys Ala Pro Ser Asn Val
            260                 265                 270

Ser Gln Gly Glu Ile Tyr Ile Asp Arg Ile Met Phe Ser Val Asp Asp
            275                 280                 285

Ala Arg Tyr Gln Trp Ser Asp Tyr Gln Val Lys Thr Arg Leu Ser Glu
290                 295                 300

Pro Glu Ile Gln Phe His Asn Val Lys Pro Gln Leu Pro Val Thr Pro
305                 310                 315                 320

Glu Asn Leu Ala Ala Ile Asp Leu Ile Arg Gln Arg Leu Ile Asn Glu
            325                 330                 335

Phe Val Gly Gly Glu Lys Glu Thr Asn Leu Ala Leu Glu Glu Asn Ile
            340                 345                 350

Ser Lys Leu Lys Ser Asp Phe Asp Ala Leu Asn Thr His Thr Leu Ala
            355                 360                 365

Asn Gly Gly Thr Gln Gly Arg His Leu Ile Thr Asp Lys Gln Ile Ile
            370                 375                 380

Ile Tyr Gln Pro Glu Asn Leu Asn Ser Gln Asp Lys Gln Leu Phe Asp
385                 390                 395                 400

Asn Tyr Val Ile Leu Gly Asn Tyr Thr Thr Leu Met Phe Asn Ile Ser
            405                 410                 415

Arg Ala Tyr Val Leu Glu Lys Asp Pro Thr Gln Lys Ala Gln Leu Lys
            420                 425                 430

Gln Met Tyr Leu Leu Met Thr Lys His Leu Leu Asp Gln Gly Phe Val
            435                 440                 445

Lys Gly Ser Ala Leu Val Thr Thr His His Trp Gly Tyr Ser Ser Arg
450                 455                 460

Trp Trp Tyr Ile Ser Thr Leu Leu Met Ser Asp Ala Leu Lys Glu Ala
465                 470                 475                 480

Asn Leu Gln Thr Gln Val Tyr Asp Ser Leu Leu Trp Tyr Ser Arg Glu
            485                 490                 495

Phe Lys Ser Ser Phe Asp Met Lys Val Ser Ala Asp Ser Ser Asp Leu
            500                 505                 510

Asp Tyr Phe Asn Thr Leu Ser Arg Gln His Leu Ala Leu Leu Leu Leu
            515                 520                 525

Glu Pro Asp Asp Gln Lys Arg Ile Asn Leu Val Asn Thr Phe Ser His
530                 535                 540

Tyr Ile Thr Gly Ala Leu Thr Gln Val Pro Pro Gly Gly Lys Asp Gly
545                 550                 555                 560

Leu Arg Pro Asp Gly Thr Ala Trp Arg His Glu Gly Asn Tyr Pro Gly
            565                 570                 575

Tyr Ser Phe Pro Ala Phe Lys Asn Ala Ser Gln Leu Ile Tyr Leu Leu
            580                 585                 590

Arg Asp Thr Pro Phe Ser Val Gly Glu Ser Gly Trp Asn Asn Leu Lys
            595                 600                 605
```

-continued

```
Lys Ala Met Val Ser Ala Trp Ile Tyr Ser Asn Pro Glu Val Gly Leu
            610                 615                 620
Pro Leu Ala Gly Arg His Pro Phe Asn Ser Pro Ser Leu Lys Ser Val
625                 630                 635                 640
Ala Gln Gly Tyr Tyr Trp Leu Ala Met Ser Ala Lys Ser Ser Pro Asp
                645                 650                 655
Lys Thr Leu Ala Ser Ile Tyr Leu Ala Ile Ser Asp Lys Thr Gln Asn
            660                 665                 670
Glu Ser Thr Ala Ile Phe Gly Glu Thr Ile Thr Pro Ala Ser Leu Pro
        675                 680                 685
Gln Gly Phe Tyr Ala Phe Asn Gly Gly Ala Phe Gly Ile His Arg Trp
690                 695                 700
Gln Asp Lys Met Val Thr Leu Lys Ala Tyr Asn Thr Asn Val Trp Ser
705                 710                 715                 720
Ser Glu Ile Tyr Asn Lys Asp Asn Arg Tyr Gly Arg Tyr Gln Ser His
                725                 730                 735
Gly Val Ala Gln Ile Val Ser Asn Gly Ser Gln Leu Ser Gln Gly Tyr
            740                 745                 750
Gln Gln Glu Gly Trp Asp Trp Asn Arg Met Glu Gly Ala Thr Thr Ile
        755                 760                 765
His Leu Pro Leu Lys Asp Leu Asp Ser Pro Lys Pro His Thr Leu Met
770                 775                 780
Gln Arg Gly Glu Arg Gly Phe Ser Gly Thr Ser Ser Leu Glu Gly Gln
785                 790                 795                 800
Tyr Gly Met Met Ala Phe Asn Leu Ile Tyr Pro Ala Asn Leu Glu Arg
                805                 810                 815
Phe Asp Pro Asn Phe Thr Ala Lys Lys Ser Val Leu Ala Ala Asp Asn
            820                 825                 830
His Leu Ile Phe Ile Gly Ser Asn Ile Asn Ser Ser Asp Lys Asn Lys
        835                 840                 845
Asn Val Glu Thr Thr Leu Phe Gln His Ala Ile Thr Pro Thr Leu Asn
850                 855                 860
Thr Leu Trp Ile Asn Gly Gln Lys Ile Glu Asn Met Pro Tyr Gln Thr
865                 870                 875                 880
Thr Leu Gln Gln Gly Asp Trp Leu Ile Asp Ser Asn Gly Asn Gly Tyr
                885                 890                 895
Leu Ile Thr Gln Ala Glu Lys Val Asn Val Ser Arg Gln His Gln Val
            900                 905                 910
Ser Ala Glu Asn Lys Asn Arg Gln Pro Thr Glu Gly Asn Phe Ser Ser
        915                 920                 925
Ala Trp Ile Asp His Ser Thr Arg Pro Lys Asp Ala Ser Tyr Glu Tyr
930                 935                 940
Met Val Phe Leu Asp Ala Thr Pro Glu Lys Met Gly Glu Met Ala Gln
945                 950                 955                 960
Lys Phe Arg Glu Asn Asn Gly Leu Tyr Gln Val Leu Arg Lys Asp Lys
                965                 970                 975
Asp Val His Ile Ile Leu Asp Lys Leu Ser Asn Val Thr Gly Tyr Ala
            980                 985                 990
Phe Tyr Gln Pro Ala Ser Ile Glu  Asp Lys Trp Ile Lys  Lys Val Asn
        995                 1000                 1005
Lys Pro Ala
    1010
```

-continued

```
<210> SEQ ID NO 21
<211> LENGTH: 1031
<212> TYPE: PRT
<213> ORGANISM: Artificial
<220> FEATURE:
<223> OTHER INFORMATION: Synthetic polypeptide, N terminal fusion
      chimera between ABCI-N(delta)60- C(delta)80 and
      GGF2-L(sub)250-E(sub)422

<400> SEQUENCE: 21
```

Cys Ile Ala Leu Leu Val Val Gly Ile Met Cys Val Val Ala Tyr Cys
1               5                   10                  15

Lys Thr Lys Lys Gln Arg Lys Lys Leu His Asp Arg Leu Arg Gln Ser
            20                  25                  30

Leu Arg Ser Glu Arg Asn Asn Met Met Asn Ile Ala Asn Gly Pro His
        35                  40                  45

His Pro Asn Pro Pro Glu Asn Val Gln Leu Val Asn Gln Tyr Val
    50                  55                  60

Ser Lys Asn Val Ile Ser Ser Glu His Ile Val Glu Arg Glu Ala Glu
65                  70                  75                  80

Thr Ser Phe Ser Thr Ser His Tyr Thr Ser Thr Ala His His Ser Thr
                85                  90                  95

Thr Val Thr Gln Thr Pro Ser His Ser Trp Ser Asn Gly His Thr Glu
            100                 105                 110

Ser Ile Leu Ser Glu Ser His Ser Val Ile Val Met Ser Ser Val Glu
        115                 120                 125

Asn Ser Arg His Ser Ser Pro Thr Gly Gly Pro Arg Gly Arg Leu Asn
    130                 135                 140

Gly Thr Gly Gly Pro Arg Glu Cys Asn Ser Phe Leu Arg His Ala Arg
145                 150                 155                 160

Glu Thr Pro Asp Ser Tyr Arg Asp Ser Pro His Ser Glu Phe Thr Leu
                165                 170                 175

His Lys Lys Leu Ile Val Pro Thr Asp Lys Glu Ala Ser Lys Ala Trp
            180                 185                 190

Gly Arg Ser Ser Thr Pro Val Phe Ser Phe Trp Leu Tyr Asn Glu Lys
        195                 200                 205

Pro Ile Asp Gly Tyr Leu Thr Ile Asp Phe Gly Glu Lys Leu Ile Ser
    210                 215                 220

Thr Ser Glu Ala Gln Ala Gly Phe Lys Val Lys Leu Asp Phe Thr Gly
225                 230                 235                 240

Trp Arg Thr Val Gly Val Ser Leu Asn Asn Asp Leu Glu Asn Arg Glu
                245                 250                 255

Met Thr Leu Asn Ala Thr Asn Thr Ser Ser Asp Gly Thr Gln Asp Ser
            260                 265                 270

Ile Gly Arg Ser Leu Gly Ala Lys Val Asp Ser Ile Arg Phe Lys Ala
        275                 280                 285

Pro Ser Asn Val Ser Gln Gly Glu Ile Tyr Ile Asp Arg Ile Met Phe
    290                 295                 300

Ser Val Asp Asp Ala Arg Tyr Gln Trp Ser Asp Tyr Gln Val Lys Thr
305                 310                 315                 320

Arg Leu Ser Glu Pro Glu Ile Gln Phe His Asn Val Lys Pro Gln Leu
                325                 330                 335

Pro Val Thr Pro Glu Asn Leu Ala Ala Ile Asp Leu Ile Arg Gln Arg
            340                 345                 350

Leu Ile Asn Glu Phe Val Gly Gly Glu Lys Glu Thr Asn Leu Ala Leu
        355                 360                 365

-continued

```
Glu Glu Asn Ile Ser Lys Leu Lys Ser Asp Phe Asp Ala Leu Asn Thr
    370                 375                 380
His Thr Leu Ala Asn Gly Gly Thr Gln Gly Arg His Leu Ile Thr Asp
385                 390                 395                 400
Lys Gln Ile Ile Ile Tyr Gln Pro Glu Asn Leu Asn Ser Gln Asp Lys
                405                 410                 415
Gln Leu Phe Asp Asn Tyr Val Ile Leu Gly Asn Tyr Thr Thr Leu Met
            420                 425                 430
Phe Asn Ile Ser Arg Ala Tyr Val Leu Glu Lys Asp Pro Thr Gln Lys
        435                 440                 445
Ala Gln Leu Lys Gln Met Tyr Leu Leu Met Thr Lys His Leu Leu Asp
450                 455                 460
Gln Gly Phe Val Lys Gly Ser Ala Leu Val Thr Thr His His Trp Gly
465                 470                 475                 480
Tyr Ser Ser Arg Trp Trp Tyr Ile Ser Thr Leu Leu Met Ser Asp Ala
                485                 490                 495
Leu Lys Glu Ala Asn Leu Gln Thr Gln Val Tyr Asp Ser Leu Leu Trp
            500                 505                 510
Tyr Ser Arg Glu Phe Lys Ser Ser Phe Asp Met Lys Val Ser Ala Asp
        515                 520                 525
Ser Ser Asp Leu Asp Tyr Phe Asn Thr Leu Ser Arg Gln His Leu Ala
530                 535                 540
Leu Leu Leu Leu Glu Pro Asp Asp Gln Lys Arg Ile Asn Leu Val Asn
545                 550                 555                 560
Thr Phe Ser His Tyr Ile Thr Gly Ala Leu Thr Gln Val Pro Pro Gly
                565                 570                 575
Gly Lys Asp Gly Leu Arg Pro Asp Gly Thr Ala Trp Arg His Glu Gly
            580                 585                 590
Asn Tyr Pro Gly Tyr Ser Phe Pro Ala Phe Lys Asn Ala Ser Gln Leu
        595                 600                 605
Ile Tyr Leu Leu Arg Asp Thr Pro Phe Ser Val Gly Glu Ser Gly Trp
610                 615                 620
Asn Asn Leu Lys Lys Ala Met Val Ser Ala Trp Ile Tyr Ser Asn Pro
625                 630                 635                 640
Glu Val Gly Leu Pro Leu Ala Gly Arg His Pro Phe Asn Ser Pro Ser
                645                 650                 655
Leu Lys Ser Val Ala Gln Gly Tyr Tyr Trp Leu Ala Met Ser Ala Lys
            660                 665                 670
Ser Ser Pro Asp Lys Thr Leu Ala Ser Ile Tyr Leu Ala Ile Ser Asp
        675                 680                 685
Lys Thr Gln Asn Glu Ser Thr Ala Ile Phe Gly Glu Thr Ile Thr Pro
690                 695                 700
Ala Ser Leu Pro Gln Gly Phe Tyr Ala Phe Asn Gly Gly Ala Phe Gly
705                 710                 715                 720
Ile His Arg Trp Gln Asp Lys Met Val Thr Leu Lys Ala Tyr Asn Thr
                725                 730                 735
Asn Val Trp Ser Ser Glu Ile Tyr Asn Lys Asp Asn Arg Tyr Gly Arg
            740                 745                 750
Tyr Gln Ser His Gly Val Ala Gln Ile Val Ser Asn Gly Ser Gln Leu
        755                 760                 765
Ser Gln Gly Tyr Gln Gln Glu Gly Trp Asp Trp Asn Arg Met Glu Gly
770                 775                 780
```

```
Ala Thr Thr Ile His Leu Pro Leu Lys Asp Leu Asp Ser Pro Lys Pro
785                 790                 795                 800

His Thr Leu Met Gln Arg Gly Glu Arg Gly Phe Ser Gly Thr Ser Ser
            805                 810                 815

Leu Glu Gly Gln Tyr Gly Met Met Ala Phe Asn Leu Ile Tyr Pro Ala
        820                 825                 830

Asn Leu Glu Arg Phe Asp Pro Asn Phe Thr Ala Lys Lys Ser Val Leu
    835                 840                 845

Ala Ala Asp Asn His Leu Ile Phe Ile Gly Ser Asn Ile Asn Ser Ser
850                 855                 860

Asp Lys Asn Lys Asn Val Glu Thr Thr Leu Phe Gln His Ala Ile Thr
865                 870                 875                 880

Pro Thr Leu Asn Thr Leu Trp Ile Asn Gly Gln Lys Ile Glu Asn Met
            885                 890                 895

Pro Tyr Gln Thr Thr Leu Gln Gln Gly Asp Trp Leu Ile Asp Ser Asn
        900                 905                 910

Gly Asn Gly Tyr Leu Ile Thr Gln Ala Glu Lys Val Asn Val Ser Arg
    915                 920                 925

Gln His Gln Val Ser Ala Glu Asn Lys Asn Arg Gln Pro Thr Glu Gly
930                 935                 940

Asn Phe Ser Ser Ala Trp Ile Asp His Ser Thr Arg Pro Lys Asp Ala
945                 950                 955                 960

Ser Tyr Glu Tyr Met Val Phe Leu Asp Ala Thr Pro Glu Lys Met Gly
            965                 970                 975

Glu Met Ala Gln Lys Phe Arg Glu Asn Asn Gly Leu Tyr Gln Val Leu
        980                 985                 990

Arg Lys Asp Lys Asp Val His Ile Ile Leu Asp Lys Leu Ser Asn Val
    995                 1000                1005

Thr Gly Tyr Ala Phe Tyr Gln Pro Ala Ser Ile Glu Asp Lys Trp
   1010                1015                1020

Ile Lys Lys Val Asn Lys Pro Ala
   1025                1030

<210> SEQ ID NO 22
<211> LENGTH: 911
<212> TYPE: PRT
<213> ORGANISM: Artificial
<220> FEATURE:
<223> OTHER INFORMATION: Synthetic polypeptide, N terminal fusion
      chimera between ABCI-N(delta)-C(delta)80 and
      GGF2-T(sub)350-C(sub)402

<400> SEQUENCE: 22

Thr Pro Ser His Ser Trp Ser Asn Gly His Thr Glu Ser Ile Leu Ser
1               5                   10                  15

Glu Ser His Ser Val Ile Val Met Ser Ser Val Glu Asn Ser Arg His
            20                  25                  30

Ser Ser Pro Thr Gly Gly Pro Arg Gly Arg Leu Asn Gly Thr Gly Gly
        35                  40                  45

Pro Arg Glu Cys Asn Phe Thr Leu His Lys Lys Leu Ile Val Pro Thr
    50                  55                  60

Asp Lys Glu Ala Ser Lys Ala Trp Gly Arg Ser Ser Thr Pro Val Phe
65                  70                  75                  80

Ser Phe Trp Leu Tyr Asn Glu Lys Pro Ile Asp Gly Tyr Leu Thr Ile
                85                  90                  95

Asp Phe Gly Glu Lys Leu Ile Ser Thr Ser Glu Ala Gln Ala Gly Phe
```

-continued

```
            100                 105                 110
    Lys Val Lys Leu Asp Phe Thr Gly Trp Arg Thr Val Gly Val Ser Leu
            115                 120                 125

Asn Asn Asp Leu Glu Asn Arg Glu Met Thr Leu Asn Ala Thr Asn Thr
            130                 135                 140

Ser Ser Asp Gly Thr Gln Asp Ser Ile Gly Arg Ser Leu Gly Ala Lys
    145                 150                 155                 160

Val Asp Ser Ile Arg Phe Lys Ala Pro Ser Asn Val Ser Gln Gly Glu
                        165                 170                 175

Ile Tyr Ile Asp Arg Ile Met Phe Ser Val Asp Ala Arg Tyr Gln
                180                 185                 190

Trp Ser Asp Tyr Gln Val Lys Thr Arg Leu Ser Glu Pro Glu Ile Gln
                195                 200                 205

Phe His Asn Val Lys Pro Gln Leu Pro Val Thr Pro Glu Asn Leu Ala
                210                 215                 220

Ala Ile Asp Leu Ile Arg Gln Arg Leu Ile Asn Glu Phe Val Gly Gly
    225                 230                 235                 240

Glu Lys Glu Thr Asn Leu Ala Leu Glu Glu Asn Ile Ser Lys Leu Lys
                        245                 250                 255

Ser Asp Phe Asp Ala Leu Asn Thr His Thr Leu Ala Asn Gly Gly Thr
                        260                 265                 270

Gln Gly Arg His Leu Ile Thr Asp Lys Gln Ile Ile Tyr Gln Pro
                275                 280                 285

Glu Asn Leu Asn Ser Gln Asp Lys Gln Leu Phe Asp Asn Tyr Val Ile
                290                 295                 300

Leu Gly Asn Tyr Thr Thr Leu Met Phe Asn Ile Ser Arg Ala Tyr Val
    305                 310                 315                 320

Leu Glu Lys Asp Pro Thr Gln Lys Ala Gln Leu Lys Gln Met Tyr Leu
                        325                 330                 335

Leu Met Thr Lys His Leu Leu Asp Gln Gly Phe Val Lys Gly Ser Ala
                        340                 345                 350

Leu Val Thr Thr His His Trp Gly Tyr Ser Ser Arg Trp Trp Tyr Ile
                355                 360                 365

Ser Thr Leu Leu Met Ser Asp Ala Leu Lys Glu Ala Asn Leu Gln Thr
                370                 375                 380

Gln Val Tyr Asp Ser Leu Leu Trp Tyr Ser Arg Glu Phe Lys Ser Ser
    385                 390                 395                 400

Phe Asp Met Lys Val Ser Ala Asp Ser Ser Asp Leu Asp Tyr Phe Asn
                        405                 410                 415

Thr Leu Ser Arg Gln His Leu Ala Leu Leu Leu Glu Pro Asp Asp
                        420                 425                 430

Gln Lys Arg Ile Asn Leu Val Asn Thr Phe Ser His Tyr Ile Thr Gly
                435                 440                 445

Ala Leu Thr Gln Val Pro Pro Gly Gly Lys Asp Gly Leu Arg Pro Asp
                450                 455                 460

Gly Thr Ala Trp Arg His Glu Gly Asn Tyr Pro Gly Tyr Ser Phe Pro
    465                 470                 475                 480

Ala Phe Lys Asn Ala Ser Gln Leu Ile Tyr Leu Leu Arg Asp Thr Pro
                        485                 490                 495

Phe Ser Val Gly Glu Ser Gly Trp Asn Asn Leu Lys Lys Ala Met Val
                        500                 505                 510

Ser Ala Trp Ile Tyr Ser Asn Pro Glu Val Gly Leu Pro Leu Ala Gly
                515                 520                 525
```

Arg His Pro Phe Asn Ser Pro Ser Leu Lys Ser Val Ala Gln Gly Tyr
530                 535                 540

Tyr Trp Leu Ala Met Ser Ala Lys Ser Ser Pro Asp Lys Thr Leu Ala
545                 550                 555                 560

Ser Ile Tyr Leu Ala Ile Ser Asp Lys Thr Gln Asn Glu Ser Thr Ala
                565                 570                 575

Ile Phe Gly Glu Thr Ile Thr Pro Ala Ser Leu Pro Gln Gly Phe Tyr
            580                 585                 590

Ala Phe Asn Gly Gly Ala Phe Gly Ile His Arg Trp Gln Asp Lys Met
        595                 600                 605

Val Thr Leu Lys Ala Tyr Asn Thr Asn Val Trp Ser Ser Glu Ile Tyr
610                 615                 620

Asn Lys Asp Asn Arg Tyr Gly Arg Tyr Gln Ser His Gly Val Ala Gln
625                 630                 635                 640

Ile Val Ser Asn Gly Ser Gln Leu Ser Gln Gly Tyr Gln Gln Glu Gly
                645                 650                 655

Trp Asp Trp Asn Arg Met Glu Gly Ala Thr Thr Ile His Leu Pro Leu
            660                 665                 670

Lys Asp Leu Asp Ser Pro Lys Pro His Thr Leu Met Gln Arg Gly Glu
        675                 680                 685

Arg Gly Phe Ser Gly Thr Ser Ser Leu Glu Gly Gln Tyr Gly Met Met
690                 695                 700

Ala Phe Asn Leu Ile Tyr Pro Ala Asn Leu Glu Arg Phe Asp Pro Asn
705                 710                 715                 720

Phe Thr Ala Lys Lys Ser Val Leu Ala Ala Asp Asn His Leu Ile Phe
                725                 730                 735

Ile Gly Ser Asn Ile Asn Ser Ser Asp Lys Asn Lys Asn Val Glu Thr
            740                 745                 750

Thr Leu Phe Gln His Ala Ile Thr Pro Thr Leu Asn Thr Leu Trp Ile
        755                 760                 765

Asn Gly Gln Lys Ile Glu Asn Met Pro Tyr Gln Thr Thr Leu Gln Gln
770                 775                 780

Gly Asp Trp Leu Ile Asp Ser Asn Gly Asn Gly Tyr Leu Ile Thr Gln
785                 790                 795                 800

Ala Glu Lys Val Asn Val Ser Arg Gln His Gln Val Ser Ala Glu Asn
                805                 810                 815

Lys Asn Arg Gln Pro Thr Glu Gly Asn Phe Ser Ser Ala Trp Ile Asp
            820                 825                 830

His Ser Thr Arg Pro Lys Asp Ala Ser Tyr Glu Tyr Met Val Phe Leu
        835                 840                 845

Asp Ala Thr Pro Glu Lys Met Gly Glu Met Ala Gln Lys Phe Arg Glu
850                 855                 860

Asn Asn Gly Leu Tyr Gln Val Leu Arg Lys Asp Lys Asp Val His Ile
865                 870                 875                 880

Ile Leu Asp Lys Leu Ser Asn Val Thr Gly Tyr Ala Phe Tyr Gln Pro
                885                 890                 895

Ala Ser Ile Glu Asp Lys Trp Ile Lys Lys Val Asn Lys Pro Ala
            900                 905                 910

<210> SEQ ID NO 23
<211> LENGTH: 1637
<212> TYPE: PRT
<213> ORGANISM: Artificial
<220> FEATURE:

<223> OTHER INFORMATION: Synthetic polypeptide, C terminal fusion
Chimera between ABCI-FL and GGF2-FL

<400> SEQUENCE: 23

```
Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45

Gln Ser Leu Leu Trp Lys Trp Lys Gly Gly Ser Ser Phe Thr Leu His
    50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95

Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Thr Val Gly Val Ser Leu Asn Asn Asp Leu Glu Asn Arg Glu Met
    130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gln Gly Glu Ile Tyr Ile Asp Arg Ile Met Phe Ser
            180                 185                 190

Val Asp Asp Ala Arg Tyr Gln Trp Ser Asp Tyr Gln Val Lys Thr Arg
        195                 200                 205

Leu Ser Glu Pro Glu Ile Gln Phe His Asn Val Lys Pro Gln Leu Pro
    210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Glu
                245                 250                 255

Glu Asn Ile Ser Lys Leu Lys Ser Asp Phe Asp Ala Leu Asn Thr His
            260                 265                 270

Thr Leu Ala Asn Gly Gly Thr Gln Gly Arg His Leu Ile Thr Asp Lys
        275                 280                 285

Gln Ile Ile Ile Tyr Gln Pro Glu Asn Leu Asn Ser Gln Asp Lys Gln
    290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                325                 330                 335

Gln Leu Lys Gln Met Tyr Leu Leu Met Thr Lys His Leu Leu Asp Gln
            340                 345                 350

Gly Phe Val Lys Gly Ser Ala Leu Val Thr Thr His His Trp Gly Tyr
        355                 360                 365

Ser Ser Arg Trp Trp Tyr Ile Ser Thr Leu Leu Met Ser Asp Ala Leu
    370                 375                 380

Lys Glu Ala Asn Leu Gln Thr Gln Val Tyr Asp Ser Leu Leu Trp Tyr
385                 390                 395                 400
```

-continued

```
Ser Arg Glu Phe Lys Ser Ser Phe Asp Met Lys Val Ser Ala Asp Ser
                405                 410                 415

Ser Asp Leu Asp Tyr Phe Asn Thr Leu Ser Arg Gln His Leu Ala Leu
            420                 425                 430

Leu Leu Leu Glu Pro Asp Asp Gln Lys Arg Ile Asn Leu Val Asn Thr
        435                 440                 445

Phe Ser His Tyr Ile Thr Gly Ala Leu Thr Gln Val Pro Pro Gly Gly
    450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                485                 490                 495

Tyr Leu Leu Arg Asp Thr Pro Phe Ser Val Gly Glu Ser Gly Trp Asn
            500                 505                 510

Asn Leu Lys Lys Ala Met Val Ser Ala Trp Ile Tyr Ser Asn Pro Glu
        515                 520                 525

Val Gly Leu Pro Leu Ala Gly Arg His Pro Phe Asn Ser Pro Ser Leu
    530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gln Asn Glu Ser Thr Ala Ile Phe Gly Glu Thr Ile Thr Pro Ala
            580                 585                 590

Ser Leu Pro Gln Gly Phe Tyr Ala Phe Asn Gly Gly Ala Phe Gly Ile
        595                 600                 605

His Arg Trp Gln Asp Lys Met Val Thr Leu Lys Ala Tyr Asn Thr Asn
    610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
                645                 650                 655

Gln Gly Tyr Gln Gln Glu Gly Trp Asp Trp Asn Arg Met Glu Gly Ala
            660                 665                 670

Thr Thr Ile His Leu Pro Leu Lys Asp Leu Asp Ser Pro Lys Pro His
        675                 680                 685

Thr Leu Met Gln Arg Gly Glu Arg Gly Phe Ser Gly Thr Ser Ser Leu
    690                 695                 700

Glu Gly Gln Tyr Gly Met Met Ala Phe Asn Leu Ile Tyr Pro Ala Asn
705                 710                 715                 720

Leu Glu Arg Phe Asp Pro Asn Phe Thr Ala Lys Lys Ser Val Leu Ala
                725                 730                 735

Ala Asp Asn His Leu Ile Phe Ile Gly Ser Asn Ile Asn Ser Ser Asp
            740                 745                 750

Lys Asn Lys Asn Val Glu Thr Thr Leu Phe Gln His Ala Ile Thr Pro
        755                 760                 765

Thr Leu Asn Thr Leu Trp Ile Asn Gly Gln Lys Ile Glu Asn Met Pro
    770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
                805                 810                 815
```

-continued

```
His Gln Val Ser Ala Glu Asn Lys Asn Arg Gln Pro Thr Glu Gly Asn
                820                 825                 830

Phe Ser Ser Ala Trp Ile Asp His Ser Thr Arg Pro Lys Asp Ala Ser
            835                 840                 845

Tyr Glu Tyr Met Val Phe Leu Asp Ala Thr Pro Glu Lys Met Gly Glu
        850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                885                 890                 895

Gly Tyr Ala Phe Tyr Gln Pro Ala Ser Ile Glu Asp Lys Trp Ile Lys
            900                 905                 910

Lys Val Asn Lys Pro Ala Ile Val Met Thr His Arg Gln Lys Asp Thr
        915                 920                 925

Leu Ile Val Ser Ala Val Thr Pro Asp Leu Asn Met Thr Arg Gln Lys
    930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
                965                 970                 975

Thr Glu Leu Thr Phe Thr Ser Tyr Phe Gly Ile Pro Gln Glu Ile Lys
            980                 985                 990

Leu Ser Pro Leu Pro Met Ser Glu Arg Lys Glu Gly Arg Gly Lys Gly
        995                 1000                1005

Lys Gly Lys Lys Lys Glu Arg Gly Ser Gly Lys Lys Pro Glu Ser
    1010                1015                1020

Ala Ala Gly Ser Gln Ser Pro Ala Leu Pro Pro Arg Leu Lys Glu
    1025                1030                1035

Met Lys Ser Gln Glu Ser Ala Ala Gly Ser Lys Leu Val Leu Arg
    1040                1045                1050

Cys Glu Thr Ser Ser Glu Tyr Ser Ser Leu Arg Phe Lys Trp Phe
    1055                1060                1065

Lys Asn Gly Asn Glu Leu Asn Arg Lys Asn Lys Pro Gln Asn Ile
    1070                1075                1080

Lys Ile Gln Lys Lys Pro Gly Lys Ser Glu Leu Arg Ile Asn Lys
    1085                1090                1095

Ala Ser Leu Ala Asp Ser Gly Glu Tyr Met Cys Lys Val Ile Ser
    1100                1105                1110

Lys Leu Gly Asn Asp Ser Ala Ser Ala Asn Ile Thr Ile Val Glu
    1115                1120                1125

Ser Asn Glu Ile Ile Thr Gly Met Pro Ala Ser Thr Glu Gly Ala
    1130                1135                1140

Tyr Val Ser Ser Glu Ser Pro Ile Arg Ile Ser Val Ser Thr Glu
    1145                1150                1155

Gly Ala Asn Thr Ser Ser Ser Thr Ser Thr Ser Thr Thr Gly Thr
    1160                1165                1170

Ser His Leu Val Lys Cys Ala Glu Lys Glu Lys Thr Phe Cys Val
    1175                1180                1185

Asn Gly Gly Glu Cys Phe Met Val Lys Asp Leu Ser Asn Pro Ser
    1190                1195                1200

Arg Tyr Leu Cys Lys Cys Gln Pro Gly Phe Thr Gly Ala Arg Cys
    1205                1210                1215

Thr Glu Asn Val Pro Met Lys Val Gln Asn Gln Glu Lys Ala Glu
```

```
            1220                1225                1230
   Glu Leu Tyr Gln Lys Arg Val Leu Thr Ile Thr Gly Ile Cys Ile
            1235                1240                1245

Ala Leu Leu Val Val Gly Ile Met Cys Val Val Ala Tyr Cys Lys
            1250                1255                1260

Thr Lys Lys Gln Arg Lys Lys Leu His Asp Arg Leu Arg Gln Ser
            1265                1270                1275

Leu Arg Ser Glu Arg Asn Asn Met Met Asn Ile Ala Asn Gly Pro
            1280                1285                1290

His His Pro Asn Pro Pro Glu Asn Val Gln Leu Val Asn Gln
            1295                1300                1305

Tyr Val Ser Lys Asn Val Ile Ser Ser Glu His Ile Val Glu Arg
            1310                1315                1320

Glu Ala Glu Thr Ser Phe Ser Thr Ser His Tyr Thr Ser Thr Ala
            1325                1330                1335

His His Ser Thr Thr Val Thr Gln Thr Pro Ser His Ser Trp Ser
            1340                1345                1350

Asn Gly His Thr Glu Ser Ile Leu Ser Glu Ser His Ser Val Ile
            1355                1360                1365

Val Met Ser Ser Val Glu Asn Ser Arg His Ser Ser Pro Thr Gly
            1370                1375                1380

Gly Pro Arg Gly Arg Leu Asn Gly Thr Gly Gly Pro Arg Glu Cys
            1385                1390                1395

Asn Ser Phe Leu Arg His Ala Arg Glu Thr Pro Asp Ser Tyr Arg
            1400                1405                1410

Asp Ser Pro His Ser Glu Arg Tyr Val Ser Ala Met Thr Thr Pro
            1415                1420                1425

Ala Arg Met Ser Pro Val Asp Phe His Thr Pro Ser Ser Pro Lys
            1430                1435                1440

Ser Pro Pro Ser Glu Met Ser Pro Pro Val Ser Ser Met Thr Val
            1445                1450                1455

Ser Met Pro Ser Met Ala Val Ser Pro Phe Met Glu Glu Glu Arg
            1460                1465                1470

Pro Leu Leu Leu Val Thr Pro Pro Arg Leu Arg Glu Lys Lys Phe
            1475                1480                1485

Asp His His Pro Gln Gln Phe Ser Ser Phe His His Asn Pro Ala
            1490                1495                1500

His Asp Ser Asn Ser Leu Pro Ala Ser Pro Leu Arg Ile Val Glu
            1505                1510                1515

Asp Glu Glu Tyr Glu Thr Thr Gln Glu Tyr Glu Pro Ala Gln Glu
            1520                1525                1530

Pro Val Lys Lys Leu Ala Asn Ser Arg Arg Ala Lys Arg Thr Lys
            1535                1540                1545

Pro Asn Gly His Ile Ala Asn Arg Leu Glu Val Asp Ser Asn Thr
            1550                1555                1560

Ser Ser Gln Ser Ser Asn Ser Glu Ser Glu Thr Glu Asp Glu Arg
            1565                1570                1575

Val Gly Glu Asp Thr Pro Phe Leu Gly Ile Gln Asn Pro Leu Ala
            1580                1585                1590

Ala Ser Leu Glu Ala Thr Pro Ala Phe Arg Leu Ala Asp Ser Arg
            1595                1600                1605

Thr Asn Pro Ala Gly Arg Phe Ser Thr Gln Glu Glu Ile Gln Ala
            1610                1615                1620
```

-continued

```
Arg Leu Ser Ser Val Ile Ala Asn Gln Asp Pro Ile Ala Val
    1625                1630                1635

<210> SEQ ID NO 24
<211> LENGTH: 1150
<212> TYPE: PRT
<213> ORGANISM: Artificial
<220> FEATURE:
<223> OTHER INFORMATION: Synthetic polypeptide, C terminal fusion
      Chimera between chondroitinase ABCI-FL and
      GGF2-L(sub)250-C(sub)402

<400> SEQUENCE: 24

Ala Thr Ser Asn Pro Ala Phe Asp Pro Lys Asn Leu Met Gln Ser Glu
  1               5                  10                  15

Ile Tyr His Phe Ala Gln Asn Asn Pro Leu Ala Asp Phe Ser Ser Asp
             20                  25                  30

Lys Asn Ser Ile Leu Thr Leu Ser Asp Lys Arg Ser Ile Met Gly Asn
         35                  40                  45

Gln Ser Leu Leu Trp Lys Trp Lys Gly Gly Ser Ser Phe Thr Leu His
     50                  55                  60

Lys Lys Leu Ile Val Pro Thr Asp Lys Glu Ala Ser Lys Ala Trp Gly
 65                  70                  75                  80

Arg Ser Ser Thr Pro Val Phe Ser Phe Trp Leu Tyr Asn Glu Lys Pro
                 85                  90                  95

Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Thr Val Gly Val Ser Leu Asn Asn Asp Leu Glu Asn Arg Glu Met
    130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gln Gly Glu Ile Tyr Ile Asp Arg Ile Met Phe Ser
            180                 185                 190

Val Asp Asp Ala Arg Tyr Gln Trp Ser Asp Tyr Gln Val Lys Thr Arg
        195                 200                 205

Leu Ser Glu Pro Glu Ile Gln Phe His Asn Val Lys Pro Gln Leu Pro
    210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Glu
                245                 250                 255

Glu Asn Ile Ser Lys Leu Lys Ser Asp Phe Asp Ala Leu Asn Thr His
            260                 265                 270

Thr Leu Ala Asn Gly Gly Thr Gln Gly Arg His Leu Ile Thr Asp Lys
        275                 280                 285

Gln Ile Ile Ile Tyr Gln Pro Glu Asn Leu Asn Ser Gln Asp Lys Gln
    290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                325                 330                 335
```

```
Gln Leu Lys Gln Met Tyr Leu Leu Met Thr Lys His Leu Leu Asp Gln
                340                 345                 350

Gly Phe Val Lys Gly Ser Ala Leu Val Thr Thr His His Trp Gly Tyr
            355                 360                 365

Ser Ser Arg Trp Trp Tyr Ile Ser Thr Leu Leu Met Ser Asp Ala Leu
    370                 375                 380

Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
                405                 410                 415

Ser Asp Leu Asp Tyr Phe Asn Thr Leu Ser Arg Gln His Leu Ala Leu
            420                 425                 430

Leu Leu Leu Glu Pro Asp Asp Gln Lys Arg Ile Asn Leu Val Asn Thr
        435                 440                 445

Phe Ser His Tyr Ile Thr Gly Ala Leu Thr Gln Val Pro Pro Gly Gly
    450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                485                 490                 495

Tyr Leu Leu Arg Asp Thr Pro Phe Ser Val Gly Glu Ser Gly Trp Asn
            500                 505                 510

Asn Leu Lys Lys Ala Met Val Ser Ala Trp Ile Tyr Ser Asn Pro Glu
        515                 520                 525

Val Gly Leu Pro Leu Ala Gly Arg His Pro Phe Asn Ser Pro Ser Leu
    530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gln Asn Glu Ser Thr Ala Ile Phe Gly Thr Ile Thr Pro Ala
            580                 585                 590

Ser Leu Pro Gln Gly Phe Tyr Ala Phe Asn Gly Gly Ala Phe Gly Ile
        595                 600                 605

His Arg Trp Gln Asp Lys Met Val Thr Leu Lys Ala Tyr Asn Thr Asn
    610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
                645                 650                 655

Gln Gly Tyr Gln Gln Glu Gly Trp Asp Trp Asn Arg Met Glu Gly Ala
            660                 665                 670

Thr Thr Ile His Leu Pro Leu Lys Asp Leu Asp Ser Pro Lys Pro His
        675                 680                 685

Thr Leu Met Gln Arg Gly Glu Arg Gly Phe Ser Gly Thr Ser Ser Leu
    690                 695                 700

Glu Gly Gln Tyr Gly Met Met Ala Phe Asn Leu Ile Tyr Pro Ala Asn
705                 710                 715                 720

Leu Glu Arg Phe Asp Pro Asn Phe Thr Ala Lys Lys Ser Val Leu Ala
                725                 730                 735

Ala Asp Asn His Leu Ile Phe Ile Gly Ser Asn Ile Asn Ser Ser Asp
            740                 745                 750

Lys Asn Lys Asn Val Glu Thr Thr Leu Phe Gln His Ala Ile Thr Pro
```

```
                755                 760                 765
Thr Leu Asn Thr Leu Trp Ile Asn Gly Gln Lys Ile Glu Asn Met Pro
770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
                805                 810                 815

His Gln Val Ser Ala Glu Asn Lys Asn Arg Gln Pro Thr Glu Gly Asn
                820                 825                 830

Phe Ser Ser Ala Trp Ile Asp His Ser Thr Arg Pro Lys Asp Ala Ser
                835                 840                 845

Tyr Glu Tyr Met Val Phe Leu Asp Ala Thr Pro Glu Lys Met Gly Glu
850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                885                 890                 895

Gly Tyr Ala Phe Tyr Gln Pro Ala Ser Ile Glu Asp Lys Trp Ile Lys
                900                 905                 910

Lys Val Asn Lys Pro Ala Ile Val Met Thr His Arg Gln Lys Asp Thr
                915                 920                 925

Leu Ile Val Ser Ala Val Thr Pro Asp Leu Asn Met Thr Arg Gln Lys
930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
                965                 970                 975

Thr Glu Leu Thr Phe Thr Ser Tyr Phe Gly Ile Pro Gln Glu Ile Lys
                980                 985                 990

Leu Ser Pro Leu Pro Cys Ile Ala Leu Leu Val Val Gly Ile Met Cys
                995                 1000                1005

Val Val Ala Tyr Cys Lys Thr Lys Lys Gln Arg Lys Lys Leu His
    1010                1015                1020

Asp Arg Leu Arg Gln Ser Leu Arg Ser Glu Arg Asn Asn Met Met
    1025                1030                1035

Asn Ile Ala Asn Gly Pro His His Pro Asn Pro Pro Glu Asn
    1040                1045                1050

Val Gln Leu Val Asn Gln Tyr Val Ser Lys Asn Val Ile Ser Ser
    1055                1060                1065

Glu His Ile Val Glu Arg Glu Ala Glu Thr Ser Phe Ser Thr Ser
    1070                1075                1080

His Tyr Thr Ser Thr Ala His His Ser Thr Val Thr Gln Thr
    1085                1090                1095

Pro Ser His Ser Trp Ser Asn Gly His Thr Glu Ser Ile Leu Ser
    1100                1105                1110

Glu Ser His Ser Val Ile Val Met Ser Ser Val Glu Asn Ser Arg
    1115                1120                1125

His Ser Ser Pro Thr Gly Gly Pro Arg Gly Arg Leu Asn Gly Thr
    1130                1135                1140

Gly Gly Pro Arg Glu Cys Asn
    1145                1150

<210> SEQ ID NO 25
```

<211> LENGTH: 1170
<212> TYPE: PRT
<213> ORGANISM: Artificial
<220> FEATURE:
<223> OTHER INFORMATION: Synthetic polypeptide, C terminal fusion
      Chimera between ABCI-FL and GGF2-L(sub)250-E(sub)422

<400> SEQUENCE: 25

```
Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45

Gln Ser Leu Leu Trp Lys Trp Lys Gly Gly Ser Ser Phe Thr Leu His
50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95

Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Thr Val Gly Val Ser Leu Asn Asn Asp Leu Glu Asn Arg Glu Met
130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gln Gly Glu Ile Tyr Ile Asp Arg Ile Met Phe Ser
            180                 185                 190

Val Asp Asp Ala Arg Tyr Gln Trp Ser Asp Tyr Gln Val Lys Thr Arg
        195                 200                 205

Leu Ser Glu Pro Glu Ile Gln Phe His Asn Val Lys Pro Gln Leu Pro
210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Glu
                245                 250                 255

Glu Asn Ile Ser Lys Leu Lys Ser Asp Phe Asp Ala Leu Asn Thr His
            260                 265                 270

Thr Leu Ala Asn Gly Gly Thr Gln Gly Arg His Leu Ile Thr Asp Lys
        275                 280                 285

Gln Ile Ile Ile Tyr Gln Pro Glu Asn Leu Asn Ser Gln Asp Lys Gln
290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                325                 330                 335

Gln Leu Lys Gln Met Tyr Leu Leu Met Thr Lys His Leu Leu Asp Gln
            340                 345                 350

Gly Phe Val Lys Gly Ser Ala Leu Val Thr Thr His His Trp Gly Tyr
        355                 360                 365

Ser Ser Arg Trp Trp Tyr Ile Ser Thr Leu Leu Met Ser Asp Ala Leu
```

```
                370                 375                 380
Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
                405                 410                 415

Ser Asp Leu Asp Tyr Phe Asn Thr Leu Ser Arg Gln His Leu Ala Leu
                420                 425                 430

Leu Leu Leu Glu Pro Asp Asp Gln Lys Arg Ile Asn Leu Val Asn Thr
            435                 440                 445

Phe Ser His Tyr Ile Thr Gly Ala Leu Thr Gln Val Pro Pro Gly Gly
            450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                485                 490                 495

Tyr Leu Leu Arg Asp Thr Pro Phe Ser Val Gly Glu Ser Gly Trp Asn
                500                 505                 510

Asn Leu Lys Lys Ala Met Val Ser Ala Trp Ile Tyr Ser Asn Pro Glu
            515                 520                 525

Val Gly Leu Pro Leu Ala Gly Arg His Pro Phe Asn Ser Pro Ser Leu
            530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gln Asn Glu Ser Thr Ala Ile Phe Gly Glu Thr Ile Thr Pro Ala
                580                 585                 590

Ser Leu Pro Gln Gly Phe Tyr Ala Phe Asn Gly Gly Ala Phe Gly Ile
            595                 600                 605

His Arg Trp Gln Asp Lys Met Val Thr Leu Lys Ala Tyr Asn Thr Asn
            610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
                645                 650                 655

Gln Gly Tyr Gln Gln Glu Gly Trp Asp Trp Asn Arg Met Glu Gly Ala
                660                 665                 670

Thr Thr Ile His Leu Pro Leu Lys Asp Leu Asp Ser Pro Lys Pro His
            675                 680                 685

Thr Leu Met Gln Arg Gly Glu Arg Gly Phe Ser Gly Thr Ser Ser Leu
            690                 695                 700

Glu Gly Gln Tyr Gly Met Met Ala Phe Asn Leu Ile Tyr Pro Ala Asn
705                 710                 715                 720

Leu Glu Arg Phe Asp Pro Asn Phe Thr Ala Lys Lys Ser Val Leu Ala
                725                 730                 735

Ala Asp Asn His Leu Ile Phe Ile Gly Ser Asn Ile Asn Ser Ser Asp
                740                 745                 750

Lys Asn Lys Asn Val Glu Thr Thr Leu Phe Gln His Ala Ile Thr Pro
            755                 760                 765

Thr Leu Asn Thr Leu Trp Ile Asn Gly Gln Lys Ile Glu Asn Met Pro
            770                 775                 780

Tyr Gln Thr Thr Leu Gln Gln Gly Asp Trp Leu Ile Asp Ser Asn Gly
785                 790                 795                 800
```

Asn Gly Tyr Leu Ile Thr Gln Ala Glu Lys Val Asn Val Ser Arg Gln
            805                 810                 815

His Gln Val Ser Ala Glu Asn Lys Asn Arg Gln Pro Thr Glu Gly Asn
        820                 825                 830

Phe Ser Ser Ala Trp Ile Asp His Ser Thr Arg Pro Lys Asp Ala Ser
    835                 840                 845

Tyr Glu Tyr Met Val Phe Leu Asp Ala Thr Pro Glu Lys Met Gly Glu
850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                885                 890                 895

Gly Tyr Ala Phe Tyr Gln Pro Ala Ser Ile Glu Asp Lys Trp Ile Lys
            900                 905                 910

Lys Val Asn Lys Pro Ala Ile Val Met Thr His Arg Gln Lys Asp Thr
        915                 920                 925

Leu Ile Val Ser Ala Val Thr Pro Asp Leu Asn Met Thr Arg Gln Lys
    930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
                965                 970                 975

Thr Glu Leu Thr Phe Thr Ser Tyr Phe Gly Ile Pro Gln Glu Ile Lys
            980                 985                 990

Leu Ser Pro Leu Pro Cys Ile Ala Leu Leu Val Val Gly Ile Met Cys
        995                 1000                1005

Val Val Ala Tyr Cys Lys Thr Lys Lys Gln Arg Lys Lys Leu His
        1010                1015                1020

Asp Arg Leu Arg Gln Ser Leu Arg Ser Glu Arg Asn Asn Met Met
        1025                1030                1035

Asn Ile Ala Asn Gly Pro His His Pro Asn Pro Pro Pro Glu Asn
        1040                1045                1050

Val Gln Leu Val Asn Gln Tyr Val Ser Lys Asn Val Ile Ser Ser
        1055                1060                1065

Glu His Ile Val Glu Arg Glu Ala Glu Thr Ser Phe Ser Thr Ser
        1070                1075                1080

His Tyr Thr Ser Thr Ala His His Ser Thr Thr Val Thr Gln Thr
        1085                1090                1095

Pro Ser His Ser Trp Ser Asn Gly His Thr Glu Ser Ile Leu Ser
        1100                1105                1110

Glu Ser His Ser Val Ile Val Met Ser Ser Val Glu Asn Ser Arg
        1115                1120                1125

His Ser Ser Pro Thr Gly Gly Pro Arg Gly Arg Leu Asn Gly Thr
        1130                1135                1140

Gly Gly Pro Arg Glu Cys Asn Ser Phe Leu Arg His Ala Arg Glu
        1145                1150                1155

Thr Pro Asp Ser Tyr Arg Asp Ser Pro His Ser Glu
        1160                1165                1170

<210> SEQ ID NO 26
<211> LENGTH: 1050
<212> TYPE: PRT
<213> ORGANISM: Artificial
<220> FEATURE:

<223> OTHER INFORMATION: Synthetic polypeptide, C terminal fusion
      Chimera between chondroitinase ABCI-FL and
      GGF2-T(sub)350-C(sub)402

<400> SEQUENCE: 26

| Ala | Thr | Ser | Asn | Pro | Ala | Phe | Asp | Pro | Lys | Asn | Leu | Met | Gln | Ser | Glu |
|---|---|---|---|---|---|---|---|---|---|---|---|---|---|---|---|
| 1 | | | | 5 | | | | | 10 | | | | | 15 | |

| Ile | Tyr | His | Phe | Ala | Gln | Asn | Asn | Pro | Leu | Ala | Asp | Phe | Ser | Ser | Asp |
|---|---|---|---|---|---|---|---|---|---|---|---|---|---|---|---|
| | | | 20 | | | | | 25 | | | | | 30 | | |

| Lys | Asn | Ser | Ile | Leu | Thr | Leu | Ser | Asp | Lys | Arg | Ser | Ile | Met | Gly | Asn |
|---|---|---|---|---|---|---|---|---|---|---|---|---|---|---|---|
| | | 35 | | | | | 40 | | | | | 45 | | | |

| Gln | Ser | Leu | Leu | Trp | Lys | Trp | Lys | Gly | Gly | Ser | Ser | Phe | Thr | Leu | His |
|---|---|---|---|---|---|---|---|---|---|---|---|---|---|---|---|
| | 50 | | | | | 55 | | | | | 60 | | | | |

| Lys | Lys | Leu | Ile | Val | Pro | Thr | Asp | Lys | Glu | Ala | Ser | Lys | Ala | Trp | Gly |
|---|---|---|---|---|---|---|---|---|---|---|---|---|---|---|---|
| 65 | | | | | 70 | | | | | 75 | | | | | 80 |

| Arg | Ser | Ser | Thr | Pro | Val | Phe | Ser | Phe | Trp | Leu | Tyr | Asn | Glu | Lys | Pro |
|---|---|---|---|---|---|---|---|---|---|---|---|---|---|---|---|
| | | | | 85 | | | | | 90 | | | | | 95 | |

| Ile | Asp | Gly | Tyr | Leu | Thr | Ile | Asp | Phe | Gly | Lys | Leu | Ile | Ser | Thr |
|---|---|---|---|---|---|---|---|---|---|---|---|---|---|---|
| | | | 100 | | | | | 105 | | | | | 110 | |

| Ser | Glu | Ala | Gln | Ala | Gly | Phe | Lys | Val | Lys | Leu | Asp | Phe | Thr | Gly | Trp |
|---|---|---|---|---|---|---|---|---|---|---|---|---|---|---|---|
| | | 115 | | | | | 120 | | | | | 125 | | | |

| Arg | Thr | Val | Gly | Val | Ser | Leu | Asn | Asn | Asp | Leu | Glu | Asn | Arg | Glu | Met |
|---|---|---|---|---|---|---|---|---|---|---|---|---|---|---|---|
| | 130 | | | | | 135 | | | | | 140 | | | | |

| Thr | Leu | Asn | Ala | Thr | Asn | Thr | Ser | Ser | Asp | Gly | Thr | Gln | Asp | Ser | Ile |
|---|---|---|---|---|---|---|---|---|---|---|---|---|---|---|---|
| 145 | | | | | 150 | | | | | 155 | | | | | 160 |

| Gly | Arg | Ser | Leu | Gly | Ala | Lys | Val | Asp | Ser | Ile | Arg | Phe | Lys | Ala | Pro |
|---|---|---|---|---|---|---|---|---|---|---|---|---|---|---|---|
| | | | | 165 | | | | | 170 | | | | | 175 | |

| Ser | Asn | Val | Ser | Gln | Gly | Glu | Ile | Tyr | Ile | Asp | Arg | Ile | Met | Phe | Ser |
|---|---|---|---|---|---|---|---|---|---|---|---|---|---|---|---|
| | | | 180 | | | | | 185 | | | | | 190 | | |

| Val | Asp | Asp | Ala | Arg | Tyr | Gln | Trp | Ser | Asp | Tyr | Gln | Val | Lys | Thr | Arg |
|---|---|---|---|---|---|---|---|---|---|---|---|---|---|---|---|
| | | 195 | | | | | 200 | | | | | 205 | | | |

| Leu | Ser | Glu | Pro | Glu | Ile | Gln | Phe | His | Asn | Val | Lys | Pro | Gln | Leu | Pro |
|---|---|---|---|---|---|---|---|---|---|---|---|---|---|---|---|
| | 210 | | | | | 215 | | | | | 220 | | | | |

| Val | Thr | Pro | Glu | Asn | Leu | Ala | Ala | Ile | Asp | Leu | Ile | Arg | Gln | Arg | Leu |
|---|---|---|---|---|---|---|---|---|---|---|---|---|---|---|---|
| 225 | | | | | 230 | | | | | 235 | | | | | 240 |

| Ile | Asn | Glu | Phe | Val | Gly | Gly | Glu | Lys | Glu | Thr | Asn | Leu | Ala | Leu | Glu |
|---|---|---|---|---|---|---|---|---|---|---|---|---|---|---|---|
| | | | | 245 | | | | | 250 | | | | | 255 | |

| Glu | Asn | Ile | Ser | Lys | Leu | Lys | Ser | Asp | Phe | Asp | Ala | Leu | Asn | Thr | His |
|---|---|---|---|---|---|---|---|---|---|---|---|---|---|---|---|
| | | | 260 | | | | | 265 | | | | | 270 | | |

| Thr | Leu | Ala | Asn | Gly | Gly | Thr | Gln | Gly | Arg | His | Leu | Ile | Thr | Asp | Lys |
|---|---|---|---|---|---|---|---|---|---|---|---|---|---|---|---|
| | | 275 | | | | | 280 | | | | | 285 | | | |

| Gln | Ile | Ile | Ile | Tyr | Gln | Pro | Glu | Asn | Leu | Asn | Ser | Gln | Asp | Lys | Gln |
|---|---|---|---|---|---|---|---|---|---|---|---|---|---|---|---|
| | 290 | | | | | 295 | | | | | 300 | | | | |

| Leu | Phe | Asp | Asn | Tyr | Val | Ile | Leu | Gly | Asn | Tyr | Thr | Thr | Leu | Met | Phe |
|---|---|---|---|---|---|---|---|---|---|---|---|---|---|---|---|
| 305 | | | | | 310 | | | | | 315 | | | | | 320 |

| Asn | Ile | Ser | Arg | Ala | Tyr | Val | Leu | Glu | Lys | Asp | Pro | Thr | Gln | Lys | Ala |
|---|---|---|---|---|---|---|---|---|---|---|---|---|---|---|---|
| | | | | 325 | | | | | 330 | | | | | 335 | |

| Gln | Leu | Lys | Gln | Met | Tyr | Leu | Leu | Met | Thr | Lys | His | Leu | Leu | Asp | Gln |
|---|---|---|---|---|---|---|---|---|---|---|---|---|---|---|---|
| | | | 340 | | | | | 345 | | | | | 350 | | |

| Gly | Phe | Val | Lys | Gly | Ser | Ala | Leu | Val | Thr | Thr | His | His | Trp | Gly | Tyr |
|---|---|---|---|---|---|---|---|---|---|---|---|---|---|---|---|
| | | | 355 | | | | | 360 | | | | | 365 | | |

| Ser | Ser | Arg | Trp | Trp | Tyr | Ile | Ser | Thr | Leu | Leu | Met | Ser | Asp | Ala | Leu |
|---|---|---|---|---|---|---|---|---|---|---|---|---|---|---|---|
| | | 370 | | | | | 375 | | | | | 380 | | | |

| Lys | Glu | Ala | Asn | Leu | Gln | Thr | Gln | Val | Tyr | Asp | Ser | Leu | Leu | Trp | Tyr |

-continued

```
                385                 390                 395                 400
        Ser Arg Glu Phe Lys Ser Ser Phe Asp Met Lys Val Ser Ala Asp Ser
                        405                 410                 415

Ser Asp Leu Asp Tyr Phe Asn Thr Leu Ser Arg Gln His Leu Ala Leu
                        420                 425                 430

Leu Leu Leu Glu Pro Asp Asp Gln Lys Arg Ile Asn Leu Val Asn Thr
                        435                 440                 445

Phe Ser His Tyr Ile Thr Gly Ala Leu Thr Gln Val Pro Pro Gly Gly
                        450                 455                 460

Lys Asp Gly Leu Arg Pro Asp Gly Thr Ala Trp Arg His Glu Gly Asn
        465                 470                 475                 480

Tyr Pro Gly Tyr Ser Phe Pro Ala Phe Lys Asn Ala Ser Gln Leu Ile
                        485                 490                 495

Tyr Leu Leu Arg Asp Thr Pro Phe Ser Val Gly Glu Ser Gly Trp Asn
                        500                 505                 510

Asn Leu Lys Lys Ala Met Val Ser Ala Trp Ile Tyr Ser Asn Pro Glu
                        515                 520                 525

Val Gly Leu Pro Leu Ala Gly Arg His Pro Phe Asn Ser Pro Ser Leu
                        530                 535                 540

Lys Ser Val Ala Gln Gly Tyr Tyr Trp Leu Ala Met Ser Ala Lys Ser
        545                 550                 555                 560

Ser Pro Asp Lys Thr Leu Ala Ser Ile Tyr Leu Ala Ile Ser Asp Lys
                        565                 570                 575

Thr Gln Asn Glu Ser Thr Ala Ile Phe Gly Glu Thr Ile Thr Pro Ala
                        580                 585                 590

Ser Leu Pro Gln Gly Phe Tyr Ala Phe Asn Gly Gly Ala Phe Gly Ile
                        595                 600                 605

His Arg Trp Gln Asp Lys Met Val Thr Leu Lys Ala Tyr Asn Thr Asn
                        610                 615                 620

Val Trp Ser Ser Glu Ile Tyr Asn Lys Asp Asn Arg Tyr Gly Arg Tyr
        625                 630                 635                 640

Gln Ser His Gly Val Ala Gln Ile Val Ser Asn Gly Ser Gln Leu Ser
                        645                 650                 655

Gln Gly Tyr Gln Gln Glu Gly Trp Asp Trp Asn Arg Met Glu Gly Ala
                        660                 665                 670

Thr Thr Ile His Leu Pro Leu Lys Asp Leu Asp Ser Pro Lys Pro His
                        675                 680                 685

Thr Leu Met Gln Arg Gly Glu Arg Gly Phe Ser Gly Thr Ser Ser Leu
                        690                 695                 700

Glu Gly Gln Tyr Gly Met Met Ala Phe Asn Leu Ile Tyr Pro Ala Asn
        705                 710                 715                 720

Leu Glu Arg Phe Asp Pro Asn Phe Thr Ala Lys Lys Ser Val Leu Ala
                        725                 730                 735

Ala Asp Asn His Leu Ile Phe Ile Gly Ser Asn Ile Asn Ser Ser Asp
                        740                 745                 750

Lys Asn Lys Asn Val Glu Thr Thr Leu Phe Gln His Ala Ile Thr Pro
                        755                 760                 765

Thr Leu Asn Thr Leu Trp Ile Asn Gly Gln Lys Ile Glu Asn Met Pro
                        770                 775                 780

Tyr Gln Thr Thr Leu Gln Gln Gly Asp Trp Leu Ile Asp Ser Asn Gly
        785                 790                 795                 800

Asn Gly Tyr Leu Ile Thr Gln Ala Glu Lys Val Asn Val Ser Arg Gln
                        805                 810                 815
```

```
His Gln Val Ser Ala Glu Asn Lys Asn Arg Gln Pro Thr Glu Gly Asn
            820                 825                 830

Phe Ser Ser Ala Trp Ile Asp His Ser Thr Arg Pro Lys Asp Ala Ser
            835                 840                 845

Tyr Glu Tyr Met Val Phe Leu Asp Ala Thr Pro Glu Lys Met Gly Glu
850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                885                 890                 895

Gly Tyr Ala Phe Tyr Gln Pro Ala Ser Ile Glu Asp Lys Trp Ile Lys
                900                 905                 910

Lys Val Asn Lys Pro Ala Ile Val Met Thr His Arg Gln Lys Asp Thr
                915                 920                 925

Leu Ile Val Ser Ala Val Thr Pro Asp Leu Asn Met Thr Arg Gln Lys
            930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
                965                 970                 975

Thr Glu Leu Thr Phe Thr Ser Tyr Phe Gly Ile Pro Gln Glu Ile Lys
                980                 985                 990

Leu Ser Pro Leu Pro Thr Pro Ser His Ser Trp Ser Asn Gly His Thr
            995                 1000                1005

Glu Ser Ile Leu Ser Glu Ser His Ser Val Ile Val Met Ser Ser
    1010                1015                1020

Val Glu Asn Ser Arg His Ser Ser Pro Thr Gly Gly Pro Arg Gly
    1025                1030                1035

Arg Leu Asn Gly Thr Gly Gly Pro Arg Glu Cys Asn
    1040                1045                1050

<210> SEQ ID NO 27
<211> LENGTH: 1281
<212> TYPE: PRT
<213> ORGANISM: Artificial
<220> FEATURE:
<223> OTHER INFORMATION: Synthetic polypeptide, N terminal fusion
      chimera between NgR(sub)27-311 and chondroitinase ABCI without a
      peptide spacer or linking group

<400> SEQUENCE: 27

Cys Pro Gly Ala Cys Val Cys Tyr Asn Glu Pro Lys Val Thr Thr Ser
1               5                   10                  15

Cys Pro Gln Gln Gly Leu Gln Ala Val Pro Val Gly Ile Pro Ala Ala
            20                  25                  30

Ser Gln Arg Ile Phe Leu His Gly Asn Arg Ile Ser His Val Pro Ala
            35                  40                  45

Ala Ser Phe Arg Ala Cys Arg Asn Leu Thr Ile Leu Trp Leu His Ser
        50                  55                  60

Asn Val Leu Ala Arg Ile Asp Ala Ala Ala Phe Thr Gly Leu Ala Leu
65                  70                  75                  80

Leu Glu Gln Leu Asp Leu Ser Asp Asn Ala Gln Leu Arg Ser Val Asp
                85                  90                  95

Pro Ala Thr Phe His Gly Leu Gly Arg Leu His Thr Leu His Leu Asp
            100                 105                 110
```

```
Arg Cys Gly Leu Gln Glu Leu Gly Pro Gly Leu Phe Arg Gly Leu Ala
            115                 120                 125

Ala Leu Gln Tyr Leu Tyr Leu Gln Asp Asn Ala Leu Gln Ala Leu Pro
    130                 135                 140

Asp Asp Thr Phe Arg Asp Leu Gly Asn Leu Thr His Leu Phe Leu His
145                 150                 155                 160

Gly Asn Arg Ile Ser Ser Val Pro Glu Arg Ala Phe Arg Gly Leu His
                165                 170                 175

Ser Leu Asp Arg Leu Leu Leu His Gln Asn Arg Val Ala His Val His
            180                 185                 190

Pro His Ala Phe Arg Asp Leu Gly Arg Leu Met Thr Leu Tyr Leu Phe
    195                 200                 205

Ala Asn Asn Leu Ser Ala Leu Pro Thr Glu Ala Leu Ala Pro Leu Arg
210                 215                 220

Ala Leu Gln Tyr Leu Arg Leu Asn Asp Asn Pro Trp Val Cys Asp Cys
225                 230                 235                 240

Arg Ala Arg Pro Leu Trp Ala Trp Leu Gln Lys Phe Arg Gly Ser Ser
                245                 250                 255

Ser Glu Val Pro Cys Ser Leu Pro Gln Arg Leu Ala Gly Arg Asp Leu
            260                 265                 270

Lys Arg Leu Ala Ala Asn Asp Leu Gln Gly Cys Ala Val Ala Thr Ser
    275                 280                 285

Asn Pro Ala Phe Asp Pro Lys Asn Leu Met Gln Ser Glu Ile Tyr His
290                 295                 300

Phe Ala Gln Asn Asn Pro Leu Ala Asp Phe Ser Ser Asp Lys Asn Ser
305                 310                 315                 320

Ile Leu Thr Leu Ser Asp Lys Arg Ser Ile Met Gly Asn Gln Ser Leu
                325                 330                 335

Leu Trp Lys Trp Lys Gly Gly Ser Ser Phe Thr Leu His Lys Lys Leu
            340                 345                 350

Ile Val Pro Thr Asp Lys Glu Ala Ser Lys Ala Trp Gly Arg Ser Ser
    355                 360                 365

Thr Pro Val Phe Ser Phe Trp Leu Tyr Asn Glu Lys Pro Ile Asp Gly
370                 375                 380

Tyr Leu Thr Ile Asp Phe Gly Glu Lys Leu Ile Ser Thr Ser Glu Ala
385                 390                 395                 400

Gln Ala Gly Phe Lys Val Lys Leu Asp Phe Thr Gly Trp Arg Thr Val
                405                 410                 415

Gly Val Ser Leu Asn Asn Asp Leu Glu Asn Arg Glu Met Thr Leu Asn
            420                 425                 430

Ala Thr Asn Thr Ser Ser Asp Gly Thr Gln Asp Ser Ile Gly Arg Ser
    435                 440                 445

Leu Gly Ala Lys Val Asp Ser Ile Arg Phe Lys Ala Pro Ser Asn Val
450                 455                 460

Ser Gln Gly Glu Ile Tyr Ile Asp Arg Ile Met Phe Ser Val Asp Asp
465                 470                 475                 480

Ala Arg Tyr Gln Trp Ser Asp Tyr Gln Val Lys Thr Arg Leu Ser Glu
                485                 490                 495

Pro Glu Ile Gln Phe His Asn Val Lys Pro Gln Leu Pro Val Thr Pro
            500                 505                 510

Glu Asn Leu Ala Ala Ile Asp Leu Ile Arg Gln Arg Leu Ile Asn Glu
    515                 520                 525

Phe Val Gly Gly Glu Lys Glu Thr Asn Leu Ala Leu Glu Glu Asn Ile
```

```
                530              535               540
Ser Lys Leu Lys Ser Asp Phe Asp Ala Leu Asn Thr His Thr Leu Ala
545                 550                 555                 560

Asn Gly Gly Thr Gln Gly Arg His Leu Ile Thr Asp Lys Gln Ile Ile
                    565                 570                 575

Ile Tyr Gln Pro Glu Asn Leu Asn Ser Gln Asp Lys Gln Leu Phe Asp
                580                 585                 590

Asn Tyr Val Ile Leu Gly Asn Tyr Thr Thr Leu Met Phe Asn Ile Ser
            595                 600                 605

Arg Ala Tyr Val Leu Glu Lys Asp Pro Thr Gln Lys Ala Gln Leu Lys
        610                 615                 620

Gln Met Tyr Leu Leu Met Thr Lys His Leu Leu Asp Gln Gly Phe Val
625                 630                 635                 640

Lys Gly Ser Ala Leu Val Thr Thr His His Trp Gly Tyr Ser Ser Arg
                    645                 650                 655

Trp Trp Tyr Ile Ser Thr Leu Leu Met Ser Asp Ala Leu Lys Glu Ala
                660                 665                 670

Asn Leu Gln Thr Gln Val Tyr Asp Ser Leu Leu Trp Tyr Ser Arg Glu
            675                 680                 685

Phe Lys Ser Ser Phe Asp Met Lys Val Ser Ala Asp Ser Ser Asp Leu
        690                 695                 700

Asp Tyr Phe Asn Thr Leu Ser Arg Gln His Leu Ala Leu Leu Leu Leu
705                 710                 715                 720

Glu Pro Asp Asp Gln Lys Arg Ile Asn Leu Val Asn Thr Phe Ser His
                    725                 730                 735

Tyr Ile Thr Gly Ala Leu Thr Gln Val Pro Pro Gly Gly Lys Asp Gly
                740                 745                 750

Leu Arg Pro Asp Gly Thr Ala Trp Arg His Glu Gly Asn Tyr Pro Gly
            755                 760                 765

Tyr Ser Phe Pro Ala Phe Lys Asn Ala Ser Gln Leu Ile Tyr Leu Leu
        770                 775                 780

Arg Asp Thr Pro Phe Ser Val Gly Glu Ser Gly Trp Asn Asn Leu Lys
785                 790                 795                 800

Lys Ala Met Val Ser Ala Trp Ile Tyr Ser Asn Pro Glu Val Gly Leu
                    805                 810                 815

Pro Leu Ala Gly Arg His Pro Phe Asn Ser Pro Ser Leu Lys Ser Val
                820                 825                 830

Ala Gln Gly Tyr Tyr Trp Leu Ala Met Ser Ala Lys Ser Ser Pro Asp
            835                 840                 845

Lys Thr Leu Ala Ser Ile Tyr Leu Ala Ile Ser Asp Lys Thr Gln Asn
        850                 855                 860

Glu Ser Thr Ala Ile Phe Gly Glu Thr Ile Thr Pro Ala Ser Leu Pro
865                 870                 875                 880

Gln Gly Phe Tyr Ala Phe Asn Gly Gly Ala Phe Gly Ile His Arg Trp
                    885                 890                 895

Gln Asp Lys Met Val Thr Leu Lys Ala Tyr Asn Thr Asn Val Trp Ser
                900                 905                 910

Ser Glu Ile Tyr Asn Lys Asp Asn Arg Tyr Gly Arg Tyr Gln Ser His
            915                 920                 925

Gly Val Ala Gln Ile Val Ser Asn Gly Ser Gln Leu Ser Gln Gly Tyr
        930                 935                 940

Gln Gln Glu Gly Trp Asp Trp Asn Arg Met Glu Gly Ala Thr Thr Ile
945                 950                 955                 960
```

```
His Leu Pro Leu Lys Asp Leu Asp Ser Pro Lys Pro His Thr Leu Met
            965                 970                 975

Gln Arg Gly Glu Arg Gly Phe Ser Gly Thr Ser Ser Leu Glu Gly Gln
            980                 985                 990

Tyr Gly Met Met Ala Phe Asn Leu Ile Tyr Pro Ala Asn Leu Glu Arg
        995                1000                1005

Phe Asp Pro Asn Phe Thr Ala Lys Lys Ser Val Leu Ala Ala Asp
    1010                1015                1020

Asn His Leu Ile Phe Ile Gly Ser Asn Ile Asn Ser Ser Asp Lys
    1025                1030                1035

Asn Lys Asn Val Glu Thr Thr Leu Phe Gln His Ala Ile Thr Pro
    1040                1045                1050

Thr Leu Asn Thr Leu Trp Ile Asn Gly Gln Lys Ile Glu Asn Met
    1055                1060                1065

Pro Tyr Gln Thr Thr Leu Gln Gln Gly Asp Trp Leu Ile Asp Ser
    1070                1075                1080

Asn Gly Asn Gly Tyr Leu Ile Thr Gln Ala Glu Lys Val Asn Val
    1085                1090                1095

Ser Arg Gln His Gln Val Ser Ala Glu Asn Lys Asn Arg Gln Pro
    1100                1105                1110

Thr Glu Gly Asn Phe Ser Ser Ala Trp Ile Asp His Ser Thr Arg
    1115                1120                1125

Pro Lys Asp Ala Ser Tyr Glu Tyr Met Val Phe Leu Asp Ala Thr
    1130                1135                1140

Pro Glu Lys Met Gly Glu Met Ala Gln Lys Phe Arg Glu Asn Asn
    1145                1150                1155

Gly Leu Tyr Gln Val Leu Arg Lys Asp Lys Asp Val His Ile Ile
    1160                1165                1170

Leu Asp Lys Leu Ser Asn Val Thr Gly Tyr Ala Phe Tyr Gln Pro
    1175                1180                1185

Ala Ser Ile Glu Asp Lys Trp Ile Lys Lys Val Asn Lys Pro Ala
    1190                1195                1200

Ile Val Met Thr His Arg Gln Lys Asp Thr Leu Ile Val Ser Ala
    1205                1210                1215

Val Thr Pro Asp Leu Asn Met Thr Arg Gln Lys Ala Ala Thr Pro
    1220                1225                1230

Val Thr Ile Asn Val Thr Ile Asn Gly Lys Trp Gln Ser Ala Asp
    1235                1240                1245

Lys Asn Ser Glu Val Lys Tyr Gln Val Ser Gly Asp Asn Thr Glu
    1250                1255                1260

Leu Thr Phe Thr Ser Tyr Phe Gly Ile Pro Gln Glu Ile Lys Leu
    1265                1270                1275

Ser Pro Leu
    1280

<210> SEQ ID NO 28
<211> LENGTH: 1287
<212> TYPE: PRT
<213> ORGANISM: Artificial
<220> FEATURE:
<223> OTHER INFORMATION: Synthetic polypeptide, N terminal fusion
      chimera between NgR(sub)27-311 and chondoitinase ABCI with a
      peptide spacer or linking group

<400> SEQUENCE: 28
```

-continued

```
Cys Pro Gly Ala Cys Val Cys Tyr Asn Glu Pro Lys Val Thr Thr Ser
1               5                   10                  15

Cys Pro Gln Gln Gly Leu Gln Ala Val Pro Val Gly Ile Pro Ala Ala
            20                  25                  30

Ser Gln Arg Ile Phe Leu His Gly Asn Arg Ile Ser His Val Pro Ala
            35                  40                  45

Ala Ser Phe Arg Ala Cys Arg Asn Leu Thr Ile Leu Trp Leu His Ser
        50                  55                  60

Asn Val Leu Ala Arg Ile Asp Ala Ala Phe Thr Gly Leu Ala Leu
65                  70                  75                  80

Leu Glu Gln Leu Asp Leu Ser Asp Asn Ala Gln Leu Arg Ser Val Asp
                85                  90                  95

Pro Ala Thr Phe His Gly Leu Gly Arg Leu His Thr Leu His Leu Asp
                100                 105                 110

Arg Cys Gly Leu Gln Glu Leu Gly Pro Gly Leu Phe Arg Gly Leu Ala
            115                 120                 125

Ala Leu Gln Tyr Leu Tyr Leu Gln Asp Asn Ala Leu Gln Ala Leu Pro
        130                 135                 140

Asp Asp Thr Phe Arg Asp Leu Gly Asn Leu Thr His Leu Phe Leu His
145                 150                 155                 160

Gly Asn Arg Ile Ser Ser Val Pro Glu Arg Ala Phe Arg Gly Leu His
                165                 170                 175

Ser Leu Asp Arg Leu Leu Leu His Gln Asn Arg Val Ala His Val His
            180                 185                 190

Pro His Ala Phe Arg Asp Leu Gly Arg Leu Met Thr Leu Tyr Leu Phe
        195                 200                 205

Ala Asn Asn Leu Ser Ala Leu Pro Thr Glu Ala Leu Ala Pro Leu Arg
        210                 215                 220

Ala Leu Gln Tyr Leu Arg Leu Asn Asp Asn Pro Trp Val Cys Asp Cys
225                 230                 235                 240

Arg Ala Arg Pro Leu Trp Ala Trp Leu Gln Lys Phe Arg Gly Ser Ser
                245                 250                 255

Ser Glu Val Pro Cys Ser Leu Pro Gln Arg Leu Ala Gly Arg Asp Leu
            260                 265                 270

Lys Arg Leu Ala Ala Asn Asp Leu Gln Gly Cys Ala Val Gly Gly Gly
        275                 280                 285

Gly Gly Ala Thr Ser Asn Pro Ala Phe Asp Pro Lys Asn Leu Met Gln
        290                 295                 300

Ser Glu Ile Tyr His Phe Ala Gln Asn Asn Pro Leu Ala Asp Phe Ser
305                 310                 315                 320

Ser Asp Lys Asn Ser Ile Leu Thr Leu Ser Asp Lys Arg Ser Ile Met
                325                 330                 335

Gly Asn Gln Ser Leu Leu Trp Lys Trp Lys Gly Gly Ser Ser Phe Thr
            340                 345                 350

Leu His Lys Lys Leu Ile Val Pro Thr Asp Lys Glu Ala Ser Lys Ala
        355                 360                 365

Trp Gly Arg Ser Ser Thr Pro Val Phe Ser Phe Trp Leu Tyr Asn Glu
        370                 375                 380

Lys Pro Ile Asp Gly Tyr Leu Thr Ile Asp Phe Gly Glu Lys Leu Ile
385                 390                 395                 400

Ser Thr Ser Glu Ala Gln Ala Gly Phe Lys Val Lys Leu Asp Phe Thr
                405                 410                 415

Gly Trp Arg Thr Val Gly Val Ser Leu Asn Asn Asp Leu Glu Asn Arg
```

```
                    420                 425                 430
Glu Met Thr Leu Asn Ala Thr Asn Thr Ser Ser Asp Gly Thr Gln Asp
            435                 440                 445

Ser Ile Gly Arg Ser Leu Gly Ala Lys Val Asp Ser Ile Arg Phe Lys
    450                 455                 460

Ala Pro Ser Asn Val Ser Gln Gly Glu Ile Tyr Ile Asp Arg Ile Met
465                 470                 475                 480

Phe Ser Val Asp Asp Ala Arg Tyr Gln Trp Ser Asp Tyr Gln Val Lys
                485                 490                 495

Thr Arg Leu Ser Glu Pro Glu Ile Gln Phe His Asn Val Lys Pro Gln
            500                 505                 510

Leu Pro Val Thr Pro Glu Asn Leu Ala Ala Ile Asp Leu Ile Arg Gln
        515                 520                 525

Arg Leu Ile Asn Glu Phe Val Gly Gly Glu Lys Glu Thr Asn Leu Ala
    530                 535                 540

Leu Glu Glu Asn Ile Ser Lys Leu Lys Ser Asp Phe Asp Ala Leu Asn
545                 550                 555                 560

Thr His Thr Leu Ala Asn Gly Gly Thr Gln Gly Arg His Leu Ile Thr
                565                 570                 575

Asp Lys Gln Ile Ile Tyr Gln Pro Glu Asn Leu Asn Ser Gln Asp
            580                 585                 590

Lys Gln Leu Phe Asp Asn Tyr Val Ile Leu Gly Asn Tyr Thr Thr Leu
        595                 600                 605

Met Phe Asn Ile Ser Arg Ala Tyr Val Leu Glu Lys Asp Pro Thr Gln
    610                 615                 620

Lys Ala Gln Leu Lys Gln Met Tyr Leu Leu Met Thr Lys His Leu Leu
625                 630                 635                 640

Asp Gln Gly Phe Val Lys Gly Ser Ala Leu Val Thr Thr His His Trp
                645                 650                 655

Gly Tyr Ser Ser Arg Trp Trp Tyr Ile Ser Thr Leu Leu Met Ser Asp
            660                 665                 670

Ala Leu Lys Glu Ala Asn Leu Gln Thr Gln Val Tyr Asp Ser Leu Leu
        675                 680                 685

Trp Tyr Ser Arg Glu Phe Lys Ser Ser Phe Asp Met Lys Val Ser Ala
    690                 695                 700

Asp Ser Ser Asp Leu Asp Tyr Phe Asn Thr Leu Ser Arg Gln His Leu
705                 710                 715                 720

Ala Leu Leu Leu Leu Glu Pro Asp Asp Gln Lys Arg Ile Asn Leu Val
                725                 730                 735

Asn Thr Phe Ser His Tyr Ile Thr Gly Ala Leu Thr Gln Val Pro Pro
            740                 745                 750

Gly Gly Lys Asp Gly Leu Arg Pro Asp Gly Thr Ala Trp Arg His Glu
        755                 760                 765

Gly Asn Tyr Pro Gly Tyr Ser Phe Pro Ala Phe Lys Asn Ala Ser Gln
    770                 775                 780

Leu Ile Tyr Leu Leu Arg Asp Thr Pro Phe Ser Val Gly Glu Ser Gly
785                 790                 795                 800

Trp Asn Asn Leu Lys Lys Ala Met Val Ser Ala Trp Ile Tyr Ser Asn
                805                 810                 815

Pro Glu Val Gly Leu Pro Leu Ala Gly Arg His Pro Phe Asn Ser Pro
            820                 825                 830

Ser Leu Lys Ser Val Ala Gln Gly Tyr Tyr Trp Leu Ala Met Ser Ala
        835                 840                 845
```

```
Lys Ser Ser Pro Asp Lys Thr Leu Ala Ser Ile Tyr Leu Ala Ile Ser
850                 855                 860

Asp Lys Thr Gln Asn Glu Ser Thr Ala Ile Phe Gly Glu Thr Ile Thr
865                 870                 875                 880

Pro Ala Ser Leu Pro Gln Gly Phe Tyr Ala Phe Asn Gly Gly Ala Phe
                885                 890                 895

Gly Ile His Arg Trp Gln Asp Lys Met Val Thr Leu Lys Ala Tyr Asn
                900                 905                 910

Thr Asn Val Trp Ser Ser Glu Ile Tyr Asn Lys Asp Asn Arg Tyr Gly
            915                 920                 925

Arg Tyr Gln Ser His Gly Val Ala Gln Ile Val Ser Asn Gly Ser Gln
            930                 935                 940

Leu Ser Gln Gly Tyr Gln Gln Glu Gly Trp Asp Trp Asn Arg Met Glu
945                 950                 955                 960

Gly Ala Thr Thr Ile His Leu Pro Leu Lys Asp Leu Asp Ser Pro Lys
                965                 970                 975

Pro His Thr Leu Met Gln Arg Gly Glu Arg Gly Phe Ser Gly Thr Ser
                980                 985                 990

Ser Leu Glu Gly Gln Tyr Gly Met Met Ala Phe Asn Leu Ile Tyr Pro
            995                 1000                1005

Ala Asn Leu Glu Arg Phe Asp Pro Asn Phe Thr Ala Lys Lys Ser
            1010                1015                1020

Val Leu Ala Ala Asp Asn His Leu Ile Phe Ile Gly Ser Asn Ile
            1025                1030                1035

Asn Ser Ser Asp Lys Asn Lys Asn Val Glu Thr Thr Leu Phe Gln
            1040                1045                1050

His Ala Ile Thr Pro Thr Leu Asn Thr Leu Trp Ile Asn Gly Gln
            1055                1060                1065

Lys Ile Glu Asn Met Pro Tyr Gln Thr Thr Leu Gln Gln Gly Asp
            1070                1075                1080

Trp Leu Ile Asp Ser Asn Gly Asn Gly Tyr Leu Ile Thr Gln Ala
            1085                1090                1095

Glu Lys Val Asn Val Ser Arg Gln His Gln Val Ser Ala Glu Asn
            1100                1105                1110

Lys Asn Arg Gln Pro Thr Glu Gly Asn Phe Ser Ser Ala Trp Ile
            1115                1120                1125

Asp His Ser Thr Arg Pro Lys Asp Ala Ser Tyr Glu Tyr Met Val
            1130                1135                1140

Phe Leu Asp Ala Thr Pro Glu Lys Met Gly Glu Met Ala Gln Lys
            1145                1150                1155

Phe Arg Glu Asn Asn Gly Leu Tyr Gln Val Leu Arg Lys Asp Lys
            1160                1165                1170

Asp Val His Ile Ile Leu Asp Lys Leu Ser Asn Val Thr Gly Tyr
            1175                1180                1185

Ala Phe Tyr Gln Pro Ala Ser Ile Glu Asp Lys Trp Ile Lys Lys
            1190                1195                1200

Val Asn Lys Pro Ala Ile Val Met Thr His Arg Gln Lys Asp Thr
            1205                1210                1215

Leu Ile Val Ser Ala Val Thr Pro Asp Leu Asn Met Thr Arg Gln
            1220                1225                1230

Lys Ala Ala Thr Pro Val Thr Ile Asn Val Thr Ile Asn Gly Lys
            1235                1240                1245
```

-continued

```
Trp Gln Ser Ala Asp Lys Asn Ser Glu Val Lys Tyr Gln Val Ser
    1250                1255                1260

Gly Asp Asn Thr Glu Leu Thr Phe Thr Ser Tyr Phe Gly Ile Pro
    1265                1270                1275

Gln Glu Ile Lys Leu Ser Pro Leu Pro
    1280                1285

<210> SEQ ID NO 29
<211> LENGTH: 1282
<212> TYPE: PRT
<213> ORGANISM: Artificial
<220> FEATURE:
<223> OTHER INFORMATION: Synthetic Polypeptide, C terminal fusion
      chimera between NgR(sub)27-311 and chondroitinase ABCI protein
      without a peptide spacer or linking group

<400> SEQUENCE: 29

Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45

Gln Ser Leu Leu Trp Lys Trp Lys Gly Gly Ser Ser Phe Thr Leu His
    50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95

Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Thr Val Gly Val Ser Leu Asn Asn Asp Leu Glu Asn Arg Glu Met
    130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gln Gly Glu Ile Tyr Ile Asp Arg Ile Met Phe Ser
            180                 185                 190

Val Asp Asp Ala Arg Tyr Gln Trp Ser Asp Tyr Gln Val Lys Thr Arg
        195                 200                 205

Leu Ser Glu Pro Glu Ile Gln Phe His Asn Val Lys Pro Gln Leu Pro
    210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Glu
                245                 250                 255

Glu Asn Ile Ser Lys Leu Lys Ser Asp Phe Asp Ala Leu Asn Thr His
            260                 265                 270

Thr Leu Ala Asn Gly Gly Thr Gln Gly Arg His Leu Ile Thr Asp Lys
        275                 280                 285

Gln Ile Ile Ile Tyr Gln Pro Glu Asn Leu Asn Ser Gln Asp Lys Gln
    290                 295                 300

Leu Phe Asp Asn Tyr Val Ile Leu Gly Asn Tyr Thr Thr Leu Met Phe
```

-continued

| | | | | | | | | | | | | | | | |
|---|---|---|---|---|---|---|---|---|---|---|---|---|---|---|---|
| | | 305 | | | | 310 | | | | 315 | | | | 320 | |
| Asn | Ile | Ser | Arg | Ala | Tyr | Val | Leu | Glu | Lys | Asp | Pro | Thr | Gln | Lys | Ala |
| | | | | 325 | | | | | 330 | | | | | 335 | |
| Gln | Leu | Lys | Gln | Met | Tyr | Leu | Leu | Met | Thr | Lys | His | Leu | Leu | Asp | Gln |
| | | | | 340 | | | | | 345 | | | | | 350 | |
| Gly | Phe | Val | Lys | Gly | Ser | Ala | Leu | Val | Thr | Thr | His | His | Trp | Gly | Tyr |
| | | | | 355 | | | | | 360 | | | | | 365 | |
| Ser | Ser | Arg | Trp | Trp | Tyr | Ile | Ser | Thr | Leu | Leu | Met | Ser | Asp | Ala | Leu |
| | | 370 | | | | | 375 | | | | | 380 | | | |
| Lys | Glu | Ala | Asn | Leu | Gln | Thr | Gln | Val | Tyr | Asp | Ser | Leu | Leu | Trp | Tyr |
| 385 | | | | | 390 | | | | | 395 | | | | | 400 |
| Ser | Arg | Glu | Phe | Lys | Ser | Ser | Phe | Asp | Met | Lys | Val | Ser | Ala | Asp | Ser |
| | | | | 405 | | | | | 410 | | | | | 415 | |
| Ser | Asp | Leu | Asp | Tyr | Phe | Asn | Thr | Leu | Ser | Arg | Gln | His | Leu | Ala | Leu |
| | | | | 420 | | | | | 425 | | | | | 430 | |
| Leu | Leu | Leu | Glu | Pro | Asp | Asp | Gln | Lys | Arg | Ile | Asn | Leu | Val | Asn | Thr |
| | | | 435 | | | | | 440 | | | | | 445 | | |
| Phe | Ser | His | Tyr | Ile | Thr | Gly | Ala | Leu | Thr | Gln | Val | Pro | Pro | Gly | Gly |
| | | | 450 | | | | | 455 | | | | | 460 | | |
| Lys | Asp | Gly | Leu | Arg | Pro | Asp | Gly | Thr | Ala | Trp | Arg | His | Glu | Gly | Asn |
| 465 | | | | | 470 | | | | | 475 | | | | | 480 |
| Tyr | Pro | Gly | Tyr | Ser | Phe | Pro | Ala | Phe | Lys | Asn | Ala | Ser | Gln | Leu | Ile |
| | | | | 485 | | | | | 490 | | | | | 495 | |
| Tyr | Leu | Leu | Arg | Asp | Thr | Pro | Phe | Ser | Val | Gly | Glu | Ser | Gly | Trp | Asn |
| | | | 500 | | | | | 505 | | | | | 510 | | |
| Asn | Leu | Lys | Lys | Ala | Met | Val | Ser | Ala | Trp | Ile | Tyr | Ser | Asn | Pro | Glu |
| | | 515 | | | | | 520 | | | | | 525 | | | |
| Val | Gly | Leu | Pro | Leu | Ala | Gly | Arg | His | Pro | Phe | Asn | Ser | Pro | Ser | Leu |
| | | 530 | | | | | 535 | | | | | 540 | | | |
| Lys | Ser | Val | Ala | Gln | Gly | Tyr | Tyr | Trp | Leu | Ala | Met | Ser | Ala | Lys | Ser |
| 545 | | | | | 550 | | | | | 555 | | | | | 560 |
| Ser | Pro | Asp | Lys | Thr | Leu | Ala | Ser | Ile | Tyr | Leu | Ala | Ile | Ser | Asp | Lys |
| | | | | 565 | | | | | 570 | | | | | 575 | |
| Thr | Gln | Asn | Glu | Ser | Thr | Ala | Ile | Phe | Gly | Glu | Thr | Ile | Thr | Pro | Ala |
| | | | | 580 | | | | | 585 | | | | | 590 | |
| Ser | Leu | Pro | Gln | Gly | Phe | Tyr | Ala | Phe | Asn | Gly | Gly | Ala | Phe | Gly | Ile |
| | | | 595 | | | | | 600 | | | | | 605 | | |
| His | Arg | Trp | Gln | Asp | Lys | Met | Val | Thr | Leu | Lys | Ala | Tyr | Asn | Thr | Asn |
| | | 610 | | | | | 615 | | | | | 620 | | | |
| Val | Trp | Ser | Ser | Glu | Ile | Tyr | Asn | Lys | Asp | Asn | Arg | Tyr | Gly | Arg | Tyr |
| 625 | | | | | 630 | | | | | 635 | | | | | 640 |
| Gln | Ser | His | Gly | Val | Ala | Gln | Ile | Val | Ser | Asn | Gly | Ser | Gln | Leu | Ser |
| | | | | 645 | | | | | 650 | | | | | 655 | |
| Gln | Gly | Tyr | Gln | Gln | Glu | Gly | Trp | Asp | Trp | Asn | Arg | Met | Glu | Gly | Ala |
| | | | 660 | | | | | 665 | | | | | 670 | | |
| Thr | Thr | Ile | His | Leu | Pro | Leu | Lys | Asp | Leu | Asp | Ser | Pro | Lys | Pro | His |
| | | | 675 | | | | | 680 | | | | | 685 | | |
| Thr | Leu | Met | Gln | Arg | Gly | Glu | Arg | Gly | Phe | Ser | Gly | Thr | Ser | Ser | Leu |
| | | | | 690 | | | | | 695 | | | | | 700 | |
| Glu | Gly | Gln | Tyr | Gly | Met | Met | Ala | Phe | Asn | Leu | Ile | Tyr | Pro | Ala | Asn |
| 705 | | | | | 710 | | | | | 715 | | | | | 720 |
| Leu | Glu | Arg | Phe | Asp | Pro | Asn | Phe | Thr | Ala | Lys | Lys | Ser | Val | Leu | Ala |
| | | | | 725 | | | | | 730 | | | | | 735 | |

```
Ala Asp Asn His Leu Ile Phe Ile Gly Ser Asn Ile Asn Ser Ser Asp
                740                 745                 750

Lys Asn Lys Asn Val Glu Thr Thr Leu Phe Gln His Ala Ile Thr Pro
            755                 760                 765

Thr Leu Asn Thr Leu Trp Ile Asn Gly Gln Lys Ile Glu Asn Met Pro
    770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
                805                 810                 815

His Gln Val Ser Ala Glu Asn Lys Asn Arg Gln Pro Thr Glu Gly Asn
            820                 825                 830

Phe Ser Ser Ala Trp Ile Asp His Ser Thr Arg Pro Lys Asp Ala Ser
        835                 840                 845

Tyr Glu Tyr Met Val Phe Leu Asp Ala Thr Pro Glu Lys Met Gly Glu
    850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                885                 890                 895

Gly Tyr Ala Phe Tyr Gln Pro Ala Ser Ile Glu Asp Lys Trp Ile Lys
            900                 905                 910

Lys Val Asn Lys Pro Ala Ile Val Met Thr His Arg Gln Lys Asp Thr
        915                 920                 925

Leu Ile Val Ser Ala Val Thr Pro Asp Leu Asn Met Thr Arg Gln Lys
    930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
                965                 970                 975

Thr Glu Leu Thr Phe Thr Ser Tyr Phe Gly Ile Pro Gln Glu Ile Lys
            980                 985                 990

Leu Ser Pro Leu Pro Cys Pro Gly Ala Cys Val Cys Tyr Asn Glu Pro
        995                 1000                1005

Lys Val Thr Thr Ser Cys Pro Gln Gln Gly Leu Gln Ala Val Pro
    1010                1015                1020

Val Gly Ile Pro Ala Ala Ser Gln Arg Ile Phe Leu His Gly Asn
    1025                1030                1035

Arg Ile Ser His Val Pro Ala Ala Ser Phe Arg Ala Cys Arg Asn
    1040                1045                1050

Leu Thr Ile Leu Trp Leu His Ser Asn Val Leu Ala Arg Ile Asp
    1055                1060                1065

Ala Ala Ala Phe Thr Gly Leu Ala Leu Leu Glu Gln Leu Asp Leu
    1070                1075                1080

Ser Asp Asn Ala Gln Leu Arg Ser Val Asp Pro Ala Thr Phe His
    1085                1090                1095

Gly Leu Gly Arg Leu His Thr Leu His Leu Asp Arg Cys Gly Leu
    1100                1105                1110

Gln Glu Leu Gly Pro Gly Leu Phe Arg Gly Leu Ala Ala Leu Gln
    1115                1120                1125

Tyr Leu Tyr Leu Gln Asp Asn Ala Leu Gln Ala Leu Pro Asp Asp
    1130                1135                1140
```

-continued

Thr Phe Arg Asp Leu Gly Asn Leu Thr His Leu Phe Leu His Gly
    1145                1150                1155

Asn Arg Ile Ser Ser Val Pro Glu Arg Ala Phe Arg Gly Leu His
    1160                1165                1170

Ser Leu Asp Arg Leu Leu Leu His Gln Asn Arg Val Ala His Val
    1175                1180                1185

His Pro His Ala Phe Arg Asp Leu Gly Arg Leu Met Thr Leu Tyr
    1190                1195                1200

Leu Phe Ala Asn Asn Leu Ser Ala Leu Pro Thr Glu Ala Leu Ala
    1205                1210                1215

Pro Leu Arg Ala Leu Gln Tyr Leu Arg Leu Asn Asp Asn Pro Trp
    1220                1225                1230

Val Cys Asp Cys Arg Ala Arg Pro Leu Trp Ala Trp Leu Gln Lys
    1235                1240                1245

Phe Arg Gly Ser Ser Ser Glu Val Pro Cys Ser Leu Pro Gln Arg
    1250                1255                1260

Leu Ala Gly Arg Asp Leu Lys Arg Leu Ala Ala Asn Asp Leu Gln
    1265                1270                1275

Gly Cys Ala Val
    1280

<210> SEQ ID NO 30
<211> LENGTH: 1287
<212> TYPE: PRT
<213> ORGANISM: Artificial
<220> FEATURE:
<223> OTHER INFORMATION: Synthetic polypeptide, C terminal fusion
      chimera between NgR(sub)27-311 and chondroitinase ABCI protein
      with a peptide spacer or linking group

<400> SEQUENCE: 30

Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45

Gln Ser Leu Leu Trp Lys Trp Lys Gly Gly Ser Ser Phe Thr Leu His
    50                  55                  60

Lys Lys Leu Ile Val Pro Thr Asp Lys Glu Ala Ser Lys Ala Trp Gly
65                  70                  75                  80

Arg Ser Thr Pro Val Phe Ser Phe Trp Leu Tyr Asn Glu Lys Pro
                85                  90                  95

Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Thr Val Gly Val Ser Leu Asn Asn Asp Leu Glu Asn Arg Glu Met
    130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gln Gly Glu Ile Tyr Ile Asp Arg Ile Met Phe Ser
            180                 185                 190

Val Asp Asp Ala Arg Tyr Gln Trp Ser Asp Tyr Gln Val Lys Thr Arg

```
                195                 200                 205
Leu Ser Glu Pro Glu Ile Gln Phe His Asn Val Lys Pro Gln Leu Pro
    210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Glu
                245                 250                 255

Glu Asn Ile Ser Lys Leu Lys Ser Asp Phe Asp Ala Leu Asn Thr His
            260                 265                 270

Thr Leu Ala Asn Gly Gly Thr Gln Gly Arg His Leu Ile Thr Asp Lys
        275                 280                 285

Gln Ile Ile Ile Tyr Gln Pro Glu Asn Leu Asn Ser Gln Asp Lys Gln
    290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                325                 330                 335

Gln Leu Lys Gln Met Tyr Leu Leu Met Thr Lys His Leu Leu Asp Gln
            340                 345                 350

Gly Phe Val Lys Gly Ser Ala Leu Val Thr Thr His Trp Gly Tyr
        355                 360                 365

Ser Ser Arg Trp Trp Tyr Ile Ser Thr Leu Leu Met Ser Asp Ala Leu
    370                 375                 380

Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
                405                 410                 415

Ser Asp Leu Asp Tyr Phe Asn Thr Leu Ser Arg Gln His Leu Ala Leu
            420                 425                 430

Leu Leu Leu Glu Pro Asp Asp Gln Lys Arg Ile Asn Leu Val Asn Thr
        435                 440                 445

Phe Ser His Tyr Ile Thr Gly Ala Leu Thr Gln Val Pro Pro Gly Gly
    450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                485                 490                 495

Tyr Leu Leu Arg Asp Thr Pro Phe Ser Val Gly Glu Ser Gly Trp Asn
            500                 505                 510

Asn Leu Lys Lys Ala Met Val Ser Ala Trp Ile Tyr Ser Asn Pro Glu
        515                 520                 525

Val Gly Leu Pro Leu Ala Gly Arg His Pro Phe Asn Ser Pro Ser Leu
    530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gln Asn Glu Ser Thr Ala Ile Phe Gly Glu Thr Ile Thr Pro Ala
            580                 585                 590

Ser Leu Pro Gln Gly Phe Tyr Ala Phe Asn Gly Gly Ala Phe Gly Ile
        595                 600                 605

His Arg Trp Gln Asp Lys Met Val Thr Leu Lys Ala Tyr Asn Thr Asn
    610                 615                 620
```

```
Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
            645                 650                 655

Gln Gly Tyr Gln Gln Glu Gly Trp Asp Trp Asn Arg Met Glu Gly Ala
        660                 665                 670

Thr Thr Ile His Leu Pro Leu Lys Asp Leu Asp Ser Pro Lys Pro His
        675                 680                 685

Thr Leu Met Gln Arg Gly Glu Arg Gly Phe Ser Gly Thr Ser Ser Leu
690                 695                 700

Glu Gly Gln Tyr Gly Met Met Ala Phe Asn Leu Ile Tyr Pro Ala Asn
705                 710                 715                 720

Leu Glu Arg Phe Asp Pro Asn Phe Thr Ala Lys Lys Ser Val Leu Ala
                725                 730                 735

Ala Asp Asn His Leu Ile Phe Ile Gly Ser Asn Ile Asn Ser Ser Asp
            740                 745                 750

Lys Asn Lys Asn Val Glu Thr Thr Leu Phe Gln His Ala Ile Thr Pro
        755                 760                 765

Thr Leu Asn Thr Leu Trp Ile Asn Gly Gln Lys Ile Glu Asn Met Pro
770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
                805                 810                 815

His Gln Val Ser Ala Glu Asn Lys Asn Arg Gln Pro Thr Glu Gly Asn
            820                 825                 830

Phe Ser Ser Ala Trp Ile Asp His Ser Thr Arg Pro Lys Asp Ala Ser
        835                 840                 845

Tyr Glu Tyr Met Val Phe Leu Asp Ala Thr Pro Glu Lys Met Gly Glu
850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                885                 890                 895

Gly Tyr Ala Phe Tyr Gln Pro Ala Ser Ile Glu Asp Lys Trp Ile Lys
            900                 905                 910

Lys Val Asn Lys Pro Ala Ile Val Met Thr His Arg Gln Lys Asp Thr
        915                 920                 925

Leu Ile Val Ser Ala Val Thr Pro Asp Leu Asn Met Thr Arg Gln Lys
930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
                965                 970                 975

Thr Glu Leu Thr Phe Thr Ser Tyr Phe Gly Ile Pro Gln Glu Ile Lys
            980                 985                 990

Leu Ser Pro Leu Pro Gly Gly Gly  Gly Gly Cys Pro Gly  Ala Cys Val
        995                 1000                1005

Cys Tyr  Asn Glu Pro Lys Val  Thr Thr Ser Cys Pro  Gln Gln Gly
        1010                1015                1020

Leu Gln  Ala Val Pro Val Gly  Ile Pro Ala Ala Ser  Gln Arg Ile
        1025                1030                1035
```

-continued

```
Phe Leu His Gly Asn Arg Ile Ser His Val Pro Ala Ala Ser Phe
    1040                1045                1050

Arg Ala Cys Arg Asn Leu Thr Ile Leu Trp Leu His Ser Asn Val
    1055                1060                1065

Leu Ala Arg Ile Asp Ala Ala Ala Phe Thr Gly Leu Ala Leu Leu
    1070                1075                1080

Glu Gln Leu Asp Leu Ser Asp Asn Ala Gln Leu Arg Ser Val Asp
    1085                1090                1095

Pro Ala Thr Phe His Gly Leu Gly Arg Leu His Thr Leu His Leu
    1100                1105                1110

Asp Arg Cys Gly Leu Gln Glu Leu Gly Pro Gly Leu Phe Arg Gly
    1115                1120                1125

Leu Ala Ala Leu Gln Tyr Leu Tyr Leu Gln Asp Asn Ala Leu Gln
    1130                1135                1140

Ala Leu Pro Asp Asp Thr Phe Arg Asp Leu Gly Asn Leu Thr His
    1145                1150                1155

Leu Phe Leu His Gly Asn Arg Ile Ser Ser Val Pro Glu Arg Ala
    1160                1165                1170

Phe Arg Gly Leu His Ser Leu Asp Arg Leu Leu Leu His Gln Asn
    1175                1180                1185

Arg Val Ala His Val His Pro His Ala Phe Arg Asp Leu Gly Arg
    1190                1195                1200

Leu Met Thr Leu Tyr Leu Phe Ala Asn Asn Leu Ser Ala Leu Pro
    1205                1210                1215

Thr Glu Ala Leu Ala Pro Leu Arg Ala Leu Gln Tyr Leu Arg Leu
    1220                1225                1230

Asn Asp Asn Pro Trp Val Cys Asp Cys Arg Ala Arg Pro Leu Trp
    1235                1240                1245

Ala Trp Leu Gln Lys Phe Arg Gly Ser Ser Ser Glu Val Pro Cys
    1250                1255                1260

Ser Leu Pro Gln Arg Leu Ala Gly Arg Asp Leu Lys Arg Leu Ala
    1265                1270                1275

Ala Asn Asp Leu Gln Gly Cys Ala Val
    1280                1285

<210> SEQ ID NO 31
<211> LENGTH: 2254
<212> TYPE: PRT
<213> ORGANISM: Artificial
<220> FEATURE:
<223> OTHER INFORMATION: Synthetic polypeptide, N terminal chimeric
      fusion between extracellular domain L1 and chondroitinase ABCI
      protein without a spacer or linking peptide

<400> SEQUENCE: 31

Met Val Val Ala Leu Arg Tyr Val Trp Pro Leu Leu Leu Cys Ser Pro
1               5                   10                  15

Cys Leu Leu Ile Gln Ile Pro Glu Glu Tyr Glu Gly His His Val Met
                20                  25                  30

Glu Pro Pro Val Ile Thr Glu Gln Ser Pro Arg Arg Leu Val Val Phe
            35                  40                  45

Pro Thr Asp Asp Ile Ser Leu Lys Cys Glu Ala Ser Gly Lys Pro Glu
        50                  55                  60

Val Gln Phe Arg Trp Thr Arg Asp Gly Val His Phe Lys Pro Lys Glu
65                  70                  75                  80

Glu Leu Gly Val Thr Val Tyr Gln Ser Pro His Ser Gly Ser Phe Thr
```

```
                85                  90                  95
Ile Thr Gly Asn Asn Ser Asn Phe Ala Gln Arg Phe Gln Gly Ile Tyr
            100                 105                 110
Arg Cys Phe Ala Ser Asn Lys Leu Gly Thr Ala Met Ser His Glu Ile
            115                 120                 125
Arg Leu Met Ala Glu Gly Ala Pro Lys Trp Pro Lys Glu Thr Val Lys
            130                 135                 140
Pro Val Glu Val Glu Gly Glu Ser Val Val Leu Pro Cys Asn Pro
145                 150                 155                 160
Pro Pro Ser Ala Glu Pro Leu Arg Ile Tyr Trp Met Asn Ser Lys Ile
            165                 170                 175
Leu His Ile Lys Gln Asp Glu Arg Val Thr Met Gly Gln Asn Gly Asn
            180                 185                 190
Leu Tyr Phe Ala Asn Val Leu Thr Ser Asp Asn His Ser Asp Tyr Ile
            195                 200                 205
Cys His Ala His Phe Pro Gly Thr Arg Thr Ile Ile Gln Lys Glu Pro
            210                 215                 220
Ile Asp Leu Arg Val Lys Ala Thr Asn Ser Met Ile Asp Arg Lys Pro
225                 230                 235                 240
Arg Leu Leu Phe Pro Thr Asn Ser Ser Ser His Leu Val Ala Leu Gln
            245                 250                 255
Gly Gln Pro Leu Val Leu Glu Cys Ile Ala Glu Gly Phe Pro Thr Pro
            260                 265                 270
Thr Ile Lys Trp Leu Arg Pro Ser Gly Pro Met Pro Ala Asp Arg Val
            275                 280                 285
Thr Tyr Gln Asn His Asn Lys Thr Leu Gln Leu Leu Lys Val Gly Glu
            290                 295                 300
Glu Asp Asp Gly Glu Tyr Arg Cys Leu Ala Glu Asn Ser Leu Gly Ser
305                 310                 315                 320
Ala Arg His Ala Tyr Tyr Val Thr Val Glu Ala Ala Pro Tyr Trp Leu
            325                 330                 335
His Lys Pro Gln Ser His Leu Tyr Gly Pro Gly Glu Thr Ala Arg Leu
            340                 345                 350
Asp Cys Gln Val Gln Gly Arg Pro Gln Pro Glu Val Thr Trp Arg Ile
            355                 360                 365
Asn Gly Ile Pro Val Glu Glu Leu Ala Lys Asp Gln Lys Tyr Arg Ile
            370                 375                 380
Gln Arg Gly Ala Leu Ile Leu Ser Asn Val Gln Pro Ser Asp Thr Met
385                 390                 395                 400
Val Thr Gln Cys Glu Ala Arg Asn Arg His Gly Leu Leu Leu Ala Asn
            405                 410                 415
Ala Tyr Ile Tyr Val Val Gln Leu Pro Ala Lys Ile Leu Thr Ala Asp
            420                 425                 430
Asn Gln Thr Tyr Met Ala Val Gln Gly Ser Thr Ala Tyr Leu Leu Cys
            435                 440                 445
Lys Ala Phe Gly Ala Pro Val Pro Ser Val Gln Trp Leu Asp Glu Asp
            450                 455                 460
Gly Thr Thr Val Leu Gln Asp Glu Arg Phe Phe Pro Tyr Ala Asn Gly
465                 470                 475                 480
Thr Leu Gly Ile Arg Asp Leu Gln Ala Asn Asp Thr Gly Arg Tyr Phe
            485                 490                 495
Cys Leu Ala Ala Asn Asp Gln Asn Asn Val Thr Ile Met Ala Asn Leu
            500                 505                 510
```

```
Lys Val Lys Asp Ala Thr Gln Ile Thr Gln Gly Pro Arg Ser Thr Ile
            515                 520                 525

Glu Lys Lys Gly Ser Arg Val Thr Phe Thr Cys Gln Ala Ser Phe Asp
        530                 535                 540

Pro Ser Leu Gln Pro Ser Ile Thr Trp Arg Gly Asp Gly Arg Asp Leu
545                 550                 555                 560

Gln Glu Leu Gly Asp Ser Asp Lys Tyr Phe Ile Glu Asp Gly Arg Leu
                565                 570                 575

Val Ile His Ser Leu Asp Tyr Ser Asp Gln Gly Asn Tyr Ser Cys Val
            580                 585                 590

Ala Ser Thr Glu Leu Asp Val Val Glu Ser Arg Ala Gln Leu Leu Val
        595                 600                 605

Val Gly Ser Pro Gly Pro Val Pro Arg Leu Val Leu Ser Asp Leu His
            610                 615                 620

Leu Leu Thr Gln Ser Gln Val Arg Val Ser Trp Ser Pro Ala Glu Asp
625                 630                 635                 640

His Asn Ala Pro Ile Glu Lys Tyr Asp Ile Glu Phe Glu Asp Lys Glu
                645                 650                 655

Met Ala Pro Glu Lys Trp Tyr Ser Leu Gly Lys Val Pro Gly Asn Gln
            660                 665                 670

Thr Ser Thr Thr Leu Lys Leu Ser Pro Tyr Val His Tyr Thr Phe Arg
        675                 680                 685

Val Thr Ala Ile Asn Lys Tyr Gly Pro Gly Glu Pro Ser Pro Val Ser
    690                 695                 700

Glu Thr Val Val Thr Pro Glu Ala Ala Pro Glu Lys Asn Pro Val Asp
705                 710                 715                 720

Val Lys Gly Glu Gly Asn Glu Thr Thr Asn Met Val Ile Thr Trp Lys
                725                 730                 735

Pro Leu Arg Trp Met Asp Trp Asn Ala Pro Gln Val Gln Tyr Arg Val
            740                 745                 750

Gln Trp Arg Pro Gln Gly Thr Arg Gly Pro Trp Gln Glu Gln Ile Val
        755                 760                 765

Ser Asp Pro Phe Leu Val Val Ser Asn Thr Ser Thr Phe Val Pro Tyr
    770                 775                 780

Glu Ile Lys Val Gln Ala Val Asn Ser Gln Gly Lys Gly Pro Glu Pro
785                 790                 795                 800

Gln Val Thr Ile Gly Tyr Ser Gly Glu Asp Tyr Pro Gln Ala Ile Pro
                805                 810                 815

Glu Leu Glu Gly Ile Glu Ile Leu Asn Ser Ser Ala Val Leu Val Lys
            820                 825                 830

Trp Arg Pro Val Asp Leu Ala Gln Val Lys Gly His Leu Arg Gly Tyr
        835                 840                 845

Asn Val Thr Tyr Trp Arg Glu Gly Ser Gln Arg Lys His Ser Lys Arg
    850                 855                 860

His Ile His Lys Asp His Val Val Val Pro Ala Asn Thr Thr Ser Val
865                 870                 875                 880

Ile Leu Ser Gly Leu Arg Pro Tyr Ser Ser Tyr His Leu Glu Val Gln
                885                 890                 895

Ala Phe Asn Gly Arg Gly Ser Gly Pro Ala Ser Glu Phe Thr Phe Ser
            900                 905                 910

Thr Pro Glu Gly Val Pro Gly His Pro Glu Ala Leu His Leu Glu Cys
        915                 920                 925
```

```
Gln Ser Asn Thr Ser Leu Leu Leu Arg Trp Gln Pro Leu Ser His
    930             935             940

Asn Gly Val Leu Thr Gly Tyr Val Leu Ser Tyr His Pro Leu Asp Glu
945             950             955             960

Gly Gly Lys Gly Gln Leu Ser Phe Asn Leu Arg Asp Pro Glu Leu Arg
                965             970             975

Thr His Asn Leu Thr Asp Leu Ser Pro His Leu Arg Tyr Arg Phe Gln
            980             985             990

Leu Gln Ala Thr Thr Lys Glu Gly Pro Gly Glu Ala Ile Val Arg Glu
            995             1000            1005

Gly Gly Thr Met Ala Leu Ser Gly Ile Ser Asp Phe Gly Asn Ile
    1010            1015            1020

Ser Ala Thr Ala Gly Glu Asn Tyr Ser Val Val Ser Trp Val Pro
    1025            1030            1035

Lys Glu Gly Gln Cys Asn Phe Arg Phe His Ile Leu Phe Lys Ala
    1040            1045            1050

Leu Gly Glu Glu Lys Gly Gly Ala Ser Leu Ser Pro Gln Tyr Val
    1055            1060            1065

Ser Tyr Asn Gln Ser Ser Tyr Thr Gln Trp Asp Leu Gln Pro Asp
    1070            1075            1080

Thr Asp Tyr Glu Ile His Leu Phe Lys Glu Arg Met Phe Arg His
    1085            1090            1095

Gln Met Ala Val Lys Thr Asn Gly Thr Gly Arg Val Arg Leu Pro
    1100            1105            1110

Pro Ala Gly Phe Ala Thr Glu Gly Trp Phe Ile Gly Phe Val Ser
    1115            1120            1125

Ala Ile Ile Leu Leu Leu Leu Val Leu Leu Ile Leu Cys Phe Ile
    1130            1135            1140

Lys Arg Ser Lys Gly Gly Lys Tyr Ser Val Lys Asp Lys Glu Asp
    1145            1150            1155

Thr Gln Val Asp Ser Glu Ala Arg Pro Met Lys Asp Glu Thr Phe
    1160            1165            1170

Gly Glu Tyr Arg Ser Leu Glu Ser Asp Asn Glu Glu Lys Ala Phe
    1175            1180            1185

Gly Ser Ser Gln Pro Ser Leu Asn Gly Asp Ile Lys Pro Leu Gly
    1190            1195            1200

Ser Asp Asp Ser Leu Ala Asp Tyr Gly Gly Ser Val Asp Val Gln
    1205            1210            1215

Phe Asn Glu Asp Gly Ser Phe Ile Gly Gln Tyr Ser Gly Lys Lys
    1220            1225            1230

Glu Lys Glu Ala Ala Gly Gly Asn Asp Ser Ser Gly Ala Thr Ser
    1235            1240            1245

Pro Ile Asn Pro Ala Val Ala Leu Glu Ala Thr Ser Asn Pro Ala
    1250            1255            1260

Phe Asp Pro Lys Asn Leu Met Gln Ser Glu Ile Tyr His Phe Ala
    1265            1270            1275

Gln Asn Asn Pro Leu Ala Asp Phe Ser Ser Asp Lys Asn Ser Ile
    1280            1285            1290

Leu Thr Leu Ser Asp Lys Arg Ser Ile Met Gly Asn Gln Ser Leu
    1295            1300            1305

Leu Trp Lys Trp Lys Gly Gly Ser Ser Phe Thr Leu His Lys Lys
    1310            1315            1320

Leu Ile Val Pro Thr Asp Lys Glu Ala Ser Lys Ala Trp Gly Arg
```

```
                  1325                1330                1335

Ser  Ser  Thr  Pro  Val  Phe  Ser  Phe  Trp  Leu  Tyr  Asn  Glu  Lys  Pro
     1340                1345                1350

Ile  Asp  Gly  Tyr  Leu  Thr  Ile  Asp  Phe  Gly  Glu  Lys  Leu  Ile  Ser
     1355                1360                1365

Thr  Ser  Glu  Ala  Gln  Ala  Gly  Phe  Lys  Val  Lys  Leu  Asp  Phe  Thr
     1370                1375                1380

Gly  Trp  Arg  Thr  Val  Gly  Val  Ser  Leu  Asn  Asn  Asp  Leu  Glu  Asn
     1385                1390                1395

Arg  Glu  Met  Thr  Leu  Asn  Ala  Thr  Asn  Thr  Ser  Ser  Asp  Gly  Thr
     1400                1405                1410

Gln  Asp  Ser  Ile  Gly  Arg  Ser  Leu  Gly  Ala  Lys  Val  Asp  Ser  Ile
     1415                1420                1425

Arg  Phe  Lys  Ala  Pro  Ser  Asn  Val  Ser  Gln  Gly  Glu  Ile  Tyr  Ile
     1430                1435                1440

Asp  Arg  Ile  Met  Phe  Ser  Val  Asp  Asp  Ala  Arg  Tyr  Gln  Trp  Ser
     1445                1450                1455

Asp  Tyr  Gln  Val  Lys  Thr  Arg  Leu  Ser  Glu  Pro  Glu  Ile  Gln  Phe
     1460                1465                1470

His  Asn  Val  Lys  Pro  Gln  Leu  Pro  Val  Thr  Pro  Glu  Asn  Leu  Ala
     1475                1480                1485

Ala  Ile  Asp  Leu  Ile  Arg  Gln  Arg  Leu  Ile  Asn  Glu  Phe  Val  Gly
     1490                1495                1500

Gly  Glu  Lys  Glu  Thr  Asn  Leu  Ala  Leu  Glu  Glu  Asn  Ile  Ser  Lys
     1505                1510                1515

Leu  Lys  Ser  Asp  Phe  Asp  Ala  Leu  Asn  Thr  His  Thr  Leu  Ala  Asn
     1520                1525                1530

Gly  Gly  Thr  Gln  Gly  Arg  His  Leu  Ile  Thr  Asp  Lys  Gln  Ile  Ile
     1535                1540                1545

Ile  Tyr  Gln  Pro  Glu  Asn  Leu  Asn  Ser  Gln  Asp  Lys  Gln  Leu  Phe
     1550                1555                1560

Asp  Asn  Tyr  Val  Ile  Leu  Gly  Asn  Tyr  Thr  Thr  Leu  Met  Phe  Asn
     1565                1570                1575

Ile  Ser  Arg  Ala  Tyr  Val  Leu  Glu  Lys  Asp  Pro  Thr  Gln  Lys  Ala
     1580                1585                1590

Gln  Leu  Lys  Gln  Met  Tyr  Leu  Leu  Met  Thr  Lys  His  Leu  Leu  Asp
     1595                1600                1605

Gln  Gly  Phe  Val  Lys  Gly  Ser  Ala  Leu  Val  Thr  Thr  His  His  Trp
     1610                1615                1620

Gly  Tyr  Ser  Ser  Arg  Trp  Trp  Tyr  Ile  Ser  Thr  Leu  Leu  Met  Ser
     1625                1630                1635

Asp  Ala  Leu  Lys  Glu  Ala  Asn  Leu  Gln  Thr  Gln  Val  Tyr  Asp  Ser
     1640                1645                1650

Leu  Leu  Trp  Tyr  Ser  Arg  Glu  Phe  Lys  Ser  Ser  Phe  Asp  Met  Lys
     1655                1660                1665

Val  Ser  Ala  Asp  Ser  Ser  Asp  Leu  Asp  Tyr  Phe  Asn  Thr  Leu  Ser
     1670                1675                1680

Arg  Gln  His  Leu  Ala  Leu  Leu  Leu  Glu  Pro  Asp  Asp  Gln  Lys
     1685                1690                1695

Arg  Ile  Asn  Leu  Val  Asn  Thr  Phe  Ser  His  Tyr  Ile  Thr  Gly  Ala
     1700                1705                1710

Leu  Thr  Gln  Val  Pro  Pro  Gly  Gly  Lys  Asp  Gly  Leu  Arg  Pro  Asp
     1715                1720                1725
```

-continued

Gly Thr Ala Trp Arg His Glu Gly Asn Tyr Pro Gly Tyr Ser Phe
1730                1735                1740

Pro Ala Phe Lys Asn Ala Ser Gln Leu Ile Tyr Leu Leu Arg Asp
    1745                1750                1755

Thr Pro Phe Ser Val Gly Glu Ser Gly Trp Asn Leu Lys Lys
1760                1765                1770

Ala Met Val Ser Ala Trp Ile Tyr Ser Asn Pro Glu Val Gly Leu
    1775                1780                1785

Pro Leu Ala Gly Arg His Pro Phe Asn Ser Pro Ser Leu Lys Ser
    1790                1795                1800

Val Ala Gln Gly Tyr Tyr Trp Leu Ala Met Ser Ala Lys Ser Ser
    1805                1810                1815

Pro Asp Lys Thr Leu Ala Ser Ile Tyr Leu Ala Ile Ser Asp Lys
    1820                1825                1830

Thr Gln Asn Glu Ser Thr Ala Ile Phe Gly Glu Thr Ile Thr Pro
1835                1840                1845

Ala Ser Leu Pro Gln Gly Phe Tyr Ala Phe Asn Gly Gly Ala Phe
    1850                1855                1860

Gly Ile His Arg Trp Gln Asp Lys Met Val Thr Leu Lys Ala Tyr
    1865                1870                1875

Asn Thr Asn Val Trp Ser Ser Glu Ile Tyr Asn Lys Asp Asn Arg
    1880                1885                1890

Tyr Gly Arg Tyr Gln Ser His Gly Val Ala Gln Ile Val Ser Asn
1895                1900                1905

Gly Ser Gln Leu Ser Gln Gly Tyr Gln Gln Glu Gly Trp Asp Trp
    1910                1915                1920

Asn Arg Met Glu Gly Ala Thr Thr Ile His Leu Pro Leu Lys Asp
    1925                1930                1935

Leu Asp Ser Pro Lys Pro His Thr Leu Met Gln Arg Gly Glu Arg
    1940                1945                1950

Gly Phe Ser Gly Thr Ser Ser Leu Glu Gly Gln Tyr Gly Met Met
    1955                1960                1965

Ala Phe Asn Leu Ile Tyr Pro Ala Asn Leu Glu Arg Phe Asp Pro
    1970                1975                1980

Asn Phe Thr Ala Lys Lys Ser Val Leu Ala Ala Asp Asn His Leu
    1985                1990                1995

Ile Phe Ile Gly Ser Asn Ile Asn Ser Ser Asp Lys Asn Lys Asn
    2000                2005                2010

Val Glu Thr Thr Leu Phe Gln His Ala Ile Thr Pro Thr Leu Asn
    2015                2020                2025

Thr Leu Trp Ile Asn Gly Gln Lys Ile Glu Asn Met Pro Tyr Gln
    2030                2035                2040

Thr Thr Leu Gln Gln Gly Asp Trp Leu Ile Asp Ser Asn Gly Asn
    2045                2050                2055

Gly Tyr Leu Ile Thr Gln Ala Glu Lys Val Asn Val Ser Arg Gln
    2060                2065                2070

His Gln Val Ser Ala Glu Asn Lys Asn Arg Gln Pro Thr Glu Gly
    2075                2080                2085

Asn Phe Ser Ser Ala Trp Ile Asp His Ser Thr Arg Pro Lys Asp
    2090                2095                2100

Ala Ser Tyr Glu Tyr Met Val Phe Leu Asp Ala Thr Pro Glu Lys
    2105                2110                2115

```
Met Gly Glu Met Ala Gln Lys Phe Arg Glu Asn Asn Gly Leu Tyr
    2120                2125                2130

Gln Val Leu Arg Lys Asp Lys Asp Val His Ile Ile Leu Asp Lys
    2135                2140                2145

Leu Ser Asn Val Thr Gly Tyr Ala Phe Tyr Gln Pro Ala Ser Ile
    2150                2155                2160

Glu Asp Lys Trp Ile Lys Lys Val Asn Lys Pro Ala Ile Val Met
    2165                2170                2175

Thr His Arg Gln Lys Asp Thr Leu Ile Val Ser Ala Val Thr Pro
    2180                2185                2190

Asp Leu Asn Met Thr Arg Gln Lys Ala Ala Thr Pro Val Thr Ile
    2195                2200                2205

Asn Val Thr Ile Asn Gly Lys Trp Gln Ser Ala Asp Lys Asn Ser
    2210                2215                2220

Glu Val Lys Tyr Gln Val Ser Gly Asp Asn Thr Glu Leu Thr Phe
    2225                2230                2235

Thr Ser Tyr Phe Gly Ile Pro Gln Glu Ile Lys Leu Ser Pro Leu
    2240                2245                2250

Pro
```

<210> SEQ ID NO 32
<211> LENGTH: 2259
<212> TYPE: PRT
<213> ORGANISM: Artificial
<220> FEATURE:
<223> OTHER INFORMATION: Synthetic polypeptide, N terminal fusion
      chimera between extracellular domain L1 and chondroitinase ABCI
      protein with a spacer or linking peptide

<400> SEQUENCE: 32

```
Met Val Val Ala Leu Arg Tyr Val Trp Pro Leu Leu Leu Cys Ser Pro
1               5                   10                  15

Cys Leu Leu Ile Gln Ile Pro Glu Glu Tyr Glu Gly His His Val Met
                20                  25                  30

Glu Pro Pro Val Ile Thr Glu Gln Ser Pro Arg Arg Leu Val Val Phe
                35                  40                  45

Pro Thr Asp Asp Ile Ser Leu Lys Cys Glu Ala Ser Gly Lys Pro Glu
    50                  55                  60

Val Gln Phe Arg Trp Thr Arg Asp Gly Val His Phe Lys Pro Lys Glu
65                  70                  75                  80

Glu Leu Gly Val Thr Val Tyr Gln Ser Pro His Ser Gly Ser Phe Thr
                85                  90                  95

Ile Thr Gly Asn Asn Ser Asn Phe Ala Gln Arg Phe Gln Gly Ile Tyr
                100                 105                 110

Arg Cys Phe Ala Ser Asn Lys Leu Gly Thr Ala Met Ser His Glu Ile
            115                 120                 125

Arg Leu Met Ala Glu Gly Ala Pro Lys Trp Pro Lys Glu Thr Val Lys
        130                 135                 140

Pro Val Glu Val Glu Glu Gly Glu Ser Val Val Leu Pro Cys Asn Pro
145                 150                 155                 160

Pro Pro Ser Ala Glu Pro Leu Arg Ile Tyr Trp Met Asn Ser Lys Ile
                165                 170                 175

Leu His Ile Lys Gln Asp Glu Arg Val Thr Met Gly Gln Asn Gly Asn
                180                 185                 190

Leu Tyr Phe Ala Asn Val Leu Thr Ser Asp Asn His Ser Asp Tyr Ile
                195                 200                 205
```

-continued

```
Cys His Ala His Phe Pro Gly Thr Arg Thr Ile Ile Gln Lys Glu Pro
    210                 215                 220
Ile Asp Leu Arg Val Lys Ala Thr Asn Ser Met Ile Asp Arg Lys Pro
225                 230                 235                 240
Arg Leu Leu Phe Pro Thr Asn Ser Ser Ser His Leu Val Ala Leu Gln
                245                 250                 255
Gly Gln Pro Leu Val Leu Glu Cys Ile Ala Glu Gly Phe Pro Thr Pro
            260                 265                 270
Thr Ile Lys Trp Leu Arg Pro Ser Gly Pro Met Pro Ala Asp Arg Val
        275                 280                 285
Thr Tyr Gln Asn His Asn Lys Thr Leu Gln Leu Leu Lys Val Gly Glu
    290                 295                 300
Glu Asp Asp Gly Glu Tyr Arg Cys Leu Ala Glu Asn Ser Leu Gly Ser
305                 310                 315                 320
Ala Arg His Ala Tyr Tyr Val Thr Val Glu Ala Pro Tyr Trp Leu
                325                 330                 335
His Lys Pro Gln Ser His Leu Tyr Gly Pro Gly Glu Thr Ala Arg Leu
            340                 345                 350
Asp Cys Gln Val Gln Gly Arg Pro Gln Pro Glu Val Thr Trp Arg Ile
        355                 360                 365
Asn Gly Ile Pro Val Glu Glu Leu Ala Lys Asp Gln Lys Tyr Arg Ile
    370                 375                 380
Gln Arg Gly Ala Leu Ile Leu Ser Asn Val Gln Pro Ser Asp Thr Met
385                 390                 395                 400
Val Thr Gln Cys Glu Ala Arg Asn Arg His Gly Leu Leu Leu Ala Asn
                405                 410                 415
Ala Tyr Ile Tyr Val Val Gln Leu Pro Ala Lys Ile Leu Thr Ala Asp
            420                 425                 430
Asn Gln Thr Tyr Met Ala Val Gln Gly Ser Thr Ala Tyr Leu Leu Cys
        435                 440                 445
Lys Ala Phe Gly Ala Pro Val Pro Ser Val Gln Trp Leu Asp Glu Asp
    450                 455                 460
Gly Thr Thr Val Leu Gln Asp Glu Arg Phe Phe Pro Tyr Ala Asn Gly
465                 470                 475                 480
Thr Leu Gly Ile Arg Asp Leu Gln Ala Asn Asp Thr Gly Arg Tyr Phe
                485                 490                 495
Cys Leu Ala Ala Asn Asp Gln Asn Asn Val Thr Ile Met Ala Asn Leu
            500                 505                 510
Lys Val Lys Asp Ala Thr Gln Ile Thr Gln Gly Pro Arg Ser Thr Ile
    515                 520                 525
Glu Lys Lys Gly Ser Arg Val Thr Phe Thr Cys Gln Ala Ser Phe Asp
530                 535                 540
Pro Ser Leu Gln Pro Ser Ile Thr Trp Arg Gly Asp Gly Arg Asp Leu
545                 550                 555                 560
Gln Glu Leu Gly Asp Ser Asp Lys Tyr Phe Ile Glu Asp Gly Arg Leu
                565                 570                 575
Val Ile His Ser Leu Asp Tyr Ser Asp Gln Gly Asn Tyr Ser Cys Val
            580                 585                 590
Ala Ser Thr Glu Leu Asp Val Val Glu Ser Arg Ala Gln Leu Leu Val
        595                 600                 605
Val Gly Ser Pro Gly Pro Val Pro Arg Leu Val Leu Ser Asp Leu His
    610                 615                 620
```

```
Leu Leu Thr Gln Ser Gln Val Arg Val Ser Trp Ser Pro Ala Glu Asp
625                 630                 635                 640

His Asn Ala Pro Ile Glu Lys Tyr Asp Ile Glu Phe Glu Asp Lys Glu
                645                 650                 655

Met Ala Pro Glu Lys Trp Tyr Ser Leu Gly Lys Val Pro Gly Asn Gln
            660                 665                 670

Thr Ser Thr Thr Leu Lys Leu Ser Pro Tyr Val His Tyr Thr Phe Arg
        675                 680                 685

Val Thr Ala Ile Asn Lys Tyr Gly Pro Gly Glu Pro Ser Pro Val Ser
690                 695                 700

Glu Thr Val Val Thr Pro Glu Ala Ala Pro Lys Asn Pro Val Asp
705                 710                 715                 720

Val Lys Gly Glu Gly Asn Glu Thr Thr Asn Met Val Ile Thr Trp Lys
                725                 730                 735

Pro Leu Arg Trp Met Asp Trp Asn Ala Pro Gln Val Gln Tyr Arg Val
            740                 745                 750

Gln Trp Arg Pro Gln Gly Thr Arg Gly Pro Trp Gln Glu Gln Ile Val
        755                 760                 765

Ser Asp Pro Phe Leu Val Val Ser Asn Thr Ser Thr Phe Val Pro Tyr
770                 775                 780

Glu Ile Lys Val Gln Ala Val Asn Ser Gln Gly Lys Gly Pro Glu Pro
785                 790                 795                 800

Gln Val Thr Ile Gly Tyr Ser Gly Glu Asp Tyr Pro Gln Ala Ile Pro
                805                 810                 815

Glu Leu Glu Gly Ile Glu Ile Leu Asn Ser Ser Ala Val Leu Val Lys
            820                 825                 830

Trp Arg Pro Val Asp Leu Ala Gln Val Lys Gly His Leu Arg Gly Tyr
        835                 840                 845

Asn Val Thr Tyr Trp Arg Glu Gly Ser Gln Arg Lys His Ser Lys Arg
850                 855                 860

His Ile His Lys Asp His Val Val Pro Ala Asn Thr Thr Ser Val
865                 870                 875                 880

Ile Leu Ser Gly Leu Arg Pro Tyr Ser Ser Tyr His Leu Glu Val Gln
                885                 890                 895

Ala Phe Asn Gly Arg Gly Ser Gly Pro Ala Ser Glu Phe Thr Phe Ser
            900                 905                 910

Thr Pro Glu Gly Val Pro Gly His Pro Glu Ala Leu His Leu Glu Cys
        915                 920                 925

Gln Ser Asn Thr Ser Leu Leu Leu Arg Trp Gln Pro Pro Leu Ser His
930                 935                 940

Asn Gly Val Leu Thr Gly Tyr Val Leu Ser Tyr His Pro Leu Asp Glu
945                 950                 955                 960

Gly Gly Lys Gly Gln Leu Ser Phe Asn Leu Arg Asp Pro Glu Leu Arg
                965                 970                 975

Thr His Asn Leu Thr Asp Leu Ser Pro His Leu Arg Tyr Arg Phe Gln
            980                 985                 990

Leu Gln Ala Thr Thr Lys Glu Gly Pro Gly Glu Ala Ile Val Arg Glu
        995                 1000                1005

Gly Gly Thr Met Ala Leu Ser Gly Ile Ser Asp Phe Gly Asn Ile
            1010                1015                1020

Ser Ala Thr Ala Gly Glu Asn Tyr Ser Val Val Ser Trp Val Pro
        1025                1030                1035

Lys Glu Gly Gln Cys Asn Phe Arg Phe His Ile Leu Phe Lys Ala
```

-continued

```
            1040                1045                1050
Leu Gly Glu Glu Lys Gly Gly Ala Ser Leu Ser Pro Gln Tyr Val
            1055                1060                1065
Ser Tyr Asn Gln Ser Ser Tyr Thr Gln Trp Asp Leu Gln Pro Asp
            1070                1075                1080
Thr Asp Tyr Glu Ile His Leu Phe Lys Glu Arg Met Phe Arg His
            1085                1090                1095
Gln Met Ala Val Lys Thr Asn Gly Thr Gly Arg Val Arg Leu Pro
            1100                1105                1110
Pro Ala Gly Phe Ala Thr Glu Gly Trp Phe Ile Gly Phe Val Ser
            1115                1120                1125
Ala Ile Ile Leu Leu Leu Leu Val Leu Leu Ile Leu Cys Phe Ile
            1130                1135                1140
Lys Arg Ser Lys Gly Gly Lys Tyr Ser Val Lys Asp Lys Glu Asp
            1145                1150                1155
Thr Gln Val Asp Ser Glu Ala Arg Pro Met Lys Asp Glu Thr Phe
            1160                1165                1170
Gly Glu Tyr Arg Ser Leu Glu Ser Asp Asn Glu Glu Lys Ala Phe
            1175                1180                1185
Gly Ser Ser Gln Pro Ser Leu Asn Gly Asp Ile Lys Pro Leu Gly
            1190                1195                1200
Ser Asp Asp Ser Leu Ala Asp Tyr Gly Gly Ser Val Asp Val Gln
            1205                1210                1215
Phe Asn Glu Asp Gly Ser Phe Ile Gly Gln Tyr Ser Gly Lys Lys
            1220                1225                1230
Glu Lys Glu Ala Ala Gly Gly Asn Asp Ser Ser Gly Ala Thr Ser
            1235                1240                1245
Pro Ile Asn Pro Ala Val Ala Leu Glu Gly Gly Gly Gly Gly Ala
            1250                1255                1260
Thr Ser Asn Pro Ala Phe Asp Pro Lys Asn Leu Met Gln Ser Glu
            1265                1270                1275
Ile Tyr His Phe Ala Gln Asn Asn Pro Leu Ala Asp Phe Ser Ser
            1280                1285                1290
Asp Lys Asn Ser Ile Leu Thr Leu Ser Asp Lys Arg Ser Ile Met
            1295                1300                1305
Gly Asn Gln Ser Leu Leu Trp Lys Trp Lys Gly Gly Ser Ser Phe
            1310                1315                1320
Thr Leu His Lys Lys Leu Ile Val Pro Thr Asp Lys Glu Ala Ser
            1325                1330                1335
Lys Ala Trp Gly Arg Ser Ser Thr Pro Val Phe Ser Phe Trp Leu
            1340                1345                1350
Tyr Asn Glu Lys Pro Ile Asp Gly Tyr Leu Thr Ile Asp Phe Gly
            1355                1360                1365
Glu Lys Leu Ile Ser Thr Ser Glu Ala Gln Ala Gly Phe Lys Val
            1370                1375                1380
Lys Leu Asp Phe Thr Gly Trp Arg Thr Val Gly Val Ser Leu Asn
            1385                1390                1395
Asn Asp Leu Glu Asn Arg Glu Met Thr Leu Asn Ala Thr Asn Thr
            1400                1405                1410
Ser Ser Asp Gly Thr Gln Asp Ser Ile Gly Arg Ser Leu Gly Ala
            1415                1420                1425
Lys Val Asp Ser Ile Arg Phe Lys Ala Pro Ser Asn Val Ser Gln
            1430                1435                1440
```

```
Gly Glu Ile Tyr Ile Asp Arg Ile Met Phe Ser Val Asp Asp Ala
1445                1450                1455

Arg Tyr Gln Trp Ser Asp Tyr Gln Val Lys Thr Arg Leu Ser Glu
1460                1465                1470

Pro Glu Ile Gln Phe His Asn Val Lys Pro Gln Leu Pro Val Thr
1475                1480                1485

Pro Glu Asn Leu Ala Ala Ile Asp Leu Ile Arg Gln Arg Leu Ile
1490                1495                1500

Asn Glu Phe Val Gly Gly Glu Lys Glu Thr Asn Leu Ala Leu Glu
1505                1510                1515

Glu Asn Ile Ser Lys Leu Lys Ser Asp Phe Asp Ala Leu Asn Thr
1520                1525                1530

His Thr Leu Ala Asn Gly Gly Thr Gln Gly Arg His Leu Ile Thr
1535                1540                1545

Asp Lys Gln Ile Ile Tyr Gln Pro Glu Asn Leu Asn Ser Gln
1550                1555                1560

Asp Lys Gln Leu Phe Asp Asn Tyr Val Ile Leu Gly Asn Tyr Thr
1565                1570                1575

Thr Leu Met Phe Asn Ile Ser Arg Ala Tyr Val Leu Glu Lys Asp
1580                1585                1590

Pro Thr Gln Lys Ala Gln Leu Lys Gln Met Tyr Leu Leu Met Thr
1595                1600                1605

Lys His Leu Leu Asp Gln Gly Phe Val Lys Gly Ser Ala Leu Val
1610                1615                1620

Thr Thr His His Trp Gly Tyr Ser Ser Arg Trp Trp Tyr Ile Ser
1625                1630                1635

Thr Leu Leu Met Ser Asp Ala Leu Lys Glu Ala Asn Leu Gln Thr
1640                1645                1650

Gln Val Tyr Asp Ser Leu Leu Trp Tyr Ser Arg Glu Phe Lys Ser
1655                1660                1665

Ser Phe Asp Met Lys Val Ser Ala Asp Ser Ser Asp Leu Asp Tyr
1670                1675                1680

Phe Asn Thr Leu Ser Arg Gln His Leu Ala Leu Leu Leu Leu Glu
1685                1690                1695

Pro Asp Asp Gln Lys Arg Ile Asn Leu Val Asn Thr Phe Ser His
1700                1705                1710

Tyr Ile Thr Gly Ala Leu Thr Gln Val Pro Pro Gly Gly Lys Asp
1715                1720                1725

Gly Leu Arg Pro Asp Gly Thr Ala Trp Arg His Glu Gly Asn Tyr
1730                1735                1740

Pro Gly Tyr Ser Phe Pro Ala Phe Lys Asn Ala Ser Gln Leu Ile
1745                1750                1755

Tyr Leu Leu Arg Asp Thr Pro Phe Ser Val Gly Glu Ser Gly Trp
1760                1765                1770

Asn Asn Leu Lys Lys Ala Met Val Ser Ala Trp Ile Tyr Ser Asn
1775                1780                1785

Pro Glu Val Gly Leu Pro Leu Ala Gly Arg His Pro Phe Asn Ser
1790                1795                1800

Pro Ser Leu Lys Ser Val Ala Gln Gly Tyr Tyr Trp Leu Ala Met
1805                1810                1815

Ser Ala Lys Ser Ser Pro Asp Lys Thr Leu Ala Ser Ile Tyr Leu
1820                1825                1830
```

```
Ala Ile Ser Asp Lys Thr Gln Asn Glu Ser Thr Ala Ile Phe Gly
    1835                1840                1845

Glu Thr Ile Thr Pro Ala Ser Leu Pro Gln Gly Phe Tyr Ala Phe
    1850                1855                1860

Asn Gly Gly Ala Phe Gly Ile His Arg Trp Gln Asp Lys Met Val
    1865                1870                1875

Thr Leu Lys Ala Tyr Asn Thr Asn Val Trp Ser Ser Glu Ile Tyr
    1880                1885                1890

Asn Lys Asp Asn Arg Tyr Gly Arg Tyr Gln Ser His Gly Val Ala
    1895                1900                1905

Gln Ile Val Ser Asn Gly Ser Gln Leu Ser Gln Gly Tyr Gln Gln
    1910                1915                1920

Glu Gly Trp Asp Trp Asn Arg Met Glu Gly Ala Thr Thr Ile His
    1925                1930                1935

Leu Pro Leu Lys Asp Leu Asp Ser Pro Lys Pro His Thr Leu Met
    1940                1945                1950

Gln Arg Gly Glu Arg Gly Phe Ser Gly Thr Ser Ser Leu Glu Gly
    1955                1960                1965

Gln Tyr Gly Met Met Ala Phe Asn Leu Ile Tyr Pro Ala Asn Leu
    1970                1975                1980

Glu Arg Phe Asp Pro Asn Phe Thr Ala Lys Lys Ser Val Leu Ala
    1985                1990                1995

Ala Asp Asn His Leu Ile Phe Ile Gly Ser Asn Ile Asn Ser Ser
    2000                2005                2010

Asp Lys Asn Lys Asn Val Glu Thr Thr Leu Phe Gln His Ala Ile
    2015                2020                2025

Thr Pro Thr Leu Asn Thr Leu Trp Ile Asn Gly Gln Lys Ile Glu
    2030                2035                2040

Asn Met Pro Tyr Gln Thr Thr Leu Gln Gln Gly Asp Trp Leu Ile
    2045                2050                2055

Asp Ser Asn Gly Asn Gly Tyr Leu Ile Thr Gln Ala Glu Lys Val
    2060                2065                2070

Asn Val Ser Arg Gln His Gln Val Ser Ala Glu Asn Lys Asn Arg
    2075                2080                2085

Gln Pro Thr Glu Gly Asn Phe Ser Ser Ala Trp Ile Asp His Ser
    2090                2095                2100

Thr Arg Pro Lys Asp Ala Ser Tyr Glu Tyr Met Val Phe Leu Asp
    2105                2110                2115

Ala Thr Pro Glu Lys Met Gly Glu Met Ala Gln Lys Phe Arg Glu
    2120                2125                2130

Asn Asn Gly Leu Tyr Gln Val Leu Arg Lys Asp Lys Asp Val His
    2135                2140                2145

Ile Ile Leu Asp Lys Leu Ser Asn Val Thr Gly Tyr Ala Phe Tyr
    2150                2155                2160

Gln Pro Ala Ser Ile Glu Asp Lys Trp Ile Lys Lys Val Asn Lys
    2165                2170                2175

Pro Ala Ile Val Met Thr His Arg Gln Lys Asp Thr Leu Ile Val
    2180                2185                2190

Ser Ala Val Thr Pro Asp Leu Asn Met Thr Arg Gln Lys Ala Ala
    2195                2200                2205

Thr Pro Val Thr Ile Asn Val Thr Ile Asn Gly Lys Trp Gln Ser
    2210                2215                2220

Ala Asp Lys Asn Ser Glu Val Lys Tyr Gln Val Ser Gly Asp Asn
```

```
            2225              2230              2235
    Thr  Glu  Leu  Thr  Phe  Thr  Ser  Tyr  Phe  Gly  Ile  Pro  Gln  Glu  Ile
         2240                     2245                    2250

Lys  Leu  Ser  Pro  Leu  Pro
         2255

<210> SEQ ID NO 33
<211> LENGTH: 2254
<212> TYPE: PRT
<213> ORGANISM: Artificial
<220> FEATURE:
<223> OTHER INFORMATION: Synthetic polypeptide, C terminal fusion
      chimera between extracellular domain L1 and chondroitinase ABCI
      protein without a spacer or linking peptide

<400> SEQUENCE: 33

Ala  Thr  Ser  Asn  Pro  Ala  Phe  Asp  Pro  Lys  Asn  Leu  Met  Gln  Ser  Glu
1                   5                   10                  15

Ile  Tyr  His  Phe  Ala  Gln  Asn  Asn  Pro  Leu  Ala  Asp  Phe  Ser  Ser  Asp
             20                  25                  30

Lys  Asn  Ser  Ile  Leu  Thr  Leu  Ser  Asp  Lys  Arg  Ser  Ile  Met  Gly  Asn
        35                  40                  45

Gln  Ser  Leu  Leu  Trp  Lys  Trp  Lys  Gly  Gly  Ser  Ser  Phe  Thr  Leu  His
    50                  55                  60

Lys  Lys  Leu  Ile  Val  Pro  Thr  Asp  Lys  Glu  Ala  Ser  Lys  Ala  Trp  Gly
65                  70                  75                  80

Arg  Ser  Ser  Thr  Pro  Val  Phe  Ser  Phe  Trp  Leu  Tyr  Asn  Glu  Lys  Pro
                85                  90                  95

Ile  Asp  Gly  Tyr  Leu  Thr  Ile  Asp  Phe  Gly  Glu  Lys  Leu  Ile  Ser  Thr
            100                 105                 110

Ser  Glu  Ala  Gln  Ala  Gly  Phe  Lys  Val  Lys  Leu  Asp  Phe  Thr  Gly  Trp
        115                 120                 125

Arg  Thr  Val  Gly  Val  Ser  Leu  Asn  Asn  Asp  Leu  Glu  Asn  Arg  Glu  Met
    130                 135                 140

Thr  Leu  Asn  Ala  Thr  Asn  Thr  Ser  Ser  Asp  Gly  Thr  Gln  Asp  Ser  Ile
145                 150                 155                 160

Gly  Arg  Ser  Leu  Gly  Ala  Lys  Val  Asp  Ser  Ile  Arg  Phe  Lys  Ala  Pro
                165                 170                 175

Ser  Asn  Val  Ser  Gln  Gly  Glu  Ile  Tyr  Ile  Asp  Arg  Ile  Met  Phe  Ser
            180                 185                 190

Val  Asp  Asp  Ala  Arg  Tyr  Gln  Trp  Ser  Asp  Tyr  Gln  Val  Lys  Thr  Arg
        195                 200                 205

Leu  Ser  Glu  Pro  Glu  Ile  Gln  Phe  His  Asn  Val  Lys  Pro  Gln  Leu  Pro
    210                 215                 220

Val  Thr  Pro  Glu  Asn  Leu  Ala  Ala  Ile  Asp  Leu  Ile  Arg  Gln  Arg  Leu
225                 230                 235                 240

Ile  Asn  Glu  Phe  Val  Gly  Gly  Glu  Lys  Glu  Thr  Asn  Leu  Ala  Leu  Glu
                245                 250                 255

Glu  Asn  Ile  Ser  Lys  Leu  Lys  Ser  Asp  Phe  Asp  Ala  Leu  Asn  Thr  His
            260                 265                 270

Thr  Leu  Ala  Asn  Gly  Gly  Thr  Gln  Gly  Arg  His  Leu  Ile  Thr  Asp  Lys
        275                 280                 285

Gln  Ile  Ile  Ile  Tyr  Gln  Pro  Glu  Asn  Leu  Asn  Ser  Gln  Asp  Lys  Gln
    290                 295                 300

Leu  Phe  Asp  Asn  Tyr  Val  Ile  Leu  Gly  Asn  Tyr  Thr  Thr  Leu  Met  Phe
305                 310                 315                 320
```

-continued

```
Asn Ile Ser Arg Ala Tyr Val Leu Glu Lys Asp Pro Thr Gln Lys Ala
                325                 330                 335

Gln Leu Lys Gln Met Tyr Leu Leu Met Thr Lys His Leu Leu Asp Gln
            340                 345                 350

Gly Phe Val Lys Gly Ser Ala Leu Val Thr Thr His His Trp Gly Tyr
        355                 360                 365

Ser Ser Arg Trp Trp Tyr Ile Ser Thr Leu Leu Met Ser Asp Ala Leu
    370                 375                 380

Lys Glu Ala Asn Leu Gln Thr Gln Val Tyr Asp Ser Leu Leu Trp Tyr
385                 390                 395                 400

Ser Arg Glu Phe Lys Ser Phe Asp Met Lys Val Ser Ala Asp Ser
                405                 410                 415

Ser Asp Leu Asp Tyr Phe Asn Thr Leu Ser Arg Gln His Leu Ala Leu
                420                 425                 430

Leu Leu Leu Glu Pro Asp Asp Gln Lys Arg Ile Asn Leu Val Asn Thr
            435                 440                 445

Phe Ser His Tyr Ile Thr Gly Ala Leu Thr Gln Val Pro Pro Gly Gly
        450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                485                 490                 495

Tyr Leu Leu Arg Asp Thr Pro Phe Ser Val Gly Glu Ser Gly Trp Asn
                500                 505                 510

Asn Leu Lys Lys Ala Met Val Ser Ala Trp Ile Tyr Ser Asn Pro Glu
            515                 520                 525

Val Gly Leu Pro Leu Ala Gly Arg His Pro Phe Asn Ser Pro Ser Leu
            530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gln Asn Glu Ser Thr Ala Ile Phe Gly Glu Thr Ile Thr Pro Ala
            580                 585                 590

Ser Leu Pro Gln Gly Phe Tyr Ala Phe Asn Gly Gly Ala Phe Gly Ile
            595                 600                 605

His Arg Trp Gln Asp Lys Met Val Thr Leu Lys Ala Tyr Asn Thr Asn
        610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
                645                 650                 655

Gln Gly Tyr Gln Gln Glu Gly Trp Asp Trp Asn Arg Met Glu Gly Ala
            660                 665                 670

Thr Thr Ile His Leu Pro Leu Lys Asp Leu Asp Ser Pro Lys Pro His
        675                 680                 685

Thr Leu Met Gln Arg Gly Glu Arg Gly Phe Ser Gly Thr Ser Ser Leu
    690                 695                 700

Glu Gly Gln Tyr Gly Met Met Ala Phe Asn Leu Ile Tyr Pro Ala Asn
705                 710                 715                 720

Leu Glu Arg Phe Asp Pro Asn Phe Thr Ala Lys Lys Ser Val Leu Ala
                725                 730                 735
```

-continued

Ala Asp Asn His Leu Ile Phe Ile Gly Ser Asn Ile Asn Ser Ser Asp
                740                 745                 750

Lys Asn Lys Asn Val Glu Thr Thr Leu Phe Gln His Ala Ile Thr Pro
            755                 760                 765

Thr Leu Asn Thr Leu Trp Ile Asn Gly Gln Lys Ile Glu Asn Met Pro
        770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
                805                 810                 815

His Gln Val Ser Ala Glu Asn Lys Asn Arg Gln Pro Thr Glu Gly Asn
            820                 825                 830

Phe Ser Ser Ala Trp Ile Asp His Ser Thr Arg Pro Lys Asp Ala Ser
        835                 840                 845

Tyr Glu Tyr Met Val Phe Leu Asp Ala Thr Pro Glu Lys Met Gly Glu
850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                885                 890                 895

Gly Tyr Ala Phe Tyr Gln Pro Ala Ser Ile Glu Asp Lys Trp Ile Lys
            900                 905                 910

Lys Val Asn Lys Pro Ala Ile Val Met Thr His Arg Gln Lys Asp Thr
        915                 920                 925

Leu Ile Val Ser Ala Val Thr Pro Asp Leu Asn Met Thr Arg Gln Lys
    930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
                965                 970                 975

Thr Glu Leu Thr Phe Thr Ser Tyr Phe Gly Ile Pro Gln Glu Ile Lys
            980                 985                 990

Leu Ser Pro Leu Pro Met Val Val  Ala Leu Arg Tyr Val  Trp Pro Leu
        995                 1000                1005

Leu Leu  Cys Ser Pro Cys Leu  Leu Ile Gln Ile Pro  Glu Glu Tyr
    1010                1015                1020

Glu Gly  His His Val Met Glu  Pro Pro Val Ile Thr  Glu Gln Ser
    1025                1030                1035

Pro Arg  Arg Leu Val Val Phe  Pro Thr Asp Asp Ile  Ser Leu Lys
    1040                1045                1050

Cys Glu  Ala Ser Gly Lys Pro  Glu Val Gln Phe Arg  Trp Thr Arg
    1055                1060                1065

Asp Gly  Val His Phe Lys Pro  Lys Glu Glu Leu Gly  Val Thr Val
    1070                1075                1080

Tyr Gln  Ser Pro His Ser Gly  Ser Phe Thr Ile Thr  Gly Asn Asn
    1085                1090                1095

Ser Asn  Phe Ala Gln Arg Phe  Gln Gly Ile Tyr Arg  Cys Phe Ala
    1100                1105                1110

Ser Asn  Lys Leu Gly Thr Ala  Met Ser His Glu Ile  Arg Leu Met
    1115                1120                1125

Ala Glu  Gly Ala Pro Lys Trp  Pro Lys Glu Thr Val  Lys Pro Val
    1130                1135                1140

Glu Val  Glu Glu Gly Glu Ser  Val Val Leu Pro Cys  Asn Pro Pro

```
            1145                1150                1155
Pro Ser Ala Glu Pro Leu Arg Ile Tyr Trp Met Asn Ser Lys Ile
    1160                1165                1170
Leu His Ile Lys Gln Asp Glu Arg Val Thr Met Gly Gln Asn Gly
    1175                1180                1185
Asn Leu Tyr Phe Ala Asn Val Leu Thr Ser Asp Asn His Ser Asp
    1190                1195                1200
Tyr Ile Cys His Ala His Phe Pro Gly Thr Arg Thr Ile Ile Gln
    1205                1210                1215
Lys Glu Pro Ile Asp Leu Arg Val Lys Ala Thr Asn Ser Met Ile
    1220                1225                1230
Asp Arg Lys Pro Arg Leu Leu Phe Pro Thr Asn Ser Ser Ser His
    1235                1240                1245
Leu Val Ala Leu Gln Gly Gln Pro Leu Val Leu Glu Cys Ile Ala
    1250                1255                1260
Glu Gly Phe Pro Thr Pro Thr Ile Lys Trp Leu Arg Pro Ser Gly
    1265                1270                1275
Pro Met Pro Ala Asp Arg Val Thr Tyr Gln Asn His Asn Lys Thr
    1280                1285                1290
Leu Gln Leu Leu Lys Val Gly Glu Glu Asp Gly Glu Tyr Arg
    1295                1300                1305
Cys Leu Ala Glu Asn Ser Leu Gly Ser Ala Arg His Ala Tyr Tyr
    1310                1315                1320
Val Thr Val Glu Ala Ala Pro Tyr Trp Leu His Lys Pro Gln Ser
    1325                1330                1335
His Leu Tyr Gly Pro Gly Glu Thr Ala Arg Leu Asp Cys Gln Val
    1340                1345                1350
Gln Gly Arg Pro Gln Pro Glu Val Thr Trp Arg Ile Asn Gly Ile
    1355                1360                1365
Pro Val Glu Glu Leu Ala Lys Asp Gln Lys Tyr Arg Ile Gln Arg
    1370                1375                1380
Gly Ala Leu Ile Leu Ser Asn Val Gln Pro Ser Asp Thr Met Val
    1385                1390                1395
Thr Gln Cys Glu Ala Arg Asn Arg His Gly Leu Leu Leu Ala Asn
    1400                1405                1410
Ala Tyr Ile Tyr Val Val Gln Leu Pro Ala Lys Ile Leu Thr Ala
    1415                1420                1425
Asp Asn Gln Thr Tyr Met Ala Val Gln Gly Ser Thr Ala Tyr Leu
    1430                1435                1440
Leu Cys Lys Ala Phe Gly Ala Pro Val Pro Ser Val Gln Trp Leu
    1445                1450                1455
Asp Glu Asp Gly Thr Thr Val Leu Gln Asp Glu Arg Phe Phe Pro
    1460                1465                1470
Tyr Ala Asn Gly Thr Leu Gly Ile Arg Asp Leu Gln Ala Asn Asp
    1475                1480                1485
Thr Gly Arg Tyr Phe Cys Leu Ala Ala Asn Asp Gln Asn Asn Val
    1490                1495                1500
Thr Ile Met Ala Asn Leu Lys Val Lys Asp Ala Thr Gln Ile Thr
    1505                1510                1515
Gln Gly Pro Arg Ser Thr Ile Glu Lys Lys Gly Ser Arg Val Thr
    1520                1525                1530
Phe Thr Cys Gln Ala Ser Phe Asp Pro Ser Leu Gln Pro Ser Ile
    1535                1540                1545
```

-continued

```
Thr Trp Arg Gly Asp Gly Arg Asp Leu Gln Glu Leu Gly Asp Ser
1550                1555                1560

Asp Lys Tyr Phe Ile Glu Asp Gly Arg Leu Val Ile His Ser Leu
1565                1570                1575

Asp Tyr Ser Asp Gln Gly Asn Tyr Ser Cys Val Ala Ser Thr Glu
1580                1585                1590

Leu Asp Val Val Glu Ser Arg Ala Gln Leu Leu Val Val Gly Ser
1595                1600                1605

Pro Gly Pro Val Pro Arg Leu Val Leu Ser Asp Leu His Leu Leu
1610                1615                1620

Thr Gln Ser Gln Val Arg Val Ser Trp Ser Pro Ala Glu Asp His
1625                1630                1635

Asn Ala Pro Ile Glu Lys Tyr Asp Ile Glu Phe Glu Asp Lys Glu
1640                1645                1650

Met Ala Pro Glu Lys Trp Tyr Ser Leu Gly Lys Val Pro Gly Asn
1655                1660                1665

Gln Thr Ser Thr Thr Leu Lys Leu Ser Pro Tyr Val His Tyr Thr
1670                1675                1680

Phe Arg Val Thr Ala Ile Asn Lys Tyr Gly Pro Gly Glu Pro Ser
1685                1690                1695

Pro Val Ser Glu Thr Val Val Thr Pro Glu Ala Ala Pro Glu Lys
1700                1705                1710

Asn Pro Val Asp Val Lys Gly Glu Gly Asn Glu Thr Thr Asn Met
1715                1720                1725

Val Ile Thr Trp Lys Pro Leu Arg Trp Met Asp Trp Asn Ala Pro
1730                1735                1740

Gln Val Gln Tyr Arg Val Gln Trp Arg Pro Gln Gly Thr Arg Gly
1745                1750                1755

Pro Trp Gln Glu Gln Ile Val Ser Asp Pro Phe Leu Val Val Ser
1760                1765                1770

Asn Thr Ser Thr Phe Val Pro Tyr Glu Ile Lys Val Gln Ala Val
1775                1780                1785

Asn Ser Gln Gly Lys Gly Pro Glu Pro Gln Val Thr Ile Gly Tyr
1790                1795                1800

Ser Gly Glu Asp Tyr Pro Gln Ala Ile Pro Glu Leu Glu Gly Ile
1805                1810                1815

Glu Ile Leu Asn Ser Ser Ala Val Leu Val Lys Trp Arg Pro Val
1820                1825                1830

Asp Leu Ala Gln Val Lys Gly His Leu Arg Gly Tyr Asn Val Thr
1835                1840                1845

Tyr Trp Arg Glu Gly Ser Gln Arg Lys His Ser Lys Arg His Ile
1850                1855                1860

His Lys Asp His Val Val Pro Ala Asn Thr Thr Ser Val Ile
1865                1870                1875

Leu Ser Gly Leu Arg Pro Tyr Ser Ser Tyr His Leu Glu Val Gln
1880                1885                1890

Ala Phe Asn Gly Arg Gly Ser Gly Pro Ala Ser Glu Phe Thr Phe
1895                1900                1905

Ser Thr Pro Glu Gly Val Pro Gly His Pro Glu Ala Leu His Leu
1910                1915                1920

Glu Cys Gln Ser Asn Thr Ser Leu Leu Leu Arg Trp Gln Pro Pro
1925                1930                1935
```

-continued

```
Leu Ser  His Asn Gly Val Leu  Thr Gly Tyr Val Leu  Ser Tyr His
    1940                 1945                 1950

Pro Leu  Asp Glu Gly Gly Lys  Gly Gln Leu Ser Phe  Asn Leu Arg
    1955                 1960                 1965

Asp Pro  Glu Leu Arg Thr His  Asn Leu Thr Asp Leu  Ser Pro His
    1970                 1975                 1980

Leu Arg  Tyr Arg Phe Gln Leu  Gln Ala Thr Thr Lys  Glu Gly Pro
    1985                 1990                 1995

Gly Glu  Ala Ile Val Arg Glu  Gly Gly Thr Met Ala  Leu Ser Gly
    2000                 2005                 2010

Ile Ser  Asp Phe Gly Asn Ile  Ser Ala Thr Ala Gly  Glu Asn Tyr
    2015                 2020                 2025

Ser Val  Val Ser Trp Val Pro  Lys Glu Gly Gln Cys  Asn Phe Arg
    2030                 2035                 2040

Phe His  Ile Leu Phe Lys Ala  Leu Gly Glu Glu Lys  Gly Gly Ala
    2045                 2050                 2055

Ser Leu  Ser Pro Gln Tyr Val  Ser Tyr Asn Gln Ser  Ser Tyr Thr
    2060                 2065                 2070

Gln Trp  Asp Leu Gln Pro Asp  Thr Asp Tyr Glu Ile  His Leu Phe
    2075                 2080                 2085

Lys Glu  Arg Met Phe Arg His  Gln Met Ala Val Lys  Thr Asn Gly
    2090                 2095                 2100

Thr Gly  Arg Val Arg Leu Pro  Pro Ala Gly Phe Ala  Thr Glu Gly
    2105                 2110                 2115

Trp Phe  Ile Gly Phe Val Ser  Ala Ile Ile Leu Leu  Leu Leu Val
    2120                 2125                 2130

Leu Leu  Ile Leu Cys Phe Ile  Lys Arg Ser Lys Gly  Gly Lys Tyr
    2135                 2140                 2145

Ser Val  Lys Asp Lys Glu Asp  Thr Gln Val Asp Ser  Glu Ala Arg
    2150                 2155                 2160

Pro Met  Lys Asp Glu Thr Phe  Gly Glu Tyr Arg Ser  Leu Glu Ser
    2165                 2170                 2175

Asp Asn  Glu Glu Lys Ala Phe  Gly Ser Ser Gln Pro  Ser Leu Asn
    2180                 2185                 2190

Gly Asp  Ile Lys Pro Leu Gly  Ser Asp Asp Ser Leu  Ala Asp Tyr
    2195                 2200                 2205

Gly Gly  Ser Val Asp Val Gln  Phe Asn Glu Asp Gly  Ser Phe Ile
    2210                 2215                 2220

Gly Gln  Tyr Ser Gly Lys Lys  Glu Lys Glu Ala Ala  Gly Gly Asn
    2225                 2230                 2235

Asp Ser  Ser Gly Ala Thr Ser  Pro Ile Asn Pro Ala  Val Ala Leu
    2240                 2245                 2250

Glu
```

<210> SEQ ID NO 34
<211> LENGTH: 2259
<212> TYPE: PRT
<213> ORGANISM: Artificial
<220> FEATURE:
<223> OTHER INFORMATION: Synthetic polypeptide, C terminal fusion chimera between extracellular domain L1 and chondroitinase ABCI protein with a spacer or linking peptide

<400> SEQUENCE: 34

```
Ala Thr Ser Asn Pro Ala Phe Asp Pro Lys Asn Leu Met Gln Ser Glu
1               5                   10                  15
```

-continued

```
Ile Tyr His Phe Ala Gln Asn Asn Pro Leu Ala Asp Phe Ser Ser Asp
             20                  25                  30

Lys Asn Ser Ile Leu Thr Leu Ser Asp Lys Arg Ser Ile Met Gly Asn
         35                  40                  45

Gln Ser Leu Leu Trp Lys Trp Lys Gly Ser Ser Phe Thr Leu His
     50                  55                  60

Lys Lys Leu Ile Val Pro Thr Asp Lys Glu Ala Ser Lys Ala Trp Gly
 65                  70                  75                  80

Arg Ser Ser Thr Pro Val Phe Ser Phe Trp Leu Tyr Asn Glu Lys Pro
                 85                  90                  95

Ile Asp Gly Tyr Leu Thr Ile Asp Phe Gly Glu Lys Leu Ile Ser Thr
             100                 105                 110

Ser Glu Ala Gln Ala Gly Phe Lys Val Lys Leu Asp Phe Thr Gly Trp
         115                 120                 125

Arg Thr Val Gly Val Ser Leu Asn Asn Asp Leu Glu Asn Arg Glu Met
130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                 165                 170                 175

Ser Asn Val Ser Gln Gly Glu Ile Tyr Ile Asp Arg Ile Met Phe Ser
             180                 185                 190

Val Asp Asp Ala Arg Tyr Gln Trp Ser Asp Tyr Gln Val Lys Thr Arg
         195                 200                 205

Leu Ser Glu Pro Glu Ile Gln Phe His Asn Val Lys Pro Gln Leu Pro
     210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Glu
                 245                 250                 255

Glu Asn Ile Ser Lys Leu Lys Ser Asp Phe Asp Ala Leu Asn Thr His
             260                 265                 270

Thr Leu Ala Asn Gly Gly Thr Gln Gly Arg His Leu Ile Thr Asp Lys
         275                 280                 285

Gln Ile Ile Ile Tyr Gln Pro Glu Asn Leu Asn Ser Gln Asp Lys Gln
     290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                 325                 330                 335

Gln Leu Lys Gln Met Tyr Leu Leu Met Thr Lys His Leu Leu Asp Gln
             340                 345                 350

Gly Phe Val Lys Gly Ser Ala Leu Val Thr Thr His His Trp Gly Tyr
         355                 360                 365

Ser Ser Arg Trp Trp Tyr Ile Ser Thr Leu Leu Met Ser Asp Ala Leu
     370                 375                 380

Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
                 405                 410                 415

Ser Asp Leu Asp Tyr Phe Asn Thr Leu Ser Arg Gln His Leu Ala Leu
             420                 425                 430
```

-continued

Leu Leu Leu Glu Pro Asp Asp Gln Lys Arg Ile Asn Leu Val Asn Thr
            435                 440                 445

Phe Ser His Tyr Ile Thr Gly Ala Leu Thr Gln Val Pro Pro Gly Gly
450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
            485                 490                 495

Tyr Leu Leu Arg Asp Thr Pro Phe Ser Val Gly Glu Ser Gly Trp Asn
            500                 505                 510

Asn Leu Lys Lys Ala Met Val Ser Ala Trp Ile Tyr Ser Asn Pro Glu
            515                 520                 525

Val Gly Leu Pro Leu Ala Gly Arg His Pro Phe Asn Ser Pro Ser Leu
530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
            565                 570                 575

Thr Gln Asn Glu Ser Thr Ala Ile Phe Gly Glu Thr Ile Thr Pro Ala
            580                 585                 590

Ser Leu Pro Gln Gly Phe Tyr Ala Phe Asn Gly Gly Ala Phe Gly Ile
            595                 600                 605

His Arg Trp Gln Asp Lys Met Val Thr Leu Lys Ala Tyr Asn Thr Asn
            610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
            645                 650                 655

Gln Gly Tyr Gln Gln Glu Gly Trp Asp Trp Asn Arg Met Glu Gly Ala
            660                 665                 670

Thr Thr Ile His Leu Pro Leu Lys Asp Leu Asp Ser Pro Lys Pro His
            675                 680                 685

Thr Leu Met Gln Arg Gly Glu Arg Gly Phe Ser Gly Thr Ser Ser Leu
690                 695                 700

Glu Gly Gln Tyr Gly Met Met Ala Phe Asn Leu Ile Tyr Pro Ala Asn
705                 710                 715                 720

Leu Glu Arg Phe Asp Pro Asn Phe Thr Ala Lys Lys Ser Val Leu Ala
            725                 730                 735

Ala Asp Asn His Leu Ile Phe Ile Gly Ser Asn Ile Asn Ser Ser Asp
            740                 745                 750

Lys Asn Lys Asn Val Glu Thr Thr Leu Phe Gln His Ala Ile Thr Pro
            755                 760                 765

Thr Leu Asn Thr Leu Trp Ile Asn Gly Gln Lys Ile Glu Asn Met Pro
770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
            805                 810                 815

His Gln Val Ser Ala Glu Asn Lys Asn Arg Gln Pro Thr Glu Gly Asn
            820                 825                 830

Phe Ser Ser Ala Trp Ile Asp His Ser Thr Arg Pro Lys Asp Ala Ser
835                 840                 845

Tyr Glu Tyr Met Val Phe Leu Asp Ala Thr Pro Glu Lys Met Gly Glu

```
                    850                 855                 860
Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                    885                 890                 895

Gly Tyr Ala Phe Tyr Gln Pro Ala Ser Ile Glu Asp Lys Trp Ile Lys
                900                 905                 910

Lys Val Asn Lys Pro Ala Ile Val Met Thr His Arg Gln Lys Asp Thr
                915                 920                 925

Leu Ile Val Ser Ala Val Thr Pro Asp Leu Asn Met Thr Arg Gln Lys
                930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
                965                 970                 975

Thr Glu Leu Thr Phe Thr Ser Tyr Phe Gly Ile Pro Gln Glu Ile Lys
                980                 985                 990

Leu Ser Pro Leu Pro Gly Gly Gly Gly Gly Met Val Val Ala Leu Arg
                995                 1000                1005

Tyr Val Trp Pro Leu Leu Leu Cys Ser Pro Cys Leu Leu Ile Gln
        1010                1015                1020

Ile Pro Glu Glu Tyr Glu Gly His His Val Met Glu Pro Pro Val
        1025                1030                1035

Ile Thr Glu Gln Ser Pro Arg Arg Leu Val Val Phe Pro Thr Asp
        1040                1045                1050

Asp Ile Ser Leu Lys Cys Glu Ala Ser Gly Lys Pro Glu Val Gln
        1055                1060                1065

Phe Arg Trp Thr Arg Asp Gly Val His Phe Lys Pro Lys Glu Glu
        1070                1075                1080

Leu Gly Val Thr Val Tyr Gln Ser Pro His Ser Gly Ser Phe Thr
        1085                1090                1095

Ile Thr Gly Asn Asn Ser Asn Phe Ala Gln Arg Phe Gln Gly Ile
        1100                1105                1110

Tyr Arg Cys Phe Ala Ser Asn Lys Leu Gly Thr Ala Met Ser His
        1115                1120                1125

Glu Ile Arg Leu Met Ala Glu Gly Ala Pro Lys Trp Pro Lys Glu
        1130                1135                1140

Thr Val Lys Pro Val Glu Val Glu Glu Gly Glu Ser Val Val Leu
        1145                1150                1155

Pro Cys Asn Pro Pro Ser Ala Glu Pro Leu Arg Ile Tyr Trp
        1160                1165                1170

Met Asn Ser Lys Ile Leu His Ile Lys Gln Asp Glu Arg Val Thr
        1175                1180                1185

Met Gly Gln Asn Gly Asn Leu Tyr Phe Ala Asn Val Leu Thr Ser
        1190                1195                1200

Asp Asn His Ser Asp Tyr Ile Cys His Ala His Phe Pro Gly Thr
        1205                1210                1215

Arg Thr Ile Ile Gln Lys Glu Pro Ile Asp Leu Arg Val Lys Ala
        1220                1225                1230

Thr Asn Ser Met Ile Asp Arg Lys Pro Arg Leu Leu Phe Pro Thr
        1235                1240                1245

Asn Ser Ser Ser His Leu Val Ala Leu Gln Gly Gln Pro Leu Val
        1250                1255                1260
```

```
Leu Glu Cys Ile Ala Glu Gly Phe Pro Thr Pro Thr Ile Lys Trp
1265                 1270                1275

Leu Arg Pro Ser Gly Pro Met Pro Ala Asp Arg Val Thr Tyr Gln
1280                 1285                1290

Asn His Asn Lys Thr Leu Gln Leu Leu Lys Val Gly Glu Glu Asp
1295                 1300                1305

Asp Gly Glu Tyr Arg Cys Leu Ala Glu Asn Ser Leu Gly Ser Ala
1310                 1315                1320

Arg His Ala Tyr Tyr Val Thr Val Glu Ala Ala Pro Tyr Trp Leu
1325                 1330                1335

His Lys Pro Gln Ser His Leu Tyr Gly Pro Gly Glu Thr Ala Arg
1340                 1345                1350

Leu Asp Cys Gln Val Gln Gly Arg Pro Gln Pro Glu Val Thr Trp
1355                 1360                1365

Arg Ile Asn Gly Ile Pro Val Glu Glu Leu Ala Lys Asp Gln Lys
1370                 1375                1380

Tyr Arg Ile Gln Arg Gly Ala Leu Ile Leu Ser Asn Val Gln Pro
1385                 1390                1395

Ser Asp Thr Met Val Thr Gln Cys Glu Ala Arg Asn Arg His Gly
1400                 1405                1410

Leu Leu Leu Ala Asn Ala Tyr Ile Tyr Val Val Gln Leu Pro Ala
1415                 1420                1425

Lys Ile Leu Thr Ala Asp Asn Gln Thr Tyr Met Ala Val Gln Gly
1430                 1435                1440

Ser Thr Ala Tyr Leu Leu Cys Lys Ala Phe Gly Ala Pro Val Pro
1445                 1450                1455

Ser Val Gln Trp Leu Asp Glu Asp Gly Thr Thr Val Leu Gln Asp
1460                 1465                1470

Glu Arg Phe Phe Pro Tyr Ala Asn Gly Thr Leu Gly Ile Arg Asp
1475                 1480                1485

Leu Gln Ala Asn Asp Thr Gly Arg Tyr Phe Cys Leu Ala Ala Asn
1490                 1495                1500

Asp Gln Asn Asn Val Thr Ile Met Ala Asn Leu Lys Val Lys Asp
1505                 1510                1515

Ala Thr Gln Ile Thr Gln Gly Pro Arg Ser Thr Ile Glu Lys Lys
1520                 1525                1530

Gly Ser Arg Val Thr Phe Thr Cys Gln Ala Ser Phe Asp Pro Ser
1535                 1540                1545

Leu Gln Pro Ser Ile Thr Trp Arg Gly Asp Gly Arg Asp Leu Gln
1550                 1555                1560

Glu Leu Gly Asp Ser Asp Lys Tyr Phe Ile Glu Asp Gly Arg Leu
1565                 1570                1575

Val Ile His Ser Leu Asp Tyr Ser Asp Gln Gly Asn Tyr Ser Cys
1580                 1585                1590

Val Ala Ser Thr Glu Leu Asp Val Val Glu Ser Arg Ala Gln Leu
1595                 1600                1605

Leu Val Val Gly Ser Pro Gly Pro Val Pro Arg Leu Val Leu Ser
1610                 1615                1620

Asp Leu His Leu Leu Thr Gln Ser Gln Val Arg Val Ser Trp Ser
1625                 1630                1635

Pro Ala Glu Asp His Asn Ala Pro Ile Glu Lys Tyr Asp Ile Glu
1640                 1645                1650
```

```
Phe Glu Asp Lys Glu Met Ala Pro Glu Lys Trp Tyr Ser Leu Gly
    1655                1660                1665

Lys Val Pro Gly Asn Gln Thr Ser Thr Thr Leu Lys Leu Ser Pro
    1670                1675                1680

Tyr Val His Tyr Thr Phe Arg Val Thr Ala Ile Asn Lys Tyr Gly
    1685                1690                1695

Pro Gly Glu Pro Ser Pro Val Ser Glu Thr Val Val Thr Pro Glu
    1700                1705                1710

Ala Ala Pro Glu Lys Asn Pro Val Asp Val Lys Gly Glu Gly Asn
    1715                1720                1725

Glu Thr Thr Asn Met Val Ile Thr Trp Lys Pro Leu Arg Trp Met
    1730                1735                1740

Asp Trp Asn Ala Pro Gln Val Gln Tyr Arg Val Gln Trp Arg Pro
    1745                1750                1755

Gln Gly Thr Arg Gly Pro Trp Gln Glu Gln Ile Val Ser Asp Pro
    1760                1765                1770

Phe Leu Val Val Ser Asn Thr Ser Thr Phe Val Pro Tyr Glu Ile
    1775                1780                1785

Lys Val Gln Ala Val Asn Ser Gln Gly Lys Gly Pro Glu Pro Gln
    1790                1795                1800

Val Thr Ile Gly Tyr Ser Gly Glu Asp Tyr Pro Gln Ala Ile Pro
    1805                1810                1815

Glu Leu Glu Gly Ile Glu Ile Leu Asn Ser Ser Ala Val Leu Val
    1820                1825                1830

Lys Trp Arg Pro Val Asp Leu Ala Gln Val Lys Gly His Leu Arg
    1835                1840                1845

Gly Tyr Asn Val Thr Tyr Trp Arg Glu Gly Ser Gln Arg Lys His
    1850                1855                1860

Ser Lys Arg His Ile His Lys Asp His Val Val Pro Ala Asn
    1865                1870                1875

Thr Thr Ser Val Ile Leu Ser Gly Leu Arg Pro Tyr Ser Ser Tyr
    1880                1885                1890

His Leu Glu Val Gln Ala Phe Asn Gly Arg Gly Ser Gly Pro Ala
    1895                1900                1905

Ser Glu Phe Thr Phe Ser Thr Pro Glu Gly Val Pro Gly His Pro
    1910                1915                1920

Glu Ala Leu His Leu Glu Cys Gln Ser Asn Thr Ser Leu Leu Leu
    1925                1930                1935

Arg Trp Gln Pro Pro Leu Ser His Asn Gly Val Leu Thr Gly Tyr
    1940                1945                1950

Val Leu Ser Tyr His Pro Leu Asp Glu Gly Gly Lys Gly Gln Leu
    1955                1960                1965

Ser Phe Asn Leu Arg Asp Pro Glu Leu Arg Thr His Asn Leu Thr
    1970                1975                1980

Asp Leu Ser Pro His Leu Arg Tyr Arg Phe Gln Leu Gln Ala Thr
    1985                1990                1995

Thr Lys Glu Gly Pro Gly Glu Ala Ile Val Arg Glu Gly Gly Thr
    2000                2005                2010

Met Ala Leu Ser Gly Ile Ser Asp Phe Gly Asn Ile Ser Ala Thr
    2015                2020                2025

Ala Gly Glu Asn Tyr Ser Val Val Ser Trp Val Pro Lys Glu Gly
    2030                2035                2040

Gln Cys Asn Phe Arg Phe His Ile Leu Phe Lys Ala Leu Gly Glu
```

Glu Lys Gly Gly Ala Ser Leu Ser Pro Gln Tyr Val Ser Tyr Asn
        2060            2065                2070

Gln Ser Ser Tyr Thr Gln Trp Asp Leu Gln Pro Asp Thr Asp Tyr
    2075            2080                2085

Glu Ile His Leu Phe Lys Glu Arg Met Phe Arg His Gln Met Ala
        2090            2095                2100

Val Lys Thr Asn Gly Thr Gly Arg Val Arg Leu Pro Pro Ala Gly
    2105            2110                2115

Phe Ala Thr Glu Gly Trp Phe Ile Gly Phe Val Ser Ala Ile Ile
    2120            2125                2130

Leu Leu Leu Leu Val Leu Leu Ile Leu Cys Phe Ile Lys Arg Ser
    2135            2140                2145

Lys Gly Gly Lys Tyr Ser Val Lys Asp Lys Glu Asp Thr Gln Val
    2150            2155                2160

Asp Ser Glu Ala Arg Pro Met Lys Asp Glu Thr Phe Gly Glu Tyr
    2165            2170                2175

Arg Ser Leu Glu Ser Asp Asn Glu Glu Lys Ala Phe Gly Ser Ser
    2180            2185                2190

Gln Pro Ser Leu Asn Gly Asp Ile Lys Pro Leu Gly Ser Asp Asp
    2195            2200                2205

Ser Leu Ala Asp Tyr Gly Gly Ser Val Asp Val Gln Phe Asn Glu
    2210            2215                2220

Asp Gly Ser Phe Ile Gly Gln Tyr Ser Gly Lys Lys Glu Lys Glu
    2225            2230                2235

Ala Ala Gly Gly Asn Asp Ser Ser Gly Ala Thr Ser Pro Ile Asn
    2240            2245                2250

Pro Ala Val Ala Leu Glu
    2255

<210> SEQ ID NO 35
<211> LENGTH: 990
<212> TYPE: PRT
<213> ORGANISM: Artificial
<220> FEATURE:
<223> OTHER INFORMATION: Synthetic polypeptide, Chondroitinase ABCII
      protein

<400> SEQUENCE: 35

Leu Pro Thr Leu Ser His Glu Ala Phe Gly Asp Ile Tyr Leu Phe Glu
1               5                   10                  15

Gly Glu Leu Pro Asn Ile Leu Thr Thr Ser Asn Asn Gln Leu Ser
            20                  25                  30

Leu Ser Lys Gln His Ala Lys Asp Gly Glu Gln Ser Leu Lys Trp Gln
        35                  40                  45

Tyr Gln Pro Gln Ala Thr Leu Thr Leu Asn Asn Ile Val Asn Tyr Gln
    50                  55                  60

Asp Asp Lys Asn Thr Ala Thr Pro Leu Thr Phe Met Met Trp Ile Tyr
65                  70                  75                  80

Asn Glu Lys Pro Gln Ser Ser Pro Leu Thr Leu Ala Phe Lys Gln Asn
                85                  90                  95

Asn Lys Ile Ala Leu Ser Phe Asn Ala Glu Leu Asn Phe Thr Gly Trp
            100                 105                 110

Arg Gly Ile Ala Val Pro Phe Arg Asp Met Gln Gly Ser Ala Thr Gly
        115                 120                 125

```
Gln Leu Asp Gln Leu Val Ile Thr Ala Pro Asn Gln Ala Gly Thr Leu
    130                 135                 140

Phe Phe Asp Gln Ile Ile Met Ser Val Pro Leu Asp Asn Arg Trp Ala
145                 150                 155                 160

Val Pro Asp Tyr Gln Thr Pro Tyr Val Asn Asn Ala Val Asn Thr Met
                165                 170                 175

Val Ser Lys Asn Trp Ser Ala Leu Leu Met Tyr Asp Gln Met Phe Gln
            180                 185                 190

Ala His Tyr Pro Thr Leu Asn Phe Asp Thr Glu Phe Arg Asp Asp Gln
        195                 200                 205

Thr Glu Met Ala Ser Ile Tyr Gln Arg Phe Glu Tyr Tyr Gln Gly Ile
    210                 215                 220

Arg Ser Asp Lys Lys Ile Thr Pro Asp Met Leu Asp Lys His Leu Ala
225                 230                 235                 240

Leu Trp Glu Lys Leu Gly Leu Thr Gln His Ala Asp Gly Ser Ile Thr
                245                 250                 255

Gly Lys Ala Leu Asp His Pro Asn Arg Gln His Phe Met Lys Val Glu
            260                 265                 270

Gly Val Phe Ser Glu Gly Thr Gln Lys Ala Leu Leu Asp Ala Asn Met
        275                 280                 285

Leu Arg Asp Val Gly Lys Thr Leu Leu Gln Thr Ala Ile Tyr Leu Arg
    290                 295                 300

Ser Asp Ser Leu Ser Ala Thr Gly Arg Lys Lys Leu Glu Glu Arg Tyr
305                 310                 315                 320

Leu Leu Gly Thr Arg Tyr Val Leu Glu Gln Gly Phe Thr Arg Gly Ser
                325                 330                 335

Gly Tyr Gln Ile Ile Thr His Val Gly Tyr Gln Thr Arg Glu Leu Phe
            340                 345                 350

Asp Ala Trp Phe Ile Gly Arg His Val Leu Ala Lys Asn Asn Leu Leu
        355                 360                 365

Ala Pro Thr Gln Gln Ala Met Met Trp Tyr Asn Ala Thr Gly Arg Ile
    370                 375                 380

Phe Glu Lys Asp Asn Glu Ile Val Asp Ala Asn Val Asp Ile Leu Asn
385                 390                 395                 400

Thr Gln Leu Gln Trp Met Ile Lys Ser Leu Leu Met Leu Pro Asp Tyr
                405                 410                 415

Gln Gln Arg Gln Gln Ala Leu Ala Gln Leu Gln Ser Trp Leu Asn Lys
            420                 425                 430

Thr Ile Leu Ser Ser Lys Gly Val Ala Gly Gly Phe Lys Ser Asp Gly
        435                 440                 445

Ser Ile Phe His His Ser Gln His Tyr Pro Ala Tyr Ala Lys Asp Ala
    450                 455                 460

Phe Gly Gly Leu Ala Pro Ser Val Tyr Ala Leu Ser Asp Ser Pro Phe
465                 470                 475                 480

Arg Leu Ser Thr Ser Ala His Glu His Leu Lys Asp Val Leu Leu Lys
                485                 490                 495

Met Arg Ile Tyr Thr Lys Glu Thr Gln Ile Pro Val Val Leu Ser Gly
            500                 505                 510

Arg His Pro Thr Gly Leu His Lys Ile Gly Ile Ala Pro Phe Lys Trp
        515                 520                 525

Met Ala Leu Ala Gly Thr Pro Asp Gly Lys Gln Lys Leu Asp Thr Thr
    530                 535                 540

Leu Ser Ala Ala Tyr Ala Asn Leu Asp Asn Lys Thr His Phe Glu Gly
```

```
545                 550                 555                 560
    Ile Asn Ala Glu Ser Glu Pro Val Gly Ala Trp Ala Met Asn Tyr Ala
                    565                 570                 575
    Ser Met Ala Ile Gln Arg Arg Ala Ser Thr Gln Ser Pro Gln Gln Ser
                    580                 585                 590
    Trp Leu Ala Ile Ala Arg Gly Phe Ser Arg Tyr Leu Val Gly Asn Glu
                    595                 600                 605
    Ser Tyr Glu Asn Asn Asn Arg Tyr Gly Arg Tyr Leu Gln Tyr Gly Gln
        610                 615                 620
    Leu Glu Ile Ile Pro Ala Asp Leu Thr Gln Ser Gly Phe Ser His Ala
625                 630                 635                 640
    Gly Trp Asp Trp Asn Arg Tyr Pro Gly Thr Thr Ile His Leu Pro
                    645                 650                 655
    Tyr Asn Glu Leu Glu Ala Lys Leu Asn Gln Leu Pro Ala Ala Gly Ile
                    660                 665                 670
    Glu Glu Met Leu Leu Ser Thr Glu Ser Tyr Ser Gly Ala Asn Thr Leu
                    675                 680                 685
    Asn Asn Asn Ser Met Phe Ala Met Lys Leu His Gly His Ser Lys Tyr
        690                 695                 700
    Gln Gln Gln Ser Leu Arg Ala Asn Lys Ser Tyr Phe Leu Phe Asp Asn
705                 710                 715                 720
    Arg Val Ile Ala Leu Gly Ser Gly Ile Glu Asn Asp Asp Lys Gln His
                    725                 730                 735
    Thr Thr Glu Thr Thr Leu Phe Gln Phe Ala Val Pro Lys Leu Gln Ser
                    740                 745                 750
    Val Ile Ile Asn Gly Lys Lys Val Asn Gln Leu Asp Thr Gln Leu Thr
                    755                 760                 765
    Leu Asn Asn Ala Asp Thr Leu Ile Asp Pro Ala Gly Asn Leu Tyr Lys
        770                 775                 780
    Leu Thr Lys Gly Gln Thr Val Lys Phe Ser Tyr Gln Lys Gln His Ser
785                 790                 795                 800
    Leu Asp Asp Arg Asn Ser Lys Pro Thr Glu Gln Leu Phe Ala Thr Ala
                    805                 810                 815
    Val Ile Ser His Gly Lys Ala Pro Ser Asn Glu Asn Tyr Glu Tyr Ala
                    820                 825                 830
    Ile Ala Ile Glu Ala Gln Asn Asn Lys Ala Pro Lys Tyr Thr Val Leu
                    835                 840                 845
    Gln His Asn Asp Gln Leu His Ala Val Lys Asp Lys Ile Thr Gln Glu
        850                 855                 860
    Glu Gly Tyr Gly Phe Phe Glu Ala Thr Lys Leu Lys Ser Ala Asp Ala
865                 870                 875                 880
    Thr Leu Leu Ser Ser Asp Ala Pro Val Met Val Met Ala Lys Ile Gln
                    885                 890                 895
    Asn Gln Gln Leu Thr Leu Ser Ile Val Asn Pro Asp Leu Asn Leu Tyr
                    900                 905                 910
    Gln Gly Arg Glu Lys Asp Gln Phe Asp Asp Lys Gly Asn Gln Ile Glu
                    915                 920                 925
    Val Ser Val Tyr Ser Arg His Trp Leu Thr Ala Glu Ser Gln Ser Thr
        930                 935                 940
    Asn Ser Thr Ile Thr Val Lys Gly Ile Trp Lys Leu Thr Pro Gln
945                 950                 955                 960
    Pro Gly Val Ile Ile Lys His His Asn Asn Asn Thr Leu Ile Thr Thr
                    965                 970                 975
```

```
Thr Thr Ile Gln Ala Thr Pro Thr Val Ile Asn Leu Val Lys
            980                 985                 990

<210> SEQ ID NO 36
<211> LENGTH: 700
<212> TYPE: PRT
<213> ORGANISM: Unknown
<220> FEATURE:
<223> OTHER INFORMATION: Pedobacter heparinus Chondroitinase AC protein

<400> SEQUENCE: 36

Met Lys Lys Leu Phe Val Thr Cys Ile Val Phe Phe Ser Ile Leu Ser
1               5                   10                  15

Pro Ala Leu Leu Ile Ala Gln Gln Thr Gly Thr Ala Glu Leu Ile Met
            20                  25                  30

Lys Arg Val Met Leu Asp Leu Lys Lys Pro Leu Arg Asn Met Asp Lys
        35                  40                  45

Val Ala Glu Lys Asn Leu Asn Thr Leu Gln Pro Asp Gly Ser Trp Lys
50                  55                  60

Asp Val Pro Tyr Lys Asp Ala Met Thr Asn Trp Leu Pro Asn Asn
65                  70                  75                  80

His Leu Leu Gln Leu Glu Thr Ile Ile Gln Ala Tyr Ile Glu Lys Asp
                85                  90                  95

Ser His Tyr Tyr Gly Asp Asp Lys Val Phe Asp Gln Ile Ser Lys Ala
            100                 105                 110

Phe Lys Tyr Trp Tyr Asp Ser Asp Pro Lys Ser Arg Asn Trp Trp His
        115                 120                 125

Asn Glu Ile Ala Thr Pro Gln Ala Leu Gly Glu Met Leu Ile Leu Met
130                 135                 140

Arg Tyr Gly Lys Lys Pro Leu Asp Glu Ala Leu Val His Lys Leu Thr
145                 150                 155                 160

Glu Arg Met Lys Arg Gly Glu Pro Glu Lys Lys Thr Gly Ala Asn Lys
                165                 170                 175

Thr Asp Ile Ala Leu His Tyr Phe Tyr Arg Ala Leu Leu Thr Ser Asp
            180                 185                 190

Glu Ala Leu Leu Ser Phe Ala Val Lys Glu Leu Phe Tyr Pro Val Gln
        195                 200                 205

Phe Val His Tyr Glu Glu Gly Leu Gln Tyr Asp Tyr Ser Tyr Leu Gln
210                 215                 220

His Gly Pro Gln Leu Gln Ile Ser Ser Tyr Gly Ala Val Phe Ile Thr
225                 230                 235                 240

Gly Val Leu Lys Leu Ala Asn Tyr Val Arg Asp Thr Pro Tyr Ala Leu
                245                 250                 255

Ser Thr Glu Lys Leu Ala Ile Phe Ser Lys Tyr Tyr Arg Asp Ser Tyr
            260                 265                 270

Leu Lys Ala Ile Arg Gly Ser Tyr Met Asp Phe Asn Val Glu Gly Arg
        275                 280                 285

Gly Val Ser Arg Pro Asp Ile Leu Asn Lys Lys Ala Glu Lys Lys Arg
290                 295                 300

Leu Leu Val Ala Lys Met Ile Asp Leu Lys His Thr Glu Glu Trp Ala
305                 310                 315                 320

Asp Ala Ile Ala Arg Thr Asp Ser Thr Val Ala Ala Gly Tyr Lys Ile
                325                 330                 335

Glu Pro Tyr His His Gln Phe Trp Asn Gly Asp Tyr Val Gln His Leu
            340                 345                 350
```

```
Arg Pro Ala Tyr Ser Phe Asn Val Arg Met Val Ser Lys Arg Thr Arg
            355                 360                 365

Arg Ser Glu Ser Gly Asn Lys Glu Asn Leu Leu Gly Arg Tyr Leu Ser
        370                 375                 380

Asp Gly Ala Thr Asn Ile Gln Leu Arg Gly Pro Glu Tyr Tyr Asn Ile
385                 390                 395                 400

Met Pro Val Trp Glu Trp Asp Lys Ile Pro Gly Ile Thr Ser Arg Asp
                405                 410                 415

Tyr Leu Thr Asp Arg Pro Leu Thr Lys Leu Trp Gly Glu Gln Gly Ser
            420                 425                 430

Asn Asp Phe Ala Gly Gly Val Ser Asp Gly Val Tyr Gly Ala Ser Ala
            435                 440                 445

Tyr Ala Leu Asp Tyr Asp Ser Leu Gln Ala Lys Lys Ala Trp Phe Phe
            450                 455                 460

Phe Asp Lys Glu Ile Val Cys Leu Gly Ala Gly Ile Asn Ser Asn Ala
465                 470                 475                 480

Pro Glu Asn Ile Thr Thr Thr Leu Asn Gln Ser Trp Leu Asn Gly Pro
                485                 490                 495

Val Ile Ser Thr Ala Gly Lys Thr Gly Arg Gly Lys Ile Thr Thr Phe
            500                 505                 510

Lys Ala Gln Gly Gln Phe Trp Leu Leu His Asp Ala Ile Gly Tyr Tyr
            515                 520                 525

Phe Pro Glu Gly Ala Asn Leu Ser Leu Ser Thr Gln Ser Gln Lys Gly
            530                 535                 540

Asn Trp Phe His Ile Asn Ser His Ser Lys Asp Glu Val Ser Gly
545                 550                 555                 560

Asp Val Phe Lys Leu Trp Ile Asn His Gly Ala Arg Pro Glu Asn Ala
                565                 570                 575

Gln Tyr Ala Tyr Ile Val Leu Pro Gly Ile Asn Lys Pro Glu Glu Ile
            580                 585                 590

Lys Lys Tyr Asn Gly Thr Ala Pro Lys Val Leu Ala Asn Thr Asn Gln
            595                 600                 605

Leu Gln Ala Val Tyr His Gln Gln Leu Asp Met Val Gln Ala Ile Phe
            610                 615                 620

Tyr Thr Ala Gly Lys Leu Ser Val Ala Gly Ile Glu Ile Glu Thr Asp
625                 630                 635                 640

Lys Pro Cys Ala Val Leu Ile Lys His Ile Asn Gly Lys Gln Val Ile
                645                 650                 655

Trp Ala Ala Asp Pro Leu Gln Lys Glu Lys Thr Ala Val Leu Ser Ile
            660                 665                 670

Arg Asp Leu Lys Thr Gly Lys Thr Asn Arg Val Lys Ile Asp Phe Pro
            675                 680                 685

Gln Gln Glu Phe Ala Gly Ala Thr Val Glu Leu Lys
            690                 695                 700

<210> SEQ ID NO 37
<211> LENGTH: 506
<212> TYPE: PRT
<213> ORGANISM: Unknown
<220> FEATURE:
<223> OTHER INFORMATION: Pedobacter heparinus Chondroitinase B protein

<400> SEQUENCE: 37

Met Lys Met Leu Asn Lys Leu Ala Gly Tyr Leu Leu Pro Ile Met Val
1               5                   10                  15
```

```
Leu Leu Asn Val Ala Pro Cys Leu Gly Gln Val Val Ala Ser Asn Glu
            20                  25                  30

Thr Leu Tyr Gln Val Val Lys Glu Val Lys Pro Gly Gly Leu Val Gln
        35                  40                  45

Ile Ala Asp Gly Thr Tyr Lys Asp Val Gln Leu Ile Val Ser Asn Ser
50                  55                  60

Gly Lys Ser Gly Leu Pro Ile Thr Ile Lys Ala Leu Asn Pro Gly Lys
65                  70                  75                  80

Val Phe Phe Thr Gly Asp Ala Lys Val Glu Leu Arg Gly Glu His Leu
                85                  90                  95

Ile Leu Glu Gly Ile Trp Phe Lys Asp Gly Asn Arg Ala Ile Gln Ala
            100                 105                 110

Trp Lys Ser His Gly Pro Gly Leu Val Ala Ile Tyr Gly Ser Tyr Asn
        115                 120                 125

Arg Ile Thr Ala Cys Val Phe Asp Cys Phe Asp Glu Ala Asn Ser Ala
130                 135                 140

Tyr Ile Thr Thr Ser Leu Thr Glu Asp Gly Lys Val Pro Gln His Cys
145                 150                 155                 160

Arg Ile Asp His Cys Ser Phe Thr Asp Lys Ile Thr Phe Asp Gln Val
                165                 170                 175

Ile Asn Leu Asn Asn Thr Ala Arg Ala Ile Lys Asp Gly Ser Val Gly
            180                 185                 190

Gly Pro Gly Met Tyr His Arg Val Asp His Cys Phe Phe Ser Asn Pro
        195                 200                 205

Gln Lys Pro Gly Asn Ala Gly Gly Ile Arg Ile Gly Tyr Tyr Arg
210                 215                 220

Asn Asp Ile Gly Arg Cys Leu Val Asp Ser Asn Leu Phe Met Arg Gln
225                 230                 235                 240

Asp Ser Glu Ala Glu Ile Ile Thr Ser Lys Ser Gln Glu Asn Val Tyr
                245                 250                 255

Tyr Gly Asn Thr Tyr Leu Asn Cys Gln Gly Thr Met Asn Phe Arg His
            260                 265                 270

Gly Asp His Gln Val Ala Ile Asn Asn Phe Tyr Ile Gly Asn Asp Gln
        275                 280                 285

Arg Phe Gly Tyr Gly Met Phe Val Trp Gly Ser Arg His Val Ile
290                 295                 300

Ala Cys Asn Tyr Phe Glu Leu Ser Glu Thr Ile Lys Ser Arg Gly Asn
305                 310                 315                 320

Ala Ala Leu Tyr Leu Asn Pro Gly Ala Met Ala Ser Glu His Ala Leu
                325                 330                 335

Ala Phe Asp Met Leu Ile Ala Asn Asn Ala Phe Ile Asn Val Asn Gly
            340                 345                 350

Tyr Ala Ile His Phe Asn Pro Leu Asp Glu Arg Arg Lys Glu Tyr Cys
        355                 360                 365

Ala Ala Asn Arg Leu Lys Phe Glu Thr Pro His Gln Leu Met Leu Lys
370                 375                 380

Gly Asn Leu Phe Phe Lys Asp Lys Pro Tyr Val Tyr Pro Phe Phe Lys
385                 390                 395                 400

Asp Asp Tyr Phe Ile Ala Gly Lys Asn Ser Trp Thr Gly Asn Val Ala
                405                 410                 415

Leu Gly Val Glu Lys Gly Ile Pro Val Asn Ile Ser Ala Asn Arg Ser
            420                 425                 430
```

```
Ala Tyr Lys Pro Val Lys Ile Lys Asp Ile Gln Pro Ile Glu Gly Ile
            435                 440                 445
Ala Leu Asp Leu Asn Ala Leu Ile Ser Lys Gly Ile Thr Gly Lys Pro
450                 455                 460
Leu Ser Trp Asp Glu Val Arg Pro Tyr Trp Leu Lys Glu Met Pro Gly
465                 470                 475                 480
Thr Tyr Ala Leu Thr Ala Arg Leu Ser Ala Asp Arg Ala Ala Lys Phe
                485                 490                 495
Lys Ala Val Ile Lys Arg Asn Lys Glu His
            500                 505

<210> SEQ ID NO 38
<211> LENGTH: 405
<212> TYPE: PRT
<213> ORGANISM: Unknown
<220> FEATURE:
<223> OTHER INFORMATION: Homo sapiens Hyaluronidase-1 protein

<400> SEQUENCE: 38

Met Ala Ala His Leu Leu Pro Ile Cys Ala Leu Phe Leu Thr Leu Leu
1               5                   10                  15
Asp Met Ala Gln Gly Phe Arg Gly Pro Leu Leu Pro Asn Arg Pro Phe
            20                  25                  30
Thr Thr Val Trp Asn Ala Asn Thr Gln Trp Cys Leu Glu Arg His Gly
        35                  40                  45
Val Asp Val Asp Val Ser Val Phe Asp Val Val Ala Asn Pro Gly Gln
    50                  55                  60
Thr Phe Arg Gly Pro Asp Met Thr Ile Phe Tyr Ser Ser Gln Leu Gly
65                  70                  75                  80
Thr Tyr Pro Tyr Tyr Thr Pro Thr Gly Glu Pro Val Phe Gly Gly Leu
                85                  90                  95
Pro Gln Asn Ala Ser Leu Ile Ala His Leu Ala Arg Thr Phe Gln Asp
            100                 105                 110
Ile Leu Ala Ala Ile Pro Ala Pro Asp Phe Ser Gly Leu Ala Val Ile
        115                 120                 125
Asp Trp Glu Ala Trp Arg Pro Arg Trp Ala Phe Asn Trp Asp Thr Lys
130                 135                 140
Asp Ile Tyr Arg Gln Arg Ser Arg Ala Leu Val Gln Ala Gln His Pro
145                 150                 155                 160
Asp Trp Pro Ala Pro Gln Val Glu Ala Val Ala Gln Asp Gln Phe Gln
                165                 170                 175
Gly Ala Ala Arg Ala Trp Met Ala Gly Thr Leu Gln Leu Gly Arg Ala
            180                 185                 190
Leu Arg Pro Arg Gly Leu Trp Gly Phe Tyr Gly Phe Pro Asp Cys Tyr
        195                 200                 205
Asn Tyr Asp Phe Leu Ser Pro Asn Tyr Thr Gly Gln Cys Pro Ser Gly
210                 215                 220
Ile Arg Ala Gln Asn Asp Gln Leu Gly Trp Leu Trp Gly Gln Ser Arg
225                 230                 235                 240
Ala Leu Tyr Pro Ser Ile Tyr Met Pro Ala Val Leu Glu Gly Thr Gly
                245                 250                 255
Lys Ser Gln Met Tyr Val Gln His Arg Val Ala Glu Ala Phe Arg Val
            260                 265                 270
Ala Val Ala Ala Gly Asp Pro Asn Leu Pro Val Leu Pro Tyr Val Gln
        275                 280                 285
```

```
Ile Phe Tyr Asp Thr Thr Asn His Phe Leu Pro Leu Glu Ser Cys Gln
290                 295                 300

Ala Ile Lys Glu Tyr Met Asp Thr Thr Leu Gly Pro Phe Ile Leu Asn
305                 310                 315                 320

Val Thr Ser Gly Ala Leu Leu Cys Ser Gln Ala Leu Cys Ser Gly His
            325                 330                 335

Gly Arg Cys Val Arg Arg Thr Ser His Pro Lys Ala Leu Leu Leu Leu
            340                 345                 350

Asn Pro Ala Ser Phe Ser Ile Gln Leu Thr Pro Gly Gly Pro Leu
            355                 360                 365

Ser Leu Arg Gly Ala Leu Ser Leu Glu Asp Gln Ala Gln Met Ala Val
370                 375                 380

Glu Phe Lys Cys Arg Cys Tyr Pro Gly Trp Gln Ala Pro Trp Cys Glu
385                 390                 395                 400

Arg Lys Ser Met Trp
            405

<210> SEQ ID NO 39
<211> LENGTH: 473
<212> TYPE: PRT
<213> ORGANISM: Unknown
<220> FEATURE:
<223> OTHER INFORMATION: Homo sapiens Hyaluronidase-2 protein

<400> SEQUENCE: 39

Met Arg Ala Gly Pro Gly Pro Thr Val Thr Leu Ala Leu Val Leu Ala
1               5                   10                  15

Val Ser Trp Ala Met Glu Leu Lys Pro Thr Ala Pro Pro Ile Phe Thr
            20                  25                  30

Gly Arg Pro Phe Val Val Ala Trp Asp Val Pro Thr Gln Asp Cys Gly
        35                  40                  45

Pro Arg Leu Lys Val Pro Leu Asp Leu Asn Ala Phe Asp Val Gln Ala
    50                  55                  60

Ser Pro Asn Glu Gly Phe Val Asn Gln Asn Ile Thr Ile Phe Tyr Arg
65                  70                  75                  80

Asp Arg Leu Gly Leu Tyr Pro Arg Phe Asp Ser Ala Gly Arg Ser Val
                85                  90                  95

His Gly Gly Val Pro Gln Asn Val Ser Leu Trp Ala His Arg Lys Met
            100                 105                 110

Leu Gln Lys Arg Val Glu His Tyr Ile Arg Thr Gln Glu Ser Ala Gly
        115                 120                 125

Leu Ala Val Ile Asp Trp Glu Asp Trp Arg Pro Val Trp Val Arg Asn
    130                 135                 140

Trp Gln Asp Lys Asp Val Tyr Arg Arg Leu Ser Arg Gln Leu Val Ala
145                 150                 155                 160

Ser Arg His Pro Asp Trp Pro Asp Arg Ile Val Lys Gln Ala Gln
                165                 170                 175

Tyr Glu Phe Glu Phe Ala Ala Gln Gln Phe Met Leu Glu Thr Leu Arg
            180                 185                 190

Tyr Val Lys Ala Val Arg Pro Arg His Leu Trp Gly Phe Tyr Leu Phe
        195                 200                 205

Pro Asp Cys Tyr Asn His Asp Tyr Val Gln Asn Trp Glu Ser Tyr Thr
    210                 215                 220

Gly Arg Cys Pro Asp Val Glu Val Ala Arg Asn Asp Gln Leu Ala Trp
225                 230                 235                 240
```

-continued

Leu Trp Ala Glu Ser Thr Ala Leu Phe Pro Ser Val Tyr Leu Asp Glu
              245                 250                 255

Thr Leu Ala Ser Ser Arg His Gly Arg Asn Phe Val Ser Phe Arg Val
        260                 265                 270

Gln Glu Ala Leu Arg Val Ala Arg Thr His His Ala Asn His Ala Leu
    275                 280                 285

Pro Val Tyr Val Phe Thr Arg Pro Thr Tyr Ser Arg Arg Leu Thr Gly
290                 295                 300

Leu Ser Glu Met Asp Leu Ile Ser Thr Ile Gly Glu Ser Ala Ala Leu
305                 310                 315                 320

Gly Ala Ala Gly Val Ile Leu Trp Gly Asp Ala Gly Tyr Thr Thr Ser
                325                 330                 335

Thr Glu Thr Cys Gln Tyr Leu Lys Asp Tyr Leu Thr Arg Leu Leu Val
            340                 345                 350

Pro Tyr Val Val Asn Val Ser Trp Ala Thr Gln Tyr Cys Ser Arg Ala
        355                 360                 365

Gln Cys His Gly His Gly Arg Cys Val Arg Arg Asn Pro Ser Ala Ser
    370                 375                 380

Thr Phe Leu His Leu Ser Thr Asn Ser Phe Arg Leu Val Pro Gly His
385                 390                 395                 400

Ala Pro Gly Glu Pro Gln Leu Arg Pro Val Gly Glu Leu Ser Trp Ala
                405                 410                 415

Asp Ile Asp His Leu Gln Thr His Phe Arg Cys Gln Cys Tyr Leu Gly
            420                 425                 430

Trp Ser Gly Glu Gln Cys Gln Trp Asp His Arg Gln Ala Ala Gly Gly
        435                 440                 445

Ala Ser Glu Ala Trp Ala Gly Ser His Leu Thr Ser Leu Leu Ala Leu
    450                 455                 460

Ala Ala Leu Ala Phe Thr Trp Thr Leu
465                 470

<210> SEQ ID NO 40
<211> LENGTH: 417
<212> TYPE: PRT
<213> ORGANISM: Unknown
<220> FEATURE:
<223> OTHER INFORMATION: Homo sapiens Hyaluronidase-3 protein

<400> SEQUENCE: 40

Met Thr Thr Gln Leu Gly Pro Ala Leu Val Leu Gly Val Ala Leu Cys
1               5                   10                  15

Leu Gly Cys Gly Gln Pro Leu Pro Gln Val Pro Glu Arg Pro Phe Ser
            20                  25                  30

Val Leu Trp Asn Val Pro Ser Ala His Cys Glu Ala Arg Phe Gly Val
        35                  40                  45

His Leu Pro Leu Asn Ala Leu Gly Ile Ile Ala Asn Arg Gly Gln His
    50                  55                  60

Phe His Gly Gln Asn Met Thr Ile Phe Tyr Lys Asn Gln Leu Gly Leu
65                  70                  75                  80

Tyr Pro Tyr Phe Gly Pro Arg Gly Thr Ala His Asn Gly Gly Ile Pro
                85                  90                  95

Gln Ala Leu Pro Leu Asp Arg His Leu Ala Leu Ala Ala Tyr Gln Ile
            100                 105                 110

His His Ser Leu Arg Pro Gly Phe Ala Gly Pro Ala Val Leu Asp Trp
        115                 120                 125

```
Glu Glu Trp Cys Pro Leu Trp Ala Gly Asn Trp Gly Arg Arg Arg Ala
130                 135                 140

Tyr Gln Ala Ala Ser Trp Ala Trp Ala Gln Gln Val Phe Pro Asp Leu
145                 150                 155                 160

Asp Pro Gln Glu Gln Leu Tyr Lys Ala Tyr Thr Gly Phe Glu Gln Ala
                165                 170                 175

Ala Arg Ala Leu Met Glu Asp Thr Leu Arg Val Ala Gln Ala Leu Arg
                180                 185                 190

Pro His Gly Leu Trp Gly Phe Tyr His Tyr Pro Ala Cys Gly Asn Gly
                195                 200                 205

Trp His Ser Met Ala Ser Asn Tyr Thr Gly Arg Cys His Ala Ala Thr
210                 215                 220

Leu Ala Arg Asn Thr Gln Leu His Trp Leu Trp Ala Ala Ser Ser Ala
225                 230                 235                 240

Leu Phe Pro Ser Ile Tyr Leu Pro Pro Arg Leu Pro Ala His His
                245                 250                 255

Gln Ala Phe Val Arg His Arg Leu Glu Glu Ala Phe Arg Val Ala Leu
                260                 265                 270

Val Gly His Arg His Pro Leu Pro Val Leu Ala Tyr Val Arg Leu Thr
                275                 280                 285

His Arg Arg Ser Gly Arg Phe Leu Ser Gln Asp Asp Leu Val Gln Ser
290                 295                 300

Ile Gly Val Ser Ala Ala Leu Gly Ala Ala Gly Val Val Leu Trp Gly
305                 310                 315                 320

Asp Leu Ser Leu Ser Ser Glu Glu Glu Cys Trp His Leu His Asp
                325                 330                 335

Tyr Leu Val Asp Thr Leu Gly Pro Tyr Val Ile Asn Val Thr Arg Ala
                340                 345                 350

Ala Met Ala Cys Ser His Gln Arg Cys His Gly His Gly Arg Cys Ala
                355                 360                 365

Arg Arg Asp Pro Gly Gln Met Glu Ala Phe Leu His Leu Trp Pro Asp
                370                 375                 380

Gly Ser Leu Gly Asp Trp Lys Ser Phe Ser Cys His Cys Tyr Trp Gly
385                 390                 395                 400

Trp Ala Gly Pro Thr Cys Gln Glu Pro Arg Pro Gly Pro Lys Glu Ala
                405                 410                 415

Val

<210> SEQ ID NO 41
<211> LENGTH: 481
<212> TYPE: PRT
<213> ORGANISM: Unknown
<220> FEATURE:
<223> OTHER INFORMATION: Homo sapiens Hyaluronidase-4 protein

<400> SEQUENCE: 41

Met Lys Val Leu Ser Glu Gly Gln Leu Lys Leu Cys Val Gln Pro
1               5                   10                  15

Val His Leu Thr Ser Trp Leu Leu Ile Phe Phe Ile Leu Lys Ser Ile
                20                  25                  30

Ser Cys Leu Lys Pro Ala Arg Leu Pro Ile Tyr Gln Arg Lys Pro Phe
                35                  40                  45

Ile Ala Ala Trp Asn Ala Pro Thr Asp Gln Cys Leu Ile Lys Tyr Asn
50                  55                  60

Leu Arg Leu Asn Leu Lys Met Phe Pro Val Ile Gly Ser Pro Leu Ala
```

```
            65                  70                  75                  80
Lys Ala Arg Gly Gln Asn Val Thr Ile Phe Tyr Val Asn Arg Leu Gly
                85                  90                  95
Tyr Tyr Pro Trp Tyr Thr Ser Gln Gly Val Pro Ile Asn Gly Gly Leu
                100                 105                 110
Pro Gln Asn Ile Ser Leu Gln Val His Leu Glu Lys Ala Asp Gln Asp
                115                 120                 125
Ile Asn Tyr Tyr Ile Pro Ala Glu Asp Phe Ser Gly Leu Ala Val Ile
        130                 135                 140
Asp Trp Glu Tyr Trp Arg Pro Gln Trp Ala Arg Asn Trp Asn Ser Lys
145                 150                 155                 160
Asp Val Tyr Arg Gln Lys Ser Arg Lys Leu Ile Ser Asp Met Gly Lys
                165                 170                 175
Asn Val Ser Ala Thr Asp Ile Glu Tyr Leu Ala Lys Val Thr Phe Glu
                180                 185                 190
Glu Ser Ala Lys Ala Phe Met Lys Glu Thr Ile Lys Leu Gly Ile Lys
                195                 200                 205
Ser Arg Pro Lys Gly Leu Trp Gly Tyr Tyr Leu Tyr Pro Asp Cys His
        210                 215                 220
Asn Tyr Asn Val Tyr Ala Pro Asn Tyr Ser Gly Ser Cys Pro Glu Asp
225                 230                 235                 240
Glu Val Leu Arg Asn Asn Glu Leu Ser Trp Leu Trp Asn Ser Ser Ala
                245                 250                 255
Ala Leu Tyr Pro Ser Ile Cys Val Trp Lys Ser Leu Gly Asp Ser Glu
                260                 265                 270
Asn Ile Leu Arg Phe Ser Lys Phe Arg Val His Glu Ser Met Arg Ile
        275                 280                 285
Ser Thr Met Thr Ser His Asp Tyr Ala Leu Pro Val Phe Val Tyr Thr
        290                 295                 300
Arg Leu Gly Tyr Arg Asp Glu Pro Leu Phe Phe Leu Ser Lys Gln Asp
305                 310                 315                 320
Leu Val Ser Thr Ile Gly Glu Ser Ala Ala Leu Gly Ala Ala Gly Ile
                325                 330                 335
Val Ile Trp Gly Asp Met Asn Leu Thr Ala Ser Lys Ala Asn Cys Thr
                340                 345                 350
Lys Val Lys Gln Phe Val Ser Ser Asp Leu Gly Ser Tyr Ile Ala Asn
                355                 360                 365
Val Thr Arg Ala Ala Glu Val Cys Ser Leu His Leu Cys Arg Asn Asn
        370                 375                 380
Gly Arg Cys Ile Arg Lys Met Trp Asn Ala Pro Ser Tyr Leu His Leu
385                 390                 395                 400
Asn Pro Ala Ser Tyr His Ile Glu Ala Ser Glu Asp Gly Glu Phe Thr
                405                 410                 415
Val Lys Gly Lys Ala Ser Asp Thr Asp Leu Ala Val Met Ala Asp Thr
                420                 425                 430
Phe Ser Cys His Cys Tyr Gln Gly Tyr Glu Gly Ala Asp Cys Arg Glu
            435                 440                 445
Ile Lys Thr Ala Asp Gly Cys Ser Gly Val Ser Pro Ser Pro Gly Ser
        450                 455                 460
Leu Met Thr Leu Cys Leu Leu Leu Ala Ser Tyr Arg Ser Ile Gln
465                 470                 475                 480
Leu
```

<210> SEQ ID NO 42
<211> LENGTH: 509
<212> TYPE: PRT
<213> ORGANISM: Unknown
<220> FEATURE:
<223> OTHER INFORMATION: Homo sapiens PH-20 protein

<400> SEQUENCE: 42

```
Met Gly Val Leu Lys Phe Lys His Ile Phe Arg Ser Phe Val Lys
1               5                   10                  15

Ser Ser Gly Val Ser Gln Ile Val Phe Thr Phe Leu Leu Ile Pro Cys
                20                  25                  30

Cys Leu Thr Leu Asn Phe Arg Ala Pro Pro Val Ile Pro Asn Val Pro
            35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
                100                 105                 110

Gly Ile Pro Gln Lys Ile Ser Leu Gln Asp His Leu Asp Lys Ala Lys
            115                 120                 125

Lys Asp Ile Thr Phe Tyr Met Pro Val Asp Asn Leu Gly Met Ala Val
130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365
```

-continued

```
Val Thr Leu Ala Ala Lys Met Cys Ser Gln Val Leu Cys Gln Glu Gln
            370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
                420                 425                 430

Phe Tyr Cys Ser Cys Tyr Ser Thr Leu Ser Cys Lys Glu Lys Ala Asp
                435                 440                 445

Val Lys Asp Thr Asp Ala Val Asp Val Cys Ile Ala Asp Gly Val Cys
            450                 455                 460

Ile Asp Ala Phe Leu Lys Pro Pro Met Glu Thr Glu Glu Pro Gln Ile
465                 470                 475                 480

Phe Tyr Asn Ala Ser Pro Ser Thr Leu Ser Ala Thr Met Phe Ile Val
                485                 490                 495

Ser Ile Leu Phe Leu Ile Ile Ser Ser Val Ala Ser Leu
            500                 505

<210> SEQ ID NO 43
<211> LENGTH: 16
<212> TYPE: PRT
<213> ORGANISM: Artificial
<220> FEATURE:
<223> OTHER INFORMATION: Synthetic polypeptide, amino acids 35-50 HIV-1
      Rev protein

<400> SEQUENCE: 43

Arg Gln Ala Arg Arg Asn Arg Arg Arg Trp Arg Glu Arg Gln Arg
1               5                   10                  15

<210> SEQ ID NO 44
<211> LENGTH: 19
<212> TYPE: PRT
<213> ORGANISM: Artificial
<220> FEATURE:
<223> OTHER INFORMATION: Synthetic polypeptide, amino acids 1-19 of
      HTLV-1 Rex protein

<400> SEQUENCE: 44

Met Pro Lys Thr Arg Arg Arg Pro Arg Arg Ser Gln Arg Lys Arg Pro
1               5                   10                  15

Pro Thr Pro

<210> SEQ ID NO 45
<211> LENGTH: 16
<212> TYPE: PRT
<213> ORGANISM: Artificial
<220> FEATURE:
<223> OTHER INFORMATION: Synthetic polypeptide, coresponding to the
      third helix of the homeodomain of Antennapedia (Derossi, et al.,
      J. Biol. Chem. 271:18188-93, 1996)

<400> SEQUENCE: 45

Arg Gln Ile Lys Ile Trp Phe Gln Asn Arg Arg Met Lys Trp Lys Lys
1               5                   10                  15

<210> SEQ ID NO 46
<211> LENGTH: 30
<212> TYPE: PRT
<213> ORGANISM: Artificial
<220> FEATURE:
<223> OTHER INFORMATION: Synthetic polypeptide, corresponding to the
``` heavy chain variable region of an anti-DNA monoclonal antibody
LOCUS (AAC40104)

<400> SEQUENCE: 46

Val Ala Tyr Ile Ser Arg Gly Gly Val Ser Thr Tyr Tyr Ser Asp Thr
1               5                   10                  15

Val Lys Gly Arg Phe Thr Arg Gln Lys Tyr Asn Lys Arg Ala
            20                  25                  30

<210> SEQ ID NO 47
<211> LENGTH: 246
<212> TYPE: PRT
<213> ORGANISM: Unknown
<220> FEATURE:
<223> OTHER INFORMATION: human herpesvirus HSV VP22 protein

<400> SEQUENCE: 47

Met Thr Ser Arg Arg Ser Val Lys Ser Gly Pro Arg Glu Val Pro Arg
1               5                   10                  15

Asp Glu Tyr Glu Asp Leu Tyr Tyr Thr Pro Ser Ser Gly Met Ala Ser
            20                  25                  30

Pro Asp Ser Pro Pro Asp Thr Ser Arg Arg Gly Ala Leu Gln Thr Arg
        35                  40                  45

Ser Arg Gln Arg Gly Glu Val Arg Phe Val Gln Tyr Asp Glu Ser Asp
    50                  55                  60

Tyr Ala Leu Tyr Gly Gly Ser Ser Ser Glu Asp Asp Glu His Pro Glu
65                  70                  75                  80

Val Pro Arg Thr Arg Arg Pro Val Ser Gly Ala Val Leu Ser Gly Pro
                85                  90                  95

Gly Pro Ala Arg Ala Pro Pro Pro Ala Gly Ser Gly Gly Ala Gly
            100                 105                 110

Arg Thr Pro Thr Thr Ala Pro Arg Ala Pro Arg Thr Gln Arg Val Ala
        115                 120                 125

Thr Lys Ala Pro Ala Ala Pro Ala Ala Glu Thr Thr Arg Gly Arg Lys
    130                 135                 140

Ser Ala Gln Pro Glu Ser Ala Ala Leu Pro Asp Ala Pro Ala Ser Arg
145                 150                 155                 160

Ala Pro Thr Val Gln Leu Trp Gln Met Ser Arg Pro Arg Thr Asp Glu
                165                 170                 175

Asp Leu Asn Glu Leu Leu Gly Ile Thr Thr Ile Arg Val Thr Val Cys Glu
            180                 185                 190

Gly Lys Asn Leu Leu Gln Arg Ala Asn Glu Leu Val Asn Pro Asp Val
        195                 200                 205

Val Gln Asp Val Asp Ala Ala Thr Ala Thr Arg Gly Arg Ser Ala Ala
    210                 215                 220

Ser Arg Pro Thr Glu Arg Pro Arg Ala Pro Ala Arg Ser Ala Ser Arg
225                 230                 235                 240

Pro Arg Arg Pro Val Glu
                245

<210> SEQ ID NO 48
<211> LENGTH: 36
<212> TYPE: PRT
<213> ORGANISM: Artificial
<220> FEATURE:
<223> OTHER INFORMATION: Synthetic peptide, residues 37-72 of the HIV-1
      Tat protein

<400> SEQUENCE: 48

```
Cys Phe Ile Thr Lys Ala Leu Gly Ile Ser Tyr Gly Arg Lys Lys Arg
1               5                   10                  15

Arg Gln Arg Arg Arg Pro Pro Gln Gly Ser Gln Thr His Gln Val Ser
            20                  25                  30

Leu Ser Lys Gln
        35

<210> SEQ ID NO 49
<211> LENGTH: 10
<212> TYPE: PRT
<213> ORGANISM: Artificial
<220> FEATURE:
<223> OTHER INFORMATION: Synthetic polypeptide, amino acid residues
      48-57 of (HIV-1) Tat protein

<400> SEQUENCE: 49

Gly Arg Lys Lys Arg Arg Gln Arg Arg Arg
1               5                   10

<210> SEQ ID NO 50
<211> LENGTH: 997
<212> TYPE: PRT
<213> ORGANISM: Artificial
<220> FEATURE:
<223> OTHER INFORMATION: Synthetic polypeptide, Chondroitinase ABCI
      protein

<400> SEQUENCE: 50

Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
                20                  25                  30

Lys Asn Ser Ile Leu Thr Leu Ser Asp Lys Arg Ser Ile Met Gly Asn
            35                  40                  45

Gln Ser Leu Leu Trp Lys Trp Lys Gly Gly Ser Ser Phe Thr Leu His
        50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95

Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Thr Val Gly Val Ser Leu Asn Asn Asp Leu Glu Asn Arg Glu Met
130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gln Gly Glu Ile Tyr Ile Asp Arg Ile Met Phe Ser
            180                 185                 190

Val Asp Asp Ala Arg Tyr Gln Trp Ser Asp Tyr Gln Val Lys Thr Arg
        195                 200                 205

Leu Ser Glu Pro Glu Ile Gln Phe His Asn Val Lys Pro Gln Leu Pro
210                 215                 220

Val Thr Pro Glu Asn Leu Ala Ala Ile Asp Leu Ile Arg Gln Arg Leu
225                 230                 235                 240
```

```
Ile Asn Glu Phe Val Gly Gly Glu Lys Glu Thr Asn Leu Ala Leu Glu
                245                 250                 255

Glu Asn Ile Ser Lys Leu Lys Ser Asp Phe Asp Ala Leu Asn Thr His
            260                 265                 270

Thr Leu Ala Asn Gly Gly Thr Gln Gly Arg His Leu Ile Thr Asp Lys
        275                 280                 285

Gln Ile Ile Ile Tyr Gln Pro Glu Asn Leu Asn Ser Gln Asp Lys Gln
    290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                325                 330                 335

Gln Leu Lys Gln Met Tyr Leu Leu Met Thr Lys His Leu Leu Asp Gln
            340                 345                 350

Gly Phe Val Lys Gly Ser Ala Leu Val Thr Thr His His Trp Gly Tyr
        355                 360                 365

Ser Ser Arg Trp Trp Tyr Ile Ser Thr Leu Leu Met Ser Asp Ala Leu
    370                 375                 380

Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
                405                 410                 415

Ser Asp Leu Asp Tyr Phe Asn Thr Leu Ser Arg Gln His Leu Ala Leu
            420                 425                 430

Leu Leu Leu Glu Pro Asp Asp Gln Lys Arg Ile Asn Leu Val Asn Thr
        435                 440                 445

Phe Ser His Tyr Ile Thr Gly Ala Leu Thr Gln Val Pro Pro Gly Gly
450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                485                 490                 495

Tyr Leu Leu Arg Asp Thr Pro Phe Ser Val Gly Glu Ser Gly Trp Asn
            500                 505                 510

Asn Leu Lys Lys Ala Met Val Ser Ala Trp Ile Tyr Ser Asn Pro Glu
        515                 520                 525

Val Gly Leu Pro Leu Ala Gly Arg His Pro Phe Asn Ser Pro Ser Leu
    530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gln Asn Glu Ser Thr Ala Ile Phe Gly Glu Thr Ile Thr Pro Ala
            580                 585                 590

Ser Leu Pro Gln Gly Phe Tyr Ala Phe Asn Gly Gly Ala Phe Gly Ile
        595                 600                 605

His Arg Trp Gln Asp Lys Met Val Thr Leu Lys Ala Tyr Asn Thr Asn
    610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
                645                 650                 655
```

```
Gln Gly Tyr Gln Gln Gly Trp Asp Trp Asn Arg Met Glu Gly Ala
            660                 665                 670
Thr Thr Ile His Leu Pro Leu Lys Asp Leu Asp Ser Pro Lys Pro His
        675                 680                 685
Thr Leu Met Gln Arg Gly Glu Arg Gly Phe Ser Gly Thr Ser Ser Leu
    690                 695                 700
Glu Gly Gln Tyr Gly Met Met Ala Phe Asn Leu Ile Tyr Pro Ala Asn
705                 710                 715                 720
Leu Glu Arg Phe Asp Pro Asn Phe Thr Ala Lys Lys Ser Val Leu Ala
                725                 730                 735
Ala Asp Asn His Leu Ile Phe Ile Gly Ser Asn Ile Asn Ser Ser Asp
            740                 745                 750
Lys Asn Lys Asn Val Glu Thr Thr Leu Phe Gln His Ala Ile Thr Pro
        755                 760                 765
Thr Leu Asn Thr Leu Trp Ile Asn Gly Gln Lys Ile Glu Asn Met Pro
    770                 775                 780
Tyr Gln Thr Thr Leu Gln Gln Gly Asp Trp Leu Ile Asp Ser Asn Gly
785                 790                 795                 800
Asn Gly Tyr Leu Ile Thr Gln Ala Glu Lys Val Asn Val Ser Arg Gln
                805                 810                 815
His Gln Val Ser Ala Glu Asn Lys Asn Arg Gln Pro Thr Glu Gly Asn
            820                 825                 830
Phe Ser Ser Ala Trp Ile Asp His Ser Thr Arg Pro Lys Asp Ala Ser
        835                 840                 845
Tyr Glu Tyr Met Val Phe Leu Asp Ala Thr Pro Glu Lys Met Gly Glu
    850                 855                 860
Met Ala Gln Lys Phe Arg Glu Asn Asn Gly Leu Tyr Gln Val Leu Arg
865                 870                 875                 880
Lys Asp Lys Asp Val His Ile Ile Leu Asp Lys Leu Ser Asn Val Thr
                885                 890                 895
Gly Tyr Ala Phe Tyr Gln Pro Ala Ser Ile Glu Asp Lys Trp Ile Lys
            900                 905                 910
Lys Val Asn Lys Pro Ala Ile Val Met Thr His Arg Gln Lys Asp Thr
        915                 920                 925
Leu Ile Val Ser Ala Val Thr Pro Asp Leu Asn Met Thr Arg Gln Lys
    930                 935                 940
Ala Ala Thr Pro Val Thr Ile Asn Val Thr Ile Asn Gly Lys Trp Gln
945                 950                 955                 960
Ser Ala Asp Lys Asn Ser Glu Val Lys Tyr Gln Val Ser Gly Asp Asn
                965                 970                 975
Thr Glu Leu Thr Phe Thr Ser Tyr Phe Gly Ile Pro Gln Glu Ile Lys
            980                 985                 990
Leu Ser Pro Leu Pro
        995

<210> SEQ ID NO 51
<211> LENGTH: 977
<212> TYPE: PRT
<213> ORGANISM: Artificial
<220> FEATURE:
<223> OTHER INFORMATION: Synthetic polypeptide, N(delta)20 ABCI
      (A(sub)45-N(sub)1023) protein

<400> SEQUENCE: 51

Ala Gln Asn Asn Pro Leu Ala Asp Phe Ser Ser Asp Lys Asn Ser Ile
1               5                   10                  15
```

Leu Thr Leu Ser Asp Lys Arg Ser Ile Met Gly Asn Gln Ser Leu Leu
            20                  25                  30

Trp Lys Trp Lys Gly Gly Ser Ser Phe Thr Leu His Lys Lys Leu Ile
        35                  40                  45

Val Pro Thr Asp Lys Glu Ala Ser Lys Ala Trp Gly Arg Ser Ser Thr
50                  55                  60

Pro Val Phe Ser Phe Trp Leu Tyr Asn Glu Lys Pro Ile Asp Gly Tyr
65                  70                  75                  80

Leu Thr Ile Asp Phe Gly Glu Lys Leu Ile Ser Thr Ser Glu Ala Gln
                85                  90                  95

Ala Gly Phe Lys Val Lys Leu Asp Phe Thr Gly Trp Arg Thr Val Gly
            100                 105                 110

Val Ser Leu Asn Asn Asp Leu Glu Asn Arg Glu Met Thr Leu Asn Ala
        115                 120                 125

Thr Asn Thr Ser Ser Asp Gly Thr Gln Asp Ser Ile Gly Arg Ser Leu
    130                 135                 140

Gly Ala Lys Val Asp Ser Ile Arg Phe Lys Ala Pro Ser Asn Val Ser
145                 150                 155                 160

Gln Gly Glu Ile Tyr Ile Asp Arg Ile Met Phe Ser Val Asp Asp Ala
                165                 170                 175

Arg Tyr Gln Trp Ser Asp Tyr Gln Val Lys Thr Arg Leu Ser Glu Pro
            180                 185                 190

Glu Ile Gln Phe His Asn Val Lys Pro Gln Leu Pro Val Thr Pro Glu
        195                 200                 205

Asn Leu Ala Ala Ile Asp Leu Ile Arg Gln Arg Leu Ile Asn Glu Phe
    210                 215                 220

Val Gly Gly Glu Lys Glu Thr Asn Leu Ala Leu Glu Glu Asn Ile Ser
225                 230                 235                 240

Lys Leu Lys Ser Asp Phe Asp Ala Leu Asn Thr His Thr Leu Ala Asn
                245                 250                 255

Gly Gly Thr Gln Gly Arg His Leu Ile Thr Asp Lys Gln Ile Ile Ile
            260                 265                 270

Tyr Gln Pro Glu Asn Leu Asn Ser Gln Asp Lys Gln Leu Phe Asp Asn
        275                 280                 285

Tyr Val Ile Leu Gly Asn Tyr Thr Thr Leu Met Phe Asn Ile Ser Arg
    290                 295                 300

Ala Tyr Val Leu Glu Lys Asp Pro Thr Gln Lys Ala Gln Leu Lys Gln
305                 310                 315                 320

Met Tyr Leu Leu Met Thr Lys His Leu Leu Asp Gln Gly Phe Val Lys
                325                 330                 335

Gly Ser Ala Leu Val Thr Thr His His Trp Gly Tyr Ser Ser Arg Trp
            340                 345                 350

Trp Tyr Ile Ser Thr Leu Leu Met Ser Asp Ala Leu Lys Glu Ala Asn
        355                 360                 365

Leu Gln Thr Gln Val Tyr Asp Ser Leu Leu Trp Tyr Ser Arg Glu Phe
    370                 375                 380

Lys Ser Ser Phe Asp Met Lys Val Ser Ala Asp Ser Ser Asp Leu Asp
385                 390                 395                 400

Tyr Phe Asn Thr Leu Ser Arg Gln His Leu Ala Leu Leu Leu Leu Glu
                405                 410                 415

Pro Asp Asp Gln Lys Arg Ile Asn Leu Val Asn Thr Phe Ser His Tyr
            420                 425                 430

```
Ile Thr Gly Ala Leu Thr Gln Val Pro Pro Gly Lys Asp Gly Leu
            435                 440                 445

Arg Pro Asp Gly Thr Ala Trp Arg His Glu Gly Asn Tyr Pro Gly Tyr
450                 455                 460

Ser Phe Pro Ala Phe Lys Asn Ala Ser Gln Leu Ile Tyr Leu Leu Arg
465                 470                 475                 480

Asp Thr Pro Phe Ser Val Gly Glu Ser Gly Trp Asn Leu Lys Lys
                485                 490                 495

Ala Met Val Ser Ala Trp Ile Tyr Ser Asn Pro Glu Val Gly Leu Pro
            500                 505                 510

Leu Ala Gly Arg His Pro Phe Asn Ser Pro Ser Leu Lys Ser Val Ala
            515                 520                 525

Gln Gly Tyr Tyr Trp Leu Ala Met Ser Ala Lys Ser Ser Pro Asp Lys
            530                 535                 540

Thr Leu Ala Ser Ile Tyr Leu Ala Ile Ser Asp Lys Thr Gln Asn Glu
545                 550                 555                 560

Ser Thr Ala Ile Phe Gly Glu Thr Ile Thr Pro Ala Ser Leu Pro Gln
                565                 570                 575

Gly Phe Tyr Ala Phe Asn Gly Gly Ala Phe Gly Ile His Arg Trp Gln
            580                 585                 590

Asp Lys Met Val Thr Leu Lys Ala Tyr Asn Thr Asn Val Trp Ser Ser
            595                 600                 605

Glu Ile Tyr Asn Lys Asp Asn Arg Tyr Gly Arg Tyr Gln Ser His Gly
            610                 615                 620

Val Ala Gln Ile Val Ser Asn Gly Ser Gln Leu Ser Gln Gly Tyr Gln
625                 630                 635                 640

Gln Glu Gly Trp Asp Trp Asn Arg Met Glu Gly Ala Thr Thr Ile His
                645                 650                 655

Leu Pro Leu Lys Asp Leu Asp Ser Pro Lys Pro His Thr Leu Met Gln
            660                 665                 670

Arg Gly Glu Arg Gly Phe Ser Gly Thr Ser Ser Leu Glu Gly Gln Tyr
            675                 680                 685

Gly Met Met Ala Phe Asn Leu Ile Tyr Pro Ala Asn Leu Glu Arg Phe
690                 695                 700

Asp Pro Asn Phe Thr Ala Lys Lys Ser Val Leu Ala Ala Asp Asn His
705                 710                 715                 720

Leu Ile Phe Ile Gly Ser Asn Ile Asn Ser Asp Lys Asn Lys Asn
                725                 730                 735

Val Glu Thr Thr Leu Phe Gln His Ala Ile Thr Pro Thr Leu Asn Thr
            740                 745                 750

Leu Trp Ile Asn Gly Gln Lys Ile Glu Asn Met Pro Tyr Gln Thr Thr
            755                 760                 765

Leu Gln Gln Gly Asp Trp Leu Ile Asp Ser Asn Gly Asn Gly Tyr Leu
770                 775                 780

Ile Thr Gln Ala Glu Lys Val Asn Val Ser Arg Gln His Gln Val Ser
785                 790                 795                 800

Ala Glu Asn Lys Asn Arg Gln Pro Thr Glu Gly Asn Phe Ser Ser Ala
                805                 810                 815

Trp Ile Asp His Ser Thr Arg Pro Lys Asp Ala Ser Tyr Glu Tyr Met
            820                 825                 830

Val Phe Leu Asp Ala Thr Pro Glu Lys Met Gly Glu Met Ala Gln Lys
            835                 840                 845

Phe Arg Glu Asn Asn Gly Leu Tyr Gln Val Leu Arg Lys Asp Lys Asp
```

```
            850                 855                 860
Val His Ile Ile Leu Asp Lys Leu Ser Asn Val Thr Gly Tyr Ala Phe
865                 870                 875                 880

Tyr Gln Pro Ala Ser Ile Glu Asp Lys Trp Ile Lys Lys Val Asn Lys
                885                 890                 895

Pro Ala Ile Val Met Thr His Arg Gln Lys Asp Thr Leu Ile Val Ser
                900                 905                 910

Ala Val Thr Pro Asp Leu Asn Met Thr Arg Gln Lys Ala Ala Thr Pro
                915                 920                 925

Val Thr Ile Asn Val Thr Ile Asn Gly Lys Trp Gln Ser Ala Asp Lys
                930                 935                 940

Asn Ser Glu Val Lys Tyr Gln Val Ser Gly Asp Asn Thr Glu Leu Thr
945                 950                 955                 960

Phe Thr Ser Tyr Phe Gly Ile Pro Gln Glu Ile Lys Leu Ser Pro Leu
                965                 970                 975

Pro

<210> SEQ ID NO 52
<211> LENGTH: 937
<212> TYPE: PRT
<213> ORGANISM: Artificial
<220> FEATURE:
<223> OTHER INFORMATION: Synthetic polypeptide, N(delta)60 ABCI
      (F(sub)85-N(sub)1023) protein

<400> SEQUENCE: 52

Phe Thr Leu His Lys Lys Leu Ile Val Pro Thr Asp Lys Glu Ala Ser
1               5                   10                  15

Lys Ala Trp Gly Arg Ser Ser Thr Pro Val Phe Ser Phe Trp Leu Tyr
                20                  25                  30

Asn Glu Lys Pro Ile Asp Gly Tyr Leu Thr Ile Asp Phe Gly Glu Lys
            35                  40                  45

Leu Ile Ser Thr Ser Glu Ala Gln Ala Gly Phe Lys Val Lys Leu Asp
    50                  55                  60

Phe Thr Gly Trp Arg Thr Val Gly Val Ser Leu Asn Asn Asp Leu Glu
65                  70                  75                  80

Asn Arg Glu Met Thr Leu Asn Ala Thr Asn Thr Ser Ser Asp Gly Thr
                85                  90                  95

Gln Asp Ser Ile Gly Arg Ser Leu Gly Ala Lys Val Asp Ser Ile Arg
            100                 105                 110

Phe Lys Ala Pro Ser Asn Val Ser Gln Gly Glu Ile Tyr Ile Asp Arg
        115                 120                 125

Ile Met Phe Ser Val Asp Asp Ala Arg Tyr Gln Trp Ser Asp Tyr Gln
    130                 135                 140

Val Lys Thr Arg Leu Ser Glu Pro Glu Ile Gln Phe His Asn Val Lys
145                 150                 155                 160

Pro Gln Leu Pro Val Thr Pro Glu Asn Leu Ala Ala Ile Asp Leu Ile
                165                 170                 175

Arg Gln Arg Leu Ile Asn Glu Phe Val Gly Gly Glu Lys Glu Thr Asn
            180                 185                 190

Leu Ala Leu Glu Glu Asn Ile Ser Lys Leu Lys Ser Asp Phe Asp Ala
        195                 200                 205

Leu Asn Thr His Thr Leu Ala Asn Gly Gly Thr Gln Gly Arg His Leu
    210                 215                 220

Ile Thr Asp Lys Gln Ile Ile Ile Tyr Gln Pro Glu Asn Leu Asn Ser
```

```
            225                 230                 235                 240
        Gln Asp Lys Gln Leu Phe Asp Asn Tyr Val Ile Leu Gly Asn Tyr Thr
                        245                 250                 255

Thr Leu Met Phe Asn Ile Ser Arg Ala Tyr Val Leu Glu Lys Asp Pro
                        260                 265                 270

Thr Gln Lys Ala Gln Leu Lys Gln Met Tyr Leu Leu Met Thr Lys His
                        275                 280                 285

Leu Leu Asp Gln Gly Phe Val Lys Gly Ser Ala Leu Val Thr Thr His
                        290                 295                 300

His Trp Gly Tyr Ser Ser Arg Trp Trp Tyr Ile Ser Thr Leu Leu Met
        305                 310                 315                 320

Ser Asp Ala Leu Lys Glu Ala Asn Leu Gln Thr Gln Val Tyr Asp Ser
                        325                 330                 335

Leu Leu Trp Tyr Ser Arg Glu Phe Lys Ser Ser Phe Asp Met Lys Val
                        340                 345                 350

Ser Ala Asp Ser Ser Asp Leu Asp Tyr Phe Asn Thr Leu Ser Arg Gln
                        355                 360                 365

His Leu Ala Leu Leu Leu Glu Pro Asp Asp Gln Lys Arg Ile Asn
                        370                 375                 380

Leu Val Asn Thr Phe Ser His Tyr Ile Thr Gly Ala Leu Thr Gln Val
        385                 390                 395                 400

Pro Pro Gly Gly Lys Asp Gly Leu Arg Pro Asp Gly Thr Ala Trp Arg
                        405                 410                 415

His Glu Gly Asn Tyr Pro Gly Tyr Ser Phe Pro Ala Phe Lys Asn Ala
                        420                 425                 430

Ser Gln Leu Ile Tyr Leu Leu Arg Asp Thr Pro Phe Ser Val Gly Glu
                        435                 440                 445

Ser Gly Trp Asn Asn Leu Lys Lys Ala Met Val Ser Ala Trp Ile Tyr
                        450                 455                 460

Ser Asn Pro Glu Val Gly Leu Pro Leu Ala Gly Arg His Pro Phe Asn
        465                 470                 475                 480

Ser Pro Ser Leu Lys Ser Val Ala Gln Gly Tyr Tyr Trp Leu Ala Met
                        485                 490                 495

Ser Ala Lys Ser Ser Pro Asp Lys Thr Leu Ala Ser Ile Tyr Leu Ala
                        500                 505                 510

Ile Ser Asp Lys Thr Gln Asn Glu Ser Thr Ala Ile Phe Gly Glu Thr
                        515                 520                 525

Ile Thr Pro Ala Ser Leu Pro Gln Gly Phe Tyr Ala Phe Asn Gly Gly
                        530                 535                 540

Ala Phe Gly Ile His Arg Trp Gln Asp Lys Met Val Thr Leu Lys Ala
        545                 550                 555                 560

Tyr Asn Thr Asn Val Trp Ser Ser Glu Ile Tyr Asn Lys Asp Asn Arg
                        565                 570                 575

Tyr Gly Arg Tyr Gln Ser His Gly Val Ala Gln Ile Val Ser Asn Gly
                        580                 585                 590

Ser Gln Leu Ser Gln Gly Tyr Gln Gln Glu Gly Trp Asp Trp Asn Arg
                        595                 600                 605

Met Glu Gly Ala Thr Thr Ile His Leu Pro Leu Lys Asp Leu Asp Ser
        610                 615                 620

Pro Lys Pro His Thr Leu Met Gln Arg Gly Glu Arg Gly Phe Ser Gly
        625                 630                 635                 640

Thr Ser Ser Leu Glu Gly Gln Tyr Gly Met Met Ala Phe Asn Leu Ile
                        645                 650                 655
```

Tyr Pro Ala Asn Leu Glu Arg Phe Asp Pro Asn Phe Thr Ala Lys Lys
            660                 665                 670

Ser Val Leu Ala Ala Asp Asn His Leu Ile Phe Ile Gly Ser Asn Ile
        675                 680                 685

Asn Ser Ser Asp Lys Asn Lys Asn Val Glu Thr Thr Leu Phe Gln His
    690                 695                 700

Ala Ile Thr Pro Thr Leu Asn Thr Leu Trp Ile Asn Gly Gln Lys Ile
705                 710                 715                 720

Glu Asn Met Pro Tyr Gln Thr Thr Leu Gln Gln Gly Asp Trp Leu Ile
                725                 730                 735

Asp Ser Asn Gly Asn Gly Tyr Leu Ile Thr Gln Ala Glu Lys Val Asn
            740                 745                 750

Val Ser Arg Gln His Gln Val Ser Ala Glu Asn Lys Asn Arg Gln Pro
        755                 760                 765

Thr Glu Gly Asn Phe Ser Ser Ala Trp Ile Asp His Ser Thr Arg Pro
    770                 775                 780

Lys Asp Ala Ser Tyr Glu Tyr Met Val Phe Leu Asp Ala Thr Pro Glu
785                 790                 795                 800

Lys Met Gly Glu Met Ala Gln Lys Phe Arg Glu Asn Asn Gly Leu Tyr
                805                 810                 815

Gln Val Leu Arg Lys Asp Lys Asp Val His Ile Ile Leu Asp Lys Leu
            820                 825                 830

Ser Asn Val Thr Gly Tyr Ala Phe Tyr Gln Pro Ala Ser Ile Glu Asp
        835                 840                 845

Lys Trp Ile Lys Lys Val Asn Lys Pro Ala Ile Val Met Thr His Arg
    850                 855                 860

Gln Lys Asp Thr Leu Ile Val Ser Ala Val Thr Pro Asp Leu Asn Met
865                 870                 875                 880

Thr Arg Gln Lys Ala Ala Thr Pro Val Thr Ile Asn Val Thr Ile Asn
                885                 890                 895

Gly Lys Trp Gln Ser Ala Asp Lys Asn Ser Glu Val Lys Tyr Gln Val
            900                 905                 910

Ser Gly Asp Asn Thr Glu Leu Thr Phe Thr Ser Tyr Phe Gly Ile Pro
        915                 920                 925

Gln Glu Ile Lys Leu Ser Pro Leu Pro
    930                 935

<210> SEQ ID NO 53
<211> LENGTH: 858
<212> TYPE: PRT
<213> ORGANISM: Artificial
<220> FEATURE:
<223> OTHER INFORMATION: Synthetic polypeptide, N(delta) 60 C(delta)80
      ABCI (F[sub]85 - A[sub]942)

<400> SEQUENCE: 53

Phe Thr Leu His Lys Lys Leu Ile Val Pro Thr Asp Lys Glu Ala Ser
1               5                   10                  15

Lys Ala Trp Gly Arg Ser Ser Thr Pro Val Phe Ser Phe Trp Leu Tyr
                20                  25                  30

Asn Glu Lys Pro Ile Asp Gly Tyr Leu Thr Ile Asp Phe Gly Glu Lys
            35                  40                  45

Leu Ile Ser Thr Ser Glu Ala Gln Ala Gly Phe Lys Val Lys Leu Asp
        50                  55                  60

Phe Thr Gly Trp Arg Thr Val Gly Val Ser Leu Asn Asn Asp Leu Glu

```
            65                  70                  75                  80
Asn Arg Glu Met Thr Leu Asn Ala Thr Asn Thr Ser Ser Asp Gly Thr
                85                  90                  95

Gln Asp Ser Ile Gly Arg Ser Leu Gly Ala Lys Val Asp Ser Ile Arg
            100                 105                 110

Phe Lys Ala Pro Ser Asn Val Ser Gln Gly Glu Ile Tyr Ile Asp Arg
        115                 120                 125

Ile Met Phe Ser Val Asp Asp Ala Arg Tyr Gln Trp Ser Asp Tyr Gln
    130                 135                 140

Val Lys Thr Arg Leu Ser Glu Pro Glu Ile Gln Phe His Asn Val Lys
145                 150                 155                 160

Pro Gln Leu Pro Val Thr Pro Glu Asn Leu Ala Ile Asp Leu Ile
            165                 170                 175

Arg Gln Arg Leu Ile Asn Glu Phe Val Gly Gly Glu Lys Glu Thr Asn
            180                 185                 190

Leu Ala Leu Glu Glu Asn Ile Ser Lys Leu Lys Ser Asp Phe Asp Ala
        195                 200                 205

Leu Asn Thr His Thr Leu Ala Asn Gly Gly Thr Gln Gly Arg His Leu
    210                 215                 220

Ile Thr Asp Lys Gln Ile Ile Tyr Gln Pro Glu Asn Leu Asn Ser
225                 230                 235                 240

Gln Asp Lys Gln Leu Phe Asp Asn Tyr Val Ile Leu Gly Asn Tyr Thr
            245                 250                 255

Thr Leu Met Phe Asn Ile Ser Arg Ala Tyr Val Leu Glu Lys Asp Pro
            260                 265                 270

Thr Gln Lys Ala Gln Leu Lys Gln Met Tyr Leu Leu Met Thr Lys His
        275                 280                 285

Leu Leu Asp Gln Gly Phe Val Lys Gly Ser Ala Leu Val Thr Thr His
    290                 295                 300

His Trp Gly Tyr Ser Ser Arg Trp Trp Tyr Ile Ser Thr Leu Leu Met
305                 310                 315                 320

Ser Asp Ala Leu Lys Glu Ala Asn Leu Gln Thr Gln Val Tyr Asp Ser
            325                 330                 335

Leu Leu Trp Tyr Ser Arg Glu Phe Lys Ser Ser Phe Asp Met Lys Val
            340                 345                 350

Ser Ala Asp Ser Ser Asp Leu Asp Tyr Phe Asn Thr Leu Ser Arg Gln
        355                 360                 365

His Leu Ala Leu Leu Leu Glu Pro Asp Asp Gln Lys Arg Ile Asn
    370                 375                 380

Leu Val Asn Thr Phe Ser His Tyr Ile Thr Gly Ala Leu Thr Gln Val
385                 390                 395                 400

Pro Pro Gly Gly Lys Asp Gly Leu Arg Pro Asp Gly Thr Ala Trp Arg
            405                 410                 415

His Glu Gly Asn Tyr Pro Gly Tyr Ser Phe Pro Ala Phe Lys Asn Ala
            420                 425                 430

Ser Gln Leu Ile Tyr Leu Leu Arg Asp Thr Pro Phe Ser Val Gly Glu
        435                 440                 445

Ser Gly Trp Asn Asn Leu Lys Lys Ala Met Val Ser Ala Trp Ile Tyr
    450                 455                 460

Ser Asn Pro Glu Val Gly Leu Pro Leu Ala Gly Arg His Pro Phe Asn
465                 470                 475                 480

Ser Pro Ser Leu Lys Ser Val Ala Gln Gly Tyr Tyr Trp Leu Ala Met
            485                 490                 495
```

```
Ser Ala Lys Ser Ser Pro Asp Lys Thr Leu Ala Ser Ile Tyr Leu Ala
            500                 505                 510

Ile Ser Asp Lys Thr Gln Asn Glu Ser Thr Ala Ile Phe Gly Glu Thr
        515                 520                 525

Ile Thr Pro Ala Ser Leu Pro Gln Gly Phe Tyr Ala Phe Asn Gly Gly
530                 535                 540

Ala Phe Gly Ile His Arg Trp Gln Asp Lys Met Val Thr Leu Lys Ala
545                 550                 555                 560

Tyr Asn Thr Asn Val Trp Ser Ser Glu Ile Tyr Asn Lys Asp Asn Arg
                565                 570                 575

Tyr Gly Arg Tyr Gln Ser His Gly Val Ala Gln Ile Val Ser Asn Gly
            580                 585                 590

Ser Gln Leu Ser Gln Gly Tyr Gln Gln Glu Gly Trp Asp Trp Asn Arg
        595                 600                 605

Met Glu Gly Ala Thr Thr Ile His Leu Pro Leu Lys Asp Leu Asp Ser
610                 615                 620

Pro Lys Pro His Thr Leu Met Gln Arg Gly Glu Arg Gly Phe Ser Gly
625                 630                 635                 640

Thr Ser Ser Leu Glu Gly Gln Tyr Gly Met Met Ala Phe Asn Leu Ile
                645                 650                 655

Tyr Pro Ala Asn Leu Glu Arg Phe Asp Pro Asn Phe Thr Ala Lys Lys
            660                 665                 670

Ser Val Leu Ala Ala Asp Asn His Leu Ile Phe Ile Gly Ser Asn Ile
        675                 680                 685

Asn Ser Ser Asp Lys Asn Lys Asn Val Glu Thr Thr Leu Phe Gln His
690                 695                 700

Ala Ile Thr Pro Thr Leu Asn Thr Leu Trp Ile Asn Gly Gln Lys Ile
705                 710                 715                 720

Glu Asn Met Pro Tyr Gln Thr Thr Leu Gln Gln Gly Asp Trp Leu Ile
                725                 730                 735

Asp Ser Asn Gly Asn Gly Tyr Leu Ile Thr Gln Ala Glu Lys Val Asn
            740                 745                 750

Val Ser Arg Gln His Gln Val Ser Ala Glu Asn Lys Asn Arg Gln Pro
        755                 760                 765

Thr Glu Gly Asn Phe Ser Ser Ala Trp Ile Asp His Ser Thr Arg Pro
770                 775                 780

Lys Asp Ala Ser Tyr Glu Tyr Met Val Phe Leu Asp Ala Thr Pro Glu
785                 790                 795                 800

Lys Met Gly Glu Met Ala Gln Lys Phe Arg Glu Asn Gly Leu Tyr
                805                 810                 815

Gln Val Leu Arg Lys Asp Lys Asp Val His Ile Ile Leu Asp Lys Leu
            820                 825                 830

Ser Asn Val Thr Gly Tyr Ala Phe Tyr Gln Pro Ala Ser Ile Glu Asp
        835                 840                 845

Lys Trp Ile Lys Lys Val Asn Lys Pro Ala
    850                 855
```

<210> SEQ ID NO 54
<211> LENGTH: 1021
<212> TYPE: PRT
<213> ORGANISM: Artificial
<220> FEATURE:
<223> OTHER INFORMATION: Synthetic polypeptide, ABCI a site-specific
      mutant designated as H501A and Y508A where amino acid H at
      position 501 in ABCI is replaced by A, and amino acid Y at position 508 in ABCI is replaced by A.

<400> SEQUENCE: 54

```
Met Pro Ile Phe Arg Phe Thr Ala Leu Ala Met Thr Leu Gly Leu Leu
1               5                   10                  15

Ser Ala Pro Tyr Asn Ala Met Ala Ala Thr Ser Asn Pro Ala Phe Asp
            20                  25                  30

Pro Lys Asn Leu Met Gln Ser Glu Ile Tyr His Phe Ala Gln Asn Asn
        35                  40                  45

Pro Leu Ala Asp Phe Ser Ser Asp Lys Asn Ser Ile Leu Thr Leu Ser
    50                  55                  60

Asp Lys Arg Ser Ile Met Gly Asn Gln Ser Leu Leu Trp Lys Trp Lys
65                  70                  75                  80

Gly Gly Ser Ser Phe Thr Leu His Lys Lys Leu Ile Val Pro Thr Asp
                85                  90                  95

Lys Glu Ala Ser Lys Ala Trp Gly Arg Ser Thr Pro Val Phe Ser
            100                 105                 110

Phe Trp Leu Tyr Asn Glu Lys Pro Ile Asp Gly Tyr Leu Thr Ile Asp
        115                 120                 125

Phe Gly Glu Lys Leu Ile Ser Thr Ser Glu Ala Gln Ala Gly Phe Lys
    130                 135                 140

Val Lys Leu Asp Phe Thr Gly Trp Arg Ala Val Gly Val Ser Leu Asn
145                 150                 155                 160

Asn Asp Leu Glu Asn Arg Glu Met Thr Leu Asn Ala Thr Asn Thr Ser
                165                 170                 175

Ser Asp Gly Thr Gln Asp Ser Ile Gly Arg Ser Leu Gly Ala Lys Val
            180                 185                 190

Asp Ser Ile Arg Phe Lys Ala Pro Ser Asn Val Ser Gln Gly Glu Ile
        195                 200                 205

Tyr Ile Asp Arg Ile Met Phe Ser Val Asp Asp Ala Arg Tyr Gln Trp
    210                 215                 220

Ser Asp Tyr Gln Val Lys Thr Arg Leu Ser Glu Pro Glu Ile Gln Phe
225                 230                 235                 240

His Asn Val Lys Pro Gln Leu Pro Val Thr Pro Glu Asn Leu Ala Ala
                245                 250                 255

Ile Asp Leu Ile Arg Gln Arg Leu Ile Asn Glu Phe Val Gly Gly Glu
            260                 265                 270

Lys Glu Thr Asn Leu Ala Leu Glu Glu Asn Ile Ser Lys Leu Lys Ser
        275                 280                 285

Asp Phe Asp Ala Leu Asn Ile His Thr Leu Ala Asn Gly Gly Thr Gln
    290                 295                 300

Gly Arg His Leu Ile Thr Asp Lys Gln Ile Ile Tyr Gln Pro Glu
305                 310                 315                 320

Asn Leu Asn Ser Gln Asp Lys Gln Leu Phe Asp Asn Tyr Val Ile Leu
                325                 330                 335

Gly Asn Tyr Thr Thr Leu Met Phe Asn Ile Ser Arg Ala Tyr Val Leu
            340                 345                 350

Glu Lys Asp Pro Thr Gln Lys Ala Gln Leu Lys Gln Met Tyr Leu Leu
        355                 360                 365

Met Thr Lys His Leu Leu Asp Gln Gly Phe Val Lys Gly Ser Ala Leu
    370                 375                 380

Val Thr Thr His His Trp Gly Tyr Ser Ser Arg Trp Trp Tyr Ile Ser
385                 390                 395                 400
```

```
Thr Leu Leu Met Ser Asp Ala Leu Lys Glu Ala Asn Leu Gln Thr Gln
                405                 410                 415

Val Tyr Asp Ser Leu Leu Trp Tyr Ser Arg Glu Phe Lys Ser Ser Phe
            420                 425                 430

Asp Met Lys Val Ser Ala Asp Ser Ser Asp Leu Asp Tyr Phe Asn Thr
            435                 440                 445

Leu Ser Arg Gln His Leu Ala Leu Leu Leu Glu Pro Asp Asp Gln
450                 455                 460

Lys Arg Ile Asn Leu Val Asn Thr Phe Ser His Tyr Ile Thr Gly Ala
465                 470                 475                 480

Leu Thr Gln Val Pro Pro Gly Lys Asp Gly Leu Arg Pro Asp Gly
                485                 490                 495

Thr Ala Trp Arg Ala Glu Gly Asn Tyr Pro Gly Ala Ser Phe Pro Ala
            500                 505                 510

Phe Lys Asn Ala Ser Gln Leu Ile Tyr Leu Leu Arg Asp Thr Pro Phe
            515                 520                 525

Ser Val Gly Glu Ser Gly Trp Asn Asn Leu Lys Lys Ala Met Val Ser
            530                 535                 540

Ala Trp Ile Tyr Ser Asn Pro Glu Val Gly Leu Pro Leu Ala Gly Arg
545                 550                 555                 560

His Pro Phe Asn Ser Pro Ser Leu Lys Ser Val Ala Gln Gly Tyr Tyr
                565                 570                 575

Trp Leu Ala Met Ser Ala Lys Ser Ser Pro Asp Lys Thr Leu Ala Ser
            580                 585                 590

Ile Tyr Leu Ala Ile Ser Asp Lys Thr Gln Asn Glu Ser Thr Ala Ile
            595                 600                 605

Phe Gly Glu Thr Ile Thr Pro Ala Ser Leu Pro Gln Gly Phe Tyr Ala
            610                 615                 620

Phe Asn Gly Gly Ala Phe Gly Ile His Arg Trp Gln Asp Lys Met Val
625                 630                 635                 640

Thr Leu Lys Ala Tyr Asn Thr Asn Val Trp Ser Ser Glu Ile Tyr Asn
                645                 650                 655

Lys Asp Asn Arg Tyr Gly Arg Tyr Gln Ser His Gly Val Ala Gln Ile
            660                 665                 670

Val Ser Asn Gly Ser Gln Leu Ser Gln Gly Tyr Gln Gln Glu Gly Trp
            675                 680                 685

Asp Trp Asn Arg Met Glu Gly Ala Thr Thr Ile His Leu Pro Leu Lys
            690                 695                 700

Asp Leu Asp Ser Pro Lys Pro His Thr Leu Met Gln Arg Gly Glu Arg
705                 710                 715                 720

Gly Phe Ser Gly Thr Ser Ser Leu Glu Gly Gln Tyr Gly Met Met Ala
                725                 730                 735

Phe Asn Leu Ile Tyr Pro Ala Asn Leu Glu Arg Phe Asp Pro Asn Phe
            740                 745                 750

Thr Ala Lys Lys Ser Val Leu Ala Ala Asp Asn His Leu Ile Phe Ile
            755                 760                 765

Gly Ser Asn Ile Asn Ser Ser Asp Lys Asn Lys Asn Val Glu Thr Thr
770                 775                 780

Leu Phe Gln His Ala Ile Thr Pro Thr Leu Asn Thr Leu Trp Ile Asn
785                 790                 795                 800

Gly Gln Lys Ile Glu Asn Met Pro Tyr Gln Thr Thr Leu Gln Gln Gly
                805                 810                 815

Asp Trp Leu Ile Asp Ser Asn Gly Asn Gly Tyr Leu Ile Thr Gln Ala
```

```
                820                 825                 830
Glu Lys Val Asn Val Ser Arg Gln His Gln Val Ser Ala Glu Asn Lys
        835                 840                 845

Asn Arg Gln Pro Thr Glu Gly Asn Phe Ser Ser Ala Trp Ile Asp His
    850                 855                 860

Ser Thr Arg Pro Lys Asp Ala Ser Tyr Glu Tyr Met Val Phe Leu Asp
865                 870                 875                 880

Ala Thr Pro Glu Lys Met Gly Glu Met Ala Gln Lys Phe Arg Glu Asn
                885                 890                 895

Asn Gly Leu Tyr Gln Val Leu Arg Lys Asp Lys Asp Val His Ile Ile
            900                 905                 910

Leu Asp Lys Leu Ser Asn Val Thr Gly Tyr Ala Phe Tyr Gln Pro Ala
        915                 920                 925

Ser Ile Glu Asp Lys Trp Ile Lys Lys Val Asn Lys Pro Ala Ile Val
    930                 935                 940

Met Thr His Arg Gln Lys Asp Thr Leu Ile Val Ser Ala Val Thr Pro
945                 950                 955                 960

Asp Leu Asn Met Thr Arg Gln Lys Ala Ala Thr Pro Val Thr Ile Asn
                965                 970                 975

Val Thr Ile Asn Gly Lys Trp Gln Ser Ala Asp Lys Asn Ser Glu Val
            980                 985                 990

Lys Tyr Gln Val Ser Gly Asp Asn  Thr Glu Leu Thr Phe Thr Ser Tyr
        995                 1000                1005

Phe Gly  Ile Pro Gln Glu Ile  Lys Leu Ser Pro Leu  Pro
    1010                1015                1020

<210> SEQ ID NO 55
<211> LENGTH: 40
<212> TYPE: PRT
<213> ORGANISM: Artificial
<220> FEATURE:
<223> OTHER INFORMATION: Synthetic polypeptide corresponding to amino
      acids 821-862 from Nogo-A protein short form (homo sapiens) LOCUS
      (AAG40878)

<400> SEQUENCE: 55

Arg Ile Tyr Lys Gly Val Ile Gln Ala Ile Gln Lys Ser Asp Glu Gly
1               5                   10                  15

His Pro Phe Arg Ala Tyr Leu Glu Ser Glu Val Ala Ile Ser Glu Glu
            20                  25                  30

Leu Val Gln Lys Tyr Ser Asn Ser
        35                  40

<210> SEQ ID NO 56
<211> LENGTH: 5
<212> TYPE: PRT
<213> ORGANISM: Artificial
<220> FEATURE:
<223> OTHER INFORMATION: Synthetic polypeptide, Gly penta-linker

<400> SEQUENCE: 56

Gly Gly Gly Gly Gly
1               5

<210> SEQ ID NO 57
<211> LENGTH: 5
<212> TYPE: PRT
<213> ORGANISM: Artificial
<220> FEATURE:
<223> OTHER INFORMATION: Synthetic polypeptide, Gly-Ala linker
```

-continued

<400> SEQUENCE: 57

Gly Gly Ala Gly Gly
1               5

<210> SEQ ID NO 58
<211> LENGTH: 2994
<212> TYPE: DNA
<213> ORGANISM: Artificial
<220> FEATURE:
<223> OTHER INFORMATION: Synthetic polynucleotide for Chondroitinase
      ABCI

<400> SEQUENCE: 58

```
gccaccagca atcctgcatt tgatcctaaa atctgatgc agtcagaaat ttaccatttt      60
gcacaaaata acccattagc agacttctca tcagataaaa actcaatact aacgttatct    120
gataaacgta gcattatggg aaaccaatct cttttatgga aatggaaagg tggtagtagc    180
tttactttac ataaaaaact gattgtcccc accgataaag aagcatctaa agcatgggga    240
cgctcatcca cccccgtttt ctcattttgg ctttacaatg aaaaaccgat tgatggttat    300
cttactatcg atttcggaga aaaactcatt tcaaccagtg aggctcaggc aggctttaaa    360
gtaaaattag atttcactgg ctggcgtact gtgggagtct ctttaaataa cgatcttgaa    420
aatcgagaga tgaccttaaa tgcaaccaat acctcctctg atggtactca agacagcatt    480
gggcgttctt taggtgctaa agtcgatagt attcgtttta aagcgccttc taatgtgagt    540
cagggtgaaa tctatatcga ccgtattatg ttttctgtcg atgatgctcg ctaccaatgg    600
tctgattatc aagtaaaaac tcgcttatca gaacctgaaa ttcaatttca caacgtaaag    660
ccacaactac ctgtaacacc tgaaaattta gcggccattg atcttattcg ccaacgtcta    720
attaatgaat tgtcggagg tgaaaagag acaaacctcg cattagaaga gaatatcagc    780
aaattaaaaa gtgatttcga tgctcttaat actcacactt tagcaaatgg tggaacgcaa    840
ggcagacatc tgatcactga taaacaaatc attatttatc aaccagagaa tcttaactct    900
caagataaac aactatttga taattatgtt attttaggta attacacgac attaatgttt    960
aatattagcc gtgcttatgt gctggaaaaa gatcccacac aaaaggcgca actaaagcag   1020
atgtacttat taatgacaaa gcatttatta gatcaaggct ttgttaaagg gagtgctta    1080 gtgacaaccc atcactgggg atacagttct cgttggtggt atatttccac gttattaatg   1140
tctgatgcac taaagaagc gaacctacaa actcaagttt atgattcatt actgtggtat   1200
tcacgtgagt ttaaaagtag ttttgatatg aaagtaagtg ctgatagctc tgatctagat   1260
tatttcaata ccttatctcg ccaacattta gccttattac tactagagcc tgatgatcaa   1320
aagcgtatca acttagttaa tactttcagc cattatatca ctggcgcatt aacgcaagtg   1380
ccaccgggtg gtaaagatgg tttacgccct gatggtacag catggcgaca tgaaggcaac   1440
tatccgggct actctttccc agcctttaaa aatgcctctc agcttattta tttattacgc   1500
gatacaccat tttcagtggg tgaaagtggt tggaatagcc tgaaaaagc gatggtttca   1560 gcgtggatct acagtaatcc agaagttgga ttaccgcttg caggaagaca ccctcttaac   1620
tcaccttcgt taaaatcagt cgctcaaggc tattactggg ttgccatgtc tgcaaaatca   1680
tcgcctgata aaacacttgc atctattta cttgcgatta gtgataaaac acaaaatgaa   1740
tcaactgcta ttttggaga aactattaca ccagcgtctt tacctcaagg tttctatgcc   1800
tttaatggcg gtgcttttgg tattcatcgt tggcaagata aatggtgac actgaaagct   1860
```

-continued

```
tataacacca atgtttggtc atctgaaatt tataacaaag ataaccgtta tggccgttac      1920
caaagtcatg gtgtcgctca aatagtgagt aatggctcgc agctttcaca gggctatcag      1980
caagaaggtt gggattggaa tagaatgcca ggggcaacca ctatccacct tcctcttaaa      2040
gacttagaca gtcctaaacc tcatacctta atgcaacgtg gagagcgtgg atttagcgga      2100
acatcatccc ttgaaggtca atatggcatg atggcattcg atcttattta tcccgccaat      2160
cttgagcgtt ttgatcctaa tttcactgcg aaaaagagtg tattagccgc tgataatcac      2220
ttaattttta ttggtagcaa tataaatagt agtgataaaa ataaaaatgt tgaaacgacc      2280
ttattccaac atgccattac tccaacatta aatacccttt ggattaatgg acaaaagata      2340
gaaaacatgc cttatcaaac aacacttcaa caaggtgatt ggttaattga tagcaatggc      2400
aatggttact taattactca agcagaaaaa gtaaatgtaa gtcgccaaca tcaggtttca      2460
gcggaaaata aaaatcgcca accgacagaa ggaaacttta gctcggcatg gatcgatcac      2520
agcactcgcc ccaaagatgc cagttatgag tatatggtct ttttagatgc gacacctgaa      2580
aaaatgggag agatggcaca aaaattccgt gaaaataatg ggttatatca ggttcttcgt      2640
aaggataaag acgttcatat tattctcgat aaactcagca atgtaacggg atatgccttt      2700
tatcagccag catcaattga agacaaatgg atcaaaaagg ttaataaacc tgcaattgtg      2760
atgactcatc gacaaaaaga cactcttatt gtcagtgcag ttacacctga tttaaatatg      2820
actcgccaaa aagcagcaac tcctgtcacc atcaatgtca cgattaatgg caaatggcaa      2880
tctgctgata aaaatagtga agtgaaatat caggtttctg gtgataacac tgaactgacg      2940
tttacgagtt actttggtat tccacaagaa atcaaactct cgccactccc ttga           2994
```

<210> SEQ ID NO 59
<211> LENGTH: 1924
<212> TYPE: DNA
<213> ORGANISM: Unknown
<220> FEATURE:
<223> OTHER INFORMATION: Homo sapiens NgR DNA fragment corresponding to residues 1-359

<400> SEQUENCE: 59

```
ctgtgcgccc tgcgcgccct gcgcacccgc ggcccgagcc cagccagagc cgggcggagc        60
ggagcgcgcc gagcctcgtc ccgcggccgg gccggggccg ggccgtagcg gcggcgcctg       120
gatgcggacc cggccgcggg gagacgggcg cccgccccga aacgactttc agtccccgac       180
gcgccccgcc caacccctac gatgaagagg gcgtccgctg gagggagccg gctgctggca       240
tgggtgctgt ggctgcaggc ctggcaggtg cagccccat gcccaggtgc ctgcgtatgc       300
tacaatgagc ccaaggtgac gacaagctgc ccccagcagg gcctgcaggc tgtgcccgtg       360
ggcatccctg ctgccagcca gcgcatcttc ctgcacggca accgcatctc gcatgtgcca       420
gctgccagct ccgtgcctg ccgcaacctc accatcctgt ggctgcactc gaatgtgctg       480
gcccgaattg atgcggctgc cttcactggc ctggccctcc tggagcagct ggacctcagc       540
gataatgcac agctccggtc tgtggaccct gccacattcc acggcctggg ccgcctacac       600
acgctgcacc tggaccgctg cggcctgcag gagctgggcc cggggctgtt ccgcggcctg       660
gctgccctgc agtacctcta cctgcaggac aacgcgctgc aggcactgcc tgatgacacc       720
ttccgcgacc tgggcaacct cacacacctc ttcctgcacg gcaaccgcat ctccagcgtg       780
cccgagcgcg ccttccgtgg gctgcacagc ctcgaccgtc tcctactgca ccagaaccgc       840
gtggcccatg tgcacccgca tgccttccgt gaccttggcc gcctcatgac actctatctg       900
```

```
tttgccaaca atctatcagc gctgcccact gaggccctgg ccccctgcg tgccctgcag    960
tacctgaggc tcaacgacaa ccctggtg tgtgactgcc gggcacgcc actctgggcc    1020
tggctgcaga agttccgcgg ctcctcctcc gaggtgccct gcagcctccc gcaacgcctg    1080
gctggccgtg acctcaaacg cctagctgcc aatgacctgc agggctgcgc tgtggccacc    1140
ggcccttacc atcccatctg gaccggcagg gccaccgatg aggagccgct ggggcttccc    1200
aagtgctgcc agccagatgc cgctgacaag gcctcagtac tggagcctgg aagaccagct    1260
tcggcaggca atgcgctgaa gggacgcgtg ccgcccggtg acagcccgcc gggcaacggc    1320
tctggcccac ggcacatcaa tgactcaccc tttgggactc tgcctggctc tgctgagccc    1380
ccgctcactg cagtgcggcc cgagggctcc gagccaccag ggttccccac ctcgggccct    1440
cgccggaggc caggctgttc acgcaagaac cgcacccgca gccactgccg tctgggccag    1500
gcaggcagcg ggggtggcgg gactggtgac tcagaaggct caggtgccct acccagcctc    1560
acctgcagcc tcaccccct gggcctggcg ctggtgctgt ggacagtgct tgggccctgc    1620
tgaccccag cggacacaag agcgtgctca gcagccaggt gtgtgtacat acggggtctc    1680
tctccacgcc gccaagccag ccgggcggcc gacccgtggg gcaggccagg ccaggtcctc    1740
cctgatggac gcctgccgcc cgccacccc atctccaccc catcatgttt acagggttcg    1800
gcggcagcgt tgttccaga acgccgcctc ccacccagat cgcggtatat agagatatgc    1860
attttatttt acttgtgtaa aaatatcgga cgacgtggaa taaagagctc ttttcttaaa    1920
aaaa                                                                 1924

<210> SEQ ID NO 60
<211> LENGTH: 855
<212> TYPE: DNA
<213> ORGANISM: Artificial
<220> FEATURE:
<223> OTHER INFORMATION: NgR DNA fragment corresponding to residues
      27-311

<400> SEQUENCE: 60
tgcccaggtg cctgcgtatg ctacaatgag cccaaggtga cgacaagctg ccccagcag      60
ggcctgcagg ctgtgcccgt gggcatccct gctgccagcc agcgcatctt cctgcacggc    120
aaccgcatct cgcatgtgcc agctgccagc ttcgtgcct gccgcaacct caccatcctg    180
tggctgcact cgaatgtgct ggcccgaatt gatgcggctg ccttcactgg cctggccctc    240
ctggagcagc tggacctcag cgataatgca cagctccggt ctgtggaccc tgccacattc    300
cacggcctgg gccgcctaca cacgctgcac ctggaccgct gcggcctgca ggagctgggc    360
ccggggctgt tccgcggcct ggctgccctg cagtacctct acctgcagga caacgcgctg    420
caggcactgc ctgatgacac cttccgcgac ctgggcaacc tcacacacct cttcctgcac    480
ggcaaccgca tctccagcgt gcccgagcgc gccttccgtg ggctgcacag cctcgaccgt    540
ctcctactgc accagaaccg cgtggcccat gtgcacccgc atgccttccg tgaccttggc    600
cgcctcatga cactctatct gtttgccaac aatctatcag cgctgcccac tgaggccctg    660
gcccccctgc gtgccctgca gtacctgagg ctcaacgaca ccctgggt gtgtgactgc    720
cgggcacgcc cactctgggc ctggctgcag aagttccgcg ctcctcctc cgaggtgccc    780
tgcagcctcc cgcaacgcct ggctggccgt gacctcaaac gcctagctgc caatgacctg    840
cagggctgcg ctgtg                                                     855

<210> SEQ ID NO 61
```

<211> LENGTH: 3835
<212> TYPE: DNA
<213> ORGANISM: Artificial
<220> FEATURE:
<223> OTHER INFORMATION: Synthetic polynucleotide, TAT fusion chondroitinase ABCI nucleic acid

<400> SEQUENCE: 61

| | | | | | |
|---|---|---|---|---|---|
| ggtcgtaaaa | agcgtcgtca | acgtcgtcgt | ggtggtggtg | gtggtgccac | cagcaatcct | 60 |
| gcatttgatc | ctaaaaatct | gatgcagtca | gaaatttacc | attttgcaca | aaataaccca | 120 |
| ttagcagact | tctcatcaga | taaaaactca | atactaacgt | tatctgataa | acgtagcatt | 180 |
| atgggaaacc | aatctctttt | atggaaatgg | aaggtggta | gtagctttac | tttacataaa | 240 |
| aaactgattg | tccccaccga | taaagaagca | tctaaagcat | ggggacgctc | atctaccccc | 300 |
| gttttctcat | tttggcttta | caatgaaaaa | ccgattgatg | ttatcttac | tatcgatttc | 360 |
| ggagaaaaac | tcatttcaac | cagtgaggct | caggcaggct | ttaaagtaaa | attagatttc | 420 |
| actggctggc | gtgctgtggg | agtctcttta | ataacgatc | ttgaaaatcg | agagatgacc | 480 |
| ttaaatgcaa | ccaataccctc | ctctgatggt | actcaagaca | gcattgggcg | ttctttaggt | 540 |
| gctaaagtcg | atagtattcg | ttttaaagcg | ccttctaatg | tgagtcaggg | tgaaatctat | 600 |
| atcgaccgta | ttatgttttc | tgtcgatgat | gctcgctacc | aatggtctga | ttatcaagta | 660 |
| aaaactcgct | atcagaaacc | tgaaattcaa | tttcacaacg | taaagccaca | actacctgta | 720 |
| acacctgaaa | atttagcggc | cattgatctt | attcgccaac | gtctaattaa | tgaatttgtc | 780 |
| ggaggtgaaa | aagagacaaa | cctcgcatta | aagagaata | tcagcaaatt | aaaaagtgat | 840 |
| ttcgatgctc | ttaatattca | cactttagca | aatggtggaa | cgcaaggcag | acatctgatc | 900 |
| actgataaac | aaatcattat | ttatcaacca | gagaatctta | actcccaaga | taaacaacta | 960 |
| tttgataatt | atgttatttt | aggtaattac | acgacattaa | tgtttaatat | tagccgtgct | 1020 |
| tatgtgctgg | aaaaagatcc | cacacaaaag | gcgcaactaa | agcagatgta | cttattaatg | 1080 |
| acaaagcatt | tattagatca | aggctttgtt | aagggagtg | ctttagtgac | aacccatcac | 1140 |
| tggggataca | gttctcgttg | gtggtatatt | tccacgttat | taatgtctga | tgcactaaaa | 1200 |
| gaagcgaacc | tacaaactca | agtttatgat | tcattactgt | ggtattcacg | tgagtttaaa | 1260 |
| agtagttttg | atatgaaagt | aagtgctgat | agctctgatc | tagattattt | caataccta | 1320 |
| tctcgccaac | atttagcctt | attattacta | gagcctgatg | atcaaaagcg | tatcaactta | 1380 |
| gttaatactt | tcagccatta | tatcactggc | gcattaacgc | aagtgccacc | gggtggtaaa | 1440 |
| gatggtttac | gccctgatgg | tacagcatgg | cgacatgaag | gcaactatcc | gggctactct | 1500 |
| ttcccagcct | ttaaaaatgc | ctctcagctt | atttatttat | tacgcgatac | accattttca | 1560 |
| gtgggtgaaa | gtggttggaa | taacctgaaa | aaagcgatgg | tttcagcgtg | gatctacagt | 1620 |
| aatccagaag | ttggattacc | gcttgcagga | agacaccctt | ttaactcacc | ttcgttaaaa | 1680 |
| tcagtcgctc | aaggctatta | ctggcttgcc | atgtctgcaa | aatcatcgcc | tgataaaaca | 1740 |
| cttgcatcta | tttatcttgc | gattagtgat | aaaacacaaa | atgaatcaac | tgctattttt | 1800 |
| ggagaaacta | ttacaccagc | gtctttacct | caaggtttct | atgcctttaa | tggcggtgct | 1860 |
| tttggtattc | atcgttggca | agataaaatg | gtgcacactga | aagcttataa | caccaatgtt | 1920 |
| tggtcatctg | aaatttataa | caaagataac | cgttatggcc | gttaccaaag | tcatggtgtc | 1980 |
| gctcaaatag | tgagtaatgg | ctcgcagctt | tcacagggct | atcagcaaga | aggttgggat | 2040 |
| tggaatagaa | tgcaaggggc | aaccactatt | caccttcctc | ttaaagactt | agacagtcct | 2100 |

-continued

```
aaacctcata ccttaatgca acgtggagag cgtggattta gcggaacatc atcccttgaa    2160
ggtcaatatg gcatgatggc attcgatctt atttatcccg ccaatcttga gcgttttgat    2220
cctaatttca ctgcgaaaaa gagtgtatta gccgctgata atcacttaat ttttattggt    2280
agcaatataa atagtagtga taaaaataaa aatgttgaaa cgaccttatt ccaacatgcc    2340
attactccaa cattaaatac cctttggatt aatggacaaa agatagaaaa catgccttat    2400
caaacaacac ttcaacaagg tgattggtta attgatagca atggcaatgg ttacttaatt    2460
actcaagcag aaaaagtaaa tgtaagtcgc caacatcagg tttcagcgga aaataaaaat    2520
cgccaaccga cagaaggaaa ctttagctcg catggatcg atcacagcac tcgccccaaa    2580
gatgccagtt atgagtatat ggtcttttta gatgcgacac ctgaaaaaat gggagagatg    2640
gcacaaaaat tccgtgaaaa taatgggtta tatcaggttc ttcgtaagga taaagacgtt    2700
catattattc tcgataaact cagcaatgta acgggatatg cctttatca gccagcatca    2760
attgaagaca atggatcaa aaaggttaat aaacctgcaa ttgtgatgac tcatcgacaa    2820
aaagacactc ttattgtcag tgcagttaca cctgatttaa atatgactcg ccaaaaagca    2880
gcaactcctg tcaccatcaa tgtcacgatt aatggcaaat ggcaatctgc tgataaaaat    2940
agtgaagtga aatatcaggt ttctggtgat aacactgaac tgacgtttac gagttacttt    3000
ggtattccac aagaaatcaa actctcgcca ctcccttgat ttaatcaaaa gaacgctctt    3060
gcgttccttt tttatttgca ggaaatctga ttatgctaat aaaaaaccct ttagcccacg    3120
cggttacatt aagcctctgt ttatcattac ccgcacaagc attcccact ctgtctcatg    3180
aagctttcgg cgatatttat cttttgaag gtgaattacc caatacccctt accacttcaa    3240
ataataatca attatcgcta agcaaacagc atgctaaaga tggtgaacaa tcactcaaat    3300
ggcaatatca accacaagca acattaacac taaataat tgttaattac caagatgata    3360
aaaatacagc cacaccactc acttttatga tgtggattta taatgaaaaa cctcaatctt    3420
ccccattaac gttagcattt aaacaaaata ataaaattgc actaagtttt aatgctgaac    3480
ttaattttac ggggtggcga ggtattgctg ttccttttcg tgatatgcaa ggctctgcga    3540
caggtcaact tgatcaatta gtgatcaccg ctccaaacca agccggaaca ctcttttttg    3600
atcaaatcat catgagtgta ccgttagaca atcgttgggc agtacctgac tatcaaacac    3660
cttacgtaaa taacgcagta aacacgatgg ttagtaaaaa ctggagtgca ttattgatgt    3720
acgatcagat gtttcaagcc cattaccccta ctttaaactt cgatactgaa tttcgcgatg    3780
accaaacaga aatggcttcg atttatcagc gctttgaata ttatcaagga attcc          3835
```

<210> SEQ ID NO 62
<211> LENGTH: 478
<212> TYPE: PRT
<213> ORGANISM: Artificial
<220> FEATURE:
<223> OTHER INFORMATION: Synthetic polypeptide C(delta)200
      chondroitinase AC (Q[sub]23 - T[sub]500)

<400> SEQUENCE: 62

Gln Gln Thr Gly Thr Ala Glu Leu Ile Met Lys Arg Val Met Leu Asp
1               5                   10                  15

Leu Lys Lys Pro Leu Arg Asn Met Asp Lys Val Ala Glu Lys Asn Leu
            20                  25                  30

Asn Thr Leu Gln Pro Asp Gly Ser Trp Lys Asp Val Pro Tyr Lys Asp
        35                  40                  45

Asp Ala Met Thr Asn Trp Leu Pro Asn Asn His Leu Leu Gln Leu Glu

```
                 50                  55                  60
Thr Ile Ile Gln Ala Tyr Ile Glu Lys Asp Ser His Tyr Tyr Gly Asp
 65                  70                  75                  80

Asp Lys Val Phe Asp Gln Ile Ser Lys Ala Phe Lys Tyr Trp Tyr Asp
                     85                  90                  95

Ser Asp Pro Lys Ser Arg Asn Trp Trp His Asn Glu Ile Ala Thr Pro
                100                 105                 110

Gln Ala Leu Gly Glu Met Leu Ile Leu Met Arg Tyr Gly Lys Lys Pro
                115                 120                 125

Leu Asp Glu Ala Leu Val His Lys Leu Thr Glu Arg Met Lys Arg Gly
            130                 135                 140

Glu Pro Glu Lys Lys Thr Gly Ala Asn Lys Thr Asp Ile Ala Leu His
145                 150                 155                 160

Tyr Phe Tyr Arg Ala Leu Leu Thr Ser Asp Glu Ala Leu Leu Ser Phe
                165                 170                 175

Ala Val Lys Glu Leu Phe Tyr Pro Val Gln Phe Val His Tyr Glu Glu
                180                 185                 190

Gly Leu Gln Tyr Asp Tyr Ser Tyr Leu Gln His Gly Pro Gln Leu Gln
            195                 200                 205

Ile Ser Ser Tyr Gly Ala Val Phe Ile Thr Gly Val Leu Lys Leu Ala
210                 215                 220

Asn Tyr Val Arg Asp Thr Pro Tyr Ala Leu Ser Thr Glu Lys Leu Ala
225                 230                 235                 240

Ile Phe Ser Lys Tyr Tyr Arg Asp Ser Tyr Leu Lys Ala Ile Arg Gly
                245                 250                 255

Ser Tyr Met Asp Phe Asn Val Glu Gly Arg Gly Val Ser Arg Pro Asp
                260                 265                 270

Ile Leu Asn Lys Lys Ala Glu Lys Arg Leu Leu Val Ala Lys Met
                275                 280                 285

Ile Asp Leu Lys His Thr Glu Glu Trp Ala Asp Ala Ile Ala Arg Thr
            290                 295                 300

Asp Ser Thr Val Ala Ala Gly Tyr Lys Ile Glu Pro Tyr His His Gln
305                 310                 315                 320

Phe Trp Asn Gly Asp Tyr Val Gln His Leu Arg Pro Ala Tyr Ser Phe
                325                 330                 335

Asn Val Arg Met Val Ser Lys Arg Thr Arg Arg Ser Gly Ser Gly Asn
                340                 345                 350

Lys Glu Asn Leu Leu Gly Arg Tyr Leu Ser Asp Gly Ala Thr Asn Ile
            355                 360                 365

Gln Leu Arg Gly Pro Glu Tyr Tyr Asn Ile Met Pro Val Trp Glu Trp
370                 375                 380

Asp Lys Ile Pro Gly Ile Thr Ser Arg Asp Tyr Leu Thr Asp Arg Pro
385                 390                 395                 400

Leu Thr Lys Leu Trp Gly Glu Gln Gly Ser Asn Asp Phe Ala Gly Gly
                405                 410                 415

Val Ser Asp Gly Val Tyr Gly Ala Ser Ala Tyr Ala Leu Asp Tyr Asp
                420                 425                 430

Ser Leu Gln Ala Lys Lys Ala Trp Phe Phe Asp Lys Glu Ile Val
            435                 440                 445

Cys Leu Gly Ala Gly Ile Asn Ser Asn Ala Pro Glu Asn Ile Thr Thr
            450                 455                 460

Thr Leu Asn Gln Ser Trp Leu Asn Gly Pro Val Ile Ser Thr
465                 470                 475
```

```
<210> SEQ ID NO 63
<211> LENGTH: 458
<212> TYPE: PRT
<213> ORGANISM: Artificial
<220> FEATURE:
<223> OTHER INFORMATION: Synthetic polypeptide C(delta)220
      chondroitinase AC (Q[sub]23 - A[sub]480)

<400> SEQUENCE: 63
```

Gln Gln Thr Gly Thr Ala Glu Leu Ile Met Lys Arg Val Met Leu Asp
1               5                   10                  15

Leu Lys Lys Pro Leu Arg Asn Met Asp Lys Val Ala Glu Lys Asn Leu
            20                  25                  30

Asn Thr Leu Gln Pro Asp Gly Ser Trp Lys Asp Val Pro Tyr Lys Asp
        35                  40                  45

Asp Ala Met Thr Asn Trp Leu Pro Asn Asn His Leu Leu Gln Leu Glu
    50                  55                  60

Thr Ile Ile Gln Ala Tyr Ile Glu Lys Asp Ser His Tyr Tyr Gly Asp
65                  70                  75                  80

Asp Lys Val Phe Asp Gln Ile Ser Lys Ala Phe Lys Tyr Trp Tyr Asp
                85                  90                  95

Ser Asp Pro Lys Ser Arg Asn Trp Trp His Asn Glu Ile Ala Thr Pro
            100                 105                 110

Gln Ala Leu Gly Glu Met Leu Ile Leu Met Arg Tyr Gly Lys Lys Pro
        115                 120                 125

Leu Asp Glu Ala Leu Val His Lys Leu Thr Glu Arg Met Lys Arg Gly
130                 135                 140

Glu Pro Glu Lys Lys Thr Gly Ala Asn Lys Thr Asp Ile Ala Leu His
145                 150                 155                 160

Tyr Phe Tyr Arg Ala Leu Leu Thr Ser Asp Glu Ala Leu Leu Ser Phe
                165                 170                 175

Ala Val Lys Glu Leu Phe Tyr Pro Val Gln Phe Val His Tyr Glu Glu
            180                 185                 190

Gly Leu Gln Tyr Asp Tyr Ser Tyr Leu Gln His Gly Pro Gln Leu Gln
        195                 200                 205

Ile Ser Ser Tyr Gly Ala Val Phe Ile Thr Gly Val Leu Lys Leu Ala
210                 215                 220

Asn Tyr Val Arg Asp Thr Pro Tyr Ala Leu Ser Thr Glu Lys Leu Ala
225                 230                 235                 240

Ile Phe Ser Lys Tyr Tyr Arg Asp Ser Tyr Leu Lys Ala Ile Arg Gly
                245                 250                 255

Ser Tyr Met Asp Phe Asn Val Glu Gly Arg Gly Val Ser Arg Pro Asp
            260                 265                 270

Ile Leu Asn Lys Lys Ala Glu Lys Lys Arg Leu Leu Val Ala Lys Met
        275                 280                 285

Ile Asp Leu Lys His Thr Glu Glu Trp Ala Asp Ala Ile Ala Arg Thr
290                 295                 300

Asp Ser Thr Val Ala Ala Gly Tyr Lys Ile Glu Pro Tyr His His Gln
305                 310                 315                 320

Phe Trp Asn Gly Asp Tyr Val Gln His Leu Arg Pro Ala Tyr Ser Phe
                325                 330                 335

Asn Val Arg Met Val Ser Lys Arg Thr Arg Arg Ser Glu Ser Gly Asn
            340                 345                 350

Lys Glu Asn Leu Leu Gly Arg Tyr Leu Ser Asp Gly Ala Thr Asn Ile

```
                355                 360                 365
Gln Leu Arg Gly Pro Glu Tyr Tyr Asn Ile Met Pro Val Trp Glu Trp
370                 375                 380

Asp Lys Ile Pro Gly Ile Thr Ser Arg Asp Tyr Leu Thr Asp Arg Pro
385                 390                 395                 400

Leu Thr Lys Leu Trp Gly Glu Gln Gly Ser Asn Asp Phe Ala Gly Gly
                405                 410                 415

Val Ser Asp Gly Val Tyr Gly Ala Ser Ala Tyr Ala Leu Asp Tyr Asp
            420                 425                 430

Ser Leu Gln Ala Lys Lys Ala Trp Phe Phe Phe Asp Lys Glu Ile Val
        435                 440                 445

Cys Leu Gly Ala Gly Ile Asn Ser Asn Ala
450                 455

<210> SEQ ID NO 64
<211> LENGTH: 458
<212> TYPE: PRT
<213> ORGANISM: Artificial
<220> FEATURE:
<223> OTHER INFORMATION: Synthetic polypeptide, N(delta)20 C(delta)200
      chondroitinase AC (L[sub]43 -T[sub]500)

<400> SEQUENCE: 64

Leu Arg Asn Met Asp Lys Val Ala Glu Lys Asn Leu Asn Thr Leu Gln
1               5                   10                  15

Pro Asp Gly Ser Trp Lys Asp Val Pro Tyr Lys Asp Asp Ala Met Thr
            20                  25                  30

Asn Trp Leu Pro Asn Asn His Leu Gln Leu Glu Thr Ile Ile Gln
        35                  40                  45

Ala Tyr Ile Glu Lys Asp Ser His Tyr Tyr Gly Asp Asp Lys Val Phe
50                  55                  60

Asp Gln Ile Ser Lys Ala Phe Lys Tyr Trp Tyr Asp Ser Asp Pro Lys
65                  70                  75                  80

Ser Arg Asn Trp Trp His Asn Glu Ile Ala Thr Pro Gln Ala Leu Gly
                85                  90                  95

Glu Met Leu Ile Leu Met Arg Tyr Gly Lys Lys Pro Leu Asp Glu Ala
            100                 105                 110

Leu Val His Lys Leu Thr Glu Arg Met Lys Arg Gly Glu Pro Glu Lys
        115                 120                 125

Lys Thr Gly Ala Asn Lys Thr Asp Ile Ala Leu His Tyr Phe Tyr Arg
130                 135                 140

Ala Leu Leu Thr Ser Asp Glu Ala Leu Leu Ser Phe Ala Val Lys Glu
145                 150                 155                 160

Leu Phe Tyr Pro Val Gln Phe Val His Tyr Glu Glu Gly Leu Gln Tyr
                165                 170                 175

Asp Tyr Ser Tyr Leu Gln His Gly Pro Gln Leu Gln Ile Ser Ser Tyr
            180                 185                 190

Gly Ala Val Phe Ile Thr Gly Val Leu Lys Leu Ala Asn Tyr Val Arg
        195                 200                 205

Asp Thr Pro Tyr Ala Leu Ser Thr Glu Lys Leu Ala Ile Phe Ser Lys
210                 215                 220

Tyr Tyr Arg Asp Ser Tyr Leu Lys Ala Ile Arg Gly Ser Tyr Met Asp
225                 230                 235                 240

Phe Asn Val Glu Gly Arg Gly Val Ser Arg Pro Asp Ile Leu Asn Lys
                245                 250                 255
```

Lys Ala Glu Lys Lys Arg Leu Leu Val Ala Lys Met Ile Asp Leu Lys
            260                 265                 270

His Thr Glu Glu Trp Ala Asp Ala Ile Ala Arg Thr Asp Ser Thr Val
        275                 280                 285

Ala Ala Gly Tyr Lys Ile Glu Pro Tyr His His Gln Phe Trp Asn Gly
        290                 295                 300

Asp Tyr Val Gln His Leu Arg Pro Ala Tyr Ser Phe Asn Val Arg Met
305                 310                 315                 320

Val Ser Lys Arg Thr Arg Arg Ser Glu Ser Gly Asn Lys Glu Asn Leu
                325                 330                 335

Leu Gly Arg Tyr Leu Ser Asp Gly Ala Thr Asn Ile Gln Leu Arg Gly
            340                 345                 350

Pro Glu Tyr Tyr Asn Ile Met Pro Val Trp Glu Trp Asp Lys Ile Pro
        355                 360                 365

Gly Ile Thr Ser Arg Asp Tyr Leu Thr Asp Arg Pro Leu Thr Lys Leu
        370                 375                 380

Trp Gly Glu Gln Gly Ser Asn Asp Phe Ala Gly Gly Val Ser Asp Gly
385                 390                 395                 400

Val Tyr Gly Ala Ser Ala Tyr Ala Leu Asp Tyr Asp Ser Leu Gln Ala
                405                 410                 415

Lys Lys Ala Trp Phe Phe Asp Lys Glu Ile Val Cys Leu Gly Ala
            420                 425                 430

Gly Ile Asn Ser Asn Ala Pro Glu Asn Ile Thr Thr Thr Leu Asn Gln
            435                 440                 445

Ser Trp Leu Asn Gly Pro Val Ile Ser Thr
450                 455

<210> SEQ ID NO 65
<211> LENGTH: 427
<212> TYPE: PRT
<213> ORGANISM: Artificial
<220> FEATURE:
<223> OTHER INFORMATION: Synthetic polypeptide, N(delta)50 C(delta)200
      of chondroitinase AC (T[sub]74 -T[sub]500)

<400> SEQUENCE: 65

Thr Asn Trp Leu Pro Asn Asn His Leu Leu Gln Leu Glu Thr Ile Ile
1               5                   10                  15

Gln Ala Tyr Ile Glu Lys Asp Ser His Tyr Tyr Gly Asp Asp Lys Val
            20                  25                  30

Phe Asp Gln Ile Ser Lys Ala Phe Lys Tyr Trp Tyr Asp Ser Asp Pro
        35                  40                  45

Lys Ser Arg Asn Trp Trp His Asn Glu Ile Ala Thr Pro Gln Ala Leu
50                  55                  60

Gly Glu Met Leu Ile Leu Met Arg Tyr Gly Lys Pro Leu Asp Glu
65                  70                  75                  80

Ala Leu Val His Lys Leu Thr Glu Arg Met Lys Arg Gly Glu Pro Glu
                85                  90                  95

Lys Lys Thr Gly Ala Asn Lys Thr Asp Ile Ala Leu His Tyr Phe Tyr
            100                 105                 110

Arg Ala Leu Leu Thr Ser Asp Glu Ala Leu Leu Ser Phe Ala Val Lys
        115                 120                 125

Glu Leu Phe Tyr Pro Val Gln Phe Val His Tyr Glu Glu Gly Leu Gln
130                 135                 140

Tyr Asp Tyr Ser Tyr Leu Gln His Gly Pro Gln Leu Gln Ile Ser Ser
145                 150                 155                 160

```
Tyr Gly Ala Val Phe Ile Thr Gly Val Leu Lys Leu Ala Asn Tyr Val
                165                 170                 175

Arg Asp Thr Pro Tyr Ala Leu Ser Thr Glu Lys Leu Ala Ile Phe Ser
            180                 185                 190

Lys Tyr Tyr Arg Asp Ser Tyr Leu Lys Ala Ile Arg Gly Ser Tyr Met
        195                 200                 205

Asp Phe Asn Val Glu Gly Arg Gly Val Ser Arg Pro Asp Ile Leu Asn
    210                 215                 220

Lys Lys Ala Glu Lys Lys Arg Leu Leu Val Ala Lys Met Ile Asp Leu
225                 230                 235                 240

Lys His Thr Glu Glu Trp Ala Asp Ala Ile Ala Arg Thr Asp Ser Thr
                245                 250                 255

Val Ala Ala Gly Tyr Lys Ile Glu Pro Tyr His His Gln Phe Trp Asn
            260                 265                 270

Gly Asp Tyr Val Gln His Leu Arg Pro Ala Tyr Ser Phe Asn Val Arg
        275                 280                 285

Met Val Ser Lys Arg Thr Arg Arg Ser Glu Ser Gly Asn Lys Glu Asn
    290                 295                 300

Leu Leu Gly Arg Tyr Leu Ser Asp Gly Ala Thr Asn Ile Gln Leu Arg
305                 310                 315                 320

Gly Pro Glu Tyr Tyr Asn Ile Met Pro Val Trp Glu Trp Asp Lys Ile
                325                 330                 335

Pro Gly Ile Thr Ser Arg Asp Tyr Leu Thr Asp Arg Pro Leu Thr Lys
            340                 345                 350

Leu Trp Gly Glu Gln Gly Ser Asn Asp Phe Ala Gly Val Ser Asp
        355                 360                 365

Gly Val Tyr Gly Ala Ser Ala Tyr Ala Leu Asp Tyr Asp Ser Leu Gln
    370                 375                 380

Ala Lys Lys Ala Trp Phe Phe Asp Lys Glu Ile Val Cys Leu Gly
385                 390                 395                 400

Ala Gly Ile Asn Ser Asn Ala Pro Glu Asn Ile Thr Thr Thr Leu Asn
                405                 410                 415

Gln Ser Trp Leu Asn Gly Pro Val Ile Ser Thr
            420                 425

<210> SEQ ID NO 66
<211> LENGTH: 378
<212> TYPE: PRT
<213> ORGANISM: Artificial
<220> FEATURE:
<223> OTHER INFORMATION: Synthetic polypeptide, N(delta)100 C(delta)200
      of chondroitinase AC (S[sub]123 - T[sub] 500

<400> SEQUENCE: 66

Ser Arg Asn Trp Trp His Asn Glu Ile Ala Thr Pro Gln Ala Leu Gly
1               5                   10                  15

Glu Met Leu Ile Leu Met Arg Tyr Gly Lys Lys Pro Leu Asp Glu Ala
            20                  25                  30

Leu Val His Lys Leu Thr Glu Arg Met Lys Arg Gly Glu Pro Glu Lys
        35                  40                  45

Lys Thr Gly Ala Asn Lys Thr Asp Ile Ala Leu His Tyr Phe Tyr Arg
    50                  55                  60

Ala Leu Leu Thr Ser Asp Glu Ala Leu Leu Ser Phe Ala Val Lys Glu
65                  70                  75                  80

Leu Phe Tyr Pro Val Gln Phe Val His Tyr Glu Glu Gly Leu Gln Tyr
```

```
                    85                  90                  95
Asp Tyr Ser Tyr Leu Gln His Gly Pro Gln Leu Gln Ile Ser Ser Tyr
                100                 105                 110

Gly Ala Val Phe Ile Thr Gly Val Leu Lys Leu Ala Asn Tyr Val Arg
            115                 120                 125

Asp Thr Pro Tyr Ala Leu Ser Thr Glu Lys Leu Ala Ile Phe Ser Lys
    130                 135                 140

Tyr Tyr Arg Asp Ser Tyr Leu Lys Ala Ile Arg Gly Ser Tyr Met Asp
145                 150                 155                 160

Phe Asn Val Glu Gly Arg Gly Val Ser Arg Pro Asp Ile Leu Asn Lys
                165                 170                 175

Lys Ala Glu Lys Lys Arg Leu Leu Val Ala Lys Met Ile Asp Leu Lys
            180                 185                 190

His Thr Glu Glu Trp Ala Asp Ala Ile Ala Arg Thr Asp Ser Thr Val
        195                 200                 205

Ala Ala Gly Tyr Lys Ile Glu Pro Tyr His His Gln Phe Trp Asn Gly
    210                 215                 220

Asp Tyr Val Gln His Leu Arg Pro Ala Tyr Ser Phe Asn Val Arg Met
225                 230                 235                 240

Val Ser Lys Arg Thr Arg Arg Ser Glu Ser Gly Asn Lys Glu Asn Leu
                245                 250                 255

Leu Gly Arg Tyr Leu Ser Asp Gly Ala Thr Asn Ile Gln Leu Arg Gly
            260                 265                 270

Pro Glu Tyr Tyr Asn Ile Met Pro Val Trp Glu Trp Asp Lys Ile Pro
        275                 280                 285

Gly Ile Thr Ser Arg Asp Tyr Leu Thr Asp Arg Pro Leu Thr Lys Leu
    290                 295                 300

Trp Gly Glu Gln Gly Ser Asn Asp Phe Ala Gly Gly Val Ser Asp Gly
305                 310                 315                 320

Val Tyr Gly Ala Ser Ala Tyr Ala Leu Asp Tyr Asp Ser Leu Gln Ala
                325                 330                 335

Lys Lys Ala Trp Phe Phe Phe Asp Lys Glu Ile Val Cys Leu Gly Ala
            340                 345                 350

Gly Ile Asn Ser Asn Ala Pro Glu Asn Ile Thr Thr Thr Leu Asn Gln
        355                 360                 365

Ser Trp Leu Asn Gly Pro Val Ile Ser Thr
    370                 375

<210> SEQ ID NO 67
<211> LENGTH: 353
<212> TYPE: PRT
<213> ORGANISM: Artificial
<220> FEATURE:
<223> OTHER INFORMATION: Synthetic polypeptide, N(delta)50 C(delta)275
      of chondroitinase AC (T[sub]74 - L[sub]426)

<400> SEQUENCE: 67

Thr Asn Trp Leu Pro Asn Asn His Leu Leu Gln Leu Glu Thr Ile Ile
1               5                   10                  15

Gln Ala Tyr Ile Glu Lys Asp Ser His Tyr Tyr Gly Asp Asp Lys Val
            20                  25                  30

Phe Asp Gln Ile Ser Lys Ala Phe Lys Tyr Trp Tyr Asp Ser Asp Pro
        35                  40                  45

Lys Ser Arg Asn Trp Trp His Asn Glu Ile Ala Thr Pro Gln Ala Leu
    50                  55                  60
```

Gly Glu Met Leu Ile Leu Met Arg Tyr Gly Lys Lys Pro Leu Asp Glu
65                  70                  75                  80

Ala Leu Val His Lys Leu Thr Glu Arg Met Lys Arg Gly Glu Pro Glu
                85                  90                  95

Lys Lys Thr Gly Ala Asn Lys Thr Asp Ile Ala Leu His Tyr Phe Tyr
            100                 105                 110

Arg Ala Leu Leu Thr Ser Asp Glu Ala Leu Leu Ser Phe Ala Val Lys
        115                 120                 125

Glu Leu Phe Tyr Pro Val Gln Phe Val His Tyr Glu Gly Leu Gln
    130                 135                 140

Tyr Asp Tyr Ser Tyr Leu Gln His Gly Pro Gln Leu Gln Ile Ser Ser
145                 150                 155                 160

Tyr Gly Ala Val Phe Ile Thr Gly Val Leu Lys Leu Ala Asn Tyr Val
                165                 170                 175

Arg Asp Thr Pro Tyr Ala Leu Ser Thr Glu Lys Leu Ala Ile Phe Ser
            180                 185                 190

Lys Tyr Tyr Arg Asp Ser Tyr Leu Lys Ala Ile Arg Gly Ser Tyr Met
        195                 200                 205

Asp Phe Asn Val Glu Gly Arg Gly Val Ser Arg Pro Asp Ile Leu Asn
    210                 215                 220

Lys Lys Ala Glu Lys Lys Arg Leu Leu Val Ala Lys Met Ile Asp Leu
225                 230                 235                 240

Lys His Thr Glu Glu Trp Ala Asp Ala Ile Ala Arg Thr Asp Ser Thr
                245                 250                 255

Val Ala Ala Gly Tyr Lys Ile Glu Pro Tyr His His Gln Phe Trp Asn
            260                 265                 270

Gly Asp Tyr Val Gln His Leu Arg Pro Ala Tyr Ser Phe Asn Val Arg
        275                 280                 285

Met Val Ser Lys Arg Thr Arg Arg Ser Glu Ser Gly Asn Lys Glu Asn
    290                 295                 300

Leu Leu Gly Arg Tyr Leu Ser Asp Gly Ala Thr Asn Ile Gln Leu Arg
305                 310                 315                 320

Gly Pro Glu Tyr Tyr Asn Ile Met Pro Val Trp Glu Trp Asp Lys Ile
                325                 330                 335

Pro Gly Ile Thr Ser Arg Asp Tyr Leu Thr Asp Arg Pro Leu Thr Lys
            340                 345                 350

Leu

<210> SEQ ID NO 68
<211> LENGTH: 401
<212> TYPE: PRT
<213> ORGANISM: Artificial
<220> FEATURE:
<223> OTHER INFORMATION: Synthetic polypeptide, N(delta)80
      chondroitinase B (G[sub]106 - H[sub]506)

<400> SEQUENCE: 68

Gly Asn Arg Ala Ile Gln Ala Trp Lys Ser His Gly Pro Gly Leu Val
1               5                   10                  15

Ala Ile Tyr Gly Ser Tyr Asn Arg Ile Thr Ala Cys Val Phe Asp Cys
                20                  25                  30

Phe Asp Glu Ala Asn Ser Ala Tyr Ile Thr Thr Ser Leu Thr Glu Asp
            35                  40                  45

Gly Lys Val Pro Gln His Cys Arg Ile Asp His Cys Ser Phe Thr Asp
        50                  55                  60

Lys Ile Thr Phe Asp Gln Val Ile Asn Leu Asn Thr Ala Arg Ala
 65                  70                  75                  80

Ile Lys Asp Gly Ser Val Gly Gly Pro Gly Met Tyr His Arg Val Asp
                 85                  90                  95

His Cys Phe Phe Ser Asn Pro Gln Lys Pro Gly Asn Ala Gly Gly Gly
            100                 105                 110

Ile Arg Ile Gly Tyr Tyr Arg Asn Asp Ile Gly Arg Cys Leu Val Asp
        115                 120                 125

Ser Asn Leu Phe Met Arg Gln Asp Ser Glu Ala Glu Ile Ile Thr Ser
130                 135                 140

Lys Ser Gln Glu Asn Val Tyr Tyr Gly Asn Thr Tyr Leu Asn Cys Gln
145                 150                 155                 160

Gly Thr Met Asn Phe Arg His Gly Asp His Gln Val Ala Ile Asn Asn
                165                 170                 175

Phe Tyr Ile Gly Asn Asp Gln Arg Phe Gly Tyr Gly Met Phe Val
            180                 185                 190

Trp Gly Ser Arg His Val Ile Ala Cys Asn Tyr Phe Glu Leu Ser Glu
        195                 200                 205

Thr Ile Lys Ser Arg Gly Asn Ala Ala Leu Tyr Leu Asn Pro Gly Ala
210                 215                 220

Met Ala Ser Glu His Ala Leu Ala Phe Asp Met Leu Ile Ala Asn Asn
225                 230                 235                 240

Ala Phe Ile Asn Val Asn Gly Tyr Ala Ile His Phe Asn Pro Leu Asp
                245                 250                 255

Glu Arg Arg Lys Glu Tyr Cys Ala Ala Asn Arg Leu Lys Phe Glu Thr
            260                 265                 270

Pro His Gln Leu Met Leu Lys Gly Asn Leu Phe Phe Lys Asp Lys Pro
        275                 280                 285

Tyr Val Tyr Pro Phe Phe Lys Asp Asp Tyr Phe Ile Ala Gly Lys Asn
290                 295                 300

Ser Trp Thr Gly Asn Val Ala Leu Gly Val Glu Lys Gly Ile Pro Val
305                 310                 315                 320

Asn Ile Ser Ala Asn Arg Ser Ala Tyr Lys Pro Val Lys Ile Lys Asp
                325                 330                 335

Ile Gln Pro Ile Glu Gly Ile Ala Leu Asp Leu Asn Ala Leu Ile Ser
            340                 345                 350

Lys Gly Ile Thr Gly Lys Pro Leu Ser Trp Asp Glu Val Arg Pro Tyr
        355                 360                 365

Trp Leu Lys Glu Met Pro Gly Thr Tyr Ala Leu Thr Ala Arg Leu Ser
370                 375                 380

Ala Asp Arg Ala Ala Lys Phe Lys Ala Val Ile Lys Arg Asn Lys Glu
385                 390                 395                 400

His

<210> SEQ ID NO 69
<211> LENGTH: 361
<212> TYPE: PRT
<213> ORGANISM: Artificial
<220> FEATURE:
<223> OTHER INFORMATION: Synthetic polypeptide, N(delta)120
      chondroitinase B (I[sub]146 - H[sub]506)

<400> SEQUENCE: 69

Ile Thr Thr Ser Leu Thr Glu Asp Gly Lys Val Pro Gln His Cys Arg
1               5                   10                  15

```
Ile Asp His Cys Ser Phe Thr Asp Lys Ile Thr Phe Asp Gln Val Ile
         20                  25                  30

Asn Leu Asn Asn Thr Ala Arg Ala Ile Lys Asp Gly Ser Val Gly Gly
             35                  40                  45

Pro Gly Met Tyr His Arg Val Asp His Cys Phe Phe Ser Asn Pro Gln
         50                  55                  60

Lys Pro Gly Asn Ala Gly Gly Ile Arg Ile Gly Tyr Tyr Arg Asn
 65                  70                  75                  80

Asp Ile Gly Arg Cys Leu Val Asp Ser Asn Leu Phe Met Arg Gln Asp
                 85                  90                  95

Ser Glu Ala Glu Ile Ile Thr Ser Lys Ser Gln Glu Asn Val Tyr Tyr
            100                 105                 110

Gly Asn Thr Tyr Leu Asn Cys Gln Gly Thr Met Asn Phe Arg His Gly
            115                 120                 125

Asp His Gln Val Ala Ile Asn Asn Phe Tyr Ile Gly Asn Asp Gln Arg
            130                 135                 140

Phe Gly Tyr Gly Gly Met Phe Val Trp Gly Ser Arg His Val Ile Ala
145                 150                 155                 160

Cys Asn Tyr Phe Glu Leu Ser Glu Thr Ile Lys Ser Arg Gly Asn Ala
                165                 170                 175

Ala Leu Tyr Leu Asn Pro Gly Ala Met Ala Ser Glu His Ala Leu Ala
            180                 185                 190

Phe Asp Met Leu Ile Ala Asn Ala Phe Ile Asn Val Asn Gly Tyr
            195                 200                 205

Ala Ile His Phe Asn Pro Leu Asp Glu Arg Arg Lys Glu Tyr Cys Ala
210                 215                 220

Ala Asn Arg Leu Lys Phe Glu Thr Pro His Gln Leu Met Leu Lys Gly
225                 230                 235                 240

Asn Leu Phe Phe Lys Asp Lys Pro Tyr Val Tyr Pro Phe Phe Lys Asp
                245                 250                 255

Asp Tyr Phe Ile Ala Gly Lys Asn Ser Trp Thr Gly Asn Val Ala Leu
            260                 265                 270

Gly Val Glu Lys Gly Ile Pro Val Asn Ile Ser Ala Asn Arg Ser Ala
            275                 280                 285

Tyr Lys Pro Val Lys Ile Lys Asp Ile Gln Pro Ile Glu Gly Ile Ala
290                 295                 300

Leu Asp Leu Asn Ala Leu Ile Ser Lys Gly Ile Thr Gly Lys Pro Leu
305                 310                 315                 320

Ser Trp Asp Glu Val Arg Pro Tyr Trp Leu Lys Glu Met Pro Gly Thr
                325                 330                 335

Tyr Ala Leu Thr Ala Arg Leu Ser Ala Asp Arg Ala Ala Lys Phe Lys
            340                 345                 350

Ala Val Ile Lys Arg Asn Lys Glu His
            355                 360

<210> SEQ ID NO 70
<211> LENGTH: 463
<212> TYPE: PRT
<213> ORGANISM: Artificial
<220> FEATURE:
<223> OTHER INFORMATION: Synthetic polypeptide, C(delta)19
      chondroitinase B (Q[sub]26 - L[sub]488)

<400> SEQUENCE: 70

Gln Val Val Ala Ser Asn Glu Thr Leu Tyr Gln Val Val Lys Glu Val
 1               5                  10                  15
```

-continued

Lys Pro Gly Gly Leu Val Gln Ile Ala Asp Gly Thr Tyr Lys Asp Val
            20                  25                  30

Gln Leu Ile Val Ser Asn Ser Gly Lys Ser Gly Leu Pro Ile Thr Ile
        35                  40                  45

Lys Ala Leu Asn Pro Gly Lys Val Phe Phe Thr Gly Asp Ala Lys Val
50                  55                  60

Glu Leu Arg Gly Glu His Leu Ile Leu Glu Gly Ile Trp Phe Lys Asp
65                  70                  75                  80

Gly Asn Arg Ala Ile Gln Ala Trp Lys Ser His Gly Pro Gly Leu Val
                85                  90                  95

Ala Ile Tyr Gly Ser Tyr Asn Arg Ile Thr Ala Cys Val Phe Asp Cys
            100                 105                 110

Phe Asp Glu Ala Asn Ser Ala Tyr Ile Thr Thr Ser Leu Thr Glu Asp
        115                 120                 125

Gly Lys Val Pro Gln His Cys Arg Ile Asp His Cys Ser Phe Thr Asp
130                 135                 140

Lys Ile Thr Phe Asp Gln Val Ile Asn Leu Asn Asn Thr Ala Arg Ala
145                 150                 155                 160

Ile Lys Asp Gly Ser Val Gly Gly Pro Gly Met Tyr His Arg Val Asp
                165                 170                 175

His Cys Phe Phe Ser Asn Pro Gln Lys Pro Gly Asn Ala Gly Gly Gly
            180                 185                 190

Ile Arg Ile Gly Tyr Tyr Arg Asn Asp Ile Gly Arg Cys Leu Val Asp
        195                 200                 205

Ser Asn Leu Phe Met Arg Gln Asp Ser Glu Ala Glu Ile Ile Thr Ser
210                 215                 220

Lys Ser Gln Glu Asn Val Tyr Tyr Gly Asn Thr Tyr Leu Asn Cys Gln
225                 230                 235                 240

Gly Thr Met Asn Phe Arg His Gly Asp His Gln Val Ala Ile Asn Asn
                245                 250                 255

Phe Tyr Ile Gly Asn Asp Gln Arg Phe Gly Tyr Gly Gly Met Phe Val
            260                 265                 270

Trp Gly Ser Arg His Val Ile Ala Cys Asn Tyr Phe Glu Leu Ser Glu
        275                 280                 285

Thr Ile Lys Ser Arg Gly Asn Ala Ala Leu Tyr Leu Asn Pro Gly Ala
290                 295                 300

Met Ala Ser Glu His Ala Leu Ala Phe Asp Met Leu Ile Ala Asn Asn
305                 310                 315                 320

Ala Phe Ile Asn Val Asn Gly Tyr Ala Ile His Phe Asn Pro Leu Asp
                325                 330                 335

Glu Arg Arg Lys Glu Tyr Cys Ala Ala Asn Arg Leu Lys Phe Glu Thr
            340                 345                 350

Pro His Gln Leu Met Leu Lys Gly Asn Leu Phe Phe Lys Asp Lys Pro
        355                 360                 365

Tyr Val Tyr Pro Phe Phe Lys Asp Asp Tyr Phe Ile Ala Gly Lys Asn
370                 375                 380

Ser Trp Thr Gly Asn Val Ala Leu Gly Val Glu Lys Gly Ile Pro Val
385                 390                 395                 400

Asn Ile Ser Ala Asn Arg Ser Ala Tyr Lys Pro Val Lys Ile Lys Asp
                405                 410                 415

Ile Gln Pro Ile Glu Gly Ile Ala Leu Asp Leu Asn Ala Leu Ile Ser
            420                 425                 430

Lys Gly Ile Thr Gly Lys Pro Leu Ser Trp Asp Glu Val Arg Pro Tyr
                435                 440                 445

Trp Leu Lys Glu Met Pro Gly Thr Tyr Ala Leu Thr Ala Arg Leu
    450                 455                 460

<210> SEQ ID NO 71
<211> LENGTH: 365
<212> TYPE: PRT
<213> ORGANISM: Artificial
<220> FEATURE:
<223> OTHER INFORMATION: OTHER INFORMATION; Synthetic polypeptide,
      C(delta)120 chondroitinase B (Q[sub]26 - K[sub]390)

<400> SEQUENCE: 71

Gln Val Val Ala Ser Asn Glu Thr Leu Tyr Gln Val Val Lys Glu Val
1               5                   10                  15

Lys Pro Gly Gly Leu Val Gln Ile Ala Asp Gly Thr Tyr Lys Asp Val
            20                  25                  30

Gln Leu Ile Val Ser Asn Ser Gly Lys Ser Gly Leu Pro Ile Thr Ile
        35                  40                  45

Lys Ala Leu Asn Pro Gly Lys Val Phe Phe Thr Gly Asp Ala Lys Val
    50                  55                  60

Glu Leu Arg Gly Glu His Leu Ile Leu Glu Gly Ile Trp Phe Lys Asp
65                  70                  75                  80

Gly Asn Arg Ala Ile Gln Ala Trp Lys Ser His Gly Pro Gly Leu Val
                85                  90                  95

Ala Ile Tyr Gly Ser Tyr Asn Arg Ile Thr Ala Cys Val Phe Asp Cys
            100                 105                 110

Phe Asp Glu Ala Asn Ser Ala Tyr Ile Thr Thr Ser Leu Thr Glu Asp
        115                 120                 125

Gly Lys Val Pro Gln His Cys Arg Ile Asp His Cys Ser Phe Thr Asp
    130                 135                 140

Lys Ile Thr Phe Asp Gln Val Ile Asn Leu Asn Asn Thr Ala Arg Ala
145                 150                 155                 160

Ile Lys Asp Gly Ser Val Gly Gly Pro Gly Met Tyr His Arg Val Asp
                165                 170                 175

His Cys Phe Phe Ser Asn Pro Gln Lys Pro Gly Asn Ala Gly Gly Gly
            180                 185                 190

Ile Arg Ile Gly Tyr Tyr Arg Asn Asp Ile Gly Arg Cys Leu Val Asp
        195                 200                 205

Ser Asn Leu Phe Met Arg Gln Asp Ser Glu Ala Glu Ile Ile Thr Ser
    210                 215                 220

Lys Ser Gln Glu Asn Val Tyr Tyr Gly Asn Thr Tyr Leu Asn Cys Gln
225                 230                 235                 240

Gly Thr Met Asn Phe Arg His Gly Asp His Gln Val Ala Ile Asn Asn
                245                 250                 255

Phe Tyr Ile Gly Asn Asp Gln Arg Phe Gly Tyr Gly Gly Met Phe Val
            260                 265                 270

Trp Gly Ser Arg His Val Ile Ala Cys Asn Tyr Phe Glu Leu Ser Glu
        275                 280                 285

Thr Ile Lys Ser Arg Gly Asn Ala Ala Leu Tyr Leu Asn Pro Gly Ala
    290                 295                 300

Met Ala Ser Glu His Ala Leu Ala Phe Asp Met Leu Ile Ala Asn Asn
305                 310                 315                 320

Ala Phe Ile Asn Val Asn Gly Tyr Ala Ile His Phe Asn Pro Leu Asp
                325                 330                 335

```
Glu Arg Arg Lys Glu Tyr Cys Ala Ala Asn Arg Leu Lys Phe Glu Thr
                340                 345                 350
Pro His Gln Leu Met Leu Lys Gly Asn Leu Phe Phe Lys
            355                 360                 365
```

<210> SEQ ID NO 72
<211> LENGTH: 245
<212> TYPE: PRT
<213> ORGANISM: Artificial
<220> FEATURE:
<223> OTHER INFORMATION: Synthetic polypeptide, N(delta)120 C(delta)120
      chondroitinase B (I[sub]146 - K[sub]390)

<400> SEQUENCE: 72

```
Ile Thr Thr Ser Leu Thr Glu Asp Gly Lys Val Pro Gln His Cys Arg
1               5                   10                  15
Ile Asp His Cys Ser Phe Thr Asp Lys Ile Thr Phe Asp Gln Val Ile
                20                  25                  30
Asn Leu Asn Thr Ala Arg Ala Ile Lys Asp Gly Ser Val Gly Gly
            35                  40                  45
Pro Gly Met Tyr His Arg Val Asp His Cys Phe Phe Ser Asn Pro Gln
        50                  55                  60
Lys Pro Gly Asn Ala Gly Gly Ile Arg Ile Gly Tyr Tyr Arg Asn
65              70                  75                  80
Asp Ile Gly Arg Cys Leu Val Asp Ser Asn Leu Phe Met Arg Gln Asp
                85                  90                  95
Ser Glu Ala Glu Ile Ile Thr Ser Lys Ser Gln Glu Asn Val Tyr Tyr
            100                 105                 110
Gly Asn Thr Tyr Leu Asn Cys Gln Gly Thr Met Asn Phe Arg His Gly
        115                 120                 125
Asp His Gln Val Ala Ile Asn Asn Phe Tyr Ile Gly Asn Asp Gln Arg
    130                 135                 140
Phe Gly Tyr Gly Gly Met Phe Val Trp Gly Ser Arg His Val Ile Ala
145                 150                 155                 160
Cys Asn Tyr Phe Glu Leu Ser Glu Thr Ile Lys Ser Arg Gly Asn Ala
                165                 170                 175
Ala Leu Tyr Leu Asn Pro Gly Ala Met Ala Ser Glu His Ala Leu Ala
            180                 185                 190
Phe Asp Met Leu Ile Ala Asn Ala Phe Ile Asn Val Asn Gly Tyr
        195                 200                 205
Ala Ile His Phe Asn Pro Leu Asp Glu Arg Arg Lys Glu Tyr Cys Ala
    210                 215                 220
Ala Asn Arg Leu Lys Phe Glu Thr Pro His Gln Leu Met Leu Lys Gly
225                 230                 235                 240
Asn Leu Phe Phe Lys
                245
```

<210> SEQ ID NO 73
<211> LENGTH: 2103
<212> TYPE: DNA
<213> ORGANISM: Unknown
<220> FEATURE:
<223> OTHER INFORMATION: Pedobacter heparinus Chondroitinase AC
      nucleotide sequence

<400> SEQUENCE: 73
atgaagaaat tatttgtaac ctgtatagtc tttttctcta ttttaagtcc tgctctgctt    60

| | |
|---|---|
| attgcacagc agaccggtac tgcagaactg attatgaagc gggtgatgct ggaccttaaa | 120 |
| aagcctttgc gcaatatgga taaggtggcg gaaaagaacc tgaatacgct gcagcctgac | 180 |
| ggtagctgga aggatgtgcc ttataaagat gatgccatga ccaattggtt gccaaacaac | 240 |
| cacctgctac aattggaaac tattatacag gcttatattg aaaaagatag tcactattat | 300 |
| ggcgacgata aagtgtttga ccagatttcc aaagctttta agtattggta tgacagcgac | 360 |
| ccgaaaagcc gcaactggtg gcacaatgaa attgccactc gcaggccct tggtgaaatg | 420 |
| ctgatcctga tgcgttacgg taaaaagccg cttgatgaag cattggtgca taaattgacc | 480 |
| gaaagaatga agcggggcga accggagaag aaaacggggg ccaacaaaac agatatcgcc | 540 |
| ctgcattact tttatcgtgc tttgttaacg tctgatgagg ctttgctttc cttcgccgta | 600 |
| aaagaattgt tttatcccgt acagtttgta cactatgagg aaggcctgca atacgattat | 660 |
| tcctacctgc agcacggtcc gcaattacag atatcgagct acggtgccgt atttattacc | 720 |
| ggggtactga aacttgccaa ttacgttagg gataccccct atgctttaag taccgagaaa | 780 |
| ctggctatat tttcaaagta ttaccgcgac agttatctga aagctatccg tggaagttat | 840 |
| atggatttta acgtagaagg ccgcggagta agccggccag acattctaaa taaaaaggca | 900 |
| gaaaaaaaga ggttgctggt ggcgaagatg atcgatctta agcatactga agaatgggct | 960 |
| gatgcgatag ccaggacaga tagcacagtt gcggccggct ataagattga gccctatcac | 1020 |
| catcagttct ggaatggtga ttatgtgcaa catttaagac ctgcctattc ttttaatgtt | 1080 |
| cgtatggtga gtaagcggac ccgacgcagt gaatccggca ataagaaaaa cctgctgggc | 1140 |
| aggtatttat ctgatggggc tactaacata caattgcgcg gaccagaata ctataacatt | 1200 |
| atgccggtat gggaatggga caagattcct ggcataacca gccgtgatta tttaaccgac | 1260 |
| agacctttga cgaagctttg gggagagcag gggagcaatg actttgcagg aggggtgtct | 1320 |
| gatggtgtat acggggccag tgcctacgca ttggattacg atagcttaca ggcaaagaaa | 1380 |
| gcctggttct tttttgacaa agagattgta tgtcttggtg ccggtatcaa cagcaatgcc | 1440 |
| cctgaaaaca ttaccactac ccttaaccag agctggttaa atggcccggt tataagtact | 1500 |
| gcaggtaaaa ccggccgggg taaaataaca acgtttaaag cacagggaca gttctggttg | 1560 |
| ttgcacgatg cgattggtta ttactttcct gaaggggcca accttagtct gagtacccag | 1620 |
| tcgcaaaaag gcaattggtt ccacatcaac aattcacatt caaaagatga agtttctggt | 1680 |
| gatgtatttta agctttggat caaccatggt gccaggccag aaaatgcgca gtatgcttat | 1740 |
| atcgttttgc cgggaataaa caagccggaa gaaattaaaa aatataatgg aacggcaccg | 1800 |
| aaagtccttg ccaataccaa ccagctgcag gcagtttatc atcagcagtt agatatggta | 1860 |
| caggctatct tctatacagc tggaaaatta agcgtagcgg gcatagaaat tgaaacagat | 1920 |
| aagccatgtg cagtgctgat caagcacatc aatggcaagc aggtaatttg ggctgccgat | 1980 |
| ccattgcaaa aagaaaagac tgcagtgttg agcatcaggg attaaaaac aggaaaaaca | 2040 |
| aatcgggtaa aaattgattt tccgcaacag gaatttgcag gtgcaacggt tgaactgaaa | 2100 |
| tag | 2103 |

<210> SEQ ID NO 74
<211> LENGTH: 1067
<212> TYPE: DNA
<213> ORGANISM: Artificial
<220> FEATURE:
<223> OTHER INFORMATION: Synthetic polynucleotide of chondroitinase AC
      nucleic acid deletion N(delta)50 C(delta)275
      (a[sub]220 - t[sub]1278)

<400> SEQUENCE: 74

```
atgccatgac caattggttg ccaaacaacc acctgctaca attggaaact attatacagg      60
cttatattga aaagatagt cactattatg gcgacgataa agtgtttgac cagatttcca     120
aagcttttaa gtattggtat gacagcgacc cgaaaagccg caactggtgg cacaatgaaa    180
ttgccactcc gcaggccctt ggtgaaatgc tgatcctgat gcgttacggt aaaaagccgc    240
ttgatgaagc attggtgcat aaattgaccg aaagaatgaa gcgggcgaa ccggagaaga    300
aaacgggggc caacaaaaca gatatcgccc tgcattactt ttatcgtgct tgttaacgt     360
ctgatgaggc tttgctttcc ttcgccgtaa agaattgtt ttatcccgta cagttttgtac   420
actatgagga aggcctgcaa tacgattatt cctacctgca gcacggtccg caattacaga    480
tatcgagcta cggtgccgta tttattaccg gggtactgaa acttgccaat tacgttaggg    540
ataccccta tgctttaagt accgagaaac tggctatatt ttcaaagtat taccgcgaca    600
gttatctgaa agctatccgt ggaagttata tggattttaa cgtagaaggc cgcggagtaa    660
gccggccaga cattctaaat aaaaaggcag aaaaaaagag gttgctggtg gcgaagatga    720
tcgatcttaa gcatactgaa gaatgggctg atgcgtagc caggacagat agcacagttg    780
cggccggcta aagattgag ccctatcacc atcagttctg gaatggtgat tatgtgcaac     840
atttaagacc tgcctattct tttaatgttc gtatggtgag taagcggacc cgacgcagtg    900
aatccggcaa taagaaaac ctgctgggca ggtatttatc tgatggggct actaacatac     960
aattgcgcgg accagaatac tataacatta tgccggtatg ggaatgggac aagattcctg   1020
gcataaccag ccgtgattat ttaaccgaca gacctttgac gaagctt                  1067
```

<210> SEQ ID NO 75
<211> LENGTH: 1521
<212> TYPE: DNA
<213> ORGANISM: Unknown
<220> FEATURE:
<223> OTHER INFORMATION: Pedobacter Heparinus Chondroitinase B
    Chondroitinase B nucleotide sequence

<400> SEQUENCE: 75

```
atgaagatgc tgaataaact agccggatac ttattgccga tcatggtgct gctgaatgtg      60
gcaccatgct taggtcaggt tgttgcttca aatgaaactt tataccaggt tgtaaaggag    120
gtaaaacccg gtggtctggt acagattgcc gatgggactt ataaagatgt tcagctgatt    180
gtcagcaatt caggaaaatc tggtttgccc atcactatta agccctgaa cccgggtaag    240
gtttttttta ccggagatgc taaagtagag ctgagggggcg agcacctgat actggaaggc    300
atctggttta agacgggaa cagagctatt caggcatgga atcacatgg acccggattg     360
gtggctatat atggtagcta taaccgcatt accgcatgtg tatttgattg ttttgatgaa    420
gccaattctg cttacattac tacttcgctt accgaagacg gaaaggtacc tcaacattgc    480
cgcatagacc attgcagttt taccgataag atcacttttg accaggtaat taacctgaac    540
aatacagcca gagctattaa agacggttcg gtgggaggac cggggatgta ccatcgtgtt    600
gatcactgtt ttttttccaa tccgcaaaaa ccgggtaatg ccgagggggg aatcaggatt    660
ggctattacc gtaatgatat aggccgttgt ctggtagact ctaacctgtt tatgcgtcag    720
gattcggaag cagagatcat caccagcaaa tcgcaggaaa atgttttatta tggtaatact   780
tacctgaatt gccagggcac catgaacttt cgtcacggtg atcatcaggt ggccattaac    840
aattttttata taggcaatga ccagcgattt ggatacgggg aatgtttgt ttggggaagc    900
```

```
aggcatgtca tagcctgtaa ttattttgag ctgtccgaaa ccataaagtc gagggggaac      960
gccgcattgt atttaaaccc cggtgctatg gcttcggagc atgctcttgc tttcgatatg     1020
ttgatagcca acaacgcttt catcaatgta aatgggtatg ccatccattt taatccattg     1080
gatgagcgca gaaaagaata ttgtgcagcc aataggctta agttcgaaac cccgcaccag     1140
ctaatgttaa aaggcaatct tttctttaag gataaacctt atgtttaccc atttttttaaa     1200 gatgattatt ttatagcagg gaaaaatagc tggactggta atgtagcctt aggtgtggaa     1260
aagggaatcc ctgttaacat ttcggccaat aggtctgcct ataagccggt aaaaattaaa     1320
gatatccagc ccatagaagg aatcgctctt gatctcaatg cgctgatcag caaaggcatt     1380
acaggaaagc cccttagctg ggatgaagta aggccctact ggttaaaaga aatgcccggg     1440
acgtatgctt taacggccag gctttctgca gatagggctg caaagtttaa agccgtaatt     1500
aaaagaaata aagagcactg a                                                1521

<210> SEQ ID NO 76
<211> LENGTH: 735
<212> TYPE: DNA
<213> ORGANISM: Artificial
<220> FEATURE:
<223> OTHER INFORMATION: Synthetic polynucleotide of chondroitinase B
      nucleic acid deletion N(delta)120 C(delta)120
      (a[sub]436 - g[sub]1170)

<400> SEQUENCE: 76
attactactt cgcttaccga agacggaaag gtacctcaac attgccgcat agaccattgc        60
agttttaccg ataagatcac ttttgaccag gtaattaacc tgaacaatac agccagagct       120
attaaagacg gttcggtggg aggaccgggg atgtaccatc gtgttgatca ctgtttttt        180 tccaatccgc aaaaaccggg taatgccgga gggggaatca ggattggcta ttaccgtaat       240
gatataggcc gttgtctggt agactctaac ctgtttatgc gtcaggattc ggaagcagag       300
atcatcacca gcaaatcgca ggaaaatgtt tattatggta atacttacct gaattgccag       360
ggcaccatga actttcgtca cggtgatcat caggtggcca ttaacaattt ttatataggc       420
aatgaccagc gatttggata cggggggaatg tttgtttggg gaagcaggca tgtcatagcc       480
tgtaattatt ttgagctgtc cgaaaccata aagtcgaggg ggaacgccgc attgtattta       540
aaccccggtg ctatggcttc ggagcatgct cttgctttcg atatgttgat agccaacaac       600
gctttcatca atgtaaatgg gtatgccatc cattttaatc cattggatga gcgcagaaaa       660
gaatattgtg cagccaatag gcttaagttc gaaacccccgc accagctaat gttaaaaggc       720
aatcttttct ttaag                                                        735

<210> SEQ ID NO 77
<211> LENGTH: 3980
<212> TYPE: DNA
<213> ORGANISM: Artificial
<220> FEATURE:
<223> OTHER INFORMATION: Synthetic polynucleotide Chondroitinase ABCI
      LOCUS (I29953)

<400> SEQUENCE: 77
ggaattccat cactcaatca ttaaatttag gcacaacgat gggctatcag cgttatgaca        60
aatttaatga aggacgcatt ggtttcactg ttagccagcg tttctaagga gaaaaataat       120
gccgatattt cgttttactg cacttgcaat gacattgggg ctattatcag cgccttataa       180
cgcgatggca gccaccagca atcctgcatt tgatcctaaa aatctgatgc agtcagaaat       240
```

| | | | | |
|---|---|---|---|---|
| ttaccattt | gcacaaaata | acccattagc | agacttctca | tcagataaaa | actcaatact | 300 |
| aacgttatct | gataaacgta | gcattatggg | aaaccaatct | cttttatgga | aatggaaagg | 360 |
| tggtagtagc | tttactttac | ataaaaaact | gattgtcccc | accgataaag | aagcatctaa | 420 |
| agcatgggga | cgctcatcta | cccccgtttt | ctcattttgg | ctttacaatg | aaaaaccgat | 480 |
| tgatggttat | cttactatcg | atttcggaga | aaaactcatt | tcaaccagtg | aggctcaggc | 540 |
| aggctttaaa | gtaaaattag | atttcactgg | ctggcgtgct | gtgggagtct | ctttaaataa | 600 |
| cgatcttgaa | aatcgagaga | tgaccttaaa | tgcaaccaat | acctcctctg | atggtactca | 660 |
| agacagcatt | gggcgttctt | taggtgctaa | agtcgatagt | attcgtttta | aagcgccttc | 720 |
| taatgtgagt | cagggtgaaa | tctatatcga | ccgtattatg | ttttctgtcg | atgatgctcg | 780 |
| ctaccaatgg | tctgattatc | aagtaaaaac | tcgcttatca | gaacctgaaa | ttcaatttca | 840 |
| caacgtaaag | ccacaactac | ctgtaacacc | tgaaaattta | gcggccattg | atcttattcg | 900 |
| ccaacgtcta | attaatgaat | tgtcggaggt | gaaaaagag | acaaacctcg | cattagaaga | 960 |
| gaatatcagc | aaattaaaaa | gtgatttcga | tgctcttaat | attcacactt | tagcaaatgg | 1020 |
| tggaacgcaa | ggcagacatc | tgatcactga | taaacaaatc | attatttatc | aaccagagaa | 1080 |
| tcttaactcc | caagataaac | aactatttga | taattatgtt | attttaggta | attacacgac | 1140 |
| attaatgttt | aatattagcc | gtgcttatgt | gctggaaaaa | gatcccacac | aaaaggcgca | 1200 |
| actaaagcag | atgtacttat | taatgacaaa | gcatttatta | gatcaaggct | ttgttaaagg | 1260 |
| gagtgcttta | gtgacaaccc | atcactgggg | atacagttct | cgttggtggt | atatttccac | 1320 |
| gttattaatg | tctgatgcac | taaaagaagc | gaacctacaa | actcaagttt | atgattcatt | 1380 |
| actgtggtat | tcacgtgagt | ttaaaagtag | ttttgatatg | aaagtaagtg | ctgatagctc | 1440 |
| tgatctagat | tatttcaata | ccttatctcg | ccaacattta | gccttattat | tactagagcc | 1500 |
| tgatgatcaa | aagcgtatca | acttagttaa | tactttcagc | cattatatca | ctggcgcatt | 1560 |
| aacgcaagtg | ccaccgggtg | gtaaagatgg | tttacgccct | gatggtacag | catggcgaca | 1620 |
| tgaaggcaac | tatccgggct | actctttccc | agcctttaaa | aatgcctctc | agcttatta | 1680 |
| tttattacgc | gatacaccat | tttcagtggg | tgaaagtggt | tggaataacc | tgaaaaaagc | 1740 |
| gatggtttca | gcgtggatct | acagtaatcc | agaagttgga | ttaccgcttg | caggaagaca | 1800 |
| cccttttaac | tcaccttcgt | taaaatcagt | cgctcaaggc | tattactggc | ttgccatgtc | 1860 |
| tgcaaaatca | tcgcctgata | aaacacttgc | atctatttat | cttgcgatta | gtgataaaac | 1920 |
| acaaaatgaa | tcaactgcta | tttttggaga | aactattaca | ccagcgtctt | tacctcaagg | 1980 |
| tttctatgcc | tttaatggcg | gtgcttttgg | tattcatcgt | tggcaagata | aaatggtgac | 2040 |
| actgaaagct | tataacacca | atgtttggtc | atctgaaatt | tataacaaag | ataaccgtta | 2100 |
| tggccgttac | caaagtcatg | gtgtcgctca | aatagtgagt | aatggctcgc | agctttcaca | 2160 |
| gggctatcag | caagaaggtt | gggattggaa | tagaatgcaa | gggcaacca | ctattcacct | 2220 |
| tcctcttaaa | gacttagaca | gtcctaaacc | tcataccta | atgcaacgtg | agagcgtgg | 2280 |
| atttagcgga | acatcatccc | ttgaaggtca | atatggcatg | atggcattcg | atcttattta | 2340 |
| tcccgccaat | cttgagcgtt | ttgatcctaa | tttcactgcg | aaaagagtg | tattagccgc | 2400 |
| tgataatcac | ttaattttta | ttggtagcaa | tataaatagt | agtgataaaa | ataaaaatgt | 2460 |
| tgaaacgacc | ttattccaac | atgccattac | tccaacatta | aatacccttt | ggattaatgg | 2520 |
| acaaaagata | gaaaacatgc | cttatcaaac | aacacttcaa | caaggtgatt | ggttaattga | 2580 |

-continued

```
tagcaatggc aatggttact taattactca agcagaaaaa gtaaatgtaa gtcgccaaca      2640
tcaggtttca gcggaaaata aaaatcgcca accgacagaa ggaaacttta gctcggcatg      2700
gatcgatcac agcactcgcc ccaaagatgc cagttatgag tatatggtct ttttagatgc      2760
gacacctgaa aaatgggag agatggcaca aaaattccgt gaaaataatg ggttatatca       2820
ggttcttcgt aaggataaag acgttcatat tattctcgat aaactcagca atgtaacggg      2880
atatgccttt tatcagccag catcaattga agacaaatgg atcaaaaagg ttaataaacc      2940
tgcaattgtg atgactcatc gacaaaaaga cactcttatt gtcagtgcag ttacacctga      3000
tttaaatatg actcgccaaa agcagcaac tcctgtcacc atcaatgtca cgattaatgg       3060
caaatggcaa tctgctgata aaaatagtga agtgaaatat caggtttctg gtgataacac      3120
tgaactgacg tttacgagtt actttggtat tccacaagaa atcaaactct cgccactccc      3180
ttgatttaat caaagaacg ctcttgcgtt ccttttttat ttgcaggaaa tctgattatg       3240
ctaataaaaa accctttagc ccacgcggtt acattaagcc tctgtttatc attacccgca      3300
caagcattac ccactctgtc tcatgaagct ttcggcgata tttatctttt tgaaggtgaa      3360
ttacccaata cccttaccac ttcaaataat aatcaattat cgctaagcaa acagcatgct      3420
aaagatggtg aacaatcact caaatggcaa tatcaaccac aagcaacatt aacactaaat      3480
aatattgtta attaccaaga tgataaaaat acagccacac cactcacttt tatgatgtgg      3540
atttataatg aaaaacctca atcttcccca ttaacgttag catttaaaca aataataaaa      3600
attgcactaa gttttaatgc tgaacttaat tttacggggt ggcgaggtat tgctgttcct      3660
tttcgtgata tgcaaggctc tgcgacaggt caacttgatc aattagtgat caccgctcca      3720
aaccaagccg gaacactctt ttttgatcaa atcatcatga gtgtaccgtt agacaatcgt      3780
tgggcagtac ctgactatca aacaccttac gtaaataacg cagtaaacac gatggttagt      3840
aaaaactgga gtgcattatt gatgtacgat cagatgtttc aagcccatta ccctacttta      3900
aacttcgata ctgaatttcg cgatgaccaa acagaaatgg cttcgattta tcagcgcttt      3960
gaatattatc aaggaattcc                                                  3980
```

<210> SEQ ID NO 78
<211> LENGTH: 15
<212> TYPE: PRT
<213> ORGANISM: Artificial
<220> FEATURE:
<223> OTHER INFORMATION: OTHER INFORMATION; Synthetic polypeptide, HIV
      TAT Sequence and Gly penta linker

<400> SEQUENCE: 78

Gly Arg Lys Lys Arg Arg Gln Arg Arg Arg Gly Gly Gly Gly Gly
1               5                   10                  15

<210> SEQ ID NO 79
<211> LENGTH: 45
<212> TYPE: DNA
<213> ORGANISM: Artificial
<220> FEATURE:
<223> OTHER INFORMATION: Synthetic polynucleotide, HIV-1 Tat Sequence
      and Gly penta linker nucleic acid

<400> SEQUENCE: 79
ggtcgtaaaa agcgtcgtca acgtcgtcgt ggtggtggtg gtggt                        45

<210> SEQ ID NO 80
<211> LENGTH: 2973
<212> TYPE: DNA

<213> ORGANISM: Artificial
<220> FEATURE:
<223> OTHER INFORMATION: Synthetic polynucleotide, Chondroitinase ABCII nucleic acid

<400> SEQUENCE: 80

```
ttacccactc tgtctcatga agctttcggc gatatttatc tttttgaagg cgaattaccc      60
aatatcctta ccacttcaaa taataatcaa ttatcgctaa gcaaacagca tgctaaagat     120
ggtgaacaat cactcaaatg gcaatatcaa ccacaagcaa cattaacact aaataatatt     180
gttaattacc aagatgataa aaatacagcc acaccactca cttttatgat gtggatttat     240
aatgaaaaac ctcaatcttc cccattaacg ttagcattta aacaaaataa taaaattgca     300
ctaagtttta atgctgaact taattttacg gggtggcgag gtattgctgt tccttttcgt     360
gatatgcaag gctctgcgac aggtcaactt gatcaattag tgatcaccgc tccaaaccaa     420
gccggaacac tctttttga tcaaatcatc atgagtgtac cgttagacaa tcgttgggca     480
gtacctgact atcaaacacc ttacgtaaat aacgcagtaa acacgatggt tagtaaaaac     540
tggagtgcat tattgatgta cgatcagatg tttcaagccc attccctac tttaaacttc     600
gatactgaat ttcgcgatga ccaaacagaa atggcttcga tttatcagcg ctttgaatat     660
tatcaaggaa ttcgtagtga taaaaaaatt actccagata tgctagataa acatttagcg     720
ttatgggaaa aattggggtt aacacaacac gctgatggct caatcacagg aaaagccctt     780
gatcaccctta accggcaaca tttttatgaaa gtcgaaggtg tatttagtga ggggactcaa     840
aaagcattac ttgatgccaa tatgctaaga gatgtgggca aaacgcttct tcaaactgct     900
atttacttgc gtagcgattc attatcagca actggtagaa aaaaattaga agagcgctat     960
ttattaggta ctcgttatgt ccttgaacaa ggttttacac gaggaagtgg ttatcaaatt    1020
attactcatg ttggttacca aaccagagaa ctttttgatg catggtttat tggccgtcat    1080
gttcttgcaa aaaataacct tttagccccc actcaacaag ctatgatgtg gtacaacgcc    1140
acaggacgta tttttgaaaa agataatgaa attgttgatg caaatgtcga tattctcaat    1200
actcaattgc aatggatgat aaaaagctta ttgatgctac cggattatca acaacgtcaa    1260
caagccttag cgcaactgca aagttggcta aataaaacca ttctaagctc aaaaggtgtt    1320
gctggcggtt tcaaatctga tggttctatt tttcaccatt cacaacatta ccccgcttat    1380
gctaaagatg catttggtgg tttagcaccc agtgtttatg cattaagtga ttcacctttt    1440
cgcttatcta cttcagcaca tgagcattta aaagatgttt tgttaaaaat gcggatctac    1500
accaaagaga cacaaattcc tgtggtatta agtggtcgtc atccaactgg gttgcataaa    1560
atagggatcg cgccatttaa atggatggca ttagcaggaa ccccagatgg caaacaaaag    1620
ttagatacca cattatccgc cgcttatgca aacttagaca caaaacgca ttttgaaggc    1680
attaacgctg aaagtgagcc agtcggcgca tgggcaatga attatgcatc aatggcaata    1740
caacgaagag catcgaccca atcaccacaa caaagctggc tcgccatagc gcgcggtttt    1800
agccgttatc ttgttggtaa tgaaagctat gaaaataaca accgttatgg tcgttattta    1860
caatatggac aattggaaat tattccagct gatttaactc aatcagggtt tagccatgct    1920
ggatgggatt ggaatagata tccaggtaca acaactattc atcttcccta taacgaactt    1980
gaagcaaaac ttaatcaatt acctgctgca ggtattgaag aaatgttgct ttcaacagaa    2040
agttactctg gtgcaaatac ccttaataat aacagtatgt ttgccatgaa attacacggt    2100
cacagtaaat atcaacaaca aagcttaagg gcaaataaat cctatttctt atttgataat    2160
```

-continued

```
agagttattg ctttaggctc aggtattgaa aatgatgata acaacatac gaccgaaaca    2220 acactattcc agtttgccgt ccctaaatta cagtcagtga tcattaatgg caaaaaggta    2280
aatcaattag atactcaatt aactttaaat aatgcagata cattaattga tcctgccggc    2340
aatttatata agctcactaa aggacaaact gtaaaattta gttatcaaaa acaacattca    2400
cttgatgata gaaattcaaa accaacagaa caattatttg caacagctgt tatttctcat    2460
ggtaaggcac cgagtaatga aaattatgaa tatgcaatag ctatcgaagc acaaaataat    2520
aaagctccca atacacagt attacaacat aatgatcagc tccatgcggt aaaagataaa    2580
ataacccaag aagagggata tggttttttt gaagccacta agttaaaatc agcggatgca    2640
acattattat ccagtgatgc gccggttatg gtcatggcta aaatacaaaa tcagcaatta    2700
acattaagta ttgttaatcc tgatttaaat ttatatcaag gtagagaaaa agatcaattt    2760
gatgataaag gtaatcaaat cgaagttagt gtttattctc gtcattggct tacagcagaa    2820
tcgcaatcaa caaatagtac tattaccgta aaaggaatat ggaaattaac gacacctcaa    2880
cccggtgtta ttattaagca ccacaataac aacactctta ttacgacaac aaccatacag    2940
gcaacaccta ctgttattaa tttagttaag taa                                2973
```

<210> SEQ ID NO 81
<211> LENGTH: 977
<212> TYPE: PRT
<213> ORGANISM: Artificial
<220> FEATURE:
<223> OTHER INFORMATION: Synthetic polypeptide, N(delta)20
      chondroitinase ABCI having gwra and dalni sequences

<400> SEQUENCE: 81

```
Ala Gln Asn Asn Pro Leu Ala Asp Phe Ser Ser Asp Lys Asn Ser Ile
1               5                   10                  15

Leu Thr Leu Ser Asp Lys Arg Ser Ile Met Gly Asn Gln Ser Leu Leu
            20                  25                  30

Trp Lys Trp Lys Gly Gly Ser Ser Phe Thr Leu His Lys Lys Leu Ile
        35                  40                  45

Val Pro Thr Asp Lys Glu Ala Ser Lys Ala Trp Gly Arg Ser Ser Thr
    50                  55                  60

Pro Val Phe Ser Phe Trp Leu Tyr Asn Glu Lys Pro Ile Asp Gly Tyr
65                  70                  75                  80

Leu Thr Ile Asp Phe Gly Glu Lys Leu Ile Ser Thr Ser Glu Ala Gln
                85                  90                  95

Ala Gly Phe Lys Val Lys Leu Asp Phe Thr Gly Trp Arg Ala Val Gly
            100                 105                 110

Val Ser Leu Asn Asn Asp Leu Glu Asn Arg Glu Met Thr Leu Asn Ala
        115                 120                 125

Thr Asn Thr Ser Ser Asp Gly Thr Gln Asp Ser Ile Gly Arg Ser Leu
    130                 135                 140

Gly Ala Lys Val Asp Ser Ile Arg Phe Lys Ala Pro Ser Asn Val Ser
145                 150                 155                 160

Gln Gly Glu Ile Tyr Ile Asp Arg Ile Met Phe Ser Val Asp Ala
                165                 170                 175

Arg Tyr Gln Trp Ser Asp Tyr Gln Val Lys Thr Arg Leu Ser Glu Pro
            180                 185                 190

Glu Ile Gln Phe His Asn Val Lys Pro Gln Leu Pro Val Thr Pro Glu
        195                 200                 205

Asn Leu Ala Ala Ile Asp Leu Ile Arg Gln Arg Leu Ile Asn Glu Phe
```

```
            210                 215                 220
Val Gly Gly Glu Lys Glu Thr Asn Leu Ala Leu Glu Glu Asn Ile Ser
225                 230                 235                 240

Lys Leu Lys Ser Asp Phe Asp Ala Leu Asn Ile His Thr Leu Ala Asn
                245                 250                 255

Gly Gly Thr Gln Gly Arg His Leu Ile Thr Asp Lys Gln Ile Ile Ile
                260                 265                 270

Tyr Gln Pro Glu Asn Leu Asn Ser Gln Asp Lys Gln Leu Phe Asp Asn
                275                 280                 285

Tyr Val Ile Leu Gly Asn Tyr Thr Thr Leu Met Phe Asn Ile Ser Arg
290                 295                 300

Ala Tyr Val Leu Glu Lys Asp Pro Thr Gln Lys Ala Gln Leu Lys Gln
305                 310                 315                 320

Met Tyr Leu Leu Met Thr Lys His Leu Leu Asp Gln Gly Phe Val Lys
                325                 330                 335

Gly Ser Ala Leu Val Thr Thr His His Trp Gly Tyr Ser Ser Arg Trp
                340                 345                 350

Trp Tyr Ile Ser Thr Leu Leu Met Ser Asp Ala Leu Lys Glu Ala Asn
                355                 360                 365

Leu Gln Thr Gln Val Tyr Asp Ser Leu Leu Trp Tyr Ser Arg Glu Phe
                370                 375                 380

Lys Ser Ser Phe Asp Met Lys Val Ser Ala Asp Ser Asp Leu Asp
385                 390                 395                 400

Tyr Phe Asn Thr Leu Ser Arg Gln His Leu Ala Leu Leu Leu Glu
                405                 410                 415

Pro Asp Asp Gln Lys Arg Ile Asn Leu Val Asn Thr Phe Ser His Tyr
                420                 425                 430

Ile Thr Gly Ala Leu Thr Gln Val Pro Pro Gly Gly Lys Asp Gly Leu
                435                 440                 445

Arg Pro Asp Gly Thr Ala Trp Arg His Glu Gly Asn Tyr Pro Gly Tyr
                450                 455                 460

Ser Phe Pro Ala Phe Lys Asn Ala Ser Gln Leu Ile Tyr Leu Leu Arg
465                 470                 475                 480

Asp Thr Pro Phe Ser Val Gly Glu Ser Gly Trp Asn Asn Leu Lys Lys
                485                 490                 495

Ala Met Val Ser Ala Trp Ile Tyr Ser Asn Pro Glu Val Gly Leu Pro
                500                 505                 510

Leu Ala Gly Arg His Pro Phe Asn Ser Pro Ser Leu Lys Ser Val Ala
                515                 520                 525

Gln Gly Tyr Tyr Trp Leu Ala Met Ser Ala Lys Ser Ser Pro Asp Lys
                530                 535                 540

Thr Leu Ala Ser Ile Tyr Leu Ala Ile Ser Asp Lys Thr Gln Asn Glu
545                 550                 555                 560

Ser Thr Ala Ile Phe Gly Glu Thr Ile Thr Pro Ala Ser Leu Pro Gln
                565                 570                 575

Gly Phe Tyr Ala Phe Asn Gly Ala Phe Gly Ile His Arg Trp Gln
                580                 585                 590

Asp Lys Met Val Thr Leu Lys Ala Tyr Asn Thr Asn Val Trp Ser Ser
                595                 600                 605

Glu Ile Tyr Asn Lys Asp Asn Arg Tyr Gly Arg Tyr Gln Ser His Gly
                610                 615                 620

Val Ala Gln Ile Val Ser Asn Gly Ser Gln Leu Ser Gln Gly Tyr Gln
625                 630                 635                 640
```

Gln Glu Gly Trp Asp Trp Asn Arg Met Glu Gly Ala Thr Thr Ile His
                645                 650                 655

Leu Pro Leu Lys Asp Leu Asp Ser Pro Lys Pro His Thr Leu Met Gln
            660                 665                 670

Arg Gly Glu Arg Gly Phe Ser Gly Thr Ser Ser Leu Glu Gly Gln Tyr
        675                 680                 685

Gly Met Met Ala Phe Asn Leu Ile Tyr Pro Ala Asn Leu Glu Arg Phe
    690                 695                 700

Asp Pro Asn Phe Thr Ala Lys Lys Ser Val Leu Ala Ala Asp Asn His
705                 710                 715                 720

Leu Ile Phe Ile Gly Ser Asn Ile Asn Ser Ser Asp Lys Asn Lys Asn
                725                 730                 735

Val Glu Thr Thr Leu Phe Gln His Ala Ile Thr Pro Thr Leu Asn Thr
            740                 745                 750

Leu Trp Ile Asn Gly Gln Lys Ile Glu Asn Met Pro Tyr Gln Thr Thr
        755                 760                 765

Leu Gln Gln Gly Asp Trp Leu Ile Asp Ser Asn Gly Asn Gly Tyr Leu
    770                 775                 780

Ile Thr Gln Ala Glu Lys Val Asn Val Ser Arg Gln His Gln Val Ser
785                 790                 795                 800

Ala Glu Asn Lys Asn Arg Gln Pro Thr Glu Gly Asn Phe Ser Ser Ala
                805                 810                 815

Trp Ile Asp His Ser Thr Arg Pro Lys Asp Ala Ser Tyr Glu Tyr Met
            820                 825                 830

Val Phe Leu Asp Ala Thr Pro Glu Lys Met Gly Glu Met Ala Gln Lys
        835                 840                 845

Phe Arg Glu Asn Asn Gly Leu Tyr Gln Val Leu Arg Lys Asp Lys Asp
    850                 855                 860

Val His Ile Ile Leu Asp Lys Leu Ser Asn Val Thr Gly Tyr Ala Phe
865                 870                 875                 880

Tyr Gln Pro Ala Ser Ile Glu Asp Lys Trp Ile Lys Lys Val Asn Lys
                885                 890                 895

Pro Ala Ile Val Met Thr His Arg Gln Lys Asp Thr Leu Ile Val Ser
            900                 905                 910

Ala Val Thr Pro Asp Leu Asn Met Thr Arg Gln Lys Ala Ala Thr Pro
        915                 920                 925

Val Thr Ile Asn Val Thr Ile Asn Gly Lys Trp Gln Ser Ala Asp Lys
    930                 935                 940

Asn Ser Glu Val Lys Tyr Gln Val Ser Gly Asp Asn Thr Glu Leu Thr
945                 950                 955                 960

Phe Thr Ser Tyr Phe Gly Ile Pro Gln Glu Ile Lys Leu Ser Pro Leu
                965                 970                 975

Pro

<210> SEQ ID NO 82
<211> LENGTH: 937
<212> TYPE: PRT
<213> ORGANISM: Artificial
<220> FEATURE:
<223> OTHER INFORMATION: Synthetic polypeptide, N(delta)60
      chondroitinase ABCI having gwra and dalni sequences

<400> SEQUENCE: 82

Phe Thr Leu His Lys Lys Leu Ile Val Pro Thr Asp Lys Glu Ala Ser
1               5                   10                  15

Lys Ala Trp Gly Arg Ser Ser Thr Pro Val Phe Ser Phe Trp Leu Tyr
            20                  25                  30

Asn Glu Lys Pro Ile Asp Gly Tyr Leu Thr Ile Asp Phe Gly Glu Lys
            35                  40                  45

Leu Ile Ser Thr Ser Glu Ala Gln Ala Gly Phe Lys Val Lys Leu Asp
 50                  55                  60

Phe Thr Gly Trp Arg Ala Val Gly Val Ser Leu Asn Asn Asp Leu Glu
 65                  70                  75                  80

Asn Arg Glu Met Thr Leu Asn Ala Thr Asn Thr Ser Ser Asp Gly Thr
                85                  90                  95

Gln Asp Ser Ile Gly Arg Ser Leu Gly Ala Lys Val Asp Ser Ile Arg
            100                 105                 110

Phe Lys Ala Pro Ser Asn Val Ser Gln Gly Glu Ile Tyr Ile Asp Arg
            115                 120                 125

Ile Met Phe Ser Val Asp Asp Ala Arg Tyr Gln Trp Ser Asp Tyr Gln
130                 135                 140

Val Lys Thr Arg Leu Ser Glu Pro Glu Ile Gln Phe His Asn Val Lys
145                 150                 155                 160

Pro Gln Leu Pro Val Thr Pro Glu Asn Leu Ala Ala Ile Asp Leu Ile
                165                 170                 175

Arg Gln Arg Leu Ile Asn Glu Phe Val Gly Gly Glu Lys Glu Thr Asn
            180                 185                 190

Leu Ala Leu Glu Glu Asn Ile Ser Lys Leu Lys Ser Asp Phe Asp Ala
            195                 200                 205

Leu Asn Ile His Thr Leu Ala Asn Gly Gly Thr Gln Gly Arg His Leu
            210                 215                 220

Ile Thr Asp Lys Gln Ile Ile Tyr Gln Pro Glu Asn Leu Asn Ser
225                 230                 235                 240

Gln Asp Lys Gln Leu Phe Asp Asn Tyr Val Ile Leu Gly Asn Tyr Thr
            245                 250                 255

Thr Leu Met Phe Asn Ile Ser Arg Ala Tyr Val Leu Glu Lys Asp Pro
            260                 265                 270

Thr Gln Lys Ala Gln Leu Lys Gln Met Tyr Leu Leu Met Thr Lys His
            275                 280                 285

Leu Leu Asp Gln Gly Phe Val Lys Gly Ser Ala Leu Val Thr Thr His
            290                 295                 300

His Trp Gly Tyr Ser Ser Arg Trp Trp Tyr Ile Ser Thr Leu Leu Met
305                 310                 315                 320

Ser Asp Ala Leu Lys Glu Ala Asn Leu Gln Thr Gln Val Tyr Asp Ser
                325                 330                 335

Leu Leu Trp Tyr Ser Arg Glu Phe Lys Ser Ser Phe Asp Met Lys Val
            340                 345                 350

Ser Ala Asp Ser Ser Asp Leu Asp Tyr Phe Asn Thr Leu Ser Arg Gln
            355                 360                 365

His Leu Ala Leu Leu Leu Glu Pro Asp Asp Gln Lys Arg Ile Asn
            370                 375                 380

Leu Val Asn Thr Phe Ser His Tyr Ile Thr Gly Ala Leu Thr Gln Val
385                 390                 395                 400

Pro Pro Gly Gly Lys Asp Gly Leu Arg Pro Asp Gly Thr Ala Trp Arg
                405                 410                 415

His Glu Gly Asn Tyr Pro Gly Tyr Ser Phe Pro Ala Phe Lys Asn Ala
            420                 425                 430

```
Ser Gln Leu Ile Tyr Leu Leu Arg Asp Thr Pro Phe Ser Val Gly Glu
        435                 440                 445

Ser Gly Trp Asn Asn Leu Lys Lys Ala Met Val Ser Ala Trp Ile Tyr
    450                 455                 460

Ser Asn Pro Glu Val Gly Leu Pro Leu Ala Gly Arg His Pro Phe Asn
465                 470                 475                 480

Ser Pro Ser Leu Lys Ser Val Ala Gln Gly Tyr Tyr Trp Leu Ala Met
            485                 490                 495

Ser Ala Lys Ser Ser Pro Asp Lys Thr Leu Ala Ser Ile Tyr Leu Ala
        500                 505                 510

Ile Ser Asp Lys Thr Gln Asn Glu Ser Thr Ala Ile Phe Gly Glu Thr
        515                 520                 525

Ile Thr Pro Ala Ser Leu Pro Gln Gly Phe Tyr Ala Phe Asn Gly Gly
        530                 535                 540

Ala Phe Gly Ile His Arg Trp Gln Asp Lys Met Val Thr Leu Lys Ala
545                 550                 555                 560

Tyr Asn Thr Asn Val Trp Ser Ser Glu Ile Tyr Asn Lys Asp Asn Arg
                565                 570                 575

Tyr Gly Arg Tyr Gln Ser His Gly Val Ala Gln Ile Val Ser Asn Gly
            580                 585                 590

Ser Gln Leu Ser Gln Gly Tyr Gln Gln Glu Gly Trp Asp Trp Asn Arg
        595                 600                 605

Met Glu Gly Ala Thr Thr Ile His Leu Pro Leu Lys Asp Leu Asp Ser
        610                 615                 620

Pro Lys Pro His Thr Leu Met Gln Arg Gly Glu Arg Gly Phe Ser Gly
625                 630                 635                 640

Thr Ser Ser Leu Glu Gly Gln Tyr Gly Met Met Ala Phe Asn Leu Ile
                645                 650                 655

Tyr Pro Ala Asn Leu Glu Arg Phe Asp Pro Asn Phe Thr Ala Lys Lys
                660                 665                 670

Ser Val Leu Ala Ala Asp Asn His Leu Phe Ile Gly Ser Asn Ile
                675                 680                 685

Asn Ser Ser Asp Lys Asn Lys Asn Val Glu Thr Thr Leu Phe Gln His
    690                 695                 700

Ala Ile Thr Pro Thr Leu Asn Thr Leu Trp Ile Asn Gly Gln Lys Ile
705                 710                 715                 720

Glu Asn Met Pro Tyr Gln Thr Thr Leu Gln Gln Gly Asp Trp Leu Ile
                725                 730                 735

Asp Ser Asn Gly Asn Gly Tyr Leu Ile Thr Gln Ala Glu Lys Val Asn
            740                 745                 750

Val Ser Arg Gln His Gln Val Ser Ala Glu Asn Lys Asn Arg Gln Pro
        755                 760                 765

Thr Glu Gly Asn Phe Ser Ser Ala Trp Ile Asp His Ser Thr Arg Pro
    770                 775                 780

Lys Asp Ala Ser Tyr Glu Tyr Met Val Phe Leu Asp Ala Thr Pro Glu
785                 790                 795                 800

Lys Met Gly Glu Met Ala Gln Lys Phe Arg Glu Asn Asn Gly Leu Tyr
                805                 810                 815

Gln Val Leu Arg Lys Asp Lys Asp Val His Ile Ile Leu Asp Lys Leu
            820                 825                 830

Ser Asn Val Thr Gly Tyr Ala Phe Tyr Gln Pro Ala Ser Ile Glu Asp
        835                 840                 845

Lys Trp Ile Lys Lys Val Asn Lys Pro Ala Ile Val Met Thr His Arg
```

|   |   |   |   |   |   |   |   |   |   |   |   |
|---|---|---|---|---|---|---|---|---|---|---|---|
|   |   | 850 |   |   |   | 855 |   |   |   | 860 |   |

Gln Lys Asp Thr Leu Ile Val Ser Ala Val Thr Pro Asp Leu Asn Met
865                 870                 875                 880

Thr Arg Gln Lys Ala Ala Thr Pro Val Thr Ile Asn Val Thr Ile Asn
                885                 890                 895

Gly Lys Trp Gln Ser Ala Asp Lys Asn Ser Glu Val Lys Tyr Gln Val
            900                 905                 910

Ser Gly Asp Asn Thr Glu Leu Thr Phe Thr Ser Tyr Phe Gly Ile Pro
        915                 920                 925

Gln Glu Ile Lys Leu Ser Pro Leu Pro
        930                 935

<210> SEQ ID NO 83
<211> LENGTH: 858
<212> TYPE: PRT
<213> ORGANISM: Artificial
<220> FEATURE:
<223> OTHER INFORMATION: Synthetic polypeptide, N(delta)60 C(delta)80
      chondroitinase ABCI having gwra and dalni sequences

<400> SEQUENCE: 83

Phe Thr Leu His Lys Lys Leu Ile Val Pro Thr Asp Lys Glu Ala Ser
1               5                   10                  15

Lys Ala Trp Gly Arg Ser Ser Thr Pro Val Phe Ser Phe Trp Leu Tyr
            20                  25                  30

Asn Glu Lys Pro Ile Asp Gly Tyr Leu Thr Ile Asp Phe Gly Glu Lys
        35                  40                  45

Leu Ile Ser Thr Ser Glu Ala Gln Ala Gly Phe Lys Val Lys Leu Asp
    50                  55                  60

Phe Thr Gly Trp Arg Ala Val Gly Val Ser Leu Asn Asn Asp Leu Glu
65              70                  75                  80

Asn Arg Glu Met Thr Leu Asn Ala Thr Asn Thr Ser Ser Asp Gly Thr
                85                  90                  95

Gln Asp Ser Ile Gly Arg Ser Leu Gly Ala Lys Val Asp Ser Ile Arg
            100                 105                 110

Phe Lys Ala Pro Ser Asn Val Ser Gln Gly Glu Ile Tyr Ile Asp Arg
        115                 120                 125

Ile Met Phe Ser Val Asp Asp Ala Arg Tyr Gln Trp Ser Asp Tyr Gln
130                 135                 140

Val Lys Thr Arg Leu Ser Glu Pro Glu Ile Gln Phe His Asn Val Lys
145                 150                 155                 160

Pro Gln Leu Pro Val Thr Pro Glu Asn Leu Ala Ala Ile Asp Leu Ile
                165                 170                 175

Arg Gln Arg Leu Ile Asn Glu Phe Val Gly Gly Glu Lys Glu Thr Asn
            180                 185                 190

Leu Ala Leu Glu Glu Asn Ile Ser Lys Leu Lys Ser Asp Phe Asp Ala
        195                 200                 205

Leu Asn Ile His Thr Leu Ala Asn Gly Gly Thr Gln Gly Arg His Leu
    210                 215                 220

Ile Thr Asp Lys Gln Ile Ile Tyr Gln Pro Glu Asn Leu Asn Ser
225                 230                 235                 240

Gln Asp Lys Gln Leu Phe Asp Asn Tyr Val Ile Leu Gly Asn Tyr Thr
            245                 250                 255

Thr Leu Met Phe Asn Ile Ser Arg Ala Tyr Val Leu Glu Lys Asp Pro
        260                 265                 270

```
Thr Gln Lys Ala Gln Leu Lys Gln Met Tyr Leu Leu Met Thr Lys His
            275                 280                 285

Leu Leu Asp Gln Gly Phe Val Lys Gly Ser Ala Leu Val Thr Thr His
        290                 295                 300

His Trp Gly Tyr Ser Ser Arg Trp Trp Tyr Ile Ser Thr Leu Leu Met
305                 310                 315                 320

Ser Asp Ala Leu Lys Glu Ala Asn Leu Gln Thr Gln Val Tyr Asp Ser
                325                 330                 335

Leu Leu Trp Tyr Ser Arg Glu Phe Lys Ser Ser Phe Asp Met Lys Val
            340                 345                 350

Ser Ala Asp Ser Ser Asp Leu Asp Tyr Phe Asn Thr Leu Ser Arg Gln
        355                 360                 365

His Leu Ala Leu Leu Leu Glu Pro Asp Asp Gln Lys Arg Ile Asn
    370                 375                 380

Leu Val Asn Thr Phe Ser His Tyr Ile Thr Gly Ala Leu Thr Gln Val
385                 390                 395                 400

Pro Pro Gly Gly Lys Asp Gly Leu Arg Pro Asp Gly Thr Ala Trp Arg
                405                 410                 415

His Glu Gly Asn Tyr Pro Gly Tyr Ser Phe Pro Ala Phe Lys Asn Ala
            420                 425                 430

Ser Gln Leu Ile Tyr Leu Leu Arg Asp Thr Pro Phe Ser Val Gly Glu
        435                 440                 445

Ser Gly Trp Asn Asn Leu Lys Lys Ala Met Val Ser Ala Trp Ile Tyr
    450                 455                 460

Ser Asn Pro Glu Val Gly Leu Pro Leu Ala Gly Arg His Pro Phe Asn
465                 470                 475                 480

Ser Pro Ser Leu Lys Ser Val Ala Gln Gly Tyr Tyr Trp Leu Ala Met
                485                 490                 495

Ser Ala Lys Ser Ser Pro Asp Lys Thr Leu Ala Ser Ile Tyr Leu Ala
            500                 505                 510

Ile Ser Asp Lys Thr Gln Asn Glu Ser Thr Ala Ile Phe Gly Glu Thr
        515                 520                 525

Ile Thr Pro Ala Ser Leu Pro Gln Gly Phe Tyr Ala Phe Asn Gly Gly
    530                 535                 540

Ala Phe Gly Ile His Arg Trp Gln Asp Lys Met Val Thr Leu Lys Ala
545                 550                 555                 560

Tyr Asn Thr Asn Val Trp Ser Ser Glu Ile Tyr Asn Lys Asp Asn Arg
                565                 570                 575

Tyr Gly Arg Tyr Gln Ser His Gly Val Ala Gln Ile Val Ser Asn Gly
            580                 585                 590

Ser Gln Leu Ser Gln Gly Tyr Gln Gln Glu Gly Trp Asp Trp Asn Arg
        595                 600                 605

Met Glu Gly Ala Thr Thr Ile His Leu Pro Leu Lys Asp Leu Asp Ser
    610                 615                 620

Pro Lys Pro His Thr Leu Met Gln Arg Gly Glu Arg Gly Phe Ser Gly
625                 630                 635                 640

Thr Ser Ser Leu Glu Gly Gln Tyr Gly Met Met Ala Phe Asn Leu Ile
                645                 650                 655

Tyr Pro Ala Asn Leu Glu Arg Phe Asp Pro Asn Phe Thr Ala Lys Lys
            660                 665                 670

Ser Val Leu Ala Ala Asp Asn His Leu Ile Phe Ile Gly Ser Asn Ile
        675                 680                 685

Asn Ser Ser Asp Lys Asn Lys Asn Val Glu Thr Thr Leu Phe Gln His
```

Ala Ile Thr Pro Thr Leu Asn Thr Leu Trp Ile Asn Gly Gln Lys Ile
705                 710                 715                 720

Glu Asn Met Pro Tyr Gln Thr Thr Leu Gln Gln Gly Asp Trp Leu Ile
            725                 730                 735

Asp Ser Asn Gly Asn Gly Tyr Leu Ile Thr Gln Ala Glu Lys Val Asn
        740                 745                 750

Val Ser Arg Gln His Gln Val Ser Ala Glu Asn Lys Asn Arg Gln Pro
    755                 760                 765

Thr Glu Gly Asn Phe Ser Ser Ala Trp Ile Asp His Ser Thr Arg Pro
770                 775                 780

Lys Asp Ala Ser Tyr Glu Tyr Met Val Phe Leu Asp Ala Thr Pro Glu
785                 790                 795                 800

Lys Met Gly Glu Met Ala Gln Lys Phe Arg Glu Asn Asn Gly Leu Tyr
                805                 810                 815

Gln Val Leu Arg Lys Asp Lys Asp Val His Ile Ile Leu Asp Lys Leu
            820                 825                 830

Ser Asn Val Thr Gly Tyr Ala Phe Tyr Gln Pro Ala Ser Ile Glu Asp
        835                 840                 845

Lys Trp Ile Lys Lys Val Asn Lys Pro Ala
    850                 855

<210> SEQ ID NO 84
<211> LENGTH: 2976
<212> TYPE: DNA
<213> ORGANISM: Artificial
<220> FEATURE:
<223> OTHER INFORMATION: Synthetic polynucleotide, TAT-Chondroitinase
      ABCI N(delta)20 Nucleic Acid

<400> SEQUENCE: 84
ggtcgtaaaa agcgtcgtca acgtcgtcgt cctcctcaat gcgcacaaaa taacccatta      60
gcagacttct catcagataa aaactcaata ctaacgttat ctgataaacg tagcattatg     120
ggaaaccaat ctcttttatg gaaatggaaa ggtggtagta gctttacttt acataaaaaa     180
ctgattgtcc ccaccgataa agaagcatct aaagcatggg gacgctcatc caccccgtt      240
ttctcatttt ggctttacaa tgaaaaaccg attgatggtt atcttactat cgatttcgga     300
gaaaaactca tttcaaccag tgaggctcag gcaggcttta agtaaaaatt agatttcact     360
ggctggcgta ctgtgggagt ctctttaaat aacgatcttg aaaatcgaga tgaccttaa     420
aatgcaacca atacctcctc tgatggtact caagacagca ttgggcgttc tttaggtgct     480
aaagtcgata gtattcgttt taaagcgcct tctaatgtga gtcagggtga atctatatc     540
gaccgtatta tgttttctgt cgatgatgct cgctaccaat ggtctgatta tcaagtaaaa     600
actcgcttat cagaacctga aattcaattt cacaacgtaa agccacaact acctgtaaca     660
cctgaaaatt tagcggccat tgatcttatt cgccaacgtc taattaatga atttgtcgga     720
ggtgaaaaag acaaaacct cgcattagaa gagaatatca gcaaattaaa aagtgatttc     780
gatgctctta atactcacac tttagcaaat ggtggaacgc aaggcagaca tctgatcact     840
gataaacaaa tcattattta tcaaccagag aatcttaact ctcaagataa acaactattt     900
gataattatg ttattttagg taattacacg acattaatgt ttaatattag ccgtgcttat     960
gtgctggaaa agatcccac acaaaaggcg caactaaagc agatgtactt attaatgaca    1020
aagcatttat tagatcaagg ctttgttaaa gggagtgctt tagtgacaac ccatcactgg    1080

```
ggatacagtt ctcgttggtg gtatatttcc acgttattaa tgtctgatgc actaaaagaa    1140
gcgaacctac aaactcaagt ttatgattca ttactgtggt attcacgtga gtttaaaagt    1200
agttttgata tgaaagtaag tgctgatagc tctgatctag attatttcaa taccttatct    1260
cgccaacatt tagccttatt actactagag cctgatgatc aaaagcgtat caacttagtt    1320
aatactttca gccattatat cactggcgca ttaacgcaag tgccaccggg tggtaaagat    1380
ggtttacgcc ctgatggtac agcatggcga catgaaggca actatccggg ctactctttc    1440
ccagccttta aaaatgcctc tcagcttatt tatttattac gcgatacacc attttcagtg    1500
ggtgaaagtg gttggaatag cctgaaaaaa gcgatggttt cagcgtggat ctacagtaat    1560
ccagaagttg gattaccgct tgcaggaaga caccctctta actcaccttc gttaaaatca    1620
gtcgctcaag gctattactg gcttgccatg tctgcaaaat catcgcctga taaaacactt    1680
gcatctattt atcttgcgat tagtgataaa acacaaaatg aatcaactgc tattttttgga   1740 gaaactatta caccagcgtc tttacctcaa ggtttctatg cctttaatgg cggtgctttt    1800
ggtattcatc gttggcaaga taaaatggtg acactgaaag cttataacac caatgttttgg   1860 tcatctgaaa tttataacaa agataaccgt tatggccgtt accaaagtca tggtgtcgct    1920
caaatagtga gtaatggctc gcagctttca cagggctatc agcaagaagg ttgggattgg    1980
aatagaatgc caggggcaac cactatccac cttcctctta aagacttaga cagtcctaaa    2040
cctcatacct taatgcaacg tggagagcgt ggatttagcg aacatcatc ccttgaaggt     2100 caatatggca tgatggcatt cgatcttatt tatcccgcca atcttgagcg ttttgatcct    2160
aatttcactg cgaaaaagag tgtattagcc gctgataatc acttaatttt tattggtagc    2220
aatataaata gtagtgataa aaataaaaat gttgaaacga ccttattcca acatgccatt    2280
actccaacat taaatacccct ttggattaat ggacaaaaga tagaaaacat gccttatcaa   2340
acaacacttc aacaaggtga ttggttaatt gatagcaatg gcaatggtta cttaattact    2400
caagcagaaa aagtaaatgt aagtcgccaa catcaggttt cagcggaaaa taaaaatcgc    2460
caaccgacag aaggaaactt tagctcggca tggatcgatc acagcactcg ccccaaagat    2520 gccagtatg agtatatggt cttttttagat gcgacacctg aaaaaatggg agagatggca    2580
caaaaattcc gtgaaaataa tgggttatat caggttcttc gtaaggataa agacgttcat    2640
attattctcg ataaactcag caatgtaacg ggatatgcct tttatcagcc agcatcaatt    2700
gaagacaaat ggatcaaaaa ggttaataaa cctgcaattg tgatgactca tcgacaaaaa    2760
gacactctta ttgtcagtgc agttacacct gatttaaata tgactcgcca aaaagcagca    2820
actcctgtca ccatcaatgt cacgattaat ggcaaatggc aatctgctga taaaaatagt    2880
gaagtgaaat atcaggtttc tggtgataac actgaactga cgtttacgag ttactttggt    2940
attccacaag aaatcaaact ctcgccactc ccttga                              2976
```

<210> SEQ ID NO 85
<211> LENGTH: 991
<212> TYPE: PRT
<213> ORGANISM: Artificial
<220> FEATURE:
<223> OTHER INFORMATION: Synthetic polypeptide, HIV-1 TAT chondroitinase ABCI-N(delta)20 fusion polypeptide

<400> SEQUENCE: 85

Gly Arg Lys Lys Arg Arg Gln Arg Arg Arg Pro Pro Gln Cys Ala Gln
1 5 10 15

Asn Asn Pro Leu Ala Asp Phe Ser Ser Asp Lys Asn Ser Ile Leu Thr

```
                    20                  25                  30
Leu Ser Asp Lys Arg Ser Ile Met Gly Asn Gln Ser Leu Leu Trp Lys
                35                  40                  45

Trp Lys Gly Gly Ser Ser Phe Thr Leu His Lys Lys Leu Ile Val Pro
     50                  55                  60

Thr Asp Lys Glu Ala Ser Lys Ala Trp Gly Arg Ser Ser Thr Pro Val
 65                  70                  75                  80

Phe Ser Phe Trp Leu Tyr Asn Glu Lys Pro Ile Asp Gly Tyr Leu Thr
                 85                  90                  95

Ile Asp Phe Gly Glu Lys Leu Ile Ser Thr Ser Glu Ala Gln Ala Gly
                100                 105                 110

Phe Lys Val Lys Leu Asp Phe Thr Gly Trp Arg Thr Val Gly Val Ser
                115                 120                 125

Leu Asn Asn Asp Leu Glu Asn Arg Glu Met Thr Leu Asn Ala Thr Asn
                130                 135                 140

Thr Ser Ser Asp Gly Thr Gln Asp Ser Ile Gly Arg Ser Leu Gly Ala
145                 150                 155                 160

Lys Val Asp Ser Ile Arg Phe Lys Ala Pro Ser Asn Val Ser Gln Gly
                165                 170                 175

Glu Ile Tyr Ile Asp Arg Ile Met Phe Ser Val Asp Ala Arg Tyr
                180                 185                 190

Gln Trp Ser Asp Tyr Gln Val Lys Thr Arg Leu Ser Glu Pro Glu Ile
                195                 200                 205

Gln Phe His Asn Val Lys Pro Gln Leu Pro Val Thr Pro Glu Asn Leu
                210                 215                 220

Ala Ala Ile Asp Leu Ile Arg Gln Arg Leu Ile Asn Glu Phe Val Gly
225                 230                 235                 240

Gly Glu Lys Glu Thr Asn Leu Ala Leu Glu Glu Asn Ile Ser Lys Leu
                245                 250                 255

Lys Ser Asp Phe Asp Ala Leu Asn Thr His Thr Leu Ala Asn Gly Gly
                260                 265                 270

Thr Gln Gly Arg His Leu Ile Thr Asp Lys Gln Ile Ile Ile Tyr Gln
                275                 280                 285

Pro Glu Asn Leu Asn Ser Gln Asp Lys Gln Leu Phe Asp Asn Tyr Val
                290                 295                 300

Ile Leu Gly Asn Tyr Thr Thr Leu Met Phe Asn Ile Ser Arg Ala Tyr
305                 310                 315                 320

Val Leu Glu Lys Asp Pro Thr Gln Lys Ala Gln Leu Lys Gln Met Tyr
                325                 330                 335

Leu Leu Met Thr Lys His Leu Leu Asp Gln Gly Phe Val Lys Gly Ser
                340                 345                 350

Ala Leu Val Thr Thr His His Trp Gly Tyr Ser Ser Arg Trp Trp Tyr
                355                 360                 365

Ile Ser Thr Leu Leu Met Ser Asp Ala Leu Lys Glu Ala Asn Leu Gln
                370                 375                 380

Thr Gln Val Tyr Asp Ser Leu Trp Tyr Ser Arg Glu Phe Lys Ser
385                 390                 395                 400

Ser Phe Asp Met Lys Val Ser Ala Asp Ser Ser Asp Leu Asp Tyr Phe
                405                 410                 415

Asn Thr Leu Ser Arg Gln His Leu Ala Leu Leu Leu Glu Pro Asp
                420                 425                 430

Asp Gln Lys Arg Ile Asn Leu Val Asn Thr Phe Ser His Tyr Ile Thr
                435                 440                 445
```

```
Gly Ala Leu Thr Gln Val Pro Pro Gly Lys Asp Gly Leu Arg Pro
    450                 455                 460

Asp Gly Thr Ala Trp Arg His Glu Gly Asn Tyr Pro Gly Tyr Ser Phe
465                 470                 475                 480

Pro Ala Phe Lys Asn Ala Ser Gln Leu Ile Tyr Leu Leu Arg Asp Thr
                485                 490                 495

Pro Phe Ser Val Gly Glu Ser Gly Trp Asn Ser Leu Lys Lys Ala Met
                500                 505                 510

Val Ser Ala Trp Ile Tyr Ser Asn Pro Glu Val Gly Leu Pro Leu Ala
            515                 520                 525

Gly Arg His Pro Leu Asn Ser Pro Ser Leu Lys Ser Val Ala Gln Gly
    530                 535                 540

Tyr Tyr Trp Leu Ala Met Ser Ala Lys Ser Ser Pro Asp Lys Thr Leu
545                 550                 555                 560

Ala Ser Ile Tyr Leu Ala Ile Ser Asp Lys Thr Gln Asn Glu Ser Thr
                565                 570                 575

Ala Ile Phe Gly Glu Thr Ile Thr Pro Ala Ser Leu Pro Gln Gly Phe
                580                 585                 590

Tyr Ala Phe Asn Gly Gly Ala Phe Gly Ile His Arg Trp Gln Asp Lys
            595                 600                 605

Met Val Thr Leu Lys Ala Tyr Asn Thr Asn Val Trp Ser Ser Glu Ile
    610                 615                 620

Tyr Asn Lys Asp Asn Arg Tyr Gly Arg Tyr Gln Ser His Gly Val Ala
625                 630                 635                 640

Gln Ile Val Ser Asn Gly Ser Gln Leu Ser Gln Gly Tyr Gln Gln Glu
                645                 650                 655

Gly Trp Asp Trp Asn Arg Met Pro Gly Ala Thr Thr Ile His Leu Pro
                660                 665                 670

Leu Lys Asp Leu Asp Ser Pro Lys Pro His Thr Leu Met Gln Arg Gly
            675                 680                 685

Glu Arg Gly Phe Ser Gly Thr Ser Ser Leu Glu Gly Gln Tyr Gly Met
    690                 695                 700

Met Ala Phe Asp Leu Ile Tyr Pro Ala Asn Leu Glu Arg Phe Asp Pro
705                 710                 715                 720

Asn Phe Thr Ala Lys Lys Ser Val Leu Ala Ala Asp Asn His Leu Ile
                725                 730                 735

Phe Ile Gly Ser Asn Ile Asn Ser Ser Asp Lys Asn Lys Asn Val Glu
                740                 745                 750

Thr Thr Leu Phe Gln His Ala Ile Thr Pro Thr Leu Asn Thr Leu Trp
            755                 760                 765

Ile Asn Gly Gln Lys Ile Glu Asn Met Pro Tyr Gln Thr Thr Leu Gln
    770                 775                 780

Gln Gly Asp Trp Leu Ile Asp Ser Asn Gly Asn Gly Tyr Leu Ile Thr
785                 790                 795                 800

Gln Ala Glu Lys Val Asn Val Ser Arg Gln His Gln Val Ser Ala Glu
                805                 810                 815

Asn Lys Asn Arg Gln Pro Thr Glu Gly Asn Phe Ser Ser Ala Trp Ile
                820                 825                 830

Asp His Ser Thr Arg Pro Lys Asp Ala Ser Tyr Glu Tyr Met Val Phe
            835                 840                 845

Leu Asp Ala Thr Pro Glu Lys Met Gly Glu Met Ala Gln Lys Phe Arg
    850                 855                 860
```

```
Glu Asn Asn Gly Leu Tyr Gln Val Leu Arg Lys Asp Lys Asp Val His
865                 870                 875                 880

Ile Ile Leu Asp Lys Leu Ser Asn Val Thr Gly Tyr Ala Phe Tyr Gln
                885                 890                 895

Pro Ala Ser Ile Glu Asp Lys Trp Ile Lys Lys Val Asn Lys Pro Ala
            900                 905                 910

Ile Val Met Thr His Arg Gln Lys Asp Thr Leu Ile Val Ser Ala Val
        915                 920                 925

Thr Pro Asp Leu Asn Met Thr Arg Gln Lys Ala Ala Thr Pro Val Thr
    930                 935                 940

Ile Asn Val Thr Ile Asn Gly Lys Trp Gln Ser Ala Asp Lys Asn Ser
945                 950                 955                 960

Glu Val Lys Tyr Gln Val Ser Gly Asp Asn Thr Glu Leu Thr Phe Thr
                965                 970                 975

Ser Tyr Phe Gly Ile Pro Gln Glu Ile Lys Leu Ser Pro Leu Pro
            980                 985                 990

<210> SEQ ID NO 86
<211> LENGTH: 2856
<212> TYPE: DNA
<213> ORGANISM: Artificial
<220> FEATURE:
<223> OTHER INFORMATION: Synthetic polynucleotide, HIV-1
      TAT-Chondroitinase ABCI N(delta)60 Nucleic Acid

<400> SEQUENCE: 86
```

| | | | | | |
|---|---|---|---|---|---|
| ggtcgtaaaa | agcgtcgtca | acgtcgtcgt | cctcctcaat | gctttacttt | acataaaaaa | 60 |
| ctgattgtcc | ccaccgataa | agaagcatct | aaagcatggg | gacgctcatc | cacccccgtt | 120 |
| ttctcatttt | ggctttacaa | tgaaaaaccg | attgatggtt | atcttactat | cgatttcgga | 180 |
| gaaaaactca | tttcaaccag | tgaggctcag | gcaggcttta | aagtaaaatt | agatttcact | 240 |
| ggctggcgta | ctgtgggagt | ctctttaaat | aacgatcttg | aaaatcgaga | gatgacctta | 300 |
| aatgcaacca | ataccctcctc | tgatggtact | caagacagca | ttgggcgttc | tttaggtgct | 360 |
| aaagtcgata | gtattcgttt | taaagcgcct | tctaatgtga | gtcagggtga | aatctatatc | 420 |
| gaccgtatta | tgttttctgt | cgatgatgct | cgctaccaat | ggtctgatta | tcaagtaaaa | 480 |
| actcgcttat | cagaacctga | aattcaattt | cacaacgtaa | agccacaact | acctgtaaca | 540 |
| cctgaaaatt | tagcggccat | tgatcttatt | cgccaacgtc | taattaatga | atttgtcgga | 600 |
| ggtgaaaaag | agacaaacct | cgcattagaa | gagaatatca | gcaaattaaa | aagtgatttc | 660 |
| gatgctctta | atactcacac | tttagcaaat | ggtggaacgc | aaggcagaca | tctgatcact | 720 |
| gataaacaaa | tcattattta | tcaaccagag | aatcttaact | ctcaagataa | acaactattt | 780 |
| gataattatg | ttattttagg | taattacacg | acattaatgt | ttaatattag | ccgtgcttat | 840 |
| gtgctggaaa | aagatcccac | acaaaaggcg | caactaaagc | agatgtactt | attaatgaca | 900 |
| aagcatttat | tagatcaagg | cttgttaaa | gggagtgctt | tagtgacaac | ccatcactgg | 960 |
| ggatacagtt | ctcgttggtg | gtatatttcc | acgttattaa | tgtctgatgc | actaaaagaa | 1020 |
| gcgaacctac | aaactcaagt | ttatgattca | ttactgtggt | attcacgtga | gtttaaaagt | 1080 |
| agttttgata | tgaaagtaag | tgctgatagc | tctgatctag | attatttcaa | taccttatct | 1140 |
| cgccaacatt | tagccttatt | actactagag | cctgatgatc | aaaagcgtat | caacttagtt | 1200 |
| aatactttca | gccattatat | cactggcgca | ttaacgcaag | tgccaccggg | tggtaaagat | 1260 |
| ggtttacgcc | ctgatggtac | agcatggcga | catgaaggca | actatccggg | ctactctttc | 1320 |

```
ccagccttta aaaatgcctc tcagcttatt tatttattac gcgatacacc attttcagtg   1380
ggtgaaagtg gttggaatag cctgaaaaaa gcgatggttt cagcgtggat ctacagtaat   1440
ccagaagttg gattaccgct tgcaggaaga caccctctta actcaccttc gttaaaatca   1500
gtcgctcaag gctattactg gcttgccatg tctgcaaaat catcgcctga taaaacactt   1560
gcatctattt atcttgcgat tagtgataaa acacaaaatg aatcaactgc tatttttgga   1620
gaaactatta caccagcgtc tttacctcaa ggtttctatg cctttaatgg cggtgctttt   1680
ggtattcatc gttggcaaga taaaatggtg acactgaaag cttataacac caatgtttgg   1740
tcatctgaaa tttataacaa agataaccgt tatggccgtt accaaagtca tggtgtcgct   1800
caaatagtga gtaatggctc gcagctttca cagggctatc agcaagaagg ttgggattgg   1860
aatagaatgc caggggcaac cactatccac cttcctctta aagacttaga cagtcctaaa   1920
cctcatacct taatgcaacg tggagagcgt ggatttagcg gaacatcatc ccttgaaggt   1980
caatatggca tgatggcatt cgatcttatt tatcccgcca atcttgagcg ttttgatcct   2040
aatttcactg cgaaaaagag tgtattagcc gctgataatc acttaatttt tattggtagc   2100
aatataaata gtagtgataa aaataaaaat gttgaaacga ccttattcca acatgccatt   2160
actccaacat taaataccct ttggattaat ggacaaaaga tagaaaacat gccttatcaa   2220
acaacacttc aacaaggtga ttggttaatt gatagcaatg gcaatggtta cttaattact   2280
caagcagaaa aagtaaatgt aagtcgccaa catcaggttt cagcggaaaa taaaaatcgc   2340
caaccgacag aaggaaactt tagctcggca tggatcgatc acagcactcg ccccaaagat   2400
gccagttatg agtatatggt ctttttagat gcgacacctg aaaaaatggg agagatggca   2460
caaaaattcc gtgaaaataa tgggttatat caggttcttc gtaaggataa agacgttcat   2520
attattctcg ataaactcag caatgtaacg ggatatgcct tttatcagcc agcatcaatt   2580
gaagacaaat ggatcaaaaa ggttaataaa cctgcaattg tgatgactca tcgacaaaaa   2640
gacactctta ttgtcagtgc agttacacct gatttaaata tgactcgcca aaaagcagca   2700
actcctgtca ccatcaatgt cacgattaat ggcaaatggc aatctgctga taaaaatagt   2760
gaagtgaaat atcaggtttc tggtgataac actgaactga cgtttacgag ttactttggt   2820
attccacaag aaatcaaact ctcgccactc ccttga                             2856
```

```

<210> SEQ ID NO 87
<211> LENGTH: 951
<212> TYPE: PRT
<213> ORGANISM: Artificial
<220> FEATURE:
<223> OTHER INFORMATION: Synthetic polypeptide, HIV-1 TAT chondroitinase
      ABCI-N(delta)60 fusion polypeptide

<400> SEQUENCE: 87

Gly Arg Lys Lys Arg Arg Gln Arg Arg Arg Pro Pro Gln Cys Phe Thr
1               5                   10                  15

Leu His Lys Lys Leu Ile Val Pro Thr Asp Lys Glu Ala Ser Lys Ala
            20                  25                  30

Trp Gly Arg Ser Ser Thr Pro Val Phe Ser Phe Trp Leu Tyr Asn Glu
        35                  40                  45

Lys Pro Ile Asp Gly Tyr Leu Thr Ile Asp Phe Gly Glu Lys Leu Ile
    50                  55                  60

Ser Thr Ser Glu Ala Gln Ala Gly Phe Lys Val Lys Leu Asp Phe Thr
65                  70                  75                  80

Gly Trp Arg Thr Val Gly Val Ser Leu Asn Asn Asp Leu Glu Asn Arg
```

```
                    85                  90                  95
Glu Met Thr Leu Asn Ala Thr Asn Thr Ser Ser Asp Gly Thr Gln Asp
                100                 105                 110
Ser Ile Gly Arg Ser Leu Gly Ala Lys Val Asp Ser Ile Arg Phe Lys
                115                 120                 125
Ala Pro Ser Asn Val Ser Gln Gly Glu Ile Tyr Ile Asp Arg Ile Met
            130                 135                 140
Phe Ser Val Asp Asp Ala Arg Tyr Gln Trp Ser Asp Tyr Gln Val Lys
145                 150                 155                 160
Thr Arg Leu Ser Glu Pro Glu Ile Gln Phe His Asn Val Lys Pro Gln
                165                 170                 175
Leu Pro Val Thr Pro Glu Asn Leu Ala Ala Ile Asp Leu Ile Arg Gln
            180                 185                 190
Arg Leu Ile Asn Glu Phe Val Gly Gly Lys Glu Thr Asn Leu Ala
                195                 200                 205
Leu Glu Glu Asn Ile Ser Lys Leu Lys Ser Asp Phe Asp Ala Leu Asn
            210                 215                 220
Thr His Thr Leu Ala Asn Gly Gly Thr Gln Gly Arg His Leu Ile Thr
225                 230                 235                 240
Asp Lys Gln Ile Ile Tyr Gln Pro Glu Asn Leu Asn Ser Gln Asp
                    245                 250                 255
Lys Gln Leu Phe Asp Asn Tyr Val Ile Leu Gly Asn Tyr Thr Thr Leu
                260                 265                 270
Met Phe Asn Ile Ser Arg Ala Tyr Val Leu Glu Lys Asp Pro Thr Gln
            275                 280                 285
Lys Ala Gln Leu Lys Gln Met Tyr Leu Leu Met Thr Lys His Leu Leu
            290                 295                 300
Asp Gln Gly Phe Val Lys Gly Ser Ala Leu Val Thr Thr His His Trp
305                 310                 315                 320
Gly Tyr Ser Ser Arg Trp Trp Tyr Ile Ser Thr Leu Leu Met Ser Asp
                325                 330                 335
Ala Leu Lys Glu Ala Asn Leu Gln Thr Gln Val Tyr Asp Ser Leu Leu
            340                 345                 350
Trp Tyr Ser Arg Glu Phe Lys Ser Ser Phe Asp Met Lys Val Ser Ala
            355                 360                 365
Asp Ser Asp Leu Asp Tyr Phe Asn Thr Leu Ser Arg Gln His Leu
            370                 375                 380
Ala Leu Leu Leu Leu Glu Pro Asp Asp Gln Lys Arg Ile Asn Leu Val
385                 390                 395                 400
Asn Thr Phe Ser His Tyr Ile Thr Gly Ala Leu Thr Gln Val Pro Pro
                405                 410                 415
Gly Gly Lys Asp Gly Leu Arg Pro Asp Gly Thr Ala Trp Arg His Glu
            420                 425                 430
Gly Asn Tyr Pro Gly Tyr Ser Phe Pro Ala Phe Lys Asn Ala Ser Gln
            435                 440                 445
Leu Ile Tyr Leu Leu Arg Asp Thr Pro Phe Ser Val Gly Glu Ser Gly
            450                 455                 460
Trp Asn Ser Leu Lys Lys Ala Met Val Ser Ala Trp Ile Tyr Ser Asn
465                 470                 475                 480
Pro Glu Val Gly Leu Pro Leu Ala Gly Arg His Pro Leu Asn Ser Pro
                485                 490                 495
Ser Leu Lys Ser Val Ala Gln Gly Tyr Tyr Trp Leu Ala Met Ser Ala
                500                 505                 510
```

-continued

```
Lys Ser Ser Pro Asp Lys Thr Leu Ala Ser Ile Tyr Leu Ala Ile Ser
    515                 520                 525

Asp Lys Thr Gln Asn Glu Ser Thr Ala Ile Phe Gly Glu Thr Ile Thr
    530                 535                 540

Pro Ala Ser Leu Pro Gln Gly Phe Tyr Ala Phe Asn Gly Gly Ala Phe
545                 550                 555                 560

Gly Ile His Arg Trp Gln Asp Lys Met Val Thr Leu Lys Ala Tyr Asn
                565                 570                 575

Thr Asn Val Trp Ser Ser Glu Ile Tyr Asn Lys Asp Asn Arg Tyr Gly
                580                 585                 590

Arg Tyr Gln Ser His Gly Val Ala Gln Ile Val Ser Asn Gly Ser Gln
    595                 600                 605

Leu Ser Gln Gly Tyr Gln Gln Glu Gly Trp Asp Trp Asn Arg Met Pro
    610                 615                 620

Gly Ala Thr Thr Ile His Leu Pro Leu Lys Asp Leu Asp Ser Pro Lys
625                 630                 635                 640

Pro His Thr Leu Met Gln Arg Gly Glu Arg Gly Phe Ser Gly Thr Ser
                645                 650                 655

Ser Leu Glu Gly Gln Tyr Gly Met Met Ala Phe Asp Leu Ile Tyr Pro
                660                 665                 670

Ala Asn Leu Glu Arg Phe Asp Pro Asn Phe Thr Ala Lys Lys Ser Val
    675                 680                 685

Leu Ala Ala Asp Asn His Leu Ile Phe Ile Gly Ser Asn Ile Asn Ser
    690                 695                 700

Ser Asp Lys Asn Lys Asn Val Glu Thr Thr Leu Phe Gln His Ala Ile
705                 710                 715                 720

Thr Pro Thr Leu Asn Thr Leu Trp Ile Asn Gly Gln Lys Ile Glu Asn
                725                 730                 735

Met Pro Tyr Gln Thr Thr Leu Gln Gln Gly Asp Trp Leu Ile Asp Ser
                740                 745                 750

Asn Gly Asn Gly Tyr Leu Ile Thr Gln Ala Glu Lys Val Asn Val Ser
    755                 760                 765

Arg Gln His Gln Val Ser Ala Glu Asn Lys Asn Arg Gln Pro Thr Glu
    770                 775                 780

Gly Asn Phe Ser Ser Ala Trp Ile Asp His Ser Thr Arg Pro Lys Asp
785                 790                 795                 800

Ala Ser Tyr Glu Tyr Met Val Phe Leu Asp Ala Thr Pro Glu Lys Met
                805                 810                 815

Gly Glu Met Ala Gln Lys Phe Arg Glu Asn Asn Gly Leu Tyr Gln Val
                820                 825                 830

Leu Arg Lys Asp Lys Asp Val His Ile Ile Leu Asp Lys Leu Ser Asn
    835                 840                 845

Val Thr Gly Tyr Ala Phe Tyr Gln Pro Ala Ser Ile Glu Asp Lys Trp
    850                 855                 860

Ile Lys Lys Val Asn Lys Pro Ala Ile Val Met Thr His Arg Gln Lys
865                 870                 875                 880

Asp Thr Leu Ile Val Ser Ala Val Thr Pro Asp Leu Asn Met Thr Arg
                885                 890                 895

Gln Lys Ala Ala Thr Pro Val Thr Ile Asn Val Thr Ile Asn Gly Lys
                900                 905                 910

Trp Gln Ser Ala Asp Lys Asn Ser Glu Val Lys Tyr Gln Val Ser Gly
    915                 920                 925
```

Asp Asn Thr Glu Leu Thr Phe Thr Ser Tyr Phe Gly Ile Pro Gln Glu
            930                 935                 940

Ile Lys Leu Ser Pro Leu Pro
945                 950

<210> SEQ ID NO 88
<211> LENGTH: 3036
<212> TYPE: DNA
<213> ORGANISM: Artificial
<220> FEATURE:
<223> OTHER INFORMATION: Synthetic polynucleotide, C terminal HIV-1
      TAT-Chondroitinase ABCI Nucleic acid

<400> SEQUENCE: 88

| | | | | | |
|---|---|---|---|---|---|
| gccaccagca | atcctgcatt | tgatcctaaa | aatctgatgc | agtcagaaat | ttaccatttt | 60 |
| gcacaaaata | acccattagc | agacttctca | tcagataaaa | actcaatact | aacgttatct | 120 |
| gataaacgta | gcattatggg | aaaccaatct | cttttatgga | aatggaaagg | tggtagtagc | 180 |
| tttactttac | ataaaaaact | gattgtcccc | accgataaag | aagcatctaa | agcatgggga | 240 |
| cgctcatcca | ccccgttttt | ctcatttggg | ctttacaatg | aaaaaccgat | tgatggttat | 300 |
| cttactatcg | atttcggaga | aaaactcatt | tcaaccagtg | aggctcaggc | aggctttaaa | 360 |
| gtaaaattag | atttcactgg | ctggcgtact | gtgggagtct | ctttaaataa | cgatcttgaa | 420 |
| aatcgagaga | tgaccttaaa | tgcaaccaat | acctcctctg | atggtactca | agacagcatt | 480 |
| gggcgttctt | taggtgctaa | agtcgatagt | attcgtttta | aagcgccttc | taatgtgagt | 540 |
| cagggtgaaa | tctatatcga | ccgtattatg | ttttctgtcg | atgatgctcg | ctaccaatgg | 600 |
| tctgattatc | aagtaaaaac | tcgcttatca | gaacctgaaa | ttcaatttca | caacgtaaag | 660 |
| ccacaactac | ctgtaacacc | tgaaaattta | gcggccattg | atcttattcg | ccaacgtcta | 720 |
| attaatgaat | tgtcggagg | tgaaaagag | acaaacctcg | cattagaaga | gaatatcagc | 780 |
| aaattaaaaa | gtgatttcga | tgctcttaat | actcacactt | tagcaaatgg | tggaacgcaa | 840 |
| ggcagacatc | tgatcactga | taaacaaatc | attatttatc | aaccagagaa | tcttaactct | 900 |
| caagataaac | aactatttga | taattatgtt | attttaggta | attacacgac | attaatgttt | 960 |
| aatattagcc | gtgcttatgt | gctggaaaaa | gatcccacac | aaaaggcgca | actaaagcag | 1020 |
| atgtacttat | taatgacaaa | gcatttatta | gatcaaggct | ttgttaaagg | gagtgctta | 1080 |
| gtgacaaccc | atcactgggg | atacagttct | cgttggtggt | atatttccac | gttattaatg | 1140 |
| tctgatgcac | taaagaagc | gaacctacaa | actcaagttt | atgattcatt | actgtggtat | 1200 |
| tcacgtgagt | ttaaaagtag | ttttgatatg | aaagtaagtg | ctgatagctc | tgatctagat | 1260 |
| tatttcaata | ccttatctcg | ccaacattta | gccttattac | tactagagcc | tgatgatcaa | 1320 |
| aagcgtatca | acttagttaa | tactttcagc | cattatatca | ctggcgcatt | aacgcaagtg | 1380 |
| ccaccgggtg | gtaaagatgg | tttacgccct | gatggtacag | catggcgaca | tgaaggcaac | 1440 |
| tatccgggct | actctttccc | agcctttaaa | aatgcctctc | agcttatta | tttattacgc | 1500 |
| gatacaccat | tttcagtggg | tgaaagtggt | tggaatagcc | tgaaaaaagc | gatggtttca | 1560 |
| gcgtggatct | acagtaatcc | agaagttgga | ttaccgcttg | caggaagaca | ccctcttaac | 1620 |
| tcaccttcgt | taaaatcagt | cgctcaaggc | tattactggg | ttgccatgtc | tgcaaaatca | 1680 |
| tcgcctgata | aaacacttgc | atctatttat | cttgcgatta | gtgataaaac | acaaatgaa | 1740 |
| tcaactgcta | tttttggaga | aactattaca | ccagcgtctt | tacctcaagg | tttctatgcc | 1800 |
| tttaatggcg | gtgcttttgg | tattcatcgt | tggcaagata | aatggtgac | actgaaagct | 1860 |

```
tataacacca atgtttggtc atctgaaatt tataacaaag ataaccgtta tggccgttac    1920
caaagtcatg gtgtcgctca aatagtgagt aatggctcgc agctttcaca gggctatcag    1980
caagaaggtt gggattggaa tagaatgcca ggggcaacca ctatccacct tcctcttaaa    2040
gacttagaca gtcctaaacc tcatacctta atgcaacgtg gagagcgtgg atttagcgga    2100
acatcatccc ttgaaggtca atatggcatg atggcattcg atcttattta tcccgccaat    2160
cttgagcgtt ttgatcctaa tttcactgcg aaaagagtg tattagccgc tgataatcac    2220 ttaatttta ttggtagcaa tataaatagt agtgataaaa ataaaaatgt tgaaacgacc    2280
ttattccaac atgccattac tccaacatta aatacccttt ggattaatgg acaaaagata    2340 gaaacatgc cttatcaaac aacacttcaa caaggtgatt ggttaattga tagcaatggc    2400
aatggttact aattactca agcagaaaaa gtaaatgtaa gtcgccaaca tcaggtttca    2460
gcggaaaata aaaatcgcca accgacagaa ggaaacttta gctcggcatg gatcgatcac    2520
agcactcgcc ccaaagatgc cagttatgag tatatggtct ttttagatgc gacacctgaa    2580
aaaatgggag agatggcaca aaaattccgt gaaaataatg ggttatatca ggttcttcgt    2640
aaggataaag acgttcatat tattctcgat aaactcagca atgtaacggg atatgccttt    2700
tatcagccag catcaattga agacaaatgg atcaaaaagg ttaataaacc tgcaattgtg    2760
atgactcatc gacaaaaaga cactcttatt gtcagtgcag ttacacctga tttaaatatg    2820
actcgccaaa aagcagcaac tcctgtcacc atcaatgtca cgattaatgg caaatggcaa    2880
tctgctgata aaatagtga agtgaaatat caggtttctg gtgataacac tgaactgacg    2940
tttacgagtt actttggtat tccacaagaa atcaaactct cgccactccc tggtcgtaaa    3000
aagcgtcgtc aacgtcgtcg tcctcctcaa tgctag                             3036
```

<210> SEQ ID NO 89
<211> LENGTH: 1011
<212> TYPE: PRT
<213> ORGANISM: Artificial
<220> FEATURE:
<223> OTHER INFORMATION: Synthetic polypeptide, C terminal HIV-1
      TAT-Chondroitinase ABCI

<400> SEQUENCE: 89

```
Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
                20                  25                  30

Lys Asn Ser Ile Leu Thr Leu Ser Asp Lys Arg Ser Ile Met Gly Asn
            35                  40                  45

Gln Ser Leu Leu Trp Lys Trp Lys Gly Gly Ser Ser Phe Thr Leu His
        50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95

Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Thr Val Gly Val Ser Leu Asn Asn Asp Leu Glu Asn Arg Glu Met
    130                 135                 140

Thr Leu Asn Ala Thr Asn Thr Ser Ser Asp Gly Thr Gln Asp Ser Ile
```

```
            145                 150                 155                 160
Gly Arg Ser Leu Gly Ala Lys Val Asp Ser Ile Arg Phe Lys Ala Pro
                    165                 170                 175

Ser Asn Val Ser Gln Gly Glu Ile Tyr Ile Asp Arg Ile Met Phe Ser
                    180                 185                 190

Val Asp Ala Arg Tyr Gln Trp Ser Asp Tyr Gln Val Lys Thr Arg
                    195                 200                 205

Leu Ser Glu Pro Glu Ile Gln Phe His Asn Val Lys Pro Gln Leu Pro
        210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Glu
                    245                 250                 255

Glu Asn Ile Ser Lys Leu Lys Ser Asp Phe Asp Ala Leu Asn Thr His
                260                 265                 270

Thr Leu Ala Asn Gly Gly Thr Gln Gly Arg His Leu Ile Thr Asp Lys
                275                 280                 285

Gln Ile Ile Ile Tyr Gln Pro Glu Asn Leu Asn Ser Gln Asp Lys Gln
        290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                    325                 330                 335

Gln Leu Lys Gln Met Tyr Leu Leu Met Thr Lys His Leu Leu Asp Gln
                340                 345                 350

Gly Phe Val Lys Gly Ser Ala Leu Val Thr Thr His His Trp Gly Tyr
                355                 360                 365

Ser Ser Arg Trp Trp Tyr Ile Ser Thr Leu Leu Met Ser Asp Ala Leu
        370                 375                 380

Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
                    405                 410                 415

Ser Asp Leu Asp Tyr Phe Asn Thr Leu Ser Arg Gln His Leu Ala Leu
                420                 425                 430

Leu Leu Leu Glu Pro Asp Asp Gln Lys Arg Ile Asn Leu Val Asn Thr
                435                 440                 445

Phe Ser His Tyr Ile Thr Gly Ala Leu Thr Gln Val Pro Pro Gly Gly
        450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                    485                 490                 495

Tyr Leu Leu Arg Asp Thr Pro Phe Ser Val Gly Glu Ser Gly Trp Asn
                500                 505                 510

Ser Leu Lys Lys Ala Met Val Ser Ala Trp Ile Tyr Ser Asn Pro Glu
        515                 520                 525

Val Gly Leu Pro Leu Ala Gly Arg His Pro Leu Asn Ser Pro Ser Leu
                530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                    565                 570                 575
```

```
Thr Gln Asn Glu Ser Thr Ala Ile Phe Gly Glu Thr Ile Thr Pro Ala
            580                 585                 590
Ser Leu Pro Gln Gly Phe Tyr Ala Phe Asn Gly Ala Phe Gly Ile
        595                 600                 605
His Arg Trp Gln Asp Lys Met Val Thr Leu Lys Ala Tyr Asn Thr Asn
        610                 615                 620
Val Trp Ser Ser Glu Ile Tyr Asn Lys Asp Asn Arg Tyr Gly Arg Tyr
625                 630                 635                 640
Gln Ser His Gly Val Ala Gln Ile Val Ser Asn Gly Ser Gln Leu Ser
            645                 650                 655
Gln Gly Tyr Gln Gln Glu Gly Trp Asp Trp Asn Arg Met Pro Gly Ala
            660                 665                 670
Thr Thr Ile His Leu Pro Leu Lys Asp Leu Asp Ser Pro Lys Pro His
            675                 680                 685
Thr Leu Met Gln Arg Gly Glu Arg Gly Phe Ser Gly Thr Ser Ser Leu
        690                 695                 700
Glu Gly Gln Tyr Gly Met Met Ala Phe Asp Leu Ile Tyr Pro Ala Asn
705                 710                 715                 720
Leu Glu Arg Phe Asp Pro Asn Phe Thr Ala Lys Lys Ser Val Leu Ala
                725                 730                 735
Ala Asp Asn His Leu Ile Phe Ile Gly Ser Asn Ile Asn Ser Ser Asp
            740                 745                 750
Lys Asn Lys Asn Val Glu Thr Thr Leu Phe Gln His Ala Ile Thr Pro
        755                 760                 765
Thr Leu Asn Thr Leu Trp Ile Asn Gly Gln Lys Ile Glu Asn Met Pro
        770                 775                 780
Tyr Gln Thr Thr Leu Gln Gln Gly Asp Trp Leu Ile Asp Ser Asn Gly
785                 790                 795                 800
Asn Gly Tyr Leu Ile Thr Gln Ala Glu Lys Val Asn Val Ser Arg Gln
                805                 810                 815
His Gln Val Ser Ala Glu Asn Lys Asn Arg Gln Pro Thr Glu Gly Asn
            820                 825                 830
Phe Ser Ser Ala Trp Ile Asp His Ser Thr Arg Pro Lys Asp Ala Ser
        835                 840                 845
Tyr Glu Tyr Met Val Phe Leu Asp Ala Thr Pro Glu Lys Met Gly Glu
850                 855                 860
Met Ala Gln Lys Phe Arg Glu Asn Asn Gly Leu Tyr Gln Val Leu Arg
865                 870                 875                 880
Lys Asp Lys Asp Val His Ile Ile Leu Asp Lys Leu Ser Asn Val Thr
                885                 890                 895
Gly Tyr Ala Phe Tyr Gln Pro Ala Ser Ile Glu Asp Lys Trp Ile Lys
            900                 905                 910
Lys Val Asn Lys Pro Ala Ile Val Met Thr His Arg Gln Lys Asp Thr
        915                 920                 925
Leu Ile Val Ser Ala Val Thr Pro Asp Leu Asn Met Thr Arg Gln Lys
        930                 935                 940
Ala Ala Thr Pro Val Thr Ile Asn Val Thr Ile Asn Gly Lys Trp Gln
945                 950                 955                 960
Ser Ala Asp Lys Asn Ser Glu Val Lys Tyr Gln Val Ser Gly Asp Asn
            965                 970                 975
Thr Glu Leu Thr Phe Thr Ser Tyr Phe Gly Ile Pro Gln Glu Ile Lys
        980                 985                 990
```

Leu Ser Pro Leu Pro Gly Arg Lys   Lys Arg Arg Gln   Arg Arg Pro
        995               1000                 1005

Pro Gln  Cys
    1010

<210> SEQ ID NO 90
<211> LENGTH: 2814
<212> TYPE: DNA
<213> ORGANISM: Artificial
<220> FEATURE:
<223> OTHER INFORMATION: Synthetic polynucleotide, chondroitinase
      ABCI-N(delta)60

<400> SEQUENCE: 90

| | | | | | |
|---|---|---|---|---|---|
| tttactttac | ataaaaaact | gattgtcccc | accgataaag | aagcatctaa | agcatgggga | 60 |
| cgctcatcca | ccccgtttt | ctcatttgg | ctttacaatg | aaaaaccgat | tgatggttat | 120 |
| cttactatcg | atttcggaga | aaaactcatt | tcaaccagtg | aggctcaggc | aggctttaaa | 180 |
| gtaaaattag | atttcactgg | ctggcgtact | gtgggagtct | ctttaaataa | cgatcttgaa | 240 |
| aatcgagaga | tgaccttaaa | tgcaaccaat | acctcctctg | atggtactca | agacagcatt | 300 |
| gggcgttctt | taggtgctaa | agtcgatagt | attcgtttta | aagcgccttc | taatgtgagt | 360 |
| cagggtgaaa | tctatatcga | ccgtattatg | ttttctgtcg | atgatgctcg | ctaccaatgg | 420 |
| tctgattatc | aagtaaaaac | tcgcttatca | gaacctgaaa | ttcaatttca | caacgtaaag | 480 |
| ccacaactac | ctgtaacacc | tgaaaattta | gcggccattg | atcttattcg | ccaacgtcta | 540 |
| attaatgaat | tgtcggagg | tgaaaaagag | acaaacctcg | cattagaaga | aatatcagc | 600 |
| aaattaaaaa | gtgatttcga | tgctcttaat | actcacactt | tagcaaatgg | tggaacgcaa | 660 |
| ggcagacatc | tgatcactga | taaacaaatc | attatttatc | aaccagagaa | tcttaactct | 720 |
| caagataaac | aactatttga | taattatgtt | attttaggta | attacacgac | attaatgttt | 780 |
| aatattagcc | gtgcttatgt | gctggaaaaa | gatcccacac | aaaaggcgca | actaaagcag | 840 |
| atgtacttat | taatgacaaa | gcatttatta | gatcaaggct | tgttaaagg | gagtgcttta | 900 |
| gtgacaaccc | atcactgggg | atacagttct | cgttggtggt | atatttccac | gttattaatg | 960 |
| tctgatgcac | taaagaagc | gaacctacaa | actcaagttt | atgattcatt | actgtggtat | 1020 |
| tcacgtgagt | ttaaaagtag | ttttgatatg | aaagtaagtg | ctgatagctc | tgatctagat | 1080 |
| tatttcaata | cctatctcg | ccaacattta | gccttattac | tactagagcc | tgatgatcaa | 1140 |
| aagcgtatca | acttagttaa | tactttcagc | cattatatca | ctggcgcatt | aacgcaagtg | 1200 |
| ccaccgggtg | gtaaagatgg | tttacgccct | gatggtacag | catggcgaca | tgaaggcaac | 1260 |
| tatccgggct | actctttccc | agcctttaaa | aatgcctctc | agcttattta | tttattacgc | 1320 |
| gatacaccat | tttcagtggg | tgaaagtggt | tggaatagcc | tgaaaaaagc | gatggttca | 1380 |
| gcgtggatct | acagtaatcc | agaagttgga | ttaccgcttg | caggaagaca | ccctcttaac | 1440 |
| tcaccttcgt | taaatcagt | cgctcaaggc | tattactggc | ttgccatgtc | tgcaaaatca | 1500 |
| tcgcctgata | aaacacttgc | atctatttat | cttgcgatta | gtgataaaac | acaaaatgaa | 1560 |
| tcaactgcta | tttttggaga | aactattaca | ccagcgtctt | tacctcaagg | tttctatgcc | 1620 |
| tttaatggcg | gtgcttttgg | tattcatcgt | tggcaagata | aaatggtgac | actgaaagct | 1680 |
| tataacacca | atgtttggtc | atctgaaatt | tataacaaag | ataaccgtta | tggccgttac | 1740 |
| caaagtcatg | gtgtcgctca | aatagtgagt | aatggctcgc | agctttcaca | gggctatcag | 1800 |
| caagaaggtt | gggattggaa | tagaatgcca | ggggcaacca | ctatccacct | tcctcttaaa | 1860 |

```
gacttagaca gtcctaaacc tcataccttta atgcaacgtg gagagcgtgg atttagcgga    1920
acatcatccc ttgaaggtca atatggcatg atggcattcg atcttattta tcccgccaat    1980
cttgagcgtt ttgatcctaa tttcactgcg aaaagagtg tattagccgc tgataatcac     2040
ttaattttta ttggtagcaa tataaatagt agtgataaaa ataaaaatgt tgaaacgacc    2100
ttattccaac atgccattac tccaacatta aataccctt ggattaatgg acaaaagata     2160 gaaacatgc cttatcaaac aacacttcaa caaggtgatt ggttaattga tagcaatggc     2220
aatggttact taattactca agcagaaaaa gtaaatgtaa gtcgccaaca tcaggtttca    2280
gcggaaaata aaaatcgcca accgacagaa ggaaacttta gctcggcatg gatcgatcac    2340
agcactcgcc ccaaagatgc cagttatgag tatatggtct ttttagatgc gacacctgaa    2400
aaaatgggag agatggcaca aaaattccgt gaaataatg ggttatatca ggttcttcgt     2460
aaggataaag acgttcatat tattctcgat aaactcagca atgtaacggg atatgccttt    2520
tatcagccag catcaattga agacaaatgg atcaaaaagg ttaataaacc tgcaattgtg    2580
atgactcatc gacaaaaaga cactcttatt gtcagtgcag ttacacctga tttaaatatg    2640
actcgccaaa aagcagcaac tcctgtcacc atcaatgtca cgattaatgg caaatggcaa    2700
tctgctgata aaaatagtga agtgaaatat caggtttctg gtgataacac tgaactgacg    2760
tttacgagtt actttggtat tccacaagaa atcaaactct cgccactccc ttga          2814
```

<210> SEQ ID NO 91  
<211> LENGTH: 2934  
<212> TYPE: DNA  
<213> ORGANISM: Artificial  
<220> FEATURE:  
<223> OTHER INFORMATION: Synthetic polynucleotide, chondroitinase ABCI-N(delta)20

<400> SEQUENCE: 91

```
gcacaaaata acccattagc agacttctca tcagataaaa actcaatact aacgttatct      60
gataaacgta gcattatggg aaaccaatct ctttttatgga aatggaaagg tggtagtagc    120
tttactttac ataaaaaact gattgtcccc accgataaag aagcatctaa agcatgggga    180
cgctcatcca ccccgtttt ctcattttgg ctttacaatg aaaaaccgat tgatggttat     240
cttactatcg atttcggaga aaaactcatt tcaaccagtg aggctcaggc aggctttaaa    300
gtaaaattag atttcactgg ctggcgtact gtgggagtct cttaaataa cgatcttgaa     360 aatcgagaga tgaccttaaa tgcaaccaat acctcctctg atggtactca agacagcatt    420
gggcgttctt taggtgctaa agtcgatagt attcgttta aagcgccttc taatgtgagt     480
cagggtgaaa tctatatcga ccgtattatg ttttctgtcg atgatgctcg ctaccaatgg    540
tctgattatc aagtaaaaac tcgcttatca gaacctgaaa ttcaatttca aacgtaaag    600 ccacaactac ctgtaacacc tgaaaattta gcggccattg atcttattcg ccaacgtcta    660
attaatgaat ttgtcggagg tgaaaaagag acaaacctcg cattagaaga gaatatcagc    720
aaattaaaaa gtgatttcga tgctcttaat actcacactt tagcaaatgg tggaacgcaa    780
ggcagacatc tgatcactga taacaaatc attatttatc aaccagagaa tcttaactct     840
caagataaac aactatttga taattatgtt attttaggta attacacgac attaatgttt    900
aatattagcc gtgcttatgt gctggaaaaa gatcccacac aaaaggcgca actaaagcag    960
atgtacttat taatgacaaa gcatttatta gatcaaggct tgttaaaagg gagtgcttta   1020
gtgacaaccc atcactgggg atacagttct cgttggtggt atatttccac gttattaatg   1080
```

```
tctgatgcac taaaagaagc gaacctacaa actcaagttt atgattcatt actgtggtat    1140
tcacgtgagt ttaaaagtag ttttgatatg aaagtaagtg ctgatagctc tgatctagat    1200
tatttcaata ccttatctcg ccaacattta gccttattac tactagagcc tgatgatcaa    1260
aagcgtatca acttagttaa tactttcagc cattatatca ctggcgcatt aacgcaagtg    1320
ccaccgggtg gtaaagatgg tttacgccct gatggtacag catggcgaca tgaaggcaac    1380
tatccgggct actctttccc agcctttaaa aatgcctctc agcttattta tttattacgc    1440
gatacaccat tttcagtggg tgaaagtggt tggaatagcc tgaaaaagc gatggtttca     1500 gcgtggatct acagtaatcc agaagttgga ttaccgcttg caggaagaca ccctcttaac    1560
tcaccttcgt taaaatcagt cgctcaaggc tattactggc ttgccatgtc tgcaaaatca    1620
tcgcctgata aaacacttgc atctatttat cttgcgatta gtgataaaac acaaaatgaa    1680
tcaactgcta tttttggaga aactattaca ccagcgtctt tacctcaagg tttctatgcc    1740
tttaatggcg gtgcttttgg tattcatcgt tggcaagata aaatggtgac actgaaagct    1800
tataacacca atgtttggtc atctgaaatt tataacaaag ataaccgtta tggccgttac    1860
caaagtcatg gtgtcgctca aatagtgagt aatggctcgc agctttcaca gggctatcag    1920
caagaaggtt gggattggaa tagaatgcca ggggcaacca ctatccacct tcctcttaaa    1980
gacttagaca gtcctaaacc tcataccta atgcaacgtg gagagcgtgg atttagcgga     2040
acatcatccc ttgaaggtca atatggcatg atggcattcg atcttattta tcccgccaat    2100
cttgagcgtt tgatcctaa tttcactgcg aaaaagagtg tattagccgc tgataatcac    2160
ttaattttta ttggtagcaa tataaatagt agtgataaaa ataaaaatgt tgaaacgacc    2220
ttattccaac atgccattac tccaacatta aatacccttt ggattaatgg acaaaagata    2280
gaaaacatgc cttatcaaac aacacttcaa caaggtgatt ggttaattga tagcaatggc    2340
aatggttact taattactca agcagaaaaa gtaaatgtaa gtcgccaaca tcaggttta    2400 gcggaaaata aaaatcgcca accgacagaa ggaaacttta gctcggcatg gatcgatcac    2460
agcactcgcc ccaaagatgc cagttatgag tatatggtct ttttagatgc gacacctgaa    2520
aaaatgggag atgtgcaca aaaattccgt gaaaataatg ggttatatca ggttcttcgt    2580
aaggataaag acgttcatat tattctcgat aaactcagca atgtaacggg atatgccttt    2640
tatcagccag catcaattga agacaaatgg atcaaaaagg ttaataaacc tgcaattgtg    2700
atgactcatc gacaaaaaga cactcttatt gtcagtgcag ttacacctga tttaaatatg    2760
actcgccaaa aagcagcaac tcctgtcacc atcaatgtca cgattaatgg caaatggcaa    2820
tctgctgata aaaatagtga agtgaaatat caggtttctg gtgataacac tgaactgacg    2880
tttacgagtt acctttggtat tccacaagaa atcaaactct cgccactccc ttga         2934
```

<210> SEQ ID NO 92
<211> LENGTH: 51
<212> TYPE: DNA
<213> ORGANISM: Artificial
<220> FEATURE:
<223> OTHER INFORMATION: Oligonucleotide used for cloning TAT-ABCI

<400> SEQUENCE: 92

```
tatgtatggt cgtaaaaagc gtcgtcaacg tcgtcgtggt ggtggtggtc a              51
```

<210> SEQ ID NO 93
<211> LENGTH: 54
<212> TYPE: DNA
<213> ORGANISM: Artificial

```
<220> FEATURE:
<223> OTHER INFORMATION: OTHER INFORMATION; Oligonucleotide used for
      cloning TAT-ABCI

<400> SEQUENCE: 93
tatgaccacc accaccacca cgacgacgtt gacgacgctt tttacgacca taca         54

<210> SEQ ID NO 94
<211> LENGTH: 7
<212> TYPE: PRT
<213> ORGANISM: Artificial
<220> FEATURE:
<223> OTHER INFORMATION: Artificial Sequence, Gly-Ser linker

<400> SEQUENCE: 94

Gly Gly Gly Gly Ser Ser Ser
1               5

<210> SEQ ID NO 95
<211> LENGTH: 27
<212> TYPE: DNA
<213> ORGANISM: Artificial
<220> FEATURE:
<223> OTHER INFORMATION: PCR primer

<400> SEQUENCE: 95
catatggcca ccagcmtcct gcatttg                                       27

<210> SEQ ID NO 96
<211> LENGTH: 24
<212> TYPE: DNA
<213> ORGANISM: Artificial
<220> FEATURE:
<223> OTHER INFORMATION: PCR primer

<400> SEQUENCE: 96
ggatcctcaa gggagtggcg agag                                          24
```

What is claimed is:

1. A composition comprising: a polypeptide comprising a protein transduction domain, and a proteoglycan degrading domain, wherein the proteoglycan degrading domain comprises SEQ ID NO: 51, SEQ ID NO: 52, SEQ ID NO: 53, SEQ ID NO: 81, SEQ ID NO: 82, SEQ ID NO: 83, or a combination thereof.

2. The composition of claim 1, wherein the protein transduction domain is a TAT domain.

3. The composition of claim 1, wherein two domains of said polypeptide are bonded together by a linker polypeptide domain.

4. The composition of claim 1, further comprising a pharmaceutically acceptable excipient.

5. The composition of claim 1, further comprising cells from the CNS.

6. The composition of claim 1, wherein the polypeptide further comprises a domain that promotes neural regeneration.

7. The composition of claim 6, wherein the domain that promotes neural regeneration is SEQ ID NO: 4, a functional variant capable of promoting neural regeneration that is at least 80% homologous with SEQ ID NO: 4, or a functional deletion mutant of SEQ ID NO: 4.

8. The composition of claim 1, wherein the polypeptide comprises SEQ ID NO: 85 or SEQ ID NO: 87.

* * * * *

UNITED STATES PATENT AND TRADEMARK OFFICE
CERTIFICATE OF CORRECTION

| | | |
|---|---|---|
| PATENT NO. | : 8,906,363 B2 | Page 1 of 1 |
| APPLICATION NO. | : 10/848564 | |
| DATED | : December 9, 2014 | |
| INVENTOR(S) | : Gruskin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1042 days.

Signed and Sealed this
First Day of December, 2015

Michelle K. Lee
*Director of the United States Patent and Trademark Office*